(12) United States Patent
Gray et al.

(10) Patent No.: US 12,365,677 B2
(45) Date of Patent: Jul. 22, 2025

(54) DEGRADERS THAT TARGET PROTEINS VIA KEAP1

(71) Applicant: DANA-FARBER CANCER INSTITUTE, INC., Boston, MA (US)

(72) Inventors: Nathanael S. Gray, Boston, MA (US); Tinghu Zhang, Brookline, MA (US); Eric Fischer, Chestnut Hill, MA (US); Guangyan Du, Jamaica Plain, MA (US); Nozhat Safaee, Brookline, MA (US); Nathaniel Henning, Brookline, MA (US); Katherine Donovan, Boston, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 1129 days.

(21) Appl. No.: 17/258,340

(22) PCT Filed: Jul. 18, 2019

(86) PCT No.: PCT/US2019/042403
§ 371 (c)(1),
(2) Date: Jan. 6, 2021

(87) PCT Pub. No.: WO2020/018788
PCT Pub. Date: Jan. 23, 2020

(65) Prior Publication Data
US 2021/0276996 A1   Sep. 9, 2021

Related U.S. Application Data

(60) Provisional application No. 62/737,514, filed on Sep. 27, 2018, provisional application No. 62/701,098, filed on Jul. 20, 2018.

(51) Int. Cl.
C07D 419/14   (2006.01)
C07D 403/12   (2006.01)
C07D 495/14   (2006.01)

(52) U.S. Cl.
CPC ........ C07D 419/14 (2013.01); C07D 403/12 (2013.01); C07D 495/14 (2013.01)

(58) Field of Classification Search
CPC .................................................. C07D 419/14
See application file for complete search history.

(56) References Cited

U.S. PATENT DOCUMENTS

2016/0058872 A1   3/2016   Crew et al.
2016/0318917 A1   11/2016  Boehm et al.

FOREIGN PATENT DOCUMENTS

WO   2018109646 A1   6/2018
WO   2020210229 A1   10/2020

OTHER PUBLICATIONS

Nandave. M. PROTAC-Mediated Protein Degradation: A Paradigm Shift in Cancer Therapeutics. Springer Nature Singapore Pte Ltd. 2024, pp. 1-400; ISBN 978-981-97-5077-1 (eBook).*

* cited by examiner

*Primary Examiner* — Shawquia Jackson
(74) *Attorney, Agent, or Firm* — ArentFox Schiff LLP; Daniel W. Clarke; Shawn P. Foley

(57) ABSTRACT

Disclosed are bifunctional compounds, pharmaceutical compositions containing them, and methods of making and using them to treat diseases and disorders characterized by aberrant protein activity wherein the protein is targeted for degradation by KEAP1 and the Cul3-based E3-ubiquitin ligase complex.

11 Claims, 11 Drawing Sheets

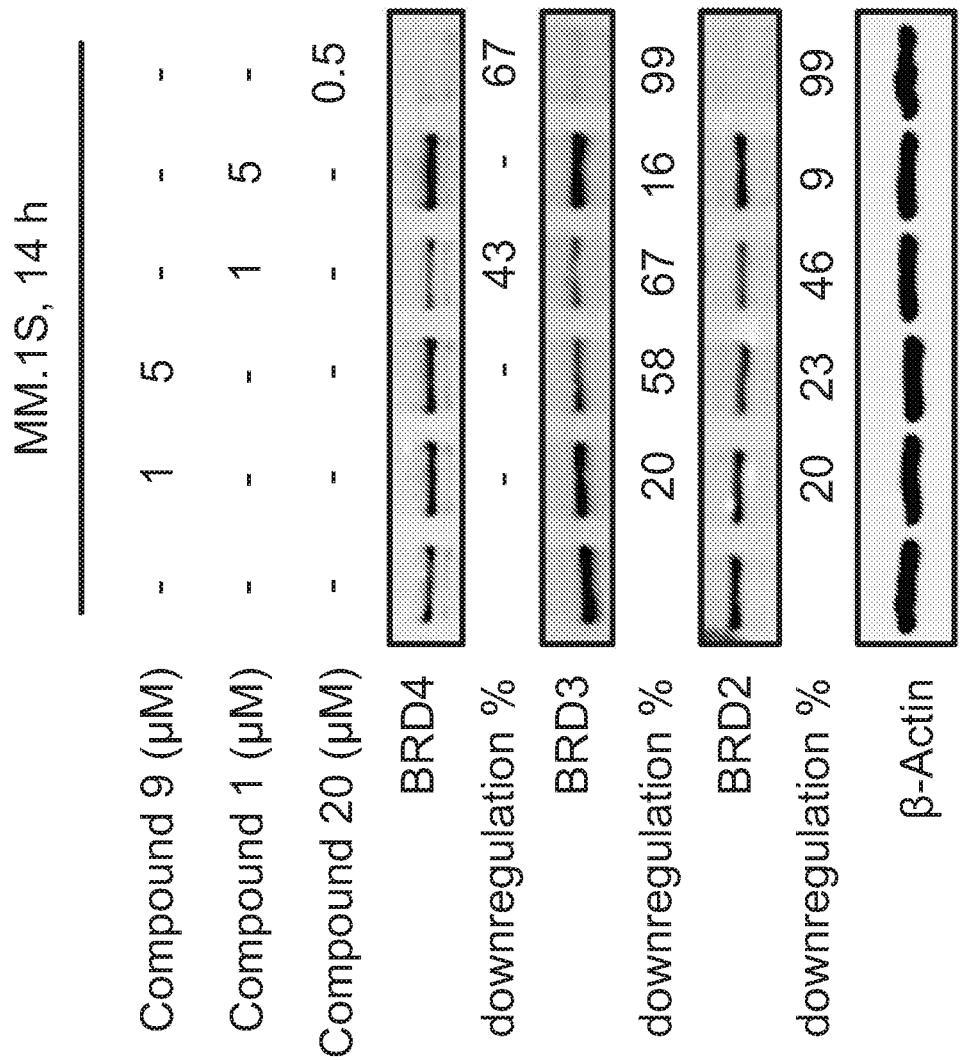

DEGRADERS THAT TARGET PROTEINS VIA KEAP1

RELATED APPLICATIONS

This application is a national stage application, filed under 35 U.S.C. § 371, of International Application No. PCT/US2019/042403, filed Jul. 18, 2019, which claims the benefit of priority under 35 U.S.C. § 119(e) to U.S. Provisional Application No: 62/701,098, filed Jul. 20, 2018 and U.S. Provisional Application No. 62/737,514, filed Sep. 27, 2018, each of which is incorporated herein by reference in its entirety.

GOVERNMENT LICENSE RIGHTS

This invention was made with government support under grant number R01 CA214608 awarded by the National Institutes of Health. The government has certain rights in the invention.

BACKGROUND OF THE INVENTION

The gene that encodes cereblon (CRBN) was first identified in the course of a study of genes related to memory and learning; the gene was assigned the name CRBN based on its supposed role in the development of cerebral tissues and because its expression in the hippocampus among other areas, is associated with memory and learning processes. Higgins et al., Neurol. 63(10):1927-31 (2004).

Cereblon is a 442-amino acid multifunctional protein located in the cytoplasm, nucleus and peripheral membrane of the human brain and other tissues (Wada et al., Biochem. & Biophys. Res. Comm. 477:388-94 (2016)). It interacts with the DNA damage-binding protein-1 (DDB1), Cullin 4 (Cul4A and Cul4B), and regulator of Cullins 1 (RoC1) to form the functional E3 ubiquitin ligase complex, which is known as the $CRL4^{CRBN}$ E3 ubiquitin ligase complex. Cereblon's role as part of this complex includes targeting proteins for proteolysis (degradation) via an ubiquitin-proteasome pathway. See, e.g., Chang et al., Int. J. Biochem. Mol. Biol. 2(3):287-94 (2011).

Cereblon is closely associated with the metabolism and proliferation of normal cells as well as tumor cells. On one hand, its existence ensures normal metabolic function and normal physiological function of ion channels, which are important to maintaining cell growth and proliferation. On the other hand, cereblon is also involved in the occurrence of many diseases, such as cancer. See, generally, Shi et al., J. Immunol. Res. Article ID 9130608 (2017).

Immunomodulatory drugs ("IMiDs") are a new class of anti-cancer drugs that are derived from thalidomide, a drug which has been approved by the FDA for treatment of multiple myeloma. In addition to thalidomide itself, two thalidomide analogs, lenalidomide and pomalidomide, have been approved by the FDA (and are being marketed under the names REVLIMID® and POMALYST®, respectively) for treatment of multiple myeloma (among other diseases). As suggested by their nomenclature, one of the first known properties of IMiDs was their immunomodulatory capacity, including cytokine modulation and T cell co-stimulation (Schafer et al., J. Pharmacol. & Exper. Ther. 305:1222-32 (2003)), resulting in interleukin-2 production in T cells. Subsequently, IMiDs were shown to have pleiotropic effects on a wide range of immune cells including natural killer (NK) cell activation and B cell and monocyte inhibition (Corral et al., J. Immunol. 163:380-6 (1999)).

Cereblon has been identified as a common primary target for IMiDs. For example, it has been reported that members of the Ikaros family of transcription factors, Ikaros and Aiolos (encoded by the genes Ikaros family zinc finger protein 1 (IKZF1) and IKZF3 respectively) are recruited as protein substrates for $CRL4^{CRBN}$ in T cells in response to treatment with lenalidomide and pomalidomide, resulting in enhanced production of IL-2 and other cytokines that regulate T cell function. See, Gandhi et al., Br. J. Hematol. 164:811-21 (2014). It has also been reported that lenalidomide, but not pomalidomide, induces the degradation of the protein kinase, casein kinase 1α (CK1α), which exploits CK1α haploinsufficiency associated with 5q-deletion associated myelodysplastic syndrome. See, Krönke et al., Nature 523:183-8 (2015). Structural studies have shown that these IMiDs bind in a shallow hydrophobic pocket on the surface of cereblon, and that the binding is mediated by the glutarimide ring that is common to thalidomide, lenalidomide and pomalidomide.

More recently, CRBN-binding compounds named "cereblon modulators" have been developed. For example, CC-122, a new chemical entity termed 'pleiotropic pathway modifier', binds cereblon and promotes degradation of Aiolos and Ikaros in diffuse large B-cell lymphoma (DLBCL) and T cells in vitro, in vivo, and in patients, resulting in both cell autonomous as well as immunostimulatory effects. See, Hagner et al., Blood 126(6):779-89 (2016). CC-885, another new cereblon modulator, has been reported to possess antitumor activity which is broader than that of thalidomide, lenalidomide and pomalidomide. CC-885 is mediated by cereblon-dependent ubiquitination and degradation of the translation termination factor glutathione S-transferase pi gene (GSTP1). See, Matyskiela et al., Nature 535:25′2-7 (2016).

The exploitation of cereblon as a mediator in disease treatment has also led to the development of hetero-bifunctional PROTACs (PROteolysis TArgeting Chimera) that recruit targeted proteins that are themselves disease mediators (e.g., bromodomain-containing protein 4 (BRD4)) to $CRL4^{CRBN}$ E3 ubiquitin ligase, leading to degradation of the targeted protein. See, e.g., Lu et al., Cell Cancer Biol. 22(6):755-63 (2015).

SUMMARY OF THE INVENTION

The protein Kelch-like ECH-associated protein (KEAP1 or $KEAP1^{KELCH}$) plays a key role in the regulation of NF-E2 related factor 2 (Nrf2). NF-E2 related factor 2 (Nrf2) is a member of the cap-n-collar (CNC) family of transcription factors containing a characteristic basic-leucine zipper motif. KEAP1 consists of three domains: 1) an N-terminal Broad-complex, Tramtrack, and the Bric-a-Brac (BTB) domain, serving as an adaptor for the E3 ubiquitin ligase Cul3/Rbx1; 2) an Intervening Region (IVR) or BTB and C-terminal Kelch (BACK) domain; and 3) a C-terminal Kelch repeat domain, which is a protein-recognition module for Nrf2 with a β-propeller fold. Under basal (normal) conditions, Nrf2 levels are tightly controlled by KEAP1 which binds Nrf2 and targets it for ubiquitylation and degradation via the Cul3-based E3-ubiquitin ligase complex. Conversely, under conditions of oxidative stress, DJ1 (Parkinsonism associated deglycase (PARK7)) is activated and stabilizes Nrf2 protein by preventing Nrf2 from interacting with KEAP1. Also, modification of reactive cysteines on KEAP1 as a result of increase in levels of electrophiles species produced as a result of oxidative stress can cause conformational changes in KEAP1 that alters Nrf2 binding and promotes Nrf2 stabilization. This perturbs the ubiquitin of Nrf2, allowing translocation to the nucleus, where it activates antioxidant response elements (AREs) which cause increased expression of cytoprotective proteins. Inadequate Nrf2 signaling in the face of chronic oxidative stress has been proposed as a pathological mechanism in inflammatory diseases.

Applicant has exploited this degradative pathway by recruiting it to target aberrant proteins that are mediators of a variety of diseases and disorders.

An aspect of the present invention is directed to a bifunctional compound, also referred to herein as a degrader or PROTAC, having a structure represented by formula (I):

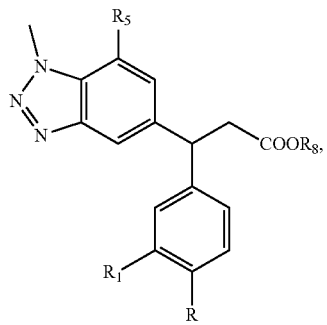

wherein:
R is methyl or halo;
R₁ is

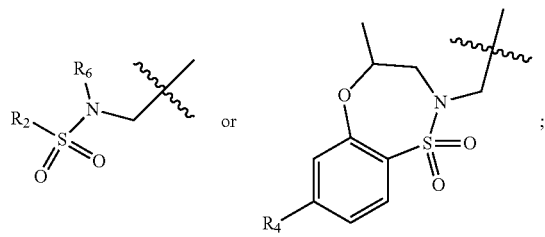

R₂ is methyl,

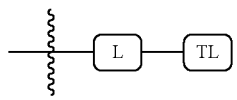

wherein L is a linker and TL is a targeting ligand that binds a protein of interest (targeted for degradation), or

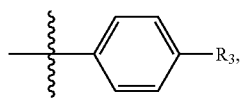

wherein
R₃ is H or

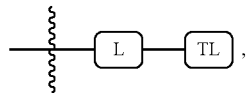

and
R₄ is H, halo or

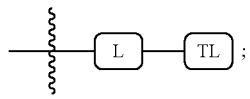

R₅ is methoxy or

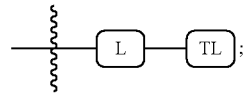

R₆ is H or methyl; and
R₈ is H, methyl or ethyl;
provided that one of R₂, R₃, R₄ and R₅ is

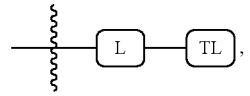

or a pharmaceutically acceptable salt or stereoisomer thereof.

Another aspect of the present invention is directed to a pharmaceutical composition including a therapeutically effective amount of a bifunctional compound of formula (I), or a pharmaceutically acceptable salt or stereoisomer thereof, and a pharmaceutically acceptable carrier. Bifunctional compounds of formula (I) may be water-soluble; hence, they may be advantageously and conveniently formulated for parenteral or oral administration, whereupon they permeate membranes of cells harboring proteins to which the bifunctional compounds bind (via the targeting ligand) resulting in degradation of the target protein.

Yet another aspect of the present invention is directed to methods of making the bifunctional compounds of formula (I), or a pharmaceutically acceptable salt or stereoisomer thereof.

A further aspect of the present invention is directed to methods of treating diseases or disorders involving aberrant protein activity, that entail administration of a therapeutically effective amount of a bifunctional compound of formula (I), or a pharmaceutically acceptable salt or stereoisomer thereof, to a subject in need thereof.

Without intending to be bound by any particular theory of operation, the bifunctional compounds of the present invention are believed to degrade aberrant proteins that are involved in the genesis and/or progression of disease via the cell's Ubiquitin/Proteasome System, including Cul3/Rbx1, whose function is to routinely identify and remove damaged proteins. The bifunctional compounds of the present invention tag the target protein (which is bound by the targeting ligand functionality) for ubiquitination and degradation via the Cul3-based E3-ubiquitin ligase complex. After destruction of the target protein, the degrader is released and continues to be active. Thus, by engaging and exploiting the body's own natural protein disposal system, the bifunctional compounds of the present invention may represent a potential improvement over traditional small molecule inhibitors of dysfunctional proteins in the treatment of cancers and other disease that have proven difficult to treat.

BRIEF DESCRIPTION OF THE DRAWINGS

FIG. 3A-FIG. 3B are Western blots that show the degradation of BRD4, BRD3 and BRD2 by inventive bifunctional compounds 1 and 9 over time (14 hours and 24 hours) and as a function of concentration (μM) as compared to controls.

DETAILED DESCRIPTION

Figure 1A:
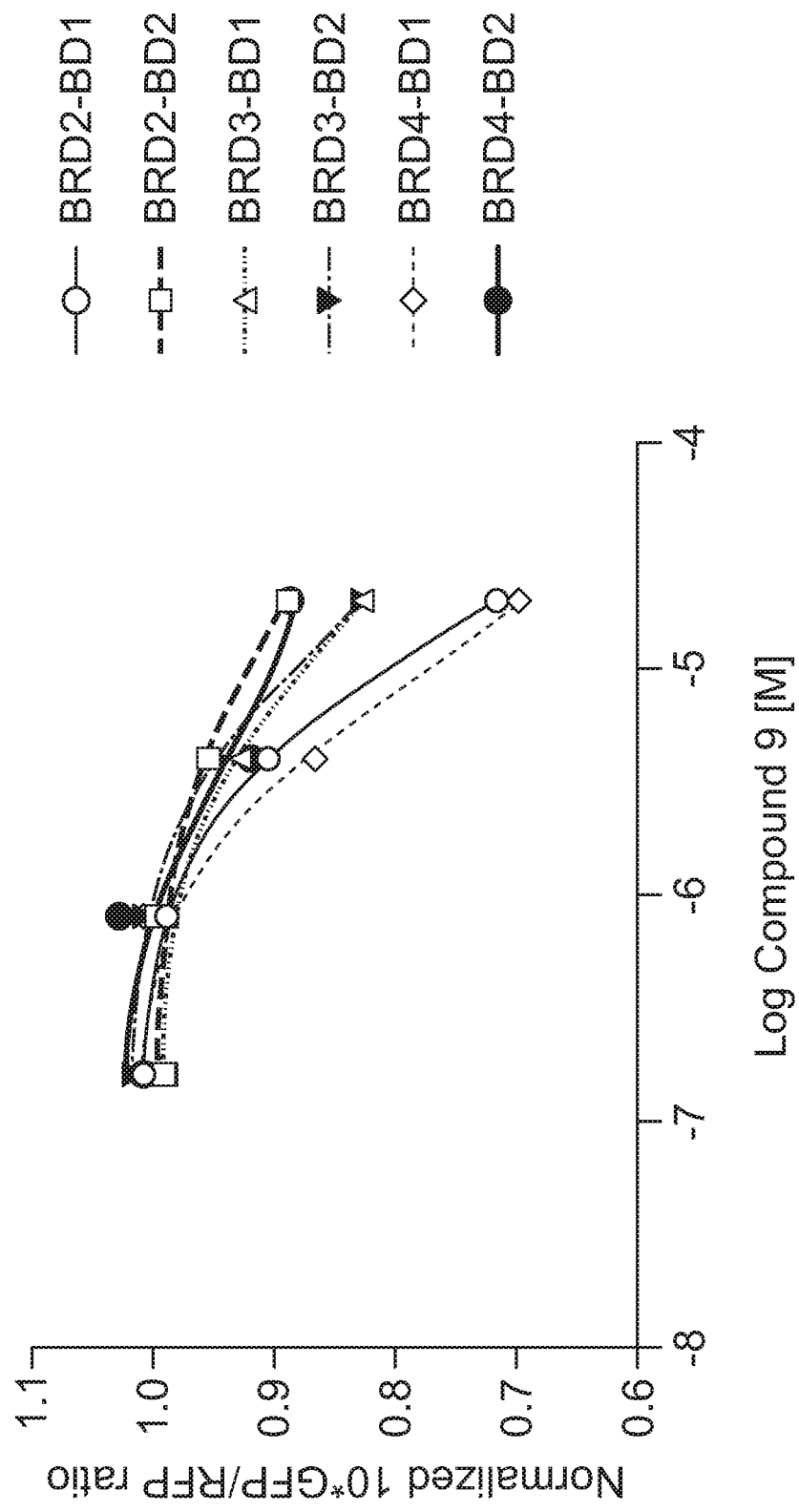
FIG. 1A is a graph that shows a comparison of the effect of inventive bifunctional compound 9 on various BRD proteins, measured in terms of normalized 10* green fluorescent protein/red fluorescent protein (GFP/RFP) ratio, as a function of concentration (expressed in units of M), assayed in reporter cell lines, each expressing one of the bromodomains (BD) of BRD2/3/4 (BRD2-BD1, BRD2-BD2, BRD3-BD1, BRD3-BD2, BRD4-BD1, BRD4-BD2) as GFP fusion proteins together with RFP.

Unless defined otherwise, all technical and scientific terms used herein have the same meaning as is commonly understood by one of skill in the art to which the subject matter herein belongs. As used in the specification and the appended claims, unless specified to the contrary, the following terms have the meaning indicated in order to facilitate the understanding of the present invention.

As used in the description and the appended claims, the singular forms "a", "an", and "the" include plural referents unless the context clearly dictates otherwise. Thus, for example, reference to "a composition" includes mixtures of two or more such compositions, reference to "an inhibitor" includes mixtures of two or more such inhibitors, and the like.

Unless stated otherwise, the term "about" means within 10% (e.g., within 5%, 2% or 1%) of the particular value modified by the term "about."

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

With respect to bifunctional compounds of the present invention, and to the extent the following terms are used herein to further describe them, the following definitions apply.

As used herein, the term "alkyl" refers to a saturated linear or branched-chain monovalent hydrocarbon radical. In one embodiment, the alkyl radical is a $C_1$-$C_{18}$ group. In other embodiments, the alkyl radical is a $C_0$-$C_6$, $C_0$-$C_5$, $C_0$-$C_3$, $C_1$-$C_{12}$, $C_1$-$C_8$, $C_1$-$C_6$, $C_1$-$C_5$, $C_1$-$C_4$ or $C_1$-$C_3$ group (wherein $C_0$ alkyl refers to a bond). Examples of alkyl groups include methyl, ethyl, 1-propyl, 2-propyl, i-propyl, 1-butyl, 2-methyl-1-propyl, 2-butyl, 2-methyl-2-propyl, 1-pentyl, n-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, heptyl, octyl, nonyl, decyl, undecyl and dodecyl. In some embodiments, an alkyl group is a $C_1$-$C_3$ alkyl group. In some embodiments, an alkyl group is a $C_1$-$C_2$ alkyl group.

As used herein, the term "alkylene" refers to a straight or branched divalent hydrocarbon chain linking the rest of the molecule to a radical group, consisting solely of carbon and hydrogen, containing no unsaturation and having from one to 12 carbon atoms, for example, methylene, ethylene, propylene, n-butylene, and the like. The alkylene chain may be attached to the rest of the molecule through a single bond and to the radical group through a single bond. In some embodiments, the alkylene group contains one to 8 carbon atoms ($C_1$-$C_8$ alkylene). In other embodiments, an alkylene group contains one to 5 carbon atoms ($C_1$-$C_5$ alkylene). In other embodiments, an alkylene group contains one to 4 carbon atoms ($C_1$-$C_4$ alkylene). In other embodiments, an alkylene contains one to three carbon atoms ($C_1$-$C_3$ alkylene). In other embodiments, an alkylene group contains one to two carbon atoms ($C_1$-$C_2$ alkylene). In other embodiments, an alkylene group contains one carbon atom ($C_1$ alkylene).

The terms "alkoxyl" or "alkoxy" as used herein refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl.

As used herein, the term "halogen" (or "halo" or "halide") refers to fluorine, chlorine, bromine, or iodine.

As used herein, the term "carbocyclic" (also "carbocyclyl") refers to a group that used alone or as part of a larger moiety, contains a saturated, partially unsaturated, or aromatic ring system having 3 to 20 carbon atoms, that is alone or part of a larger moiety (e.g., an alkcarbocyclic group). The term carbocyclyl includes mono-, bi-, tri-, fused, bridged, and spiro-ring systems, and combinations thereof. In one embodiment, carbocyclyl includes 3 to 15 carbon atoms ($C_3$-$C_{15}$). In one embodiment, carbocyclyl includes 3 to 12 carbon atoms ($C_3$-$C_{12}$). In another embodiment, carbocyclyl includes $C_3$-$C_8$, $C_3$-$C_{10}$ or $C_5$-$C_{10}$. In another embodiment, carbocyclyl, as a monocycle, includes $C_3$-$C_8$, $C_3$-$C_6$ or $C_5$-$C_6$. In some embodiments, carbocyclyl, as a bicycle, includes $C_7$-$C_{12}$. In another embodiment, carbocyclyl, as a spiro system, includes $C_5$-$C_{12}$. Representative examples of monocyclic carbocyclyls include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, phenyl, and cyclododecyl; bicyclic carbocyclyls having 7 to 12 ring atoms include [4,3], [4,4], [4,5], [5,5], [5,6] or [6,6] ring systems, such as for example bicyclo[2.2.1]heptane, bicyclo[2.2.2]octane, naphthalene, and bicyclo[3.2.2]nonane. Representative examples of spiro carbocyclyls include spiro[2.2]pentane, spiro[2.3]hexane, spiro[2.4]heptane, spiro[2.5]octane and spiro[4.5]decane. The term carbocyclyl includes aryl ring systems as defined herein. The term carbocycyl also includes cycloalkyl rings (e.g., saturated or partially unsaturated mono-, bi-, or spiro-carbocycles). The term carbocyclic group also includes a carbocyclic ring fused to one or more (e.g., 1, 2 or 3) different cyclic groups (e.g., aryl or heterocyclic rings), where the radical or point of attachment is on the carbocyclic ring.

Thus, the term carbocyclic also embraces carbocyclylalkyl groups which as used herein refer to a group of the formula —$R^c$-carbocyclyl where $R^c$ is an alkylene chain. The term carbocyclic also embraces carbocyclylalkoxy groups which as used herein refer to a group bonded through an oxygen atom of the formula —O—$R^c$-carbocyclyl where $R^c$ is an alkylene chain.

As used herein, the term "heterocyclyl" refers to a "carbocyclyl" that used alone or as part of a larger moiety, contains a saturated, partially unsaturated or aromatic ring system, wherein one or more (e.g., 1, 2, 3, or 4) carbon atoms have been replaced with a heteroatom (e.g., O, N, N(O), S, S(O), or S(O)$_2$). The term heterocyclyl includes mono-, bi-, tri-, fused, bridged, and spiro-ring systems, and combinations thereof. In some embodiments, a heterocyclyl refers to a 3 to 15 membered heterocyclyl ring system. In some embodiments, a heterocyclyl refers to a 3 to 12 membered heterocyclyl ring system. In some embodiments, a heterocyclyl refers to a saturated ring system, such as a 3 to 12 membered saturated heterocyclyl ring system. In some embodiments, a heterocyclyl refers to a heteroaryl ring system, such as a 5 to 14 membered heteroaryl ring system. The term heterocyclyl also includes $C_3$-$C_8$ heterocycloalkyl, which is a saturated or partially unsaturated mono-, bi-, or spiro-ring system containing 3-8 carbons and one or more (1, 2, 3 or 4) heteroatoms.

In some embodiments, a heterocyclyl group includes 3-12 ring atoms and includes monocycles, bicycles, tricycles and Spiro ring systems, wherein the ring atoms are carbon, and one to 5 ring atoms is a heteroatom such as nitrogen, sulfur or oxygen. In some embodiments, heterocyclyl includes 3- to 7-membered monocycles having one or more heteroatoms selected from nitrogen, sulfur or oxygen. In some embodiments, heterocyclyl includes 4- to 6-membered monocycles having one or more heteroatoms selected from nitrogen, sulfur or oxygen. In some embodiments, heterocyclyl includes 3-membered monocycles. In some embodiments, heterocyclyl includes 4-membered monocycles. In some embodiments, heterocyclyl includes 5-6 membered monocycles. In some embodiments, the heterocyclyl group includes 0 to 3 double bonds. In any of the foregoing embodiments, heterocyclyl includes 1, 2, 3 or 4 heteroatoms. Any nitrogen or sulfur heteroatom may optionally be oxidized (e.g., NO, SO, SO$_2$), and any nitrogen heteroatom may optionally be quaternized (e.g., [NR$_4$]$^+$Cl$^-$—, [NR$_4$]$^+$OH$^-$). Representative examples of heterocyclyls include oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydropyranyl, dihydrothienyl, tetrahydrothienyl, imidazolidinyl, piperidinyl, piperazinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, oxazolidinonyl, imidazolidinonyl, 4,5,6,7-tetrahydro[2H]indazolyl, tetrahydrobenzoimidazolyl, 4,5,6,7-tetrahydrobenzo[d]imidazolyl, 1,6-dihydroimidazol[4,5-d]pyrrolo[2,3-b]pyridinyl, thiazinyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptane, azaspiro[3.5]nonanyl, azaspiro[2.5]octanyl, azaspiro[4.5]decanyl, 1-azaspiro[4.5]decan-2-only, azaspiro[5.5]undecanyl, tetrahydroindolyl, octahydroindolyl, tetrahydroisoindolyl, tetrahydroindazolyl, 1,1-dioxohexahydrothiopyranyl. Examples of 5-membered heterocyclyls containing a sulfur or oxygen atom and one to three nitrogen atoms are thiazolyl, including thiazol-2-yl and thiazol-2-yl N-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5-membered ring heterocyclyls containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Representative examples of benzo-fused 5-membered heterocyclyls are benzoxazol-2-yl, benzthiazol-2-yl and benzimidazol-2-yl. Example 6-membered heterocyclyls contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are yet other examples of heterocyclyl groups. In some embodiments, a heterocyclic group includes a heterocyclic ring fused to one or more (e.g., 1, 2 or 3) different cyclic groups (e.g., carbocyclic rings or heterocyclic rings), where the radical or point of attachment is on the heterocyclic ring, and in some embodiments wherein the point of attachment is a heteroatom contained in the heterocyclic ring.

Thus, the term heterocyclic embraces N-heterocyclyl groups which as used herein refer to a heterocyclyl group containing at least one nitrogen and where the point of attachment of the heterocyclyl group to the rest of the molecule is through a nitrogen atom in the heterocyclyl group. Representative examples of N-heterocyclyl groups include 1-morpholinyl, 1-piperidinyl, 1-piperazinyl, 1-pyrrolidinyl, pyrazolidinyl, imidazolinyl and imidazolidinyl. The term heterocyclic also embraces C-heterocyclyl groups which as used herein refer to a heterocyclyl group containing at least one heteroatom and where the point of attachment of the heterocyclyl group to the rest of the molecule is through a carbon atom in the heterocyclyl group. Representative examples of C-heterocyclyl radicals include 2-morpholinyl, 2- or 3- or 4-piperidinyl, 2-piperazinyl, and 2- or 3-pyrrolidinyl. The term heterocyclic also embraces heterocyclylalkyl groups which as disclosed above refer to a group of the formula —$R^c$-heterocyclyl where $R^c$ is an alkylene chain. The term heterocyclic also embraces heterocyclylalkoxy groups which as used herein refer to a radical bonded through an oxygen atom of the formula —O—$R^c$-heterocyclyl where R is an alkylene chain.

As used herein, the term "aryl" used alone or as part of a larger moiety (e.g., "aralkyl", wherein the terminal carbon atom on the alkyl group is the point of attachment, e.g., a benzyl group), "aralkoxy" wherein the oxygen atom is the point of attachment, or "aroxyalkyl" wherein the point of attachment is on the aryl group) refers to a group that includes monocyclic, bicyclic or tricyclic, carbon ring system, that includes fused rings, wherein at least one ring in the system is aromatic. In some embodiments, the aralkoxy group is a benzoxy group. The term "aryl" may be used interchangeably with the term "aryl ring". In one embodiment, aryl includes groups having 6-18 carbon atoms. In another embodiment, aryl includes groups having 6-10 carbon atoms. Examples of aryl groups include phenyl, naphthyl, anthracyl, biphenyl, phenanthrenyl, naphthacenyl, 1,2,3,4-tetrahydronaphthalenyl, 1H-indenyl, 2,3-dihydro-1H-indenyl, and the like, which may be substituted or independently substituted by one or more substituents described herein. A particular aryl is phenyl. In some embodiments, an aryl group includes an aryl ring fused to one or more (e.g., 1, 2 or 3) different cyclic groups (e.g., carbocyclic rings or heterocyclic rings), where the radical or point of attachment is on the aryl ring.

Thus, the term aryl embraces aralkyl groups (e.g., benzyl) which as disclosed above refer to a group of the formula —$R^c$-aryl where $R^c$ is an alkylene chain such as methylene or ethylene. In some embodiments, the aralkyl group is an optionally substituted benzyl group. The term aryl also embraces aralkoxy groups which as used herein refer to a group bonded through an oxygen atom of the formula —O—$R^c$-aryl where $R^c$ is an alkylene chain such as methylene or ethylene.

As used herein, the term "heteroaryl" used alone or as part of a larger moiety (e.g., "heteroarylalkyl" (also "heteroaralkyl"), or "heteroarylalkoxy" (also "heteroaralkoxy"), refers to a monocyclic, bicyclic or tricyclic ring system having 5 to 14 ring atoms, wherein at least one ring is aromatic and contains at least one heteroatom. In one embodiment, heteroaryl includes 4-6 membered monocyclic aromatic groups where one or more ring atoms is nitrogen, sulfur or oxygen that is independently optionally substituted. In another embodiment, heteroaryl includes 5-6 membered monocyclic aromatic groups where one or more ring atoms is nitrogen, sulfur or oxygen. Representative examples of heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, tetrazolo[1,5-b]pyridazinyl, purinyl, benzoxazolyl, benzofuryl, benzothiazolyl, benzothiadiazolyl, benzotriazolyl, benzoimidazolyl, indolyl, 1,3-thiazol-2-yl, 1,3,4-triazol-5-yl, 1,3-oxazol-2-yl, 1,3,4-oxadiazol-5-yl, 1,2,4-oxadiazol-5-yl, 1,3,4-thiadiazol-5-yl, 1H-tetrazol-5-yl, 1,2,3-triazol-5-yl, and pyrid-2-yl N-oxide. The term "heteroaryl" also includes groups in which a heteroaryl is fused to one or more cyclic (e.g., carbocyclyl, or heterocyclyl) rings, where the radical or point of attachment is on the heteroaryl ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl and pyrido[2,3-b]-1,4-oxazin-3(4H)-one. A heteroaryl group may be mono-, bi- or tri-cyclic. In some embodiments, a heteroaryl group includes a heteroaryl ring fused to one or more (e.g., 1, 2 or 3) different cyclic groups (e.g., carbocyclic rings or heterocyclic rings), where the radical or point of attachment is on the heteroaryl ring, and in some embodiments wherein the point of attachment is a heteroatom contained in the heterocyclic ring.

Thus, the term heteroaryl embraces N-heteroaryl groups which as used herein refer to a heteroaryl group as defined above containing at least one nitrogen and where the point of attachment of the heteroaryl group to the rest of the molecule is through a nitrogen atom in the heteroaryl group. The term heteroaryl also embraces C-heteroaryl groups which as used herein refer to a heteroaryl group as defined above and where the point of attachment of the heteroaryl group to the rest of the molecule is through a carbon atom in the heteroaryl group. The term heteroaryl also embraces heteroarylalkyl groups which as disclosed above refer to a group of the formula —$R^c$-heteroaryl, where $R^c$ is an alkylene chain as defined above. The term heteroaryl also embraces heteroaralkoxy (or heteroarylalkoxy) groups which as used herein refer to a group bonded through an oxygen atom of the formula —O—$R^c$-heteroaryl, where $R^c$ is an alkylene group as defined above.

Any of the groups described herein may be substituted or unsubstituted. As used herein, the term "substituted" broadly refers to all permissible substituents with the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc. Representative substituents include halogens, hydroxyl groups, and any other organic groupings containing any number of carbon atoms, e.g., 1-14 carbon atoms, and which may include one or more (e.g., 1 2 3, or 4) heteroatoms such as oxygen, sulfur, and nitrogen grouped in a linear, branched, or cyclic structural format.

Representative examples of substituents may thus include alkyl, substituted alkyl, alkoxy, substituted alkoxy, alkenyl, substituted alkenyl, alkynyl, substituted alkynyl, cyclic, substituted cyclic, carbocyclic, substituted carbocyclic, heterocyclic, substituted heterocyclic, aryl (e.g., benzyl and phenyl), substituted aryl (e.g., substituted benzyl or phenyl), heteroaryl, substituted heteroaryl, aralkyl, substituted aralkyl, halo, hydroxyl, aryloxy, substituted aryloxy, alkylthio, substituted alkylthio, arylthio, substituted arylthio, cyano, carbonyl, substituted carbonyl, carboxyl, substituted carboxyl, amino, substituted amino, amido, substituted amido, sulfonyl, substituted sulfonyl, amino acid, and peptide groups.

The term "binding" as it relates to interaction between the targeting ligand and the targeted protein, typically refers to an inter-molecular interaction that is substantially specific in that binding of the targeting ligand with other proteinaceous entities present in the cell is functionally insignificant. In some embodiments, such as in the case of bromodomain-containing proteins, binding of the targeting ligand to the protein target may be selective with respect to BRD proteins. By way of example, JQ1, which as disclosed herein as a targeting ligand, selectively binds at least one member of the bromodomain and extra-terminal (BET) family (e.g., BRD2, BRD3, BRD4, and bromodomain testis-specific protein (BRDT)).

The term "binding" as it relates to interaction between the degron and the E3 ubiquitin ligase Cul3/Rbx1, typically refers to an inter-molecular interaction that may or may not exhibit an affinity level that equals or exceeds that affinity between the targeting ligand and the target protein, but nonetheless wherein the affinity is sufficient to achieve recruitment of the ligase to the targeted degradation and the selective degradation of the targeted protein.

Broadly, the bifunctional compounds of the present invention have a structure represented by formula (I):

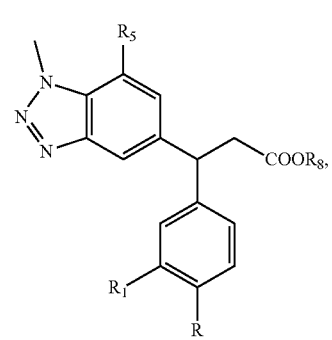

wherein:
$R$ is methyl or halo;
$R_1$ is

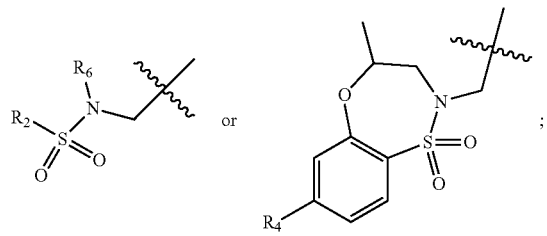

$R_2$ is methyl,

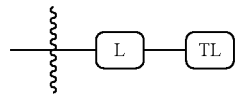

wherein L is a linker and TL is a targeting ligand, that binds a protein of interest, or

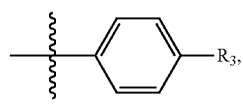

wherein
$R_3$ is H or

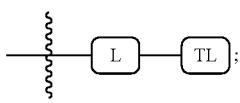

$R_4$ is H, halo or

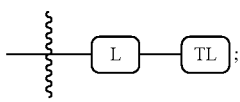

$R_5$ is methoxy or

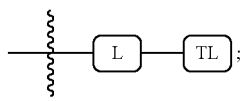

$R_6$ is H or methyl; and
$R_8$ is H, methyl or ethyl;
provided that one of $R_2$, $R_3$, $R_4$ and $R_5$ is

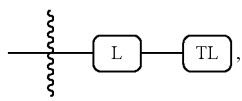

or a pharmaceutically acceptable salt or stereoisomer thereof.

In some embodiments, wherein R is methyl;
$R_1$ is

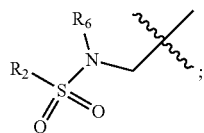

$R_2$ is

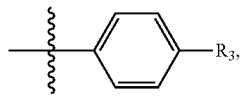

wherein
$R_3$ is

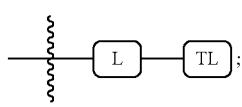

$R_5$ is methoxy;
$R_6$ is methyl; and $R_8$ is H,
the bifunctional compound is represented by formula (Ia):

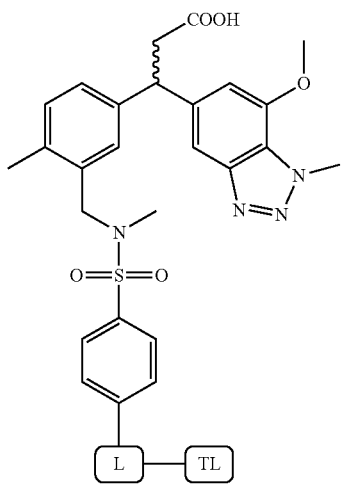

or a pharmaceutically acceptable salt or stereoisomer thereof.

In some embodiments, R is methyl;
$R_1$ is

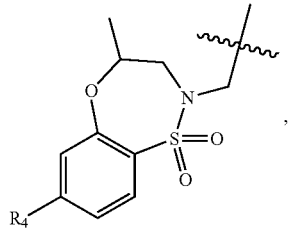

wherein
$R_4$ is

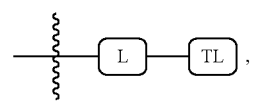

$R_5$ is methoxy; and $R_8$ is H, the bifunctional compound is represented by formula (Ib):

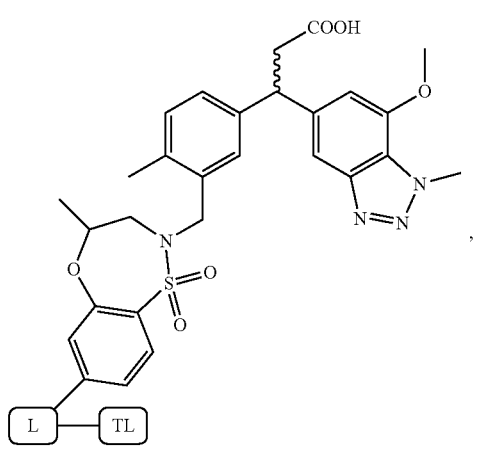

(Ib)

or a pharmaceutically acceptable salt or stereoisomer thereof.

In some embodiments, R is methyl;

$R_1$ is

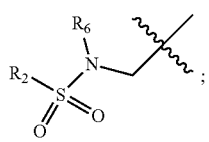

$R_2$ is

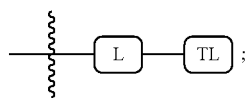

$R_5$ is methoxy;

$R_6$ is H; and $R_8$ is H, the bifunctional compound is represented by formula (Ic):

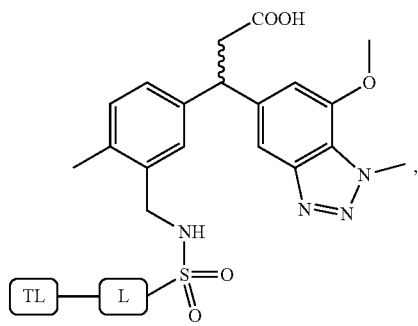

(Ic)

or a pharmaceutically acceptable salt or stereoisomer thereof.

In some embodiments, R is Cl;

$R_1$ is

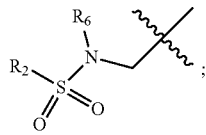

$R_2$ is

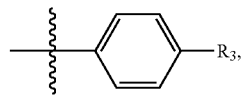

$R_3$ is

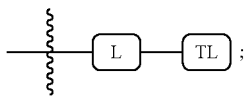

$R_5$ is methoxy;

$R_6$ is methyl; and $R_8$ is H, the bifunctional compound is represented by formula (Id):

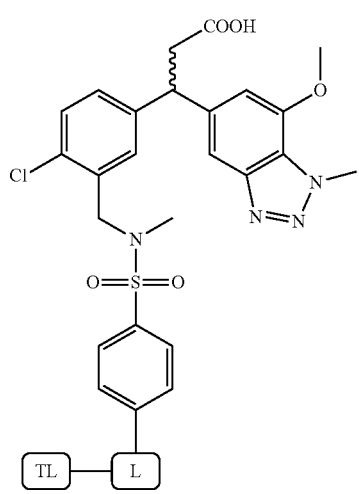

(Id)

or a pharmaceutically acceptable salt or stereoisomer thereof.

In some embodiments, R is Cl;

$R_1$ is

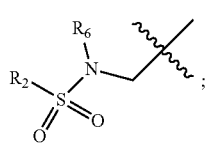

wherein $R_2$ is

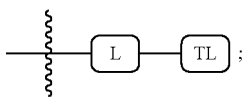

$R_5$ is methoxy;

$R_6$ is H; and $R_8$ is H, the bifunctional compound is represented by formula (Ie):

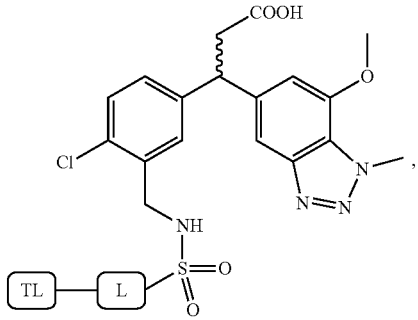

(Ie)

or a pharmaceutically acceptable salt or stereoisomer thereof.

In some embodiments, R is methyl;

$R_1$ is

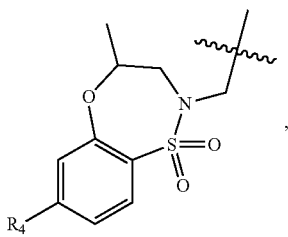

$R_4$ is H;

$R_5$ is

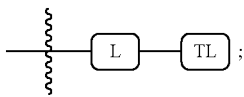

and $R_8$ is H, the bifunctional compound is represented by formula (If):

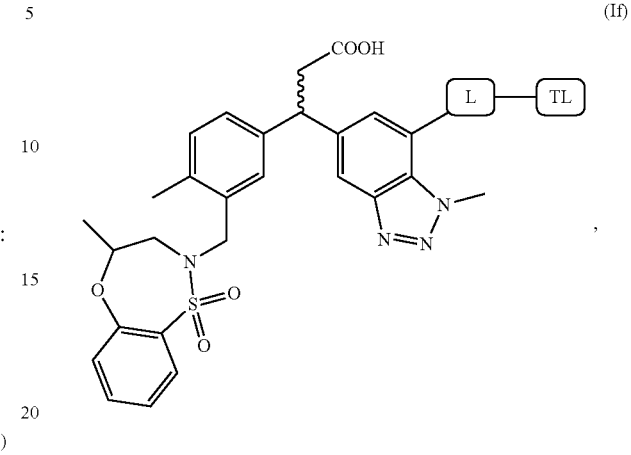

(If)

or a pharmaceutically acceptable salt or stereoisomer thereof.

Linkers

The linker ("L") provides a covalent attachment the targeting ligand and the degron. The structure of linker may not be critical, provided it does not substantially interfere with the activity of the targeting ligand or the degron. In some embodiments, the linker may be an alkylene chain or a bivalent alkylene chain, either of which may be interrupted by, and/or terminate (at either or both termini) in at least one of —O—, —S—, —N(R')—, —C≡C—, —C(O)—, —C(O)O—, —OC(O)—, —OC(O)O—, —C(NOR')—, —C(O)N(R')—, —C(O)N(R')C(O)—, —C(O)N(R')C(O)N(R')—, —N(R')C(O)—, —N(R')C(O)N(R')—, —N(R')C(O)O—, —OC(O)N(R')—, —C(NR')—, —N(R')C(NR')—, —C(NR')N(R')—, —N(R')C(NR')N(R')—, —OB(Me)O—, —S(O)$_2$—, —OS(O)—, —S(O)O—, —S(O)—, —OS(O)$_2$—, —S(O)$_2$O—, —N(R')S(O)$_2$—, —S(O)$_2$N(R')—, —N(R')S(O)—, —S(O)N(R')—, —N(R')S(O)$_2$N(R')—, —N(R')S(O)N(R')—, $C_3$-$C_{12}$ carbocyclene, 3- to 12-membered heterocyclene, 5- to 12-membered heteroarylene or any combination thereof, wherein R' is H or $C_1$-$C_6$ alkyl, wherein the interrupting and the one or both terminating groups may be the same or different.

In some embodiments, the linker may be a polyethylene glycol chain which may terminate (at either or both termini) in at least one of —S—, —N(R')—, —C≡C—, —C(O)—, —C(O)O—, —OC(O)—, —OC(O)O—, —C(NOR')—, —C(O)N(R')—, —C(O)N(R')C(O)—, —C(O)N(R')C(O)N(R')—, —N(R')C(O)—, —N(R')C(O)N(R')—, —N(R')C(O)O—, —OC(O)N(R')—, —C(NR')—, —N(R')C(NR')—, —C(NR')N(R')—, —N(R')C(NR')N(R')—, —OB(Me)O—, —S(O)$_2$—, —OS(O)—, —S(O)O—, —S(O)—, —OS(O)$_2$—, —S(O)$_2$O—, —N(R')S(O)$_2$—, —S(O)$_2$N(R')—, —N(R')S(O)—, —S(O)N(R')—, —N(R')S(O)$_2$N(R')—, —N(R')S(O)N(R')—, $C_{3-12}$ carbocyclene, 3- to 12-membered heterocyclene, 5- to 12-membered heteroarylene or any combination thereof, wherein R' is H or $C_1$-$C_6$ alkyl, wherein the one or both terminating groups may be the same or different.

"Carbocyclene" refers to a bivalent carbocycle radical, which is optionally substituted.

"Heterocyclene" refers to a bivalent heterocyclyl radical which may be optionally substituted.

"Heteroarylene" refers to a bivalent heteroaryl radical which may be optionally substituted.

Representative examples of linkers that may be suitable for use in the present invention include alkylene chain:

(L1)

wherein n is an integer of 1-10, inclusive, e.g., 1-9, 1-8, 1-7, 1-6, 1-5, 1-4, 1-3, 1-2, 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, 9-10 and 1, 2, 3, 4, 5, 6, 7, 8, 9 and 10 examples of which include:

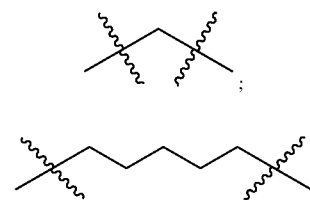
(L1-a)

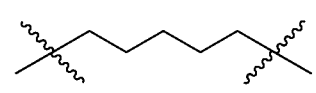
(L1-b)

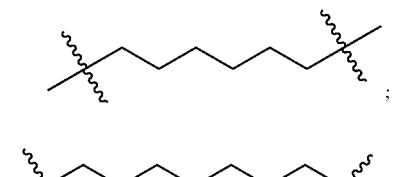
(L1-c)

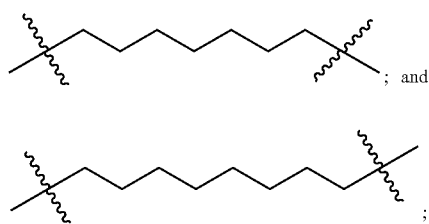
(L1-d); and (L1-e)

alkylene chains terminating in various functional groups (as described above), examples of which are as follows:

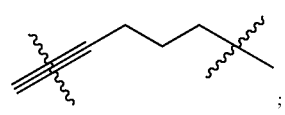
(L2-a)

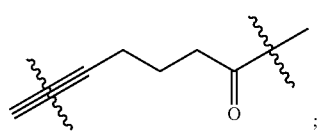
(L2-b)

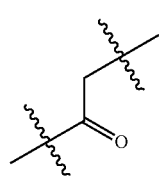
(L2-c)

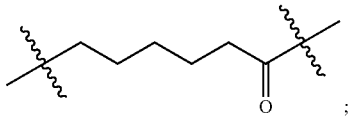
(L2-d)

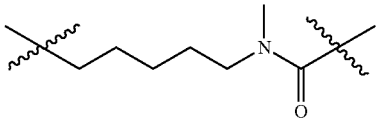
(L2-e)

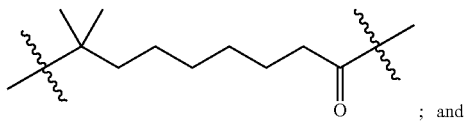
(L2-f); and

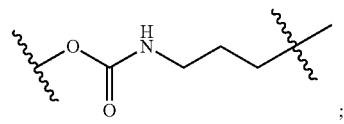
(L2-g)

alkylene chains interrupted with various functional groups (as described above), examples of which are as follows:

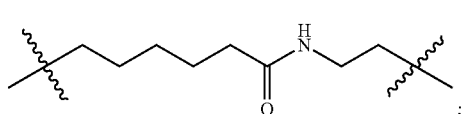
(L3-a)

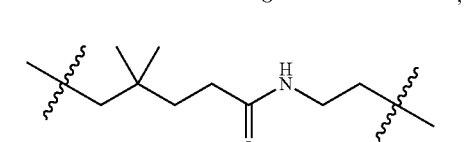
(L3-b)

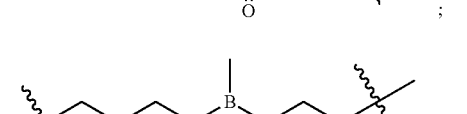
(L3-c); and

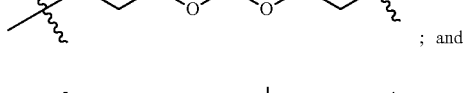
(L3-d)

alkylene chains interrupted or terminating with heterocyclene groups, e.g.,

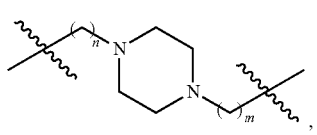
(L4)

wherein m and n are independently integers of 0-10 examples of which include:

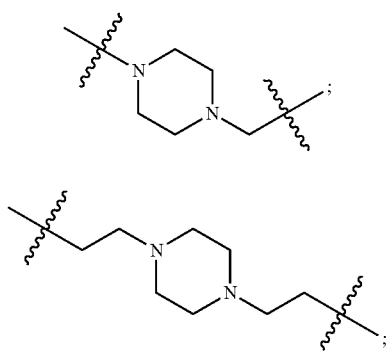
(L4-a)

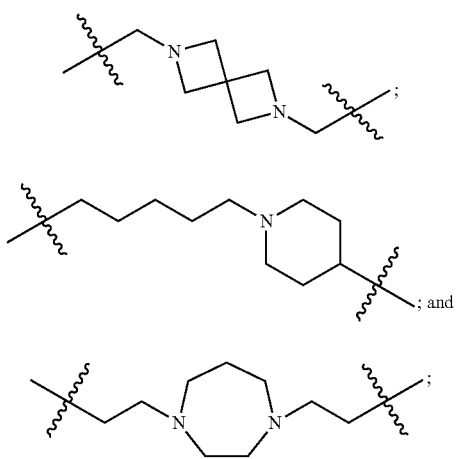
(L4-b)

(L4-c)

(L4-d)

(L4-e)

alkylene chains interrupted by amide, heterocyclene and/or aryl groups, examples of which include:

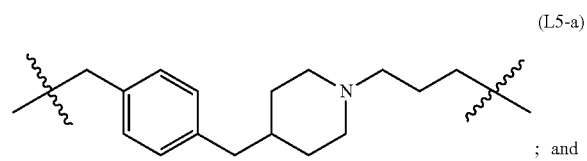
(L5-a); and

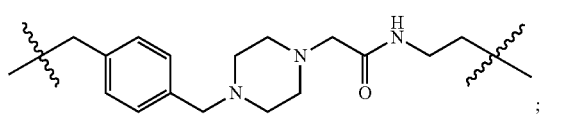
(L5-b);

alkylene chains interrupted by heterocyclene and aryl groups, and a heteroatom, examples of which include:

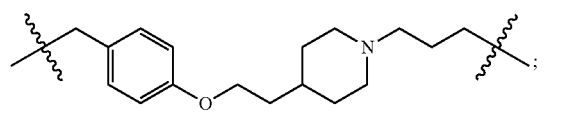
(L6-a);

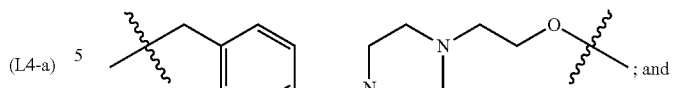
(L6-b); and

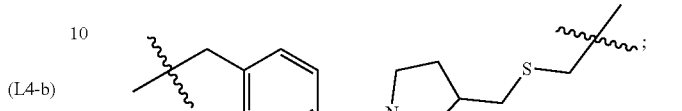
(L6-c);

alkylene chains interrupted by a heteroatom such as N, O or B, e.g.,

(L7)

wherein n is an integer of 1-10, e.g., 1-9, 1-8, 1-7, 1-6, 1-5, 1-4, 1-3, 1-2, 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, 9-10, and 1, 2, 3, 4, 5, 6, 7, 8, 9 and 10, and R is H, or C1 to C4 alkyl, an example of which is

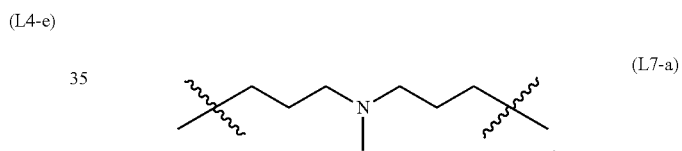
(L7-a)

In some embodiments, the linker is a polyethylene glycol chain, examples of which include:

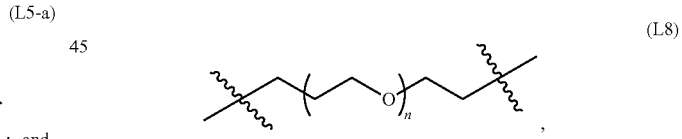
(L8)

wherein n is an integer of 2-10, examples of which include:

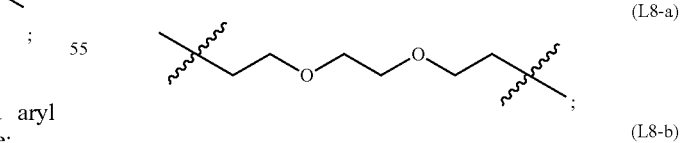
(L8-a);

(L8-b);

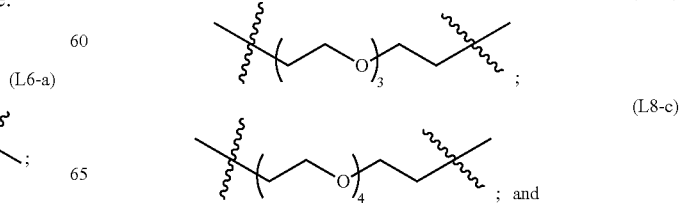
(L8-c); and (L8-d)
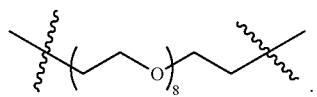
In some embodiments, the polyethylene glycol chain may terminate in a functional group, examples of which are as follows:
(L9-a)
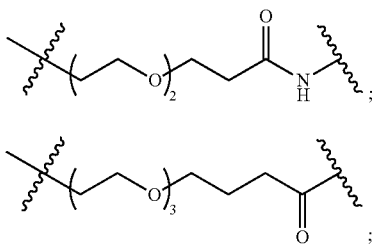
(L9-b)
(L9-c)
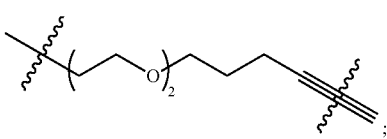
(L9-d)
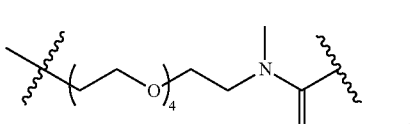
; and
(L9-e)
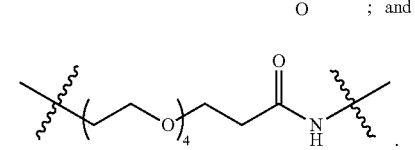
In some embodiments, the linker is represented by a structure selected from the group consisting of:
(L10-a)
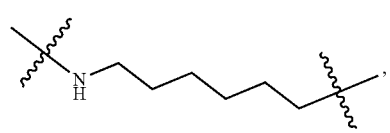
(L10-b)
(L10-c)
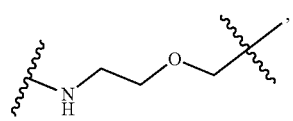
(L10-d)
(L10-e)
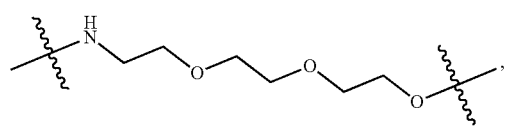
(L10-f)
(L10-g)
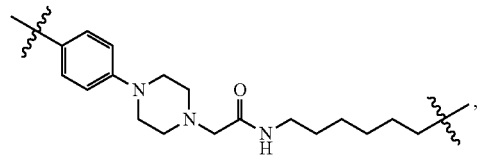
(L10-h)
(L10-i)
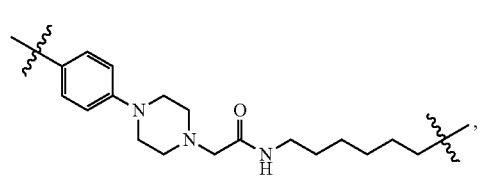
(L10-j)
(L10-k)
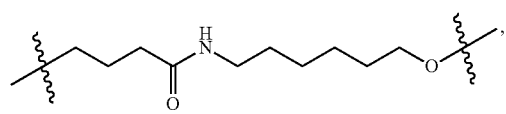

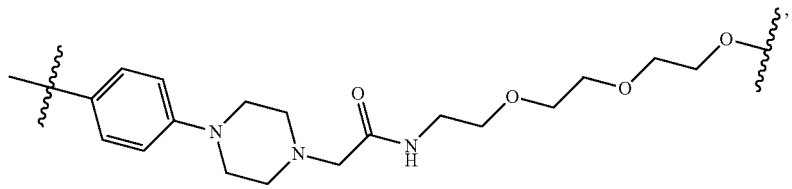

(L10-l)

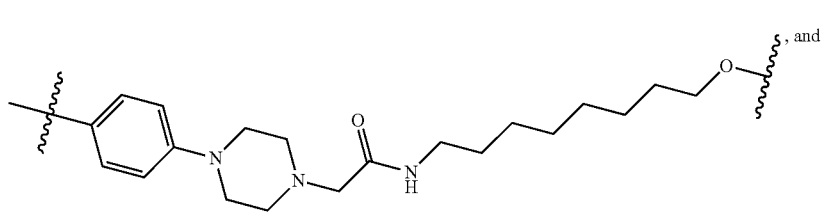

(L10-m)

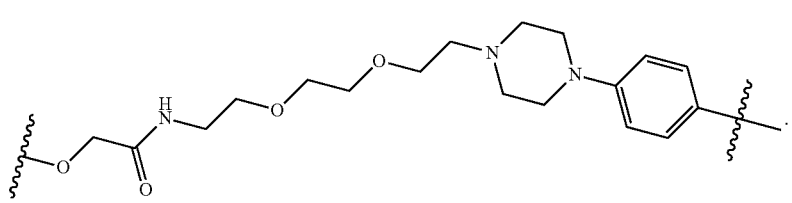

(L10-n)

Yet further examples of linkers that may be useful in the bifunctional compounds are disclosed in U.S. Patent Application Publication 2018/0125821 A1.

Targeting Ligands

Broadly, the bifunctional compounds of the present invention may be constructed to target any aberrant or dysfunctional protein. Thus, the targeting ligand may bind target proteins including for example, the expression products of IKZF1 and IKZF3, and the following proteins: CK1α, FAM83F, DTWD1, ZFP91, RNF166, IKZF1, IKZF3, ZN692, ZBTB39, SALL4, ZN653, ZN654, ZC827, RAB28, GSTP1, TIMM10, IKZF5, ZFP36L2, GZF1, GSPT2, EGR1, HIC1, HIC2, IKZF2, IKZF4, INSM2, OSR2, PRD15, SALL1, SALL3, WIZ, Z324B, ZBT17, ZBT41, ZBT49, ZBT7A, ZBT7B, ZBTB2, ZFP62, ZIK1, ZNF217, ZNF276, ZNF3, ZNF316, ZNF335, ZNF397, ZNF407, ZNF408, ZNF462, ZNF483, SNF517, ZNF526, ZNF581, ZNF587, ZNF589, ZNF618, ZNF644, ZNF646, ZNF724, ZNF771, ZNF782, ZNF784, ZNF814, ZSC10, ZSC22 and ZUFSP.

Yet other proteins that may be targeted by the bifunctional compounds of the present invention include tyrosine kinases (e.g., AATK, ABL, ABL2, ALK, AXL, BLK, BMX, BTK, CSF1R, CSK, DDR1, DDR2, EGFR, EPHA1, EPHA2, EPHA3, EPHA4, EPHA5, EPHA6, EPHA7, EPHA8, EPHA10, EPHB1, EPHB2, EPHB3, EPHB4, EPHB6, ERBB2, ERBB3, ERBB4, FER, FES, FGFR1, FGFR2, FGFR3, FGFR4, FGR, FLT1, FLT3, FLT4, FRK, FYN, GSG2, HCK, IGF1R, ILK, INSR, INSRR, ITK, JAK1, JAK2, JAK3, KDR, KIT, KSR1, LCK, LMTK2, LMTK3, LTK, LYN, MATK, MERTK, MET, MLTK, MST1R, MUSK, NPR1, NTRK1, NTRK2, NTRK3, PDGFRA, PDGFRB, PLK4, PTK2, PTK2B, PTK6, PTK7, RET, ROR1, ROR2, ROS1, RYK, SGK493, SRC, SRMS, STYK1, SYK, TEC, TEK, TEX14, TIE1, TNK1, TNK2, TNNI3K, TXK, TYK2, TYRO3, YES 1, or ZAP70), a serine/threonine kinase (e.g., casein kinase 2, protein kinase A, protein kinase B, protein kinase C, Raf kinases, CaM kinases, AKT1, AKT2, AKT3, ALK1, ALK2, ALK3, ALK4, Aurora A, Aurora B, Aurora C, CHK1, CHK2, CLK1, CLK2, CLK3, DAPK1, DAPK2, DAPK3, DMPK, ERK1, ERK2, ERK5, GCK, GSK3, HIPK, KHS1, LKB1, LOK, MAPKAPK2, MAPKAPK, MNK1, MSSK1, MST1, MST2, MST4, NDR, NEK2, NEK3, NEK6, NEK7, NEK9, NEK11, PAK1, PAK2, PAK3, PAK4, PAK5, PAK6, PIM1, PIM2, PLK1, RIP2, RIPS, RSK1, RSK2, SGK2, SGK3, SIK1, STK33, TAO1, TAO2, TGF-beta, TLK2, TSSK1, TSSK2, ULK1, or ULK2), a cyclin dependent kinase (e.g., Cdk1-Cdk11), and a leucine-rich repeat kinase (e.g., LRRK2).

In some embodiments, the bifunctional compounds of the present invention directly target IRAK 1 and/or IRAK 4, KRAS, HRAS and NRAS (particularly G12C mutants thereof), and bromodomain proteins, e.g., PB1 and BRD4, as further disclosed herein below. Yet other aberrant or dysfunctional proteins that may be targeted by the bifunctional compounds of the present invention include B7.1 and B7, TINFRlm, TNFR2, NADPH oxidase, BcllBax and other partners in the apoptosis pathway, C5a receptor, HMG-CoA reductase, PDE V phosphodiesterase type, PDE IV phosphodiesterase type 4, PDE I, PDEII, PDEIII, squalene cyclase inhibitor, CXCR1, CXCR2, nitric oxide (NO) synthase, cyclo-oxygenase 1, cyclo-oxygenase 2, 5HT receptors, dopamine receptors, G Proteins, i.e., Gq, histamine receptors, 5-lipoxygenase, tryptase serine protease, thymidylate synthase, purine nucleoside phosphorylase, GAPDH trypanosomal, glycogen phosphorylase, Carbonic anhydrase, chemokine receptors, JAW STAT, RXR and similar, HIV 1 protease, HIV 1 integrase, influenza, neuramimidase, hepatitis B reverse transcriptase, sodium channel, multi drug resistance (MDR), protein β-glycoprotein (and MRP), CD23, CD124, tyrosine kinase p56 lck, CD4, CD5, IL-2 receptor, IL-1 receptor, TNF-alphaR, ICAM1, Cat+ channels, VCAM, VLA-4 integrin, selectins, CD40/CD40L, neurokinins and receptors, inosine monophosphate dehydrogenase, p38 MAP Kinase, Ras-Raf-MEK-ERK pathway, interleukin-1 converting enzyme, caspase, HCV, NS3 protease, HCV NS3 RNA helicase, glycinamide ribonucleotide formyl transferase, rhinovirus 3C protease, herpes simplex virus-1 (HSV-I), protease, cytomegalovirus (CMV) protease, poly (ADP-ribose) polymerase, cyclin dependent kinases, vascular endothelial growth factor, oxytocin receptor, microsomal transfer protein inhibitor, bile acid transport inhibitor, 5-α reductase inhibitors, angiotensin 11, glycine receptor, noradrenaline reuptake receptor, endothelin receptors, neuropeptide Y and receptor, adenosine receptors, adenosine kinase and AMP deaminase, purinergic receptors (P2Y1, P2Y2, P2Y4, P2Y6, P2X1-7), farnesyltransferases, geranylgeranyl transferase, TrkA-α receptor for NGF, β-amyloid, tyrosine kinase Flk-IIKDR, vitronectin receptor, integrin receptor, Her-21 neu, telomerase inhibition, cytosolic phospholipaseA2 and EGF receptor tyrosine kinase, ecdysone 20-monooxygenase, ion channel of the GABA gated chloride channel, acetylcholinesterase, voltage-sensitive sodium channel protein, calcium release channel, chloride channels, acetyl-CoA carboxylase, adenylosuccinate synthetase, protoporphyrinogen oxidase and enolpyruvylshikimate-phosphate synthase. Targeting ligands that bind these proteins, e.g., small molecule inhibitors of the proteins, are known in the art.

In some embodiments, the bifunctional compound of formula (I) includes a targeting ligand that binds G12C mutants of KRas, HRas and NRas (hereinafter collectively referred to as "KRas") for degradation. Ras proteins contain a so-called G domain which contains the enzymatically active domain of the protein, namely guanine nucleotide binding and hydrolysis. The C-terminal extension, known as the CAAX box, targets Ras to the cell membrane. The G domain contains a phosphate-binding loop, known as the P-loop, which represents a pocket where guanine nucleotides are bound. It has been determined that several conserved amino acid residues in the pocket of the P-loop, namely Glycine 12, Threonine 26 and Lysine 16, are essential for guanine nucleotide binding and hydrolysis. The G domain of Ras also contains the Switch I and II regions, also known as the spring-loaded mechanism, due to their ability to switch Ras between the active and inactive state. Mutations in any one of HRas, KRas, and NRas are quite common in tumorigenesis. The majority of the mutations are found in the KRas gene. For instance, about 30% of all human tumors which have been found to carry a Ras mutation, and KRas mutations have been detected in about 25-30% of tumors. The most common KRas mutations are found at G12, G13 which are in the P-loop and at residue Q61, which is in the Switch II region. The G12C (glycine-12 to cysteine) mutation of KRas gene occurs frequently (about 13%) in cancer. It is even more prevalent (43%) in lung cancer, and has been found in almost 100% of MYH-associated polyposis (familial colon cancer syndrome). For purposes of comparison, mutations in the NRas and the HRas genes have been found to occur at a much lower frequency, i.e., about 8% and 3%, respectively.

In some embodiments, the bifunctional compound of formula (I) includes a targeting ligand that targets KRASG12C for degradation, as follows:

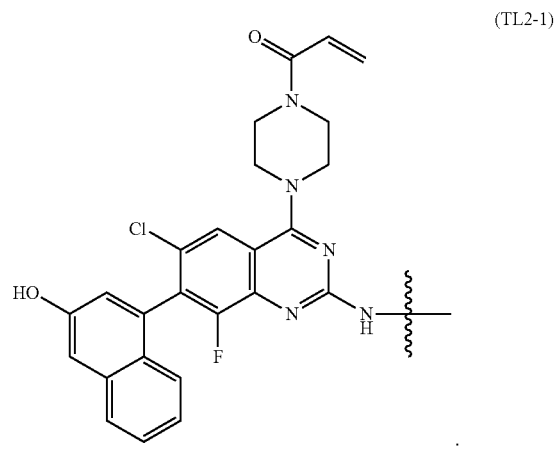 [SMILES: *Nc1nc(N2CCN(C(=O)C=C)CC2)c2cc(Cl)c(-c3cc(O)cc4ccccc34)c(F)c2n1]

(TL2-1)

Other compounds that may be useful as KRASG12C-targeting ligands are known in the art. See, e.g., U.S. Patent Application Publication 2018/0015087 (e.g., formulas II and III, including IIIA-E); WO 2013/155223; WO 2016/168540; WO 2017/058728; WO 2017/058768; WO 2017/058805; WO 2017/058792; WO 2017/058807; WO 2017/058902; WO 2017/058915 and U.S. Pub. Nos. 2014/0288045; 2015/0239900; 2016/0031898; 2016/0108019; 2016/0297774; 20160159738; 20170247376; 2017/0022184 and 2017/0197945.

A representative example of a bifunctional compound of the present invention that targets KRASG12C for degradation is as follows:

(19)

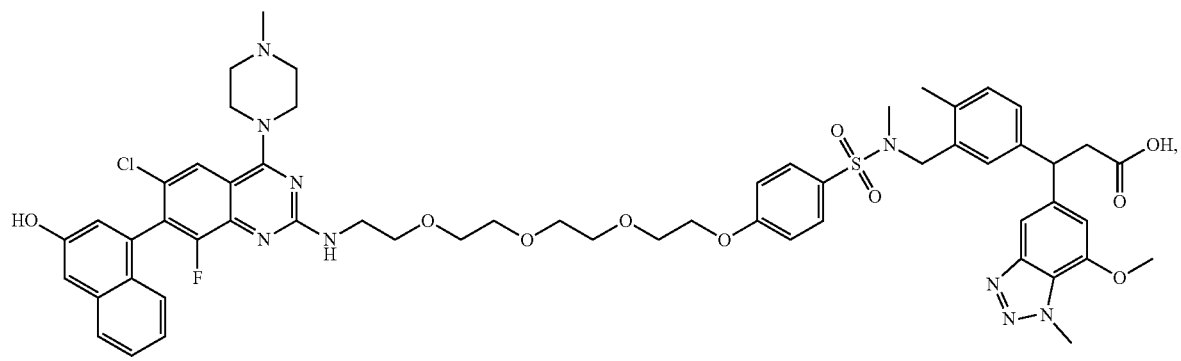

or a pharmaceutically acceptable salt or stereoisomer thereof.

In some embodiments, the compounds of formula (I) of the present invention target a bromodomain-containing protein contained in the Switch/Sucrose Non-Fermentable (SWI/SNF) chromatin-remodeling complex. This complex is a nucleosome remodeling complex that includes a group of proteins that associate to remodel the way in which DNA is packaged inside the cell. The SWI/SNF chromatin-remodeling complex has been reported to be involved in gene regulation, cell linage specification and development and comprises a number of bromodomain containing subunits, including BRG1 (also known as SMARCA4), BRM (also known as SMARCA2) and PBRM1 (also known as PB1).

Representative examples of entities that may be suitable for use as PB1-targeting ligands in the compounds of the present invention are disclosed in U.S. Patent Application Publication 2018/0086720 A1, e.g., Paragraphs 71-83 therein.

In some embodiments, the compounds of formula (I) include a targeting ligand that binds proteins that are members of the bromodomain and extra-terminal (BET) family (e.g., BRD2, BRD3, BRD4, and bromodomain testis-specific protein (BRDT)). Inventive compounds containing JQ1 (or a deuterated form of same) as the targeting ligand will target BRD4, BRD3, and BRD2 for degradation. Thus, in some embodiments, the targeting ligands of the present invention may be based on the following structure:

JQ1

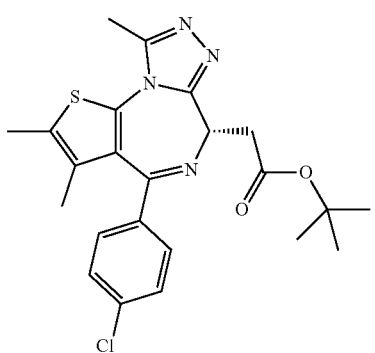

Representative examples of compounds that target BRD2, BRD3, and BRD4 may thus have the following structures:

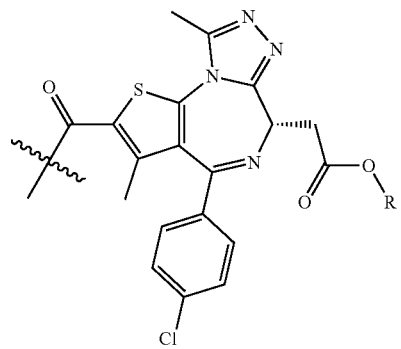

wherein R is Me or t-Bu; or

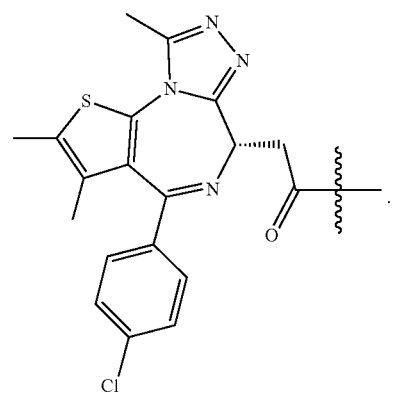 [SMILES: *C(=O)C[C@@H]1N=C(c2ccc(Cl)cc2)c2c(sc(C)c2C)-n2c(C)nnc21]

In some embodiments, bifunctional compounds of the present invention that target BRD2, BRD3, and BRD4 are represented by the following formulae (with the linker shown generically):

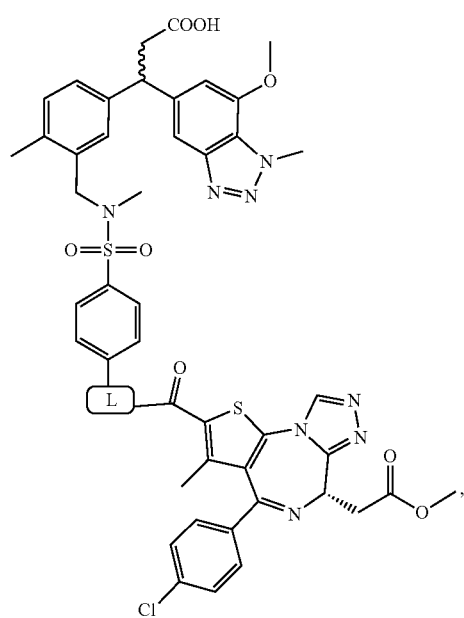
(Ia-1)
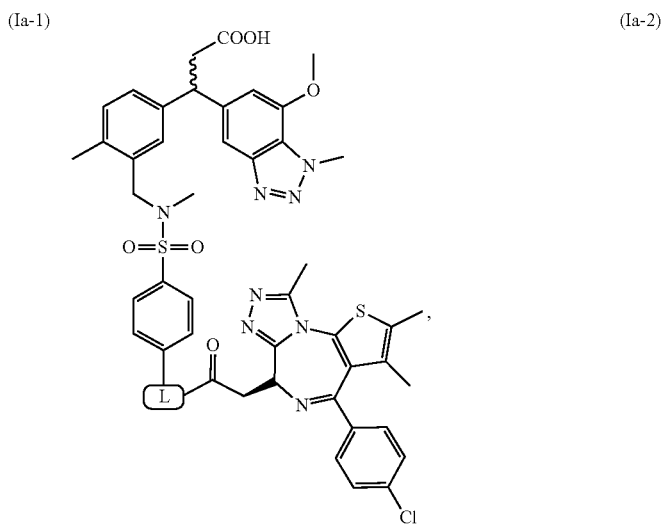
(Ia-2)
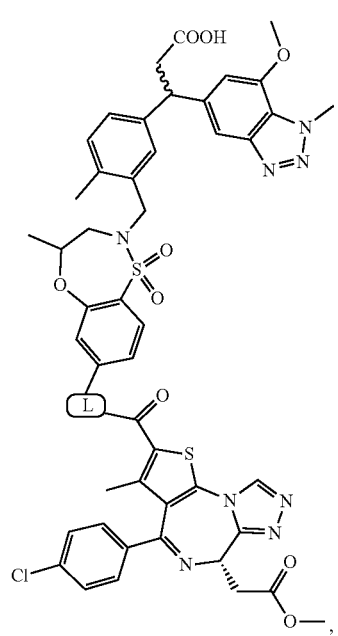
(Ib-1)
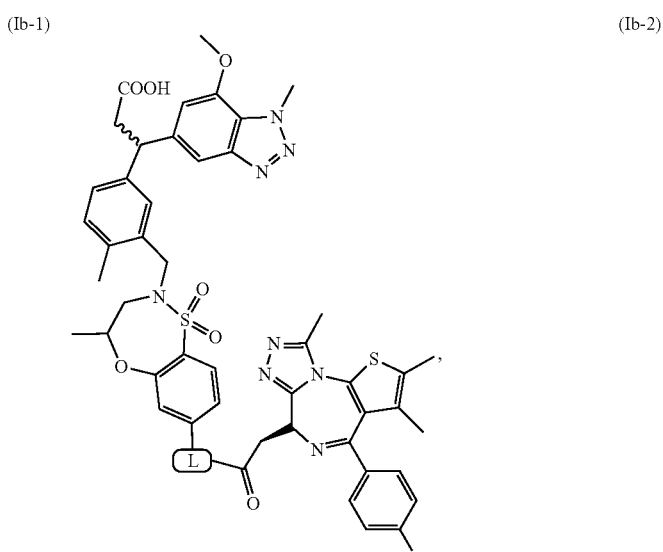
(Ib-2)

-continued
(Ic-1)
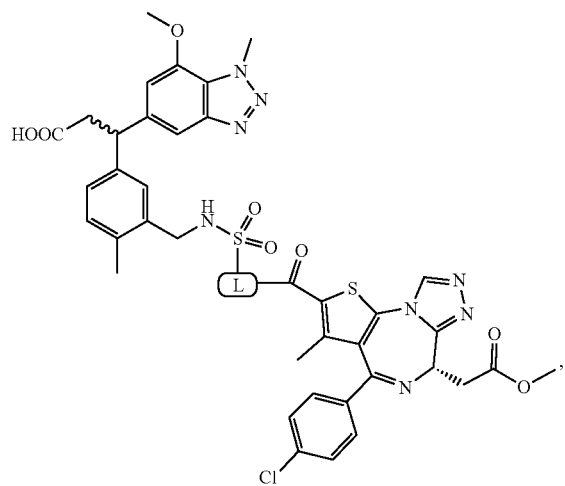
(Ic-2)
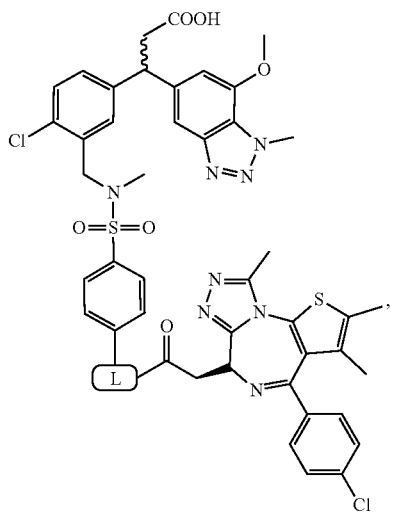
(Id-1)
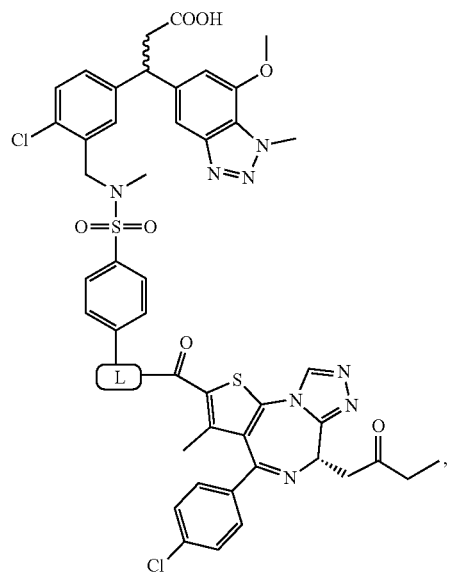
(Id-2)
(Ie-1)
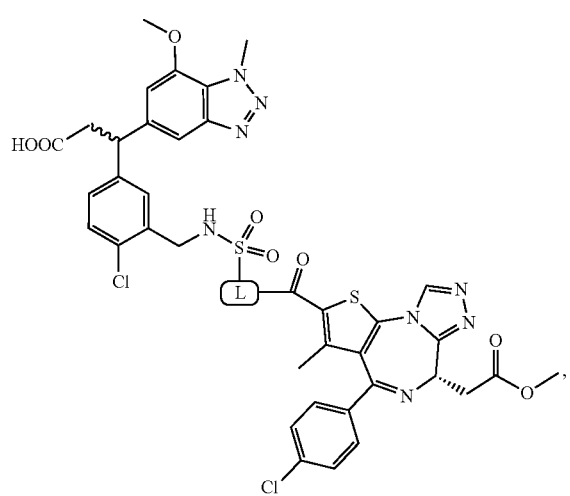
(Ie-2)
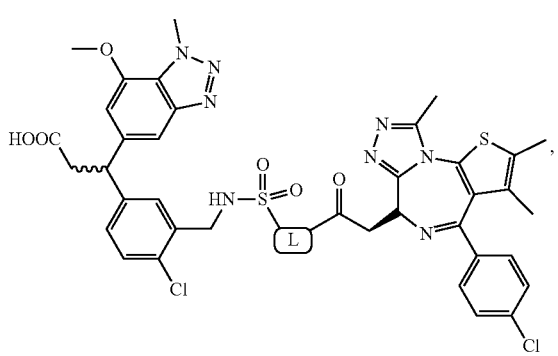

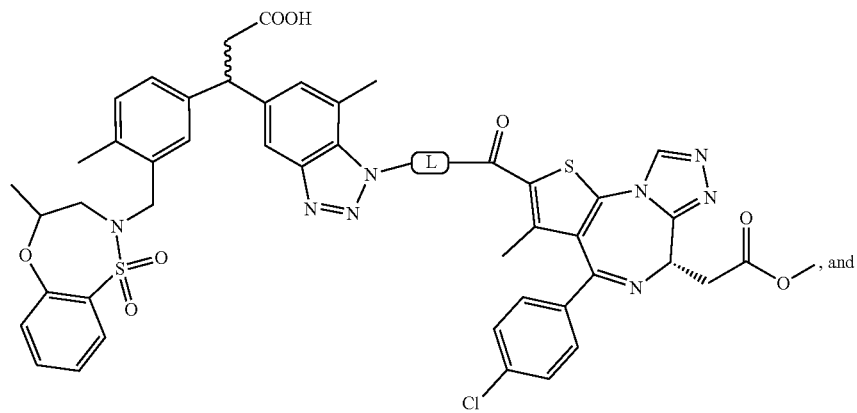
(If-1)
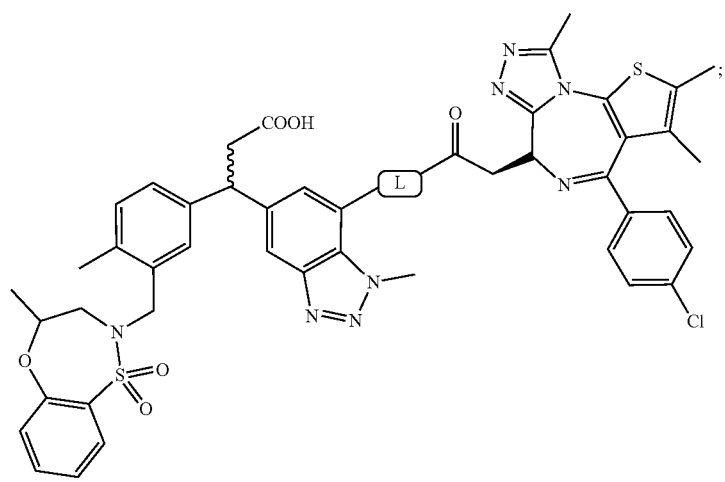
(If-2)
or a pharmaceutically acceptable salt or stereoisomer thereof.
In some embodiments, the inventive bifunctional compounds that target BRD4, BRD3, and BRD2 are represented by the following structures:

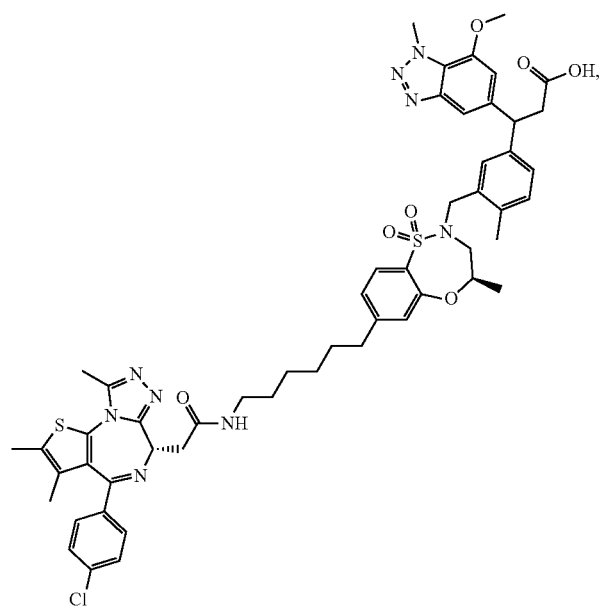
(1)
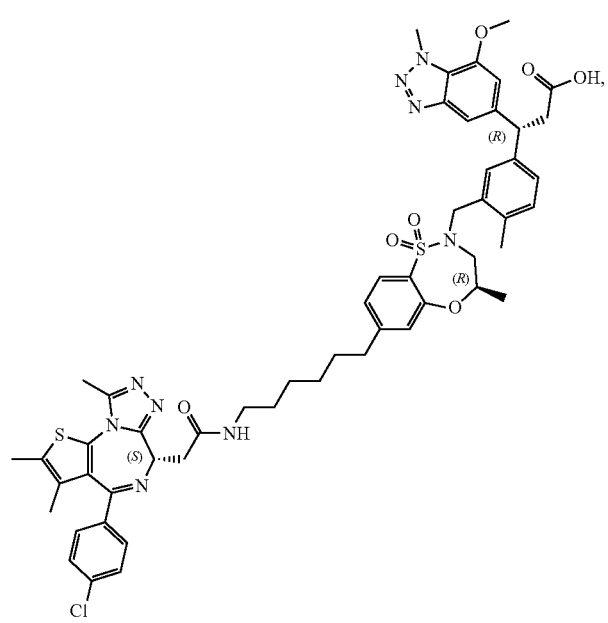
(2)

(3)
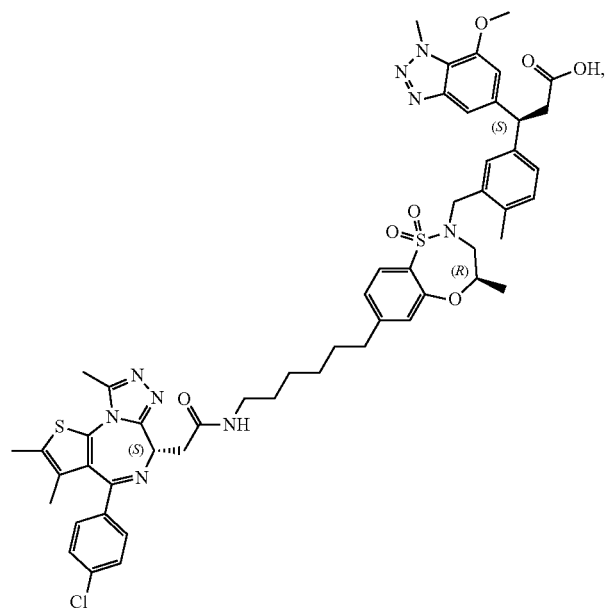
(4)
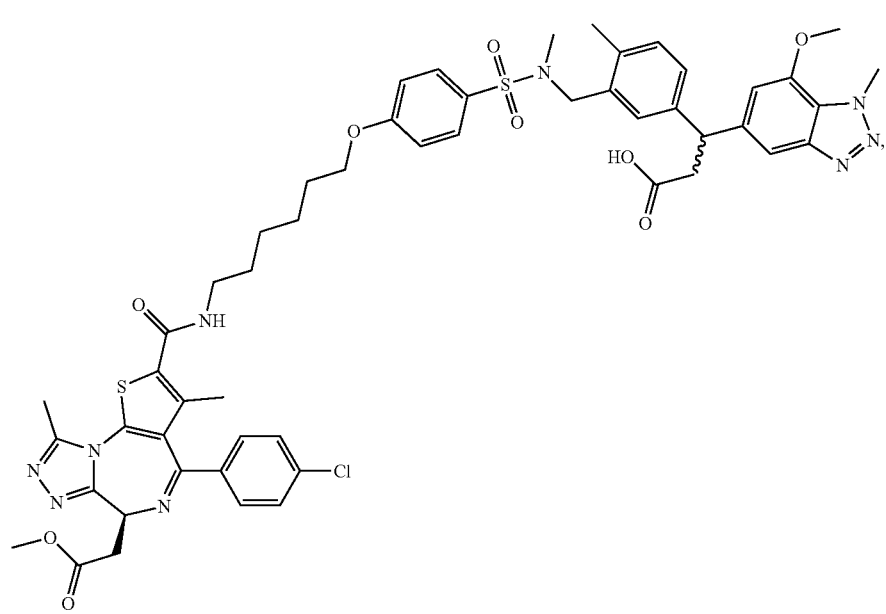

(5)
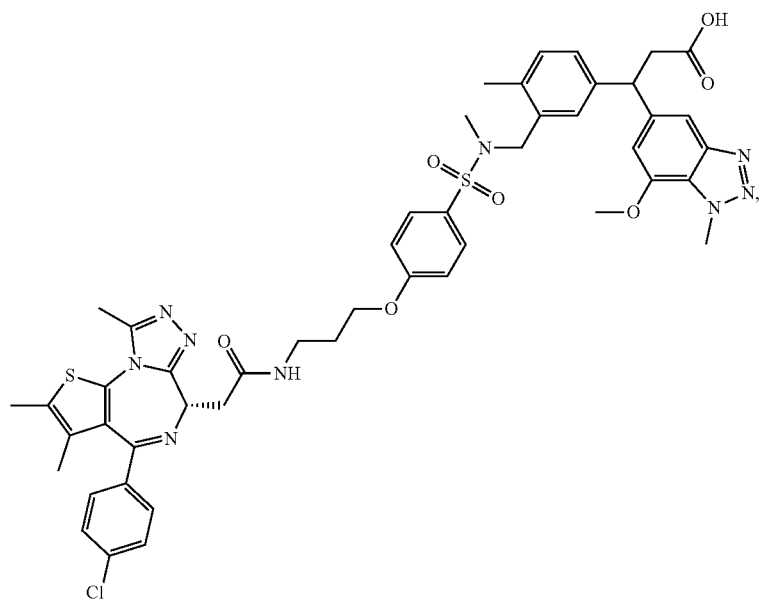
(6)
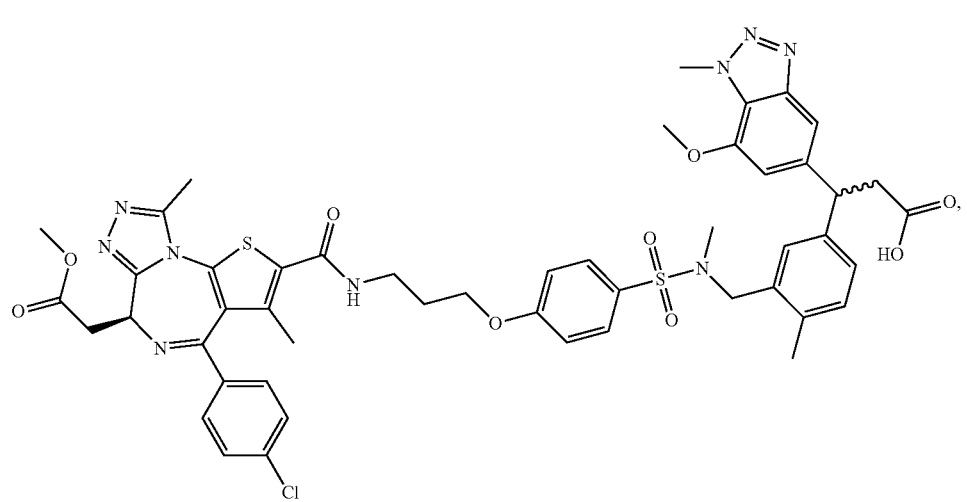

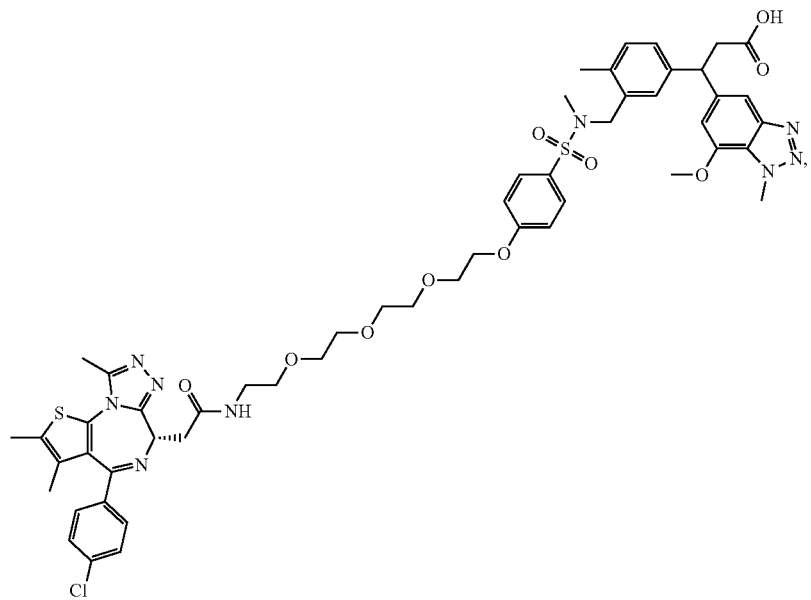
(7)
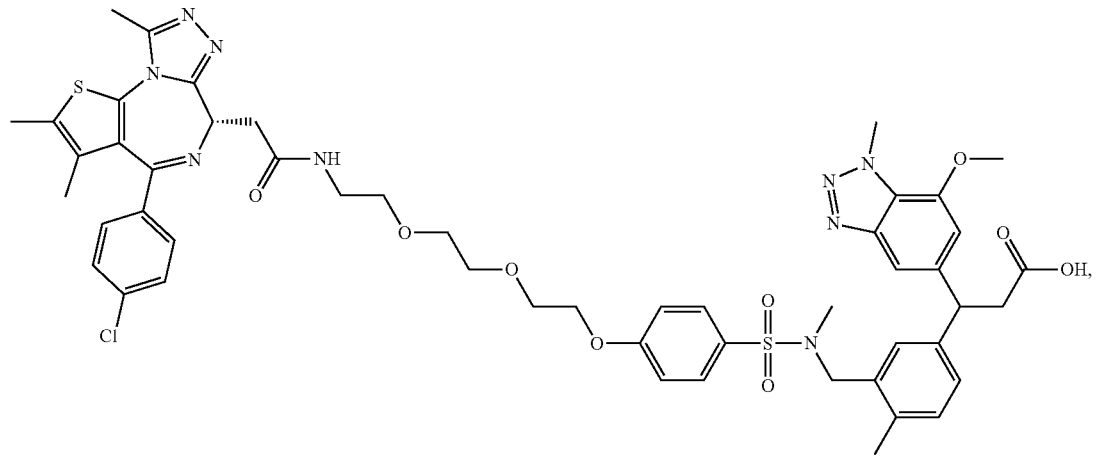
(8)
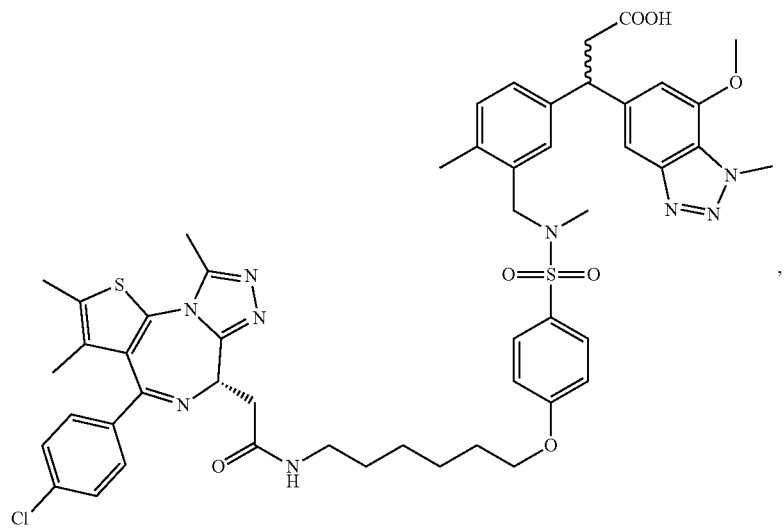
(9)

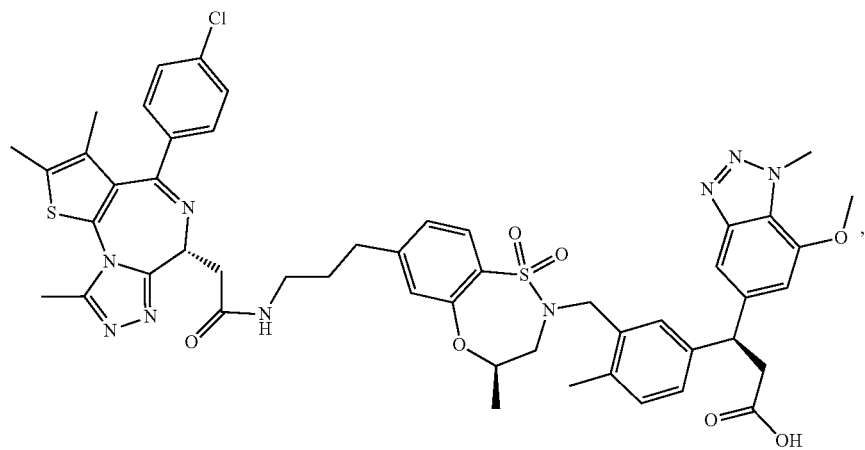
(21)
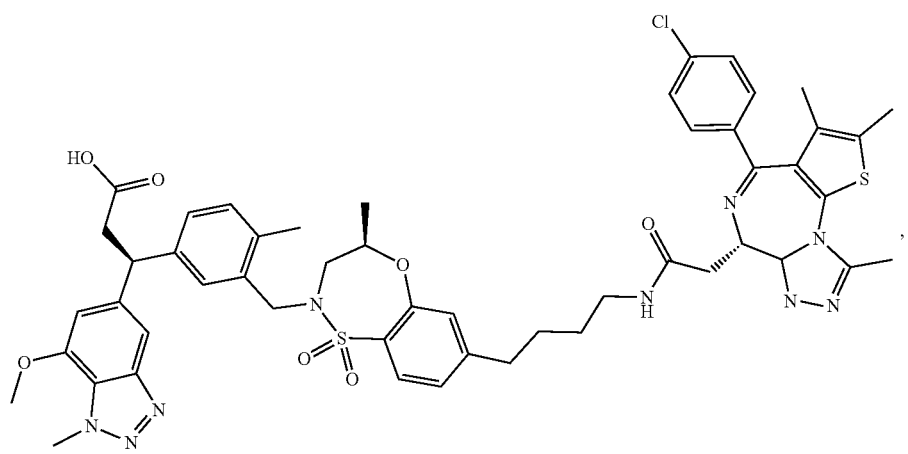
(22)
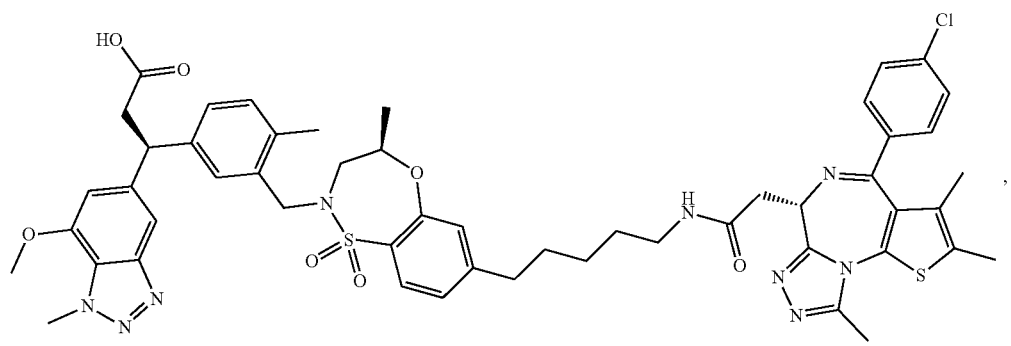
(23)

(24)
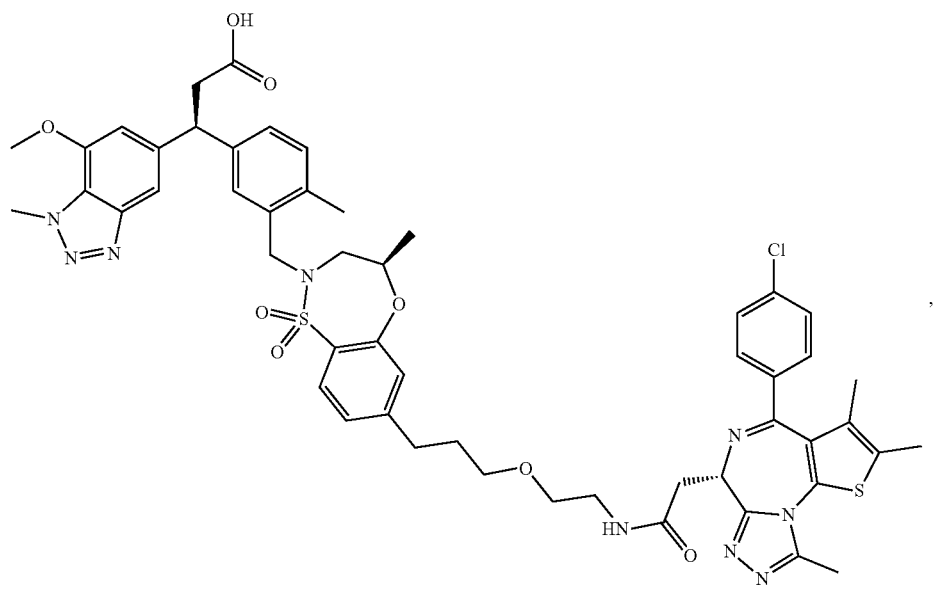
(25)
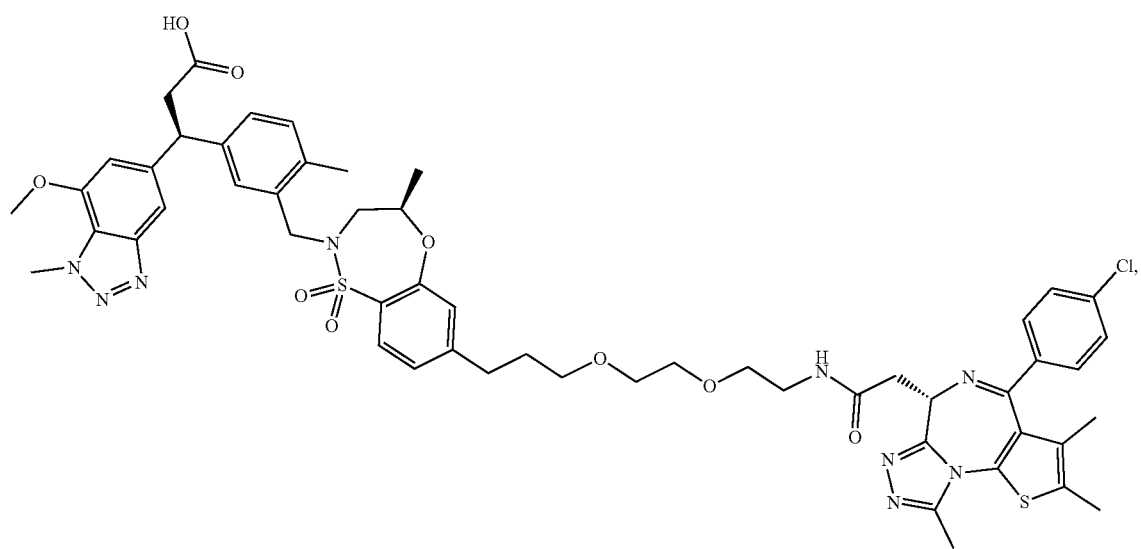
(26)
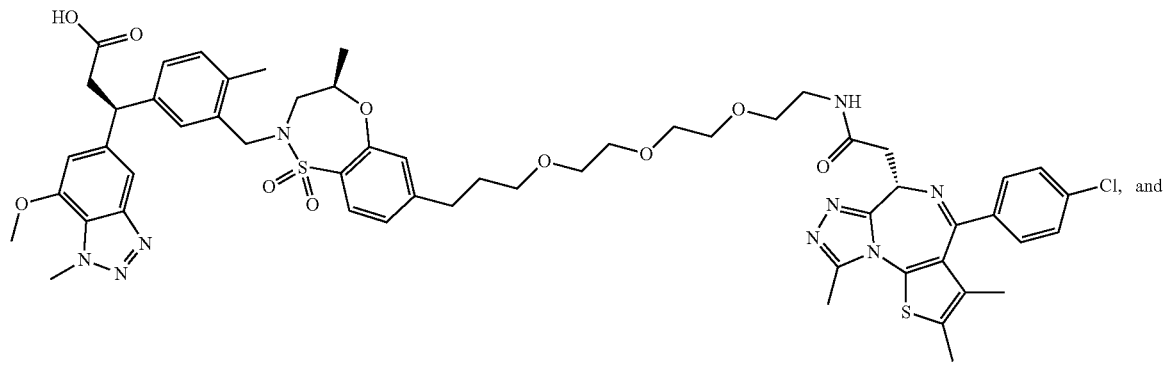

(27)

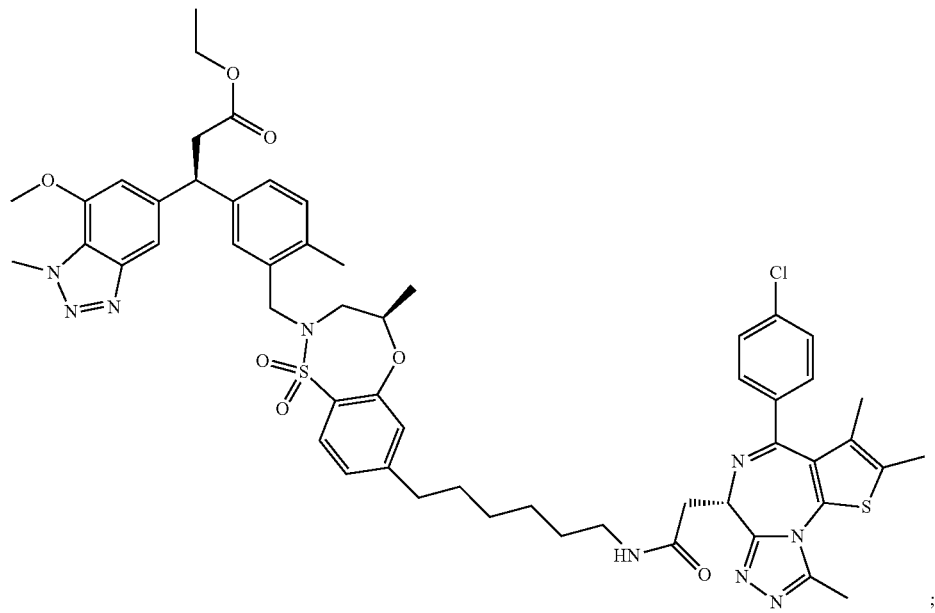

or a pharmaceutically acceptable salt or stereoisomer thereof.

In some embodiments, the inventive bifunctional compounds target multiple (e.g., two or more) kinases, including BTK, FAK, CDK7, CDK9, HCK, ALK, FLT3, EGFR, AAK1, WEE1, LIMK2, AURKA, AURKB, CDK5, ITK, CDK12, CDK13, LCK, GAK, BLK, ULK1, and BLK.

A representative example of an inventive bifunctional compound that binds these kinases is as follows:

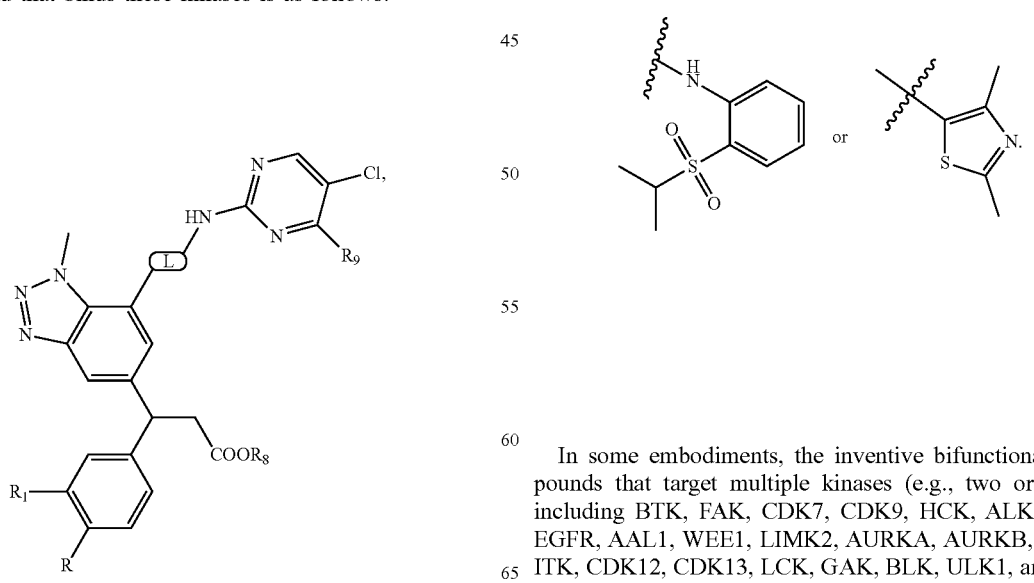

where $R_9$ is

In some embodiments, the inventive bifunctional compounds that target multiple kinases (e.g., two or more), including BTK, FAK, CDK7, CDK9, HCK, ALK, FLT3, EGFR, AAL1, WEE1, LIMK2, AURKA, AURKB, CDK5, ITK, CDK12, CDK13, LCK, GAK, BLK, ULK1, and BLK are represented by the following formulae (with the linker shown generically):

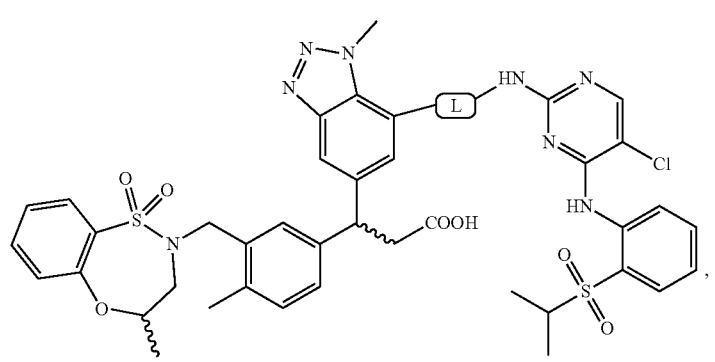
(Ig)
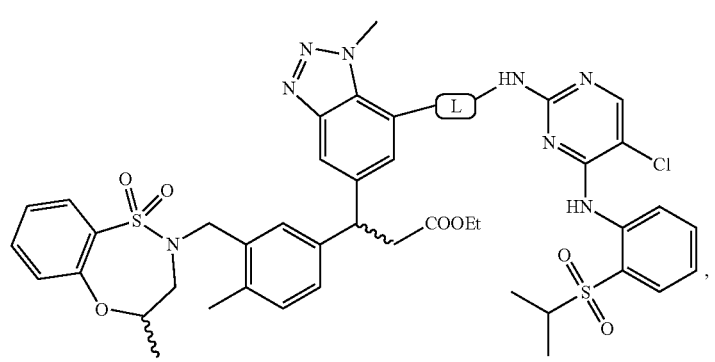
(Ih)
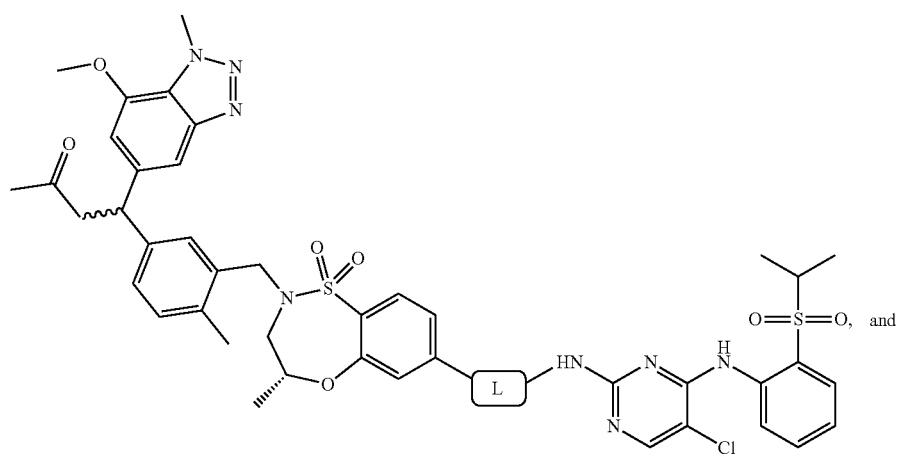
(Ii)
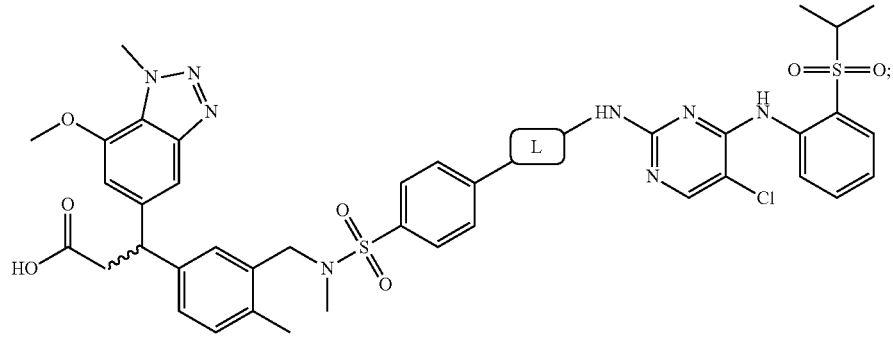
(Ij)
or a pharmaceutically acceptable salt or stereoisomer thereof.
In some embodiments, the inventive bifunctional compounds that target multiple kinases (e.g., two or more), including BTK, FAK, CDK7, CDK9, HCK, ALK, FLT3, EGFR, AAK1, WEE1, LIMK2, AURKA, AURKB, CDK5, ITK, CDK12, CDK13, LCK, GAK, BLK, ULK1 and BLK are represented by the following structures:

(10)
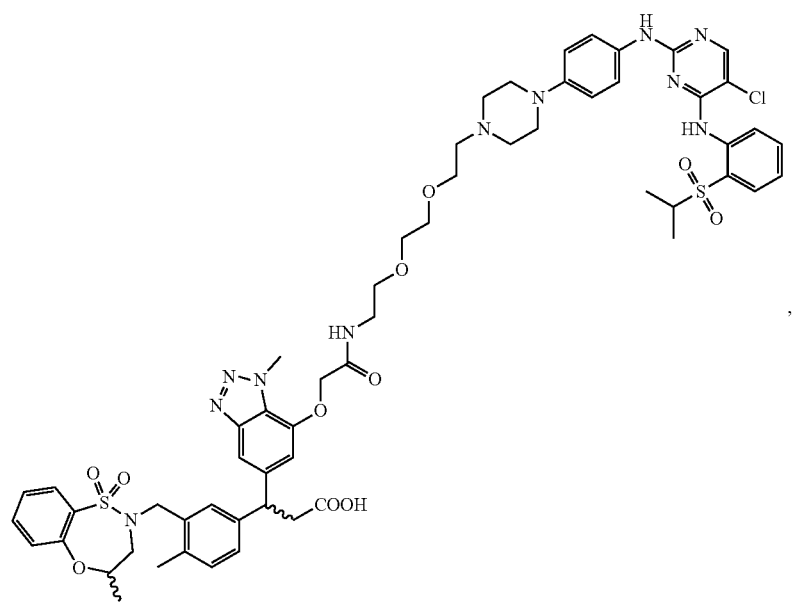
(11)
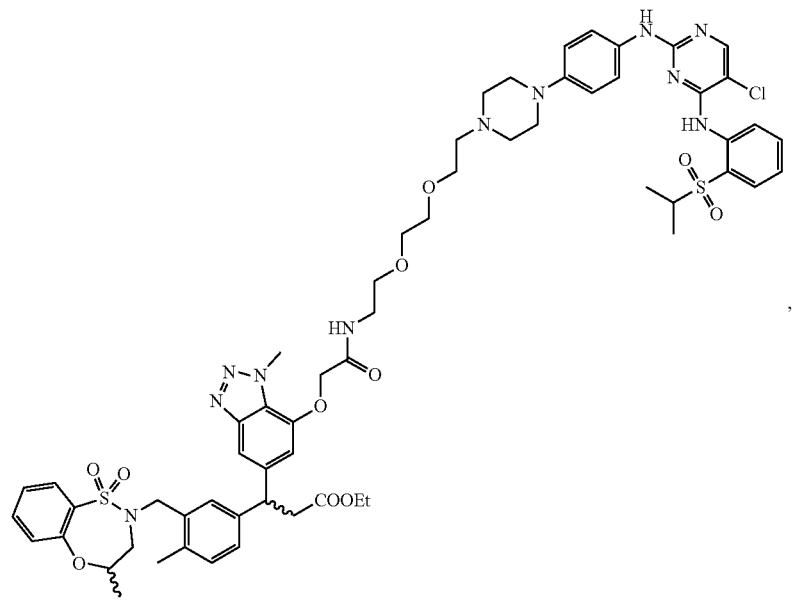
(12)
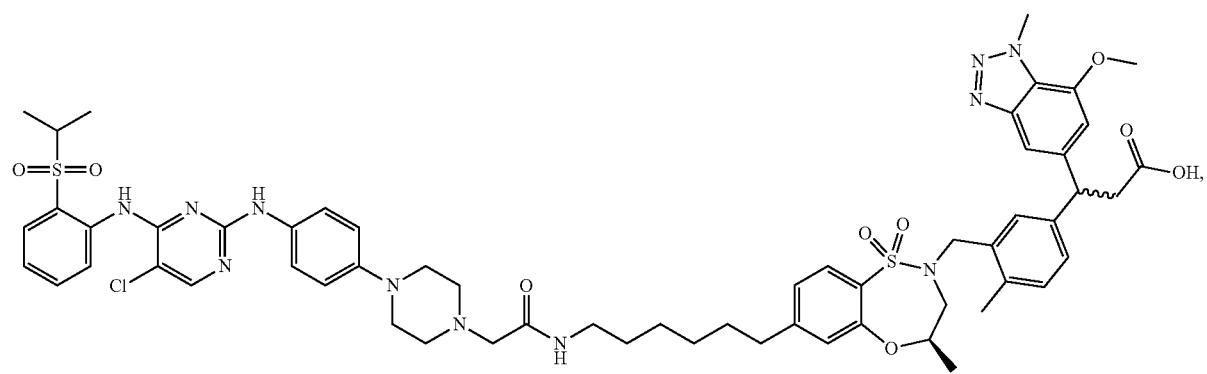

-continued
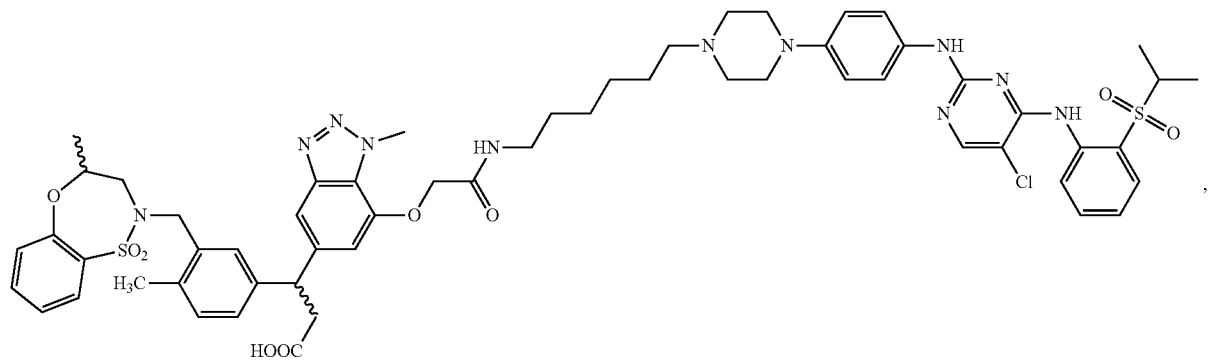
(13)
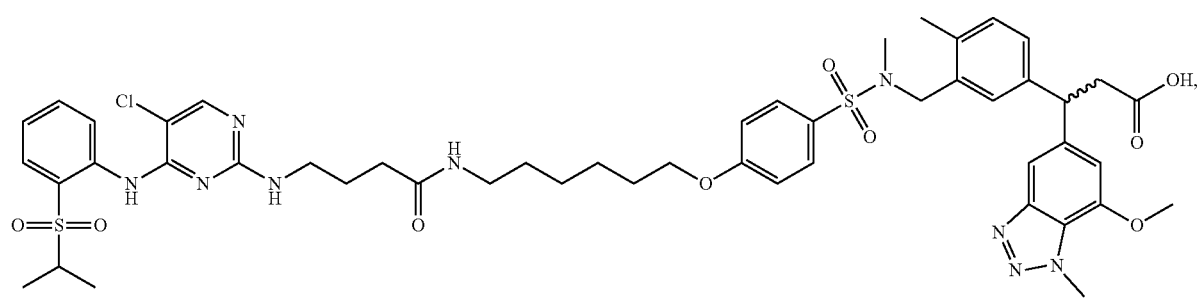
(14)
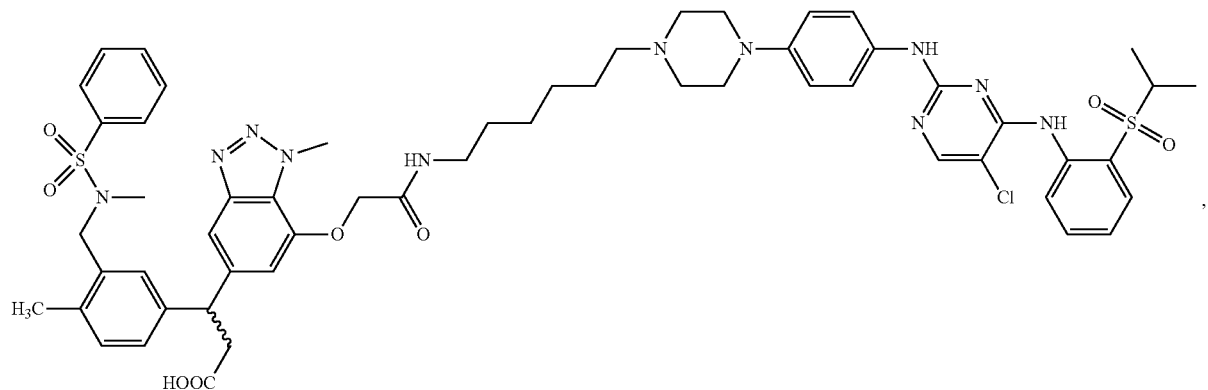
(15)
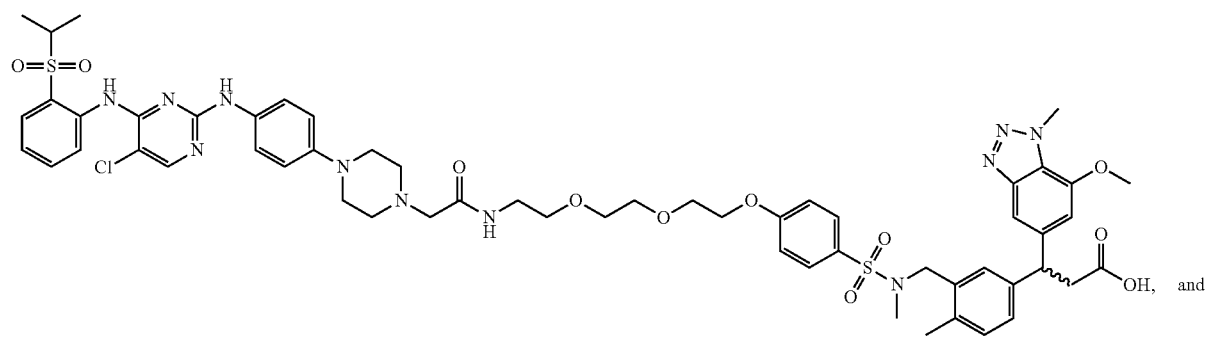
(16)
and (17)

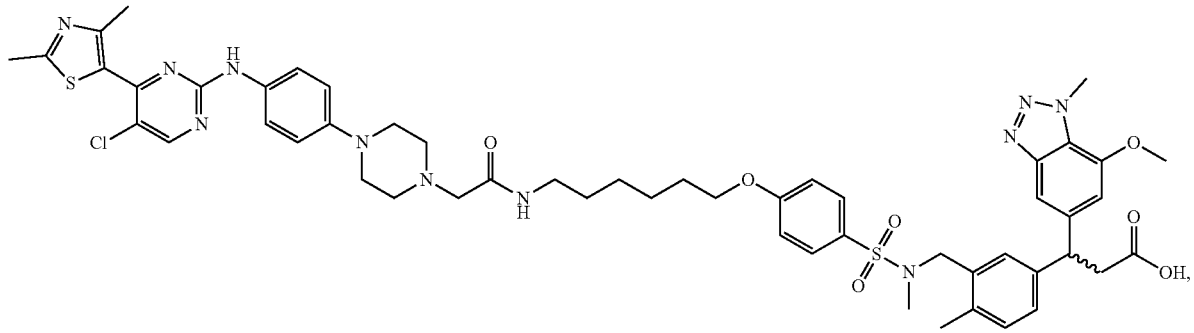

or a pharmaceutically acceptable salt or stereoisomer thereof.

In some embodiments, the inventive bifunctional compounds target Bruton's tyrosine kinase (BTK). An example of a bifunctional compound that targets BTK is represented by the following structure:

(18)

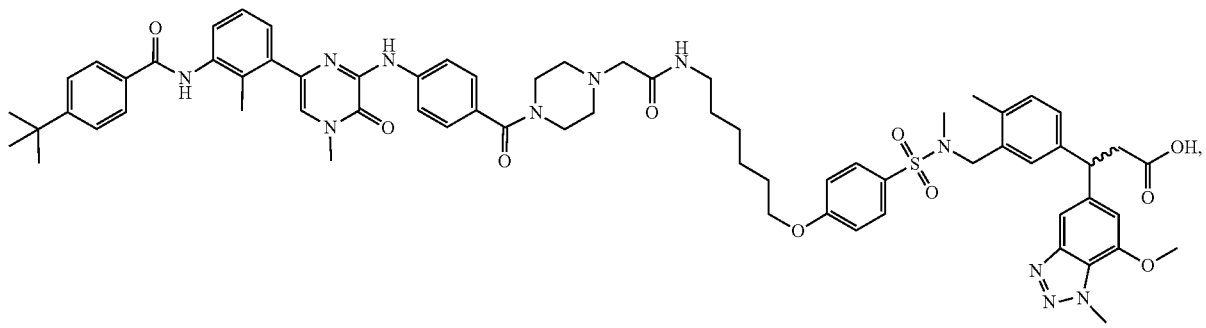

or a pharmaceutically acceptable salt or stereoisomer thereof.

Bifunctional compounds of the present invention may be in the form of a free acid or free base, or a pharmaceutically acceptable salt. As used herein, the term "pharmaceutically acceptable" refers to a material, such as a carrier or diluent, which does not abrogate the biological activity or properties of the compound, and is relatively non-toxic, i.e., the material may be administered to a subject without causing undesirable biological effects (such as dizziness or gastric upset) or interacting in a deleterious manner with any of the components of the composition in which it is contained. The term "pharmaceutically acceptable salt" refers to a product obtained by reaction of the compound of the present invention with a suitable acid or a base. Examples of pharmaceutically acceptable salts of the compounds of this invention include those derived from suitable inorganic bases such as Li, Na, K, Ca, Mg, Fe, Cu, Al, Zn and Mn salts. Examples of pharmaceutically acceptable, nontoxic acid addition salts are salts of an amino group formed with inorganic acids such as hydrochloride, hydrobromide, hydroiodide, nitrate, sulfate, bisulfate, phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, 4-methylbenzenesulfonate or p-toluenesulfonate salts and the like. Certain compounds of the invention can form pharmaceutically acceptable salts with various organic bases such as lysine, arginine, guanidine, diethanolamine or metformin.

In some embodiments, the bifunctional compounds of the present invention is an isotopic derivative in that it has at least one desired isotopic substitution of an atom, at an amount above the natural abundance of the isotope, i.e., enriched. In one embodiment, the bifunctional compound includes deuterium or multiple deuterium atoms. Substitution with heavier isotopes such as deuterium, i.e. $^2$H, may afford certain therapeutic advantages resulting from greater metabolic stability, for example, increased in vivo half-life or reduced dosage requirements, and thus may be advantageous in some circumstances. For example, in bifunctional compounds of formula (I) that target BRD4, BRD2 AND BRD3, a JQ1 moiety may be deuterated in order to increase half-life.

Bifunctional compounds of the present invention may have at least one chiral center and thus may be in the form of a stereoisomer, which as used herein, embraces all isomers of individual compounds that differ only in the orientation of their atoms in space. The term stereoisomer includes mirror image isomers (enantiomers which include the (R-) or (S-) configurations of the compounds), mixtures of mirror image isomers (physical mixtures of the enantiomers, and racemates or racemic mixtures) of compounds, geometric (cis/trans or E/Z, R/S) isomers of compounds and isomers of compounds with more than one chiral center that are not mirror images of one another (diastereoisomers). The chiral centers of the compounds may undergo epimerization in vivo; thus, for these compounds, administration of the compound in its (R-) form is considered equivalent to administration of the compound in its (S-) form. Accordingly, the compounds of the present invention may be made and used in the form of individual isomers and substantially free of other isomers, or in the form of a mixture of various isomers, e.g., racemic mixtures of stereoisomers.

Methods of Synthesis

In another aspect, the present invention is directed to a method for making a bifunctional compound of formula (I), or a pharmaceutically acceptable salt or stereoisomer thereof. Broadly, the inventive compounds or pharmaceutically-acceptable salts or stereoisomers thereof may be prepared by any process known to be applicable to the preparation of chemically related compounds. The compounds of the present invention will be better understood in connection with the synthetic schemes that described in various working examples and which illustrate non-limiting methods by which the compounds of the invention may be prepared.

Pharmaceutical Compositions

Another aspect of the present invention is directed to a pharmaceutical composition that includes a therapeutically effective amount of the bifunctional compound of formula (I) or a pharmaceutically acceptable salt or stereoisomer thereof, and a pharmaceutically acceptable carrier. The term "pharmaceutically acceptable carrier," as known in the art, refers to a pharmaceutically acceptable material, composition or vehicle, suitable for administering compounds of the present invention to mammals. Suitable carriers may include, for example, liquids (both aqueous and non-aqueous alike, and combinations thereof), solids, encapsulating materials, gases, and combinations thereof (e.g., semi-solids), and gases, that function to carry or transport the compound from one organ, or portion of the body, to another organ, or portion of the body. A carrier is "acceptable" in the sense of being physiologically inert to and compatible with the other ingredients of the formulation and not injurious to the subject or patient. Depending on the type of formulation, the composition may include one or more pharmaceutically acceptable excipients.

Broadly, bifunctional compounds of formula (I) may be formulated into a given type of composition in accordance with conventional pharmaceutical practice such as conventional mixing, dissolving, granulating, dragee-making, levigating, emulsifying, encapsulating, entrapping and compression processes (see, e.g., Remington: *The Science and Practice of Pharmacy* (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York). The type of formulation depends on the mode of administration which may include enteral (e.g., oral, buccal, sublingual and rectal), parenteral (e.g., subcutaneous (s.c.), intravenous (i.v.), intramuscular (i.m.), and intrasternal injection, or infusion techniques, intra-ocular, intra-arterial, intramedullary, intrathecal, intraventricular, transdermal, interdermal, intravaginal, intraperitoneal, mucosal, nasal, intratracheal instillation, bronchial instillation, and inhalation) and topical (e.g., transdermal). In general, the most appropriate route of administration will depend upon a variety of factors including, for example, the nature of the agent (e.g., its stability in the environment of the gastrointestinal tract), and/or the condition of the subject (e.g., whether the subject is able to tolerate oral administration). For example, parenteral (e.g., intravenous) administration may also be advantageous in that the compound may be administered relatively quickly such as in the case of a single-dose treatment and/or an acute condition.

In some embodiments, the compositions are formulated for oral or intravenous administration (e.g., systemic intravenous injection).

Accordingly, compounds of the present invention may be formulated into solid compositions (e.g., powders, tablets, dispersible granules, capsules, cachets, and suppositories), liquid compositions (e.g., solutions in which the compound is dissolved, suspensions in which solid particles of the compound are dispersed, emulsions, and solutions containing liposomes, micelles, or nanoparticles, syrups and elixirs); semi-solid compositions (e.g., gels, suspensions and creams); and gases (e.g., propellants for aerosol compositions). Compounds may also be formulated for rapid, intermediate or extended release.

Solid dosage forms for oral administration include capsules, tablets, pills, powders, and granules. In such solid dosage forms, the active compound is mixed with a carrier such as sodium citrate or dicalcium phosphate and an additional carrier or excipient such as a) fillers or extenders such as starches, lactose, sucrose, glucose, mannitol, and silicic acid, b) binders such as, for example, methylcellulose, microcrystalline cellulose, hydroxypropylmethylcellulose, carboxymethylcellulose, sodium carboxymethylcellulose, alginates, gelatin, polyvinylpyrrolidinone, sucrose, and acacia, c) humectants such as glycerol, d) disintegrating agents such as crosslinked polymers (e.g., crosslinked polyvinylpyrrolidone (crospovidone), crosslinked sodium carboxymethyl cellulose (croscarmellose sodium), sodium starch glycolate, agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also include buffering agents. Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings. They may further contain an opacifying agent.

In some embodiments, compounds of the present invention may be formulated in a hard or soft gelatin capsule. Representative excipients that may be used include pregelatinized starch, magnesium stearate, mannitol, sodium stearyl fumarate, lactose anhydrous, microcrystalline cellulose and croscarmellose sodium. Gelatin shells may include gelatin, titanium dioxide, iron oxides and colorants.

Liquid dosage forms for oral administration include solutions, suspensions, emulsions, micro-emulsions, syrups and elixirs. In addition to the compound, the liquid dosage forms may contain an aqueous or non-aqueous carrier (depending upon the solubility of the compounds) commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Oral compositions may also include an excipients such as wetting agents, suspending agents, coloring, sweetening, flavoring, and perfuming agents.

Injectable preparations may include sterile aqueous solutions or oleaginous suspensions. They may be formulated according to standard techniques using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. The effect of the compound may be prolonged by slowing its absorption, which may be accomplished by the use of a liquid suspension or crystalline or amorphous material with poor water solubility. Prolonged absorption of the compound from a parenterally administered formulation may also be accomplished by suspending the compound in an oily vehicle.

In certain embodiments, bifunctional compounds of formula (I) may be administered in a local rather than systemic manner, for example, via injection of the conjugate directly into an organ, often in a depot preparation or sustained release formulation. In specific embodiments, long acting formulations are administered by implantation (for example subcutaneously or intramuscularly) or by intramuscular injection. Injectable depot forms are made by forming microencapsule matrices of the compound in a biodegradable polymer, e.g., polylactide-polyglycolides, poly(orthoesters) and poly(anhydrides). The rate of release of the compound may be controlled by varying the ratio of compound to polymer and the nature of the particular polymer employed. Depot injectable formulations are also prepared by entrapping the compound in liposomes or microemulsions that are compatible with body tissues. Furthermore, in other embodiments, the compound is delivered in a targeted drug delivery system, for example, in a liposome coated with organ-specific antibody. In such embodiments, the liposomes are targeted to and taken up selectively by the organ.

The inventive compounds may be formulated for buccal or sublingual administration, examples of which include tablets, lozenges and gels.

The compounds may be formulated for administration by inhalation. Various forms suitable for administration by inhalation include aerosols, mists or powders. Pharmaceutical compositions may be delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In some embodiments, the dosage unit of a pressurized aerosol may be determined by providing a valve to deliver a metered amount. In some embodiments, capsules and cartridges including gelatin, for example, for use in an inhaler or insufflator, may be formulated containing a powder mix of the compound and a suitable powder base such as lactose or starch.

Bifunctional compounds of formula (I) may be formulated for topical administration which as used herein, refers to administration intradermally by application of the formulation to the epidermis. These types of compositions are typically in the form of ointments, pastes, creams, lotions, gels, solutions and sprays.

Representative examples of carriers useful in formulating compositions for topical application include solvents (e.g., alcohols, poly alcohols, water), creams, lotions, ointments, oils, plasters, liposomes, powders, emulsions, microemulsions, and buffered solutions (e.g., hypotonic or buffered saline). Creams, for example, may be formulated using saturated or unsaturated fatty acids such as stearic acid, palmitic acid, oleic acid, palmito-oleic acid, cetyl, or oleyl alcohols. Creams may also contain a non-ionic surfactant such as polyoxy-40-stearate.

In some embodiments, the topical formulations may also include an excipient, an example of which is a penetration enhancing agent. These agents are capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, *Percutaneous Penetration Enhancers*, Maibach H. I. and Smith H. E. (eds.), CRC Press, Inc., Boca Raton, Fla. (1995), which surveys the use and testing of various skin penetration enhancers, and Buyuktimkin et al., *Chemical Means of Transdermal Drug Permeation Enhancement in Transdermal and Topical Drug Delivery Systems*, Gosh T. K., Pfister W. R., Yum S. I. (Eds.), Interpharm Press Inc., Buffalo Grove, Ill. (1997). Representative examples of penetration enhancing agents include triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate), and N-methylpyrrolidone.

Representative examples of yet other excipients that may be included in topical as well as in other types of formulations (to the extent they are compatible), include preservatives, antioxidants, moisturizers, emollients, buffering agents, solubilizing agents, skin protectants, and surfactants. Suitable preservatives include alcohols, quaternary amines, organic acids, parabens, and phenols. Suitable antioxidants include ascorbic acid and its esters, sodium bisulfite, butylated hydroxytoluene, butylated hydroxyanisole, tocopherols, and chelating agents like EDTA and citric acid. Suitable moisturizers include glycerine, sorbitol, polyethylene glycols, urea, and propylene glycol. Suitable buffering agents include citric, hydrochloric, and lactic acid buffers. Suitable solubilizing agents include quaternary ammonium chlorides, cyclodextrins, benzyl benzoate, lecithin, and polysorbates. Suitable skin protectants include vitamin E oil, allatoin, dimethicone, glycerin, petrolatum, and zinc oxide.

Transdermal formulations typically employ transdermal delivery devices and transdermal delivery patches wherein the compound is formulated in lipophilic emulsions or buffered, aqueous solutions, dissolved and/or dispersed in a polymer or an adhesive. Patches may be constructed for continuous, pulsatile, or on demand delivery of pharmaceutical agents. Transdermal delivery of the compounds may be accomplished by means of an iontophoretic patch. Transdermal patches may provide controlled delivery of the compounds wherein the rate of absorption is slowed by using rate-controlling membranes or by trapping the compound within a polymer matrix or gel. Absorption enhancers may be used to increase absorption, examples of which include absorbable pharmaceutically acceptable solvents that assist passage through the skin.

Ophthalmic formulations include eye drops.

Formulations for rectal administration include enemas, rectal gels, rectal foams, rectal aerosols, and retention enemas, which may contain conventional suppository bases such as cocoa butter or other glycerides, as well as synthetic polymers such as polyvinylpyrrolidone, PEG, and the like. Compositions for rectal or vaginal administration may also be formulated as suppositories which can be prepared by mixing the compound with suitable non-irritating carriers and excipients such as cocoa butter, mixtures of fatty acid glycerides, polyethylene glycol, suppository waxes, and combinations thereof, all of which are solid at ambient temperature but liquid at body temperature and therefore melt in the rectum or vaginal cavity and release the compound.

Dosage Amounts

As used herein, the term, "therapeutically effective amount" refers to an amount of a bifunctional compound of formula (I) or a pharmaceutically acceptable salt or a stereoisomer thereof that is effective in producing the desired therapeutic response in a particular patient suffering from a disease or disorder mediated by aberrant protein activity. The term "therapeutically effective amount" thus includes the amount of the compound of the invention or a pharmaceutically acceptable salt or a stereoisomer thereof, that when administered, induces a positive modification in the disease or disorder to be treated, or is sufficient to prevent development or progression of the disease or disorder, or alleviate to some extent, one or more of the symptoms of the disease or disorder being treated in a subject, or which simply kills or inhibits the growth of diseased (e.g., cancer) cells, or reduces the amounts of aberrant protein in diseased cells.

The total daily dosage of the bifunctional compounds of formula (I) and usage thereof may be decided in accordance with standard medical practice, e.g., by the attending physician using sound medical judgment. The specific therapeutically effective dose for any particular patient will depend upon a variety of factors including the disease or disorder being treated and the severity thereof (e.g., its present status); the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts (see, for example, Goodman and Gilman's, "The Pharmacological Basis of Therapeutics", 10th Edition, A. Gilman, J. Hardman and L. Limbird, eds., McGraw-Hill Press, 155-173, 2001).

Bifunctional compounds of formula (I) and their pharmaceutically acceptable salts and stereoisomers may be effective over a wide dosage range. In some embodiments, the total daily dosage (e.g., for adult humans) may range from about 0.001 to about 1600 mg, from about 0.01 to about 1000 mg, from 0.01 to about 500 mg, from about 0.01 to about 100 mg, from about 0.5 to about 100 mg, from 1 to about 100-400 mg per day, from about 1 to about 50 mg per day, and from about 5 to about 40 mg per day, and in yet other embodiments from about 10 to about 30 mg per day. By way of example, capsules may be formulated with from about 1 to about 200 mg of compound (e.g., 1, 2, 2.5, 3, 4, 5, 10, 15, 20, 25, 50, 100, 150, and 200 mg). In some embodiments, individual dosages may be formulated to contain the desired dosage amount depending upon the number of times the compound is administered per day.

Methods of Use

In some aspects, the present invention is directed to methods of treating diseases or disorders involving aberrant or dysfunctional protein activity, that entails administration of a therapeutically effective amount of a bifunctional compound of formula (I) or a pharmaceutically acceptable salt or stereoisomer thereof, to a subject in need thereof.

The diseases or disorders may be said to be characterized or mediated by aberrant or dysfunctional protein activity (e.g., elevated levels of the proteins or otherwise functionally abnormal relative to a non-pathological state). A "disease" is generally regarded as a state of health of a subject wherein the subject cannot maintain homeostasis, and wherein if the disease is not ameliorated then the subject's health continues to deteriorate. In contrast, a "disorder" in a subject is a state of health in which the subject is able to maintain homeostasis, but in which the subject's state of health is less favorable than it would be in the absence of the disorder. Left untreated, a disorder does not necessarily cause a further decrease in the animal's state of health. In some embodiments, compounds of the invention may be useful in the treatment of cell proliferative diseases and disorders (e.g., cancer or benign neoplasms). As used herein, the term "cell proliferative disease or disorder" refers to the conditions characterized by deregulated or abnormal cell growth, or both, including noncancerous conditions such as neoplasms, precancerous conditions, benign tumors, and cancer.

The term "subject" (or "patient") as used herein includes all members of the animal kingdom prone to or suffering from the indicated disease or disorder. In some embodiments, the subject is a mammal, e.g., a human or a non-human mammal. The methods are also applicable to companion animals such as dogs and cats as well as livestock such as cows, horses, sheep, goats, pigs, and other domesticated and wild animals. A subject "in need of" treatment according to the present invention may be "suffering from or suspected of suffering from" a specific disease or disorder may have been positively diagnosed or otherwise presents with a sufficient number of risk factors or a sufficient number or combination of signs or symptoms such that a medical professional could diagnose or suspect that the subject was suffering from the disease or disorder. Thus, subjects suffering from, and suspected of suffering from, a specific disease or disorder are not necessarily two distinct groups.

The bifunctional compounds may be used to treat a disease or disorder characterized or mediated by aberrant activity of a target that may be targeted for degradation. Representative examples include diseases or disorders characterized or mediated by aberrant activity of the expression products of IKZF1 and IKZF3, and the following proteins: CK1α, FAM83F, DTWD1, ZFP91, RNF166, IKZF1, IKZF3, ZN692, ZBTB39, SALL4, ZN653, ZN654, ZC827, RAB28, GSTP1, TIMM10, IKZF5, ZFP36L2, GZF1, GSPT2, EGR1, HIC1, HIC2, IKZF2, IKZF4, INSM2, OSR2, PRD15, SALL1, SALL3, WIZ, Z324B, ZBT17, ZBT41, ZBT49, ZBT7A, ZBT7B, ZBTB2, ZFP62, ZIK1, ZNF217, ZNF276, ZNF3, ZNF316, ZNF335, ZNF397, ZNF407, ZNF408, ZNF462, ZNF483, SNF517, ZNF526, ZNF581, ZNF587, ZNF589, ZNF618, ZNF644, ZNF646, ZNF724, ZNF771, ZNF782, ZNF784, ZNF814, ZSC10, ZSC22 and ZUFSP.

Additional representative examples include diseases or disorders characterized or mediated by aberrant activity of tyrosine kinases (e.g., AATK, ABL, ABL2, ALK, AXL, BLK, BMX, BTK, CSF1R, CSK, DDR1, DDR2, EGFR, EPHA1, EPHA2, EPHA3, EPHA4, EPHA5, EPHA6, EPHA7, EPHA8, EPHA10, EPHB1, EPHB2, EPHB3, EPHB4, EPHB6, ERBB2, ERBB3, ERBB4, FER, FES, FGFR1, FGFR2, FGFR3, FGFR4, FGR, FLT1, FLT3, FLT4, FRK, FYN, GSG2, HCK, IGF1R, ILK, INSR, INSRR, ITK, JAK1, JAK2, JAK3, KDR, KIT, KSR1, LCK, LMTK2, LMTK3, LTK, LYN, MATK, MERTK, MET, MLTK, MST1R, MUSK, NPR1, NTRK1, NTRK2, NTRK3, PDGFRA, PDGFRB, PLK4, PTK2, PTK2B, PTK6, PTK7, RET, ROR1, ROR2, ROS1, RYK, SGK493, SRC, SRMS, STYK1, SYK, TEC, TEK, TEX14, TIE1, TNK1, TNK2, TNNI3K, TXK, TYK2, TYRO3, YES 1, or ZAP70), a serine/threonine kinase (e.g., casein kinase 2, protein kinase A, protein kinase B, protein kinase C, Raf kinases, CaM kinases, AKT1, AKT2, AKT3, ALK1, ALK2, ALK3, ALK4, Aurora A, Aurora B, Aurora C, CHK1, CHK2, CLK1, CLK2, CLK3, DAPK1, DAPK2, DAPK3, DMPK, ERK1, ERK2, ERK5, GCK, GSK3, HIPK, KHS1, LKB1, LOK, MAPKAPK2, MAPKAPK, MNK1, MSSK1, MST1, MST2, MST4, NDR, NEK2, NEK3, NEK6, NEK7, NEK9, NEK11, PAK1, PAK2, PAK3, PAK4, PAK5, PAK6, PIM1, PIM2, PLK1, RIP2, RIPS, RSK1, RSK2, SGK2, SGK3, SIK1, STK33, TAO1, TAO2, TGF-beta, TLK2, TSSK1, TSSK2, ULK1, or ULK2), a cyclin dependent kinase (e.g., Cdk1-Cdk11), and a leucine-rich repeat kinase (e.g., LRRK2).

Further representative examples include diseases or disorders characterized or mediated by aberrant activity of IRAK 1 and/or IRAK 4, KRAS, HRAS and NRAS (particularly G12C mutants thereof), and bromodomain proteins, e.g., PB1 and BRD4, as further disclosed herein below. Yet other aberrant or dysfunctional proteins that may be targeted by the bifunctional compounds of the present invention include B7.1 and B7, TINFR1m, TNFR2, NADPH oxidase, BclIBax and other partners in the apoptosis pathway, C5a receptor, HMG-CoA reductase, PDE V phosphodiesterase type, PDE IV phosphodiesterase type 4, PDE I, PDEII, PDEIII, squalene cyclase inhibitor, CXCR1, CXCR2, nitric oxide (NO) synthase, cyclo-oxygenase 1, cyclo-oxygenase 2, 5HT receptors, dopamine receptors, G Proteins, i.e., Gq, histamine receptors, 5-lipoxygenase, tryptase serine protease, thymidylate synthase, purine nucleoside phosphorylase, GAPDH trypanosomal, glycogen phosphorylase, Carbonic anhydrase, chemokine receptors, JAW STAT, RXR and similar, HIV 1 protease, HIV 1 integrase, influenza, neuramimidase, hepatitis B reverse transcriptase, sodium channel, multi drug resistance (MDR), protein β-glycoprotein (and MRP), CD23, CD124, tyrosine kinase p56 lck, CD4, CD5, IL-2 receptor, IL-1 receptor, TNF-alphaR, ICAM1, Cat+ channels, VCAM, VLA-4 integrin, selectins, CD40/CD40L, neurokinins and receptors, inosine monophosphate dehydrogenase, p38 MAP Kinase, Ras-Raf-MEK-ERK pathway, interleukin-1 converting enzyme, caspase, HCV, NS3 protease, HCV NS3 RNA helicase, glycinamide ribonucleotide formyl transferase, rhinovirus 3C protease, herpes simplex virus-1 (HSV-I), protease, cytomegalovirus (CMV) protease, poly (ADP-ribose) polymerase, cyclin dependent kinases, vascular endothelial growth factor, oxytocin receptor, microsomal transfer protein inhibitor, bile acid transport inhibitor, 5-α reductase inhibitors, angiotensin 11, glycine receptor, noradrenaline reuptake receptor, endothelin receptors, neuropeptide Y and receptor, adenosine receptors, adenosine kinase and AMP deaminase, purinergic receptors (P2Y1, P2Y2, P2Y4, P2Y6, P2X1-7), farnesyltransferases, geranylgeranyl transferase, TrkA-α receptor for NGF, β-amyloid, tyrosine kinase Flk-IIKDR, vitronectin receptor, integrin receptor, Her-21 neu, telomerase inhibition, cytosolic phospholipaseA2 and EGF receptor tyrosine kinase, ecdysone 20-monooxygenase, ion channel of the GABA gated chloride channel, acetylcholinesterase, voltage-sensitive sodium channel protein, calcium release channel, chloride channels, acetyl-CoA carboxylase, adenylosuccinate synthetase, protoporphyrinogen oxidase and enolpyruvylshikimate-phosphate synthase.

Exemplary types of non-cancerous (e.g., cell proliferative) diseases or disorders that may be amenable to treatment with the compounds of the present invention include inflammatory diseases and conditions, autoimmune diseases, neurodegenerative diseases, heart diseases, viral diseases, chronic and acute kidney diseases or injuries, metabolic diseases, and allergic and genetic diseases.

Representative examples of specific non-cancerous diseases and disorders include rheumatoid arthritis, alopecia areata, lymphoproliferative conditions, autoimmune hematological disorders (e.g. hemolytic anemia, aplastic anemia, anhidrotic ectodermal dysplasia, pure red cell anemia and idiopathic thrombocytopenia), cholecystitis, acromegaly, rheumatoid spondylitis, osteoarthritis, gout, scleroderma, sepsis, septic shock, dacryoadenitis, cryopyrin associated periodic syndrome (CAPS), endotoxic shock, endometritis, gram-negative sepsis, keratoconjunctivitis sicca, toxic shock syndrome, asthma, adult respiratory distress syndrome, chronic obstructive pulmonary disease, chronic pulmonary inflammation, chronic graft rejection, hidradenitis suppurativa, inflammatory bowel disease, Crohn's disease, Behcet's syndrome, systemic lupus erythematosus, glomerulonephritis, multiple sclerosis, juvenile-onset diabetes, autoimmune uveoretinitis, autoimmune vasculitis, thyroiditis, Addison's disease, lichen planus, appendicitis, bullous pemphigus, pemphigus vulgaris, pemphigus foliaceus, paraneoplastic pemphigus, myasthenia gravis, immunoglobulin A nephropathy, Hashimoto's disease, Sjogren's syndrome, vitiligo, Wegener granulomatosis, granulomatous orchitis, autoimmune oophoritis, sarcoidosis, rheumatic carditis, ankylosing spondylitis, Grave's disease, autoimmune thrombocytopenic purpura, psoriasis, psoriatic arthritis, eczema, dermatitis herpetiformis, ulcerative colitis, pancreatic fibrosis, hepatitis, hepatic fibrosis, CD14 mediated sepsis, non-CD14 mediated sepsis, acute and chronic renal disease, irritable bowel syndrome, pyresis, restenosis, cervicitis, stroke and ischemic injury, neural trauma, acute and chronic pain, allergic rhinitis, allergic conjunctivitis, chronic heart failure, congestive heart failure, acute coronary syndrome, cachexia, malaria, leprosy, leishmaniasis, Lyme disease, Reiter's syndrome, acute synovitis, muscle degeneration, bursitis, tendonitis, tenosynovitis, herniated, ruptured, or prolapsed intervertebral disk syndrome, osteopetrosis, rhinosinusitis, thrombosis, silicosis, pulmonary sarcosis, bone resorption diseases, such as osteoporosis, fibromyalgia, AIDS and other viral diseases such as Herpes Zoster, Herpes Simplex I or II, influenza virus and cytomegalovirus, diabetes Type I and II, obesity, insulin resistance and diabetic retinopathy, 22q11.2 deletion syndrome, Angelman syndrome, Canavan disease, celiac disease, Charcot-Marie-Tooth disease, color blindness, Cri du chat, Down syndrome, cystic fibrosis, Duchenne muscular dystrophy, haemophilia, Klinefleter's syndrome, neurofibromatosis, phenylketonuria, Prader-Willi syndrome, sickle cell disease, Tay-Sachs disease, Turner syndrome, urea cycle disorders, thalassemia, otitis, pancreatitis, parotitis, pericarditis, peritonitis, pharyngitis, pleuritis, phlebitis, pneumonitis, uveitis, polymyositis, proctitis, interstitial lung fibrosis, dermatomyositis, atherosclerosis, arteriosclerosis, amyotrophic lateral sclerosis, asociality, varicosis, vaginitis, depression, and Sudden Infant Death Syndrome.

In other embodiments, the methods are directed to treating subjects having cancer. Broadly, the bifunctional compounds of the present invention may be effective in the treatment of carcinomas (solid tumors including both primary and metastatic tumors), sarcomas, melanomas, and hematological cancers (cancers affecting blood including lymphocytes, bone marrow and/or lymph nodes) including leukemia, lymphoma and multiple myeloma. Adult tumors/cancers and pediatric tumors/cancers are included. The cancers may be vascularized, or not yet substantially vascularized, or non-vascularized tumors.

Representative examples of cancers includes adrenocortical carcinoma, AIDS-related cancers (e.g., Kaposi's and AIDS-related lymphoma), appendix cancer, childhood cancers (e.g., childhood cerebellar astrocytoma, childhood cerebral astrocytoma), basal cell carcinoma, skin cancer (non-melanoma), biliary cancer, extrahepatic bile duct cancer, intrahepatic bile duct cancer, bladder cancer, urinary bladder cancer, urothelial cancer, brain cancer (e.g., gliomas and glioblastomas such as brain stem glioma, cerebellar astrocytoma, cerebral astrocytoma/malignant glioma, ependymoma, medulloblastoma, supratentorial primitive neuroectodeimal tumors, visual pathway and hypothalamic glioma), breast cancer, bronchial adenomas/carcinoids, carcinoid tumor, nervous system cancer (e.g., central nervous system cancer, central nervous system lymphoma), cervical cancer, chronic myeloproliferative disorders, colorectal cancer (e.g., colon cancer, rectal cancer), lymphoid neoplasm, mycosis fungoids, Sezary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastrointestinal cancer (e.g., stomach cancer, small intestine cancer, gastrointestinal carcinoid tumor, gastrointestinal stromal tumor (GIST)), germ cell tumor, ovarian germ cell tumor, gestational trophoblastic tumor glioma, head and neck cancer, Hodgkin's lymphoma, leukemia, lymphoma, multiple myeloma, hypopharyngeal cancer, intraocular melanoma, ocular cancer, islet cell tumors (endocrine pancreas), renal cancer (e.g., Wilm's Tumor, clear cell renal cell carcinoma), liver cancer, lung cancer (e.g., non-small cell lung cancer and small cell lung cancer), Waldenstrom's macroglobulinema, melanoma, intraocular (eye) melanoma, merkel cell carcinoma, mesothelioma, metastatic squamous neck cancer with occult primary, multiple endocrine neoplasia (MEN), myelodysplastic syndromes, myelodysplastic/myeloproliferative diseases, nasopharyngeal cancer, neuroblastoma, oral cancer (e.g., mouth cancer, lip cancer, oral cavity cancer, tongue cancer, oropharyngeal cancer, throat cancer, laryngeal cancer), ovarian cancer (e.g., ovarian epithelial cancer, ovarian germ cell tumor, ovarian low malignant potential tumor), pancreatic cancer, cholangiocarcinoma, islet cell pancreatic cancer, paranasal sinus and nasal cavity cancer, parathyroid cancer, penile cancer, pharyngeal cancer, pheochromocytoma, pineoblastoma, pituitary tumor, plasma cell neoplasm/multiple myeloma, pleuropulmonary blastoma, prostate cancer, retinoblastoma rhabdomyosarcoma, salivary gland cancer, uterine cancer (e.g., endometrial uterine cancer, uterine sarcoma, uterine corpus cancer), squamous cell carcinoma, testicular cancer, thymoma, thymic carcinoma, thyroid cancer, esophageal cancer, transitional cell cancer of the renal pelvis and ureter and other urinary organs, urethral cancer, gestational trophoblastic tumor, vaginal cancer and vulvar cancer.

Sarcomas that may be treatable with bifunctional compounds of the present invention include both soft tissue and bone cancers alike, representative examples of which include osteosarcoma or osteogenic sarcoma (bone) (e.g., Ewing's sarcoma), chondrosarcoma (cartilage), leiomyosarcoma (smooth muscle), rhabdomyosarcoma (skeletal muscle), mesothelial sarcoma or mesothelioma (membranous lining of body cavities), fibrosarcoma (fibrous tissue), angiosarcoma or hemangioendothelioma (blood vessels), liposarcoma (adipose tissue), glioma or astrocytoma (neurogenic connective tissue found in the brain), myxosarcoma (primitive embryonic connective tissue) and mesenchymous or mixed mesodermal tumor (mixed connective tissue types).

In some embodiments, methods of the present invention entail treatment of subjects having cell proliferative diseases or disorders of the hematological system, liver (hepatocellular), brain, lung, colorectal (e.g., colon), pancreas, prostate, skin, ovary, breast, skin (e.g., melanoma), and endometrium.

As used herein, "cell proliferative diseases or disorders of the hematologic system" include lymphoma, leukemia, myeloid neoplasms, mast cell neoplasms, myelodysplasia, benign monoclonal gammopathy, lymphomatoid papulosis, polycythemia vera, chronic myelocytic leukemia, agnogenic myeloid metaplasia, and essential thrombocythemia. Representative examples of hematologic cancers may thus include multiple myeloma, lymphoma (including T-cell lymphoma, Hodgkin's lymphoma, non-Hodgkin's lymphoma (diffuse large B-cell lymphoma (DLBCL), follicular lymphoma (FL), mantle cell lymphoma (MCL) and ALK+ anaplastic large cell lymphoma (e.g., B-cell non-Hodgkin's lymphoma selected from diffuse large B-cell lymphoma (e.g., germinal center B-cell-like diffuse large B-cell lymphoma or activated B-cell-like diffuse large B-cell lymphoma), Burkitt's lymphoma/leukemia, mantle cell lymphoma, mediastinal (thymic) large B-cell lymphoma, follicular lymphoma, marginal zone lymphoma, lymphoplasmacytic lymphoma/Waldenstrom macroglobulinemia, metastatic pancreatic adenocarcinoma, refractory B-cell non-Hodgkin's lymphoma, and relapsed B-cell non-Hodgkin's lymphoma, childhood lymphomas, and lymphomas of lymphocytic and cutaneous origin, e.g., small lymphocytic lymphoma, leukemia, including childhood leukemia, hairy-cell leukemia, acute lymphocytic leukemia, acute myelocytic leukemia, acute myeloid leukemia (e.g., acute monocytic leukemia), chronic lymphocytic leukemia, small lymphocytic leukemia, chronic myelocytic leukemia, chronic myelogenous leukemia, and mast cell leukemia, myeloid neoplasms and mast cell neoplasms.

As used herein, "cell proliferative diseases or disorders of the liver (hepatocellular)" include all forms of cell proliferative disorders affecting the liver. Cell proliferative disorders of the liver may include liver cancer (e.g., hepatocellular carcinoma, intrahepatic cholangiocarcinoma and hepatoblastoma), a precancer or precancerous condition of the liver, benign growths or lesions of the liver, and malignant growths or lesions of the liver, and metastatic lesions in tissue and organs in the body other than the liver. Cell proliferative disorders of the liver may include hyperplasia, metaplasia, and dysplasia of the liver.

As used herein, "cell proliferative diseases or disorders of the brain" include all forms of cell proliferative disorders affecting the brain. Cell proliferative disorders of the brain may include brain cancer (e.g., gliomas, glioblastomas, meningiomas, pituitary adenomas, vestibular schwannomas, and primitive neuroectodermal tumors (medulloblastomas)), a precancer or precancerous condition of the brain, benign growths or lesions of the brain, and malignant growths or lesions of the brain, and metastatic lesions in tissue and organs in the body other than the brain. Cell proliferative disorders of the brain may include hyperplasia, metaplasia, and dysplasia of the brain.

As used herein, "cell proliferative diseases or disorders of the lung" include all forms of cell proliferative disorders affecting lung cells. Cell proliferative disorders of the lung include lung cancer, precancer and precancerous conditions of the lung, benign growths or lesions of the lung, hyperplasia, metaplasia, and dysplasia of the long, and metastatic lesions in the tissue and organs in the body other than the lung. Lung cancer includes all forms of cancer of the lung, e.g., malignant lung neoplasms, carcinoma in situ, typical carcinoid tumors, and atypical carcinoid tumors. Lung cancer includes small cell lung cancer ("SLCL"), non-small cell lung cancer ("NSCLC"), squamous cell carcinoma, adenocarcinoma, small cell carcinoma, large cell carcinoma, squamous cell carcinoma, and mesothelioma. Lung cancer can include "scar carcinoma", bronchioveolar carcinoma, giant cell carcinoma, spindle cell carcinoma, and large cell neuroendocrine carcinoma. Lung cancer also includes lung neoplasms having histologic and ultrastructural heterogeneity (e.g., mixed cell types). In some embodiments, a compound of the present invention may be used to treat non-metastatic or metastatic lung cancer (e.g., NSCLC, ALK-positive NSCLC, NSCLC harboring ROS1 Rearrangement, Lung Adenocarcinoma, and Squamous Cell Lung Carcinoma).

As used herein, "cell proliferative diseases or disorders of the colon" include all forms of cell proliferative disorders affecting colon cells, including colon cancer, a precancer or precancerous conditions of the colon, adenomatous polyps of the colon and metachronous lesions of the colon. Colon cancer includes sporadic and hereditary colon cancer, malignant colon neoplasms, carcinoma in situ, typical carcinoid tumors, and atypical carcinoid tumors, adenocarcinoma, squamous cell carcinoma, and squamous cell carcinoma. Colon cancer can be associated with a hereditary syndrome such as hereditary nonpolyposis colorectal cancer, familiar adenomatous polyposis, MYH associated polyposis, Gardner's syndrome, Peutz-Jeghers syndrome, Turcot's syndrome and juvenile polyposis. Cell proliferative disorders of the colon may also be characterized by hyperplasia, metaplasia, or dysplasia of the colon.

As used herein, "cell proliferative diseases or disorders of the pancreas" include all forms of cell proliferative disorders affecting pancreatic cells. Cell proliferative disorders of the pancreas may include pancreatic cancer, a precancer or precancerous condition of the pancreas, hyperplasia of the pancreas, dysplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas, including ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma, and pancreatic neoplasms having histologic and ultrastructural heterogeneity (e.g., mixed cell types).

As used herein, "cell proliferative diseases or disorders of the prostate" include all forms of cell proliferative disorders affecting the prostate. Cell proliferative disorders of the prostate may include prostate cancer, a precancer or precancerous condition of the prostate, benign growths or lesions of the prostate, and malignant growths or lesions of the prostate, and metastatic lesions in tissue and organs in the body other than the prostate. Cell proliferative disorders of the prostate may include hyperplasia, metaplasia, and dysplasia of the prostate.

As used herein, "cell proliferative diseases or disorders of the ovary" include all forms of cell proliferative disorders affecting cells of the ovary. Cell proliferative disorders of the ovary may include a precancer or precancerous condition of the ovary, benign growths or lesions of the ovary, ovarian cancer, and metastatic lesions in tissue and organs in the body other than the ovary. Cell proliferative disorders of the ovary may include hyperplasia, metaplasia, and dysplasia of the ovary.

As used herein, "cell proliferative diseases or disorders of the breast" include all forms of cell proliferative disorders affecting breast cells. Cell proliferative disorders of the breast may include breast cancer, a precancer or precancerous condition of the breast, benign growths or lesions of the breast, and metastatic lesions in tissue and organs in the body other than the breast. Cell proliferative disorders of the breast may include hyperplasia, metaplasia, and dysplasia of the breast.

As used herein, "cell proliferative diseases or disorders of the skin" include all forms of cell proliferative disorders affecting skin cells. Cell proliferative disorders of the skin may include a precancer or precancerous condition of the skin, benign growths or lesions of the skin, melanoma, malignant melanoma or other malignant growths or lesions of the skin, and metastatic lesions in tissue and organs in the body other than the skin. Cell proliferative disorders of the skin may include hyperplasia, metaplasia, and dysplasia of the skin.

As used herein, "cell proliferative diseases or disorders of the endometrium" include all forms of cell proliferative disorders affecting cells of the ovary. Cell proliferative disorders of the endometrium may include a precancer or precancerous condition of the endometrium, benign growths or lesions of the endometrium, endometrial cancer, and metastatic lesions in tissue and organs in the body other than the endometrium. Cell proliferative disorders of the endometrium may include hyperplasia, metaplasia, and dysplasia of the endometrium.

The bifunctional compounds of formula (I) may be administered to a patient, e.g., a cancer patient, as a monotherapy or by way of combination therapy, and as a front-line therapy or a follow-on therapy for patients who are unresponsive to front line therapy. Therapy may be "first-line", i.e., as an initial treatment in patients who have undergone no prior anti-cancer treatment regimens, either alone or in combination with other treatments; or "second-line", as a treatment in patients who have undergone a prior anti-cancer treatment regimen, either alone or in combination with other treatments; or as "third-line", "fourth-line", etc. treatments, either alone or in combination with other treatments. Therapy may also be given to patients who have had previous treatments which have been partially successful but are intolerant to the particular treatment. Therapy may also be given as an adjuvant treatment, i.e., to prevent reoccurrence of cancer in patients with no currently detectable disease or after surgical removal of a tumor. Thus, in some embodiments, the compound may be administered to a patient who has received another therapy, such as chemotherapy, radioimmunotherapy, surgical therapy, immunotherapy, radiation therapy, targeted therapy or any combination thereof.

The methods of the present invention may entail administration of bifunctional compounds of formula (I) or pharmaceutical compositions thereof to the patient in a single dose or in multiple doses (e.g., 1, 2, 3, 4, 5, 6, 7, 8, 10, 15, 20, or more doses). For example, the frequency of administration may range from once a day up to about once every eight weeks. In some embodiments, the frequency of administration ranges from about once a day for 1, 2, 3, 4, 5, or 6 weeks, and in other embodiments entails a 28-day cycle which includes daily administration for 3 weeks (21 days). In other embodiments, the bifunctional compound may be dosed twice a day (BID) over the course of two and a half days (for a total of 5 doses) or once a day (QD) over the course of two days (for a total of 2 doses). In other embodiments, the bifunctional compound may be dosed once a day (QD) over the course of five days.

Combination Therapy

Bifunctional compound of formula (I) may be used in combination or concurrently with at least one other active agent, e.g., anti-cancer agent or regimen, in treating diseases and disorders. The terms "in combination" and "concurrently in this context mean that the agents are co-administered, which includes substantially contemporaneous administration, by way of the same or separate dosage forms, and by the same or different modes of administration, or sequentially, e.g., as part of the same treatment regimen, or by way of successive treatment regimens. Thus, if given sequentially, at the onset of administration of the second compound, the first of the two compounds is in some cases still detectable at effective concentrations at the site of treatment. The sequence and time interval may be determined such that they can act together (e.g., synergistically to provide an increased benefit than if they were administered otherwise). For example, the therapeutics may be administered at the same time or sequentially in any order at different points in time; however, if not administered at the same time, they may be administered sufficiently close in time so as to provide the desired therapeutic effect, which may be in a synergistic fashion. Thus, the terms are not limited to the administration of the active agents at exactly the same time.

In some embodiments, the treatment regimen may include administration of a bifunctional compound of the invention in combination with one or more additional anticancer therapeutics. The dosage of the additional anticancer therapeutic may be the same or even lower than known or recommended doses. See, Hardman et al., eds., Goodman & Gilman's The Pharmacological Basis Of Basis Of Therapeutics, 10th ed., McGraw-Hill, New York, 2001; Physician's Desk Reference 60th ed., 2006. Anti-cancer agents that may be used in combination with the inventive compounds are known in the art. See, e.g., U.S. Pat. No. 9,101,622 (Section 5.2 thereof). Representative examples of additional active agents and treatment regimens include radiation therapy, chemotherapeutics (e.g., mitotic inhibitors, angiogenesis inhibitors, anti-hormones, autophagy inhibitors, alkylating agents, intercalating antibiotics, growth factor inhibitors, anti-androgens, signal transduction pathway inhibitors, anti-microtubule agents, platinum coordination complexes, HDAC inhibitors, proteasome inhibitors, and topoisomerase inhibitors), immunomodulators, therapeutic antibodies (e.g., mono-specific and bispecific antibodies) and CAR-T therapy.

In some embodiments, the bifunctional compound of formula (I) and the additional anticancer therapeutic may be administered less than 5 minutes apart, less than 30 minutes apart, less than 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. The two or more anticancer therapeutics may be administered within the same patient visit.

When the active components of the combination are not administered in the same pharmaceutical composition, it is understood that they can be administered in any order to a subject in need thereof. For example, a bifunctional compound of the present invention can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the additional anticancer therapeutic, to a subject in need thereof. In various aspects, the anticancer therapeutics are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one example, the anticancer therapeutics are administered within the same office visit. In another example, the combination anticancer therapeutics may be administered at 1 minute to 24 hours apart.

In some embodiments, the bifunctional compound of the present invention and the additional agent or therapeutic (e.g., an anti-cancer therapeutic) are cyclically administered. Cycling therapy involves the administration of one anticancer therapeutic for a period of time, followed by the administration of a second anti-cancer therapeutic for a period of time and repeating this sequential administration, i.e., the cycle, in order to reduce the development of resistance to one or both of the anticancer therapeutics, to avoid or reduce the side effects of one or both of the anticancer therapeutics, and/or to improve the efficacy of the therapies. In one example, cycling therapy involves the administration of a first anticancer therapeutic for a period of time, followed by the administration of a second anticancer therapeutic for a period of time, optionally, followed by the administration of a third anticancer therapeutic for a period of time and so forth, and repeating this sequential administration, i.e., the cycle in order to reduce the development of resistance to one of the anticancer therapeutics, to avoid or reduce the side effects of one of the anticancer therapeutics, and/or to improve the efficacy of the anticancer therapeutics.

Pharmaceutical Kits

The present compositions may be assembled into kits or pharmaceutical systems. Kits or pharmaceutical systems according to this aspect of the invention include a carrier or package such as a box, carton, tube or the like, having in close confinement therein one or more containers, such as vials, tubes, ampoules, or bottles, which contain the bifunctional compound of formula (I) or a pharmaceutical composition thereof. The kits or pharmaceutical systems of the invention may also include printed instructions for using the compounds and compositions.

These and other aspects of the present application will be further appreciated upon consideration of the following Examples, which are intended to illustrate certain particular embodiments of the application but are not intended to limit its scope, as defined by the claims.

EXAMPLES

Example 1: Synthesis of 3-(3-((4-(6-(2-((6S)-4-(4-chlorophenyl)-2,3,9-trimethyl-6H-thieno[3,2-f][1,2,4]triazolo[4,3-a][1,4]diazepin-6-yl)acetamido)hexyloxy)-N-methylphenylsulfonamido)methyl)-4-methylphenyl)-3-(7-methoxy-1-methyl-1H-benzo[d][1,2,3]triazol-5-yl)propanoic acid (9)

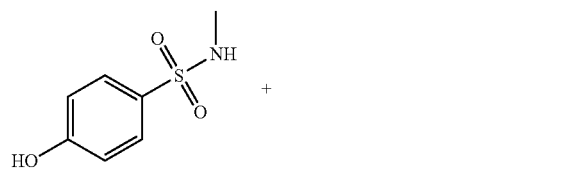

To a solution 4-hydroxy-N-methylbenzenesulfonamide (300 mg, 1.60 mmol) and 6-(tert-butoxycarbonylamino)hexyl methanesulfonate (520 mg, 1.76 mmol) in dimethylformamide (DMF) (8 mL), $K_2CO_3$ (441 mg, 3.20 mmol) was added at room temperature. Then the mixture was stirred at this temperature overnight. The mixture was filtered and the filtrate was concentrated under vacuum. The residue was purified by flash chromatography to yield tert-butyl 6-(4-(N-methylsulfamoyl)phenoxy)hexylcarbamate (600 mg, 1.55 mmol, 97%).

LC/MS m/z calculated for [M+H]$^+$ 387.2, found 387.2.

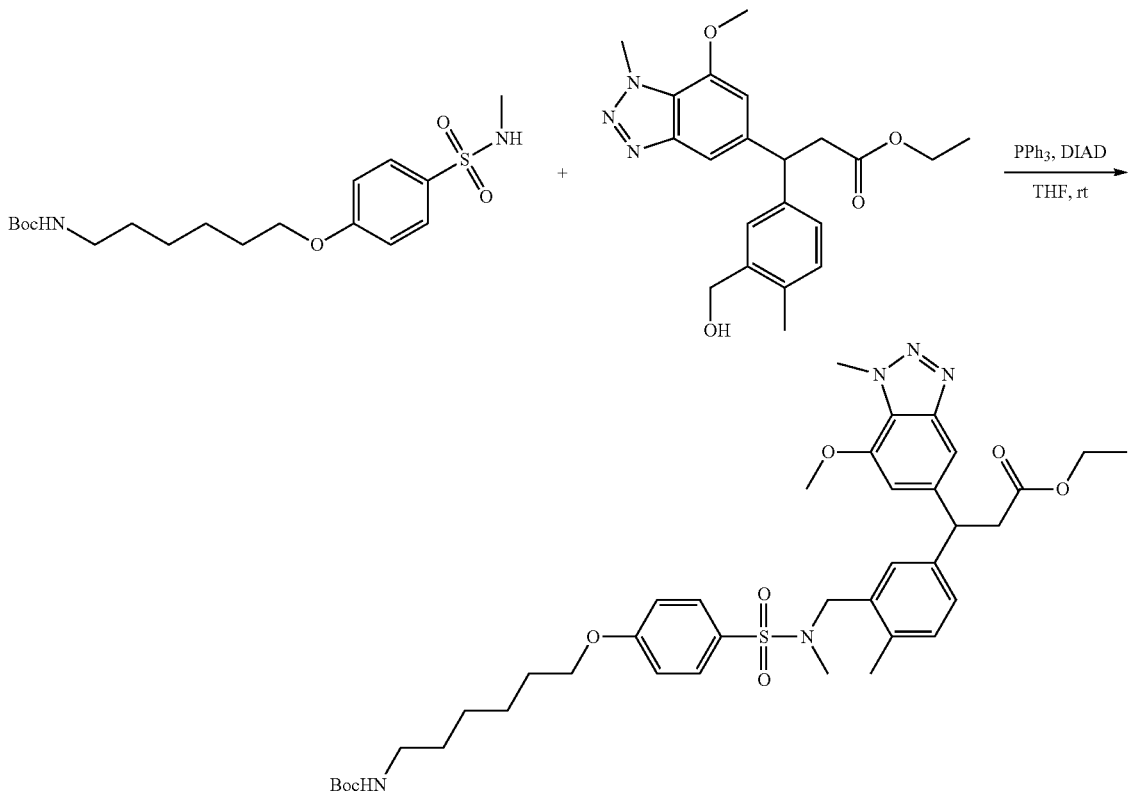

To a solution of tert-butyl 6-(4-(N-methylsulfamoyl)phenoxy)hexylcarbamate (131 mg, 0.34 mmol) and ethyl 3-(3-(hydroxymethyl)-4-methylphenyl)-3-(7-methoxy-1-methyl-1H-benzo[d][1,2,3]triazol-5-yl)propanoate (100 mg, 0.26 mmol) in THF (2 mL), diisopropyl azodicarboxylate (DIAD) (105 mg, 0.52 mmol) and PPh₃ (136 mg, 0.52 mmol) were added at room temperature. The reaction mixture was stirred for 30 mins. The mixture was evaporated under vacuum, and the residue was purified by flash chromatography to yield ethyl 3-(3-((4-(6-(tert-butoxycarbonylamino)hexyloxy)-N-methylphenylsulfonamido)methyl)-4-methylphenyl)-3-(7-methoxy-1-methyl-1H-benzo[d][1,2,3]triazol-5-yl)propanoate (27 mg, 0.036 mmol, 14%).

LC/MS m/z calculated for [M+H]⁺ 752.4, found 752.4.

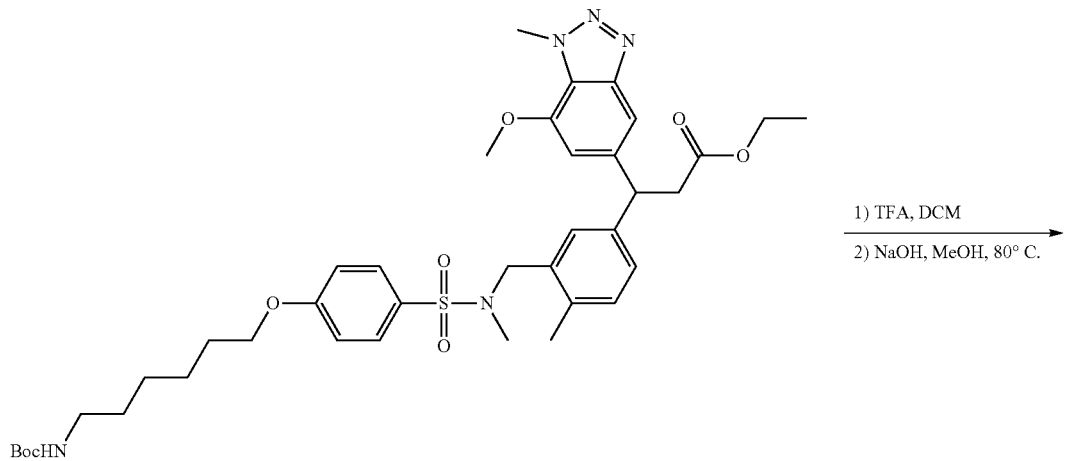

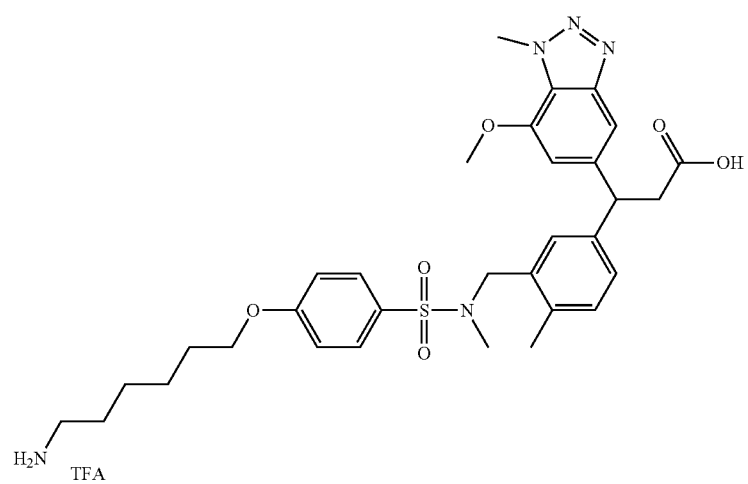

To a solution of ethyl 3-(3-((4-(6-(tert-butoxycarbonylamino)hexyloxy)-N-methylphenylsulfonamido)methyl)-4-methylphenyl)-3-(7-methoxy-1-methyl-1H-benzo[d][1,2,3]triazol-5-yl)propanoate (27 mg, 0.036 mmol) in DCM (0.5 mL), TFA (0.5 mL) was added dropwise at room temperature. After 1 hour, the mixture was evaporated under vacuum, and the residue was dissolved in MeOH (1 mL). NaOH (0.2 mL, 2N aq.) was added to the mixture at room temperature. Then the mixture was heated up to 80° C. for 30 mins. After it was allowed to cool down, the mixture was purified by HPLC to yield 3-(3-((4-(6-aminohexyloxy)-N-methylphenylsulfonamido)methyl)-4-methylphenyl)-3-(7-methoxy-1-methyl-1H-benzo[d][1,2,3]triazol-5-yl)propanoic acid (12 mg, 0.017 mmol, 46%) as a TFA salt.

LC/MS m/z calculated for $[M+H]^+$ 624.3, found 624.3.

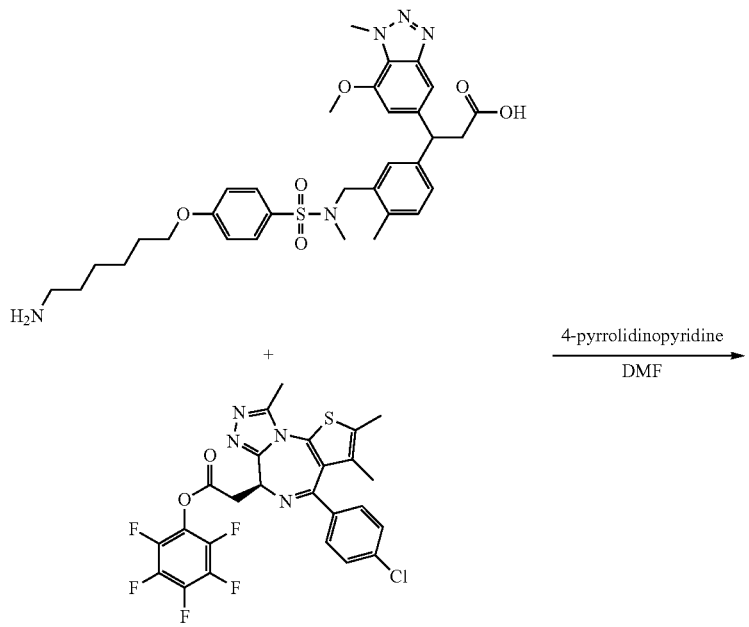

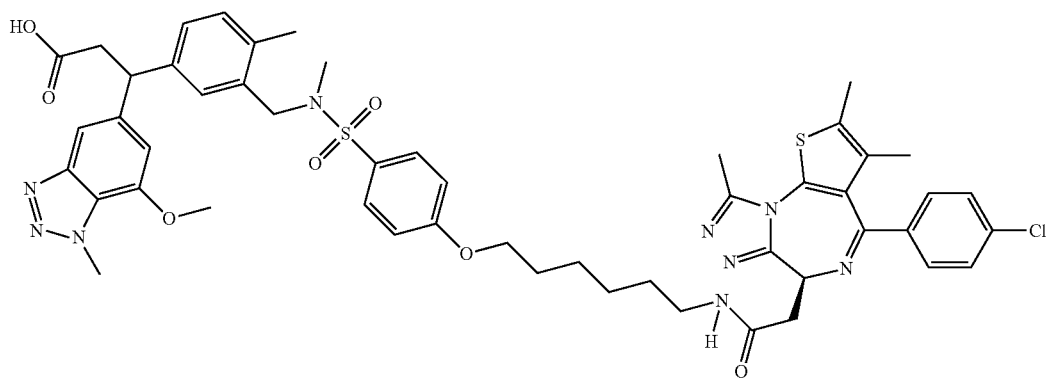

To a solution of 3-(3-((4-(6-aminohexyloxy)-N-methylphenylsulfonamido)methyl)-4-methylphenyl)-3-(7-methoxy-1-methyl-1H-benzo[d][1,2,3]triazol-5-yl)propanoic acid (12 mg, 0.017 mmol) and (S)-perfluorophenyl 2-(4-(4-chlorophenyl)-2,3,9-trimethyl-6H-thieno[3,2-f][1,2,4]triazolo[4,3-a][1,4]diazepin-6-yl)acetate (9.6 mg, 0.017 mmol) in DMF (1 mL), 4-pyrrolidinopyridine (5 mg, 0.034 mmol) was added at room temperature. After 3 hours, the mixture was purified by HPLC to yield bifunctional compound 9 (11 mg, 0.011 mmol, 63%) as a TFA salt.

LC/MS m/z calculated for [M+H]+ 1006.3, found 1006.3.

Example 2: Synthesis of 3-(3-(((R)-7-(6-(2-((S)-4-(4-chlorophenyl)-2,3,9-trimethyl-6H-thieno[3,2-f][1,2,4]triazolo[4,3-a][1,4]diazepin-6-yl)acetamido)hexyl)-4-methyl-1,1-dioxido-3,4-dihydro-2H-benzo[b][1,4,5]oxathiazepin-2-yl)methyl)-4-methylphenyl)-3-(7-methoxy-1-methyl-1H-benzo[d][1,2,3]triazol-5-yl)propanoic acid (1)

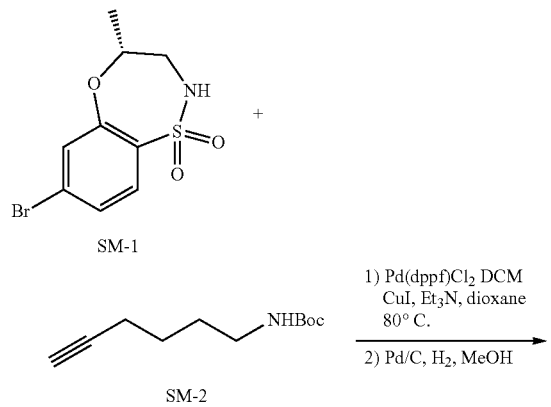

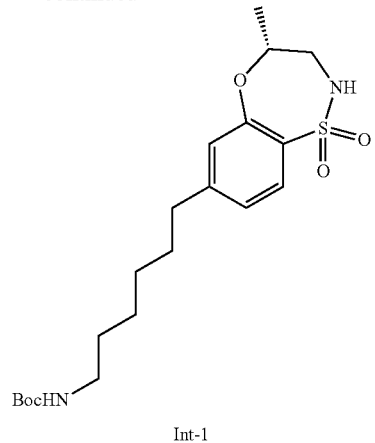

To a solution of SM-1 (50 mg, 0.17 mmol), SM-2 (67 mg, 0.34 mmol) and Et$_3$N (171 mg, 1.70 mmol) in dioxane (2 mL), CuI (13 mg, 0.068 mmol) and Pd(dppf)Cl$_2$·DCM (28 mg, 0.034 mmol) were added at room temperature under N$_2$ atmosphere. Then the reaction mixture was heated up to 80° C. for 2 hours. The mixture was filtered, and the filtrate was evaporated under vacuum. To a solution of the obtained residue in MeOH (3 mL), Pd/C (8.4 mg) was added slowly. The suspension was stirred overnight under hydrogen atmosphere. The mixture was filtered with celite to get the crude product without any further purification.

LC/MS m/z calculated for [M+H]+ 413.2, found 413.2.

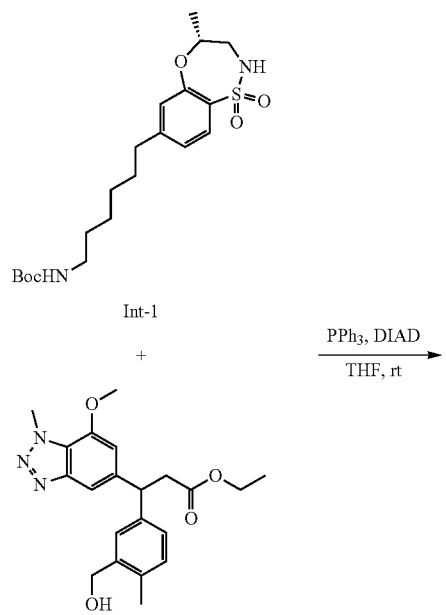

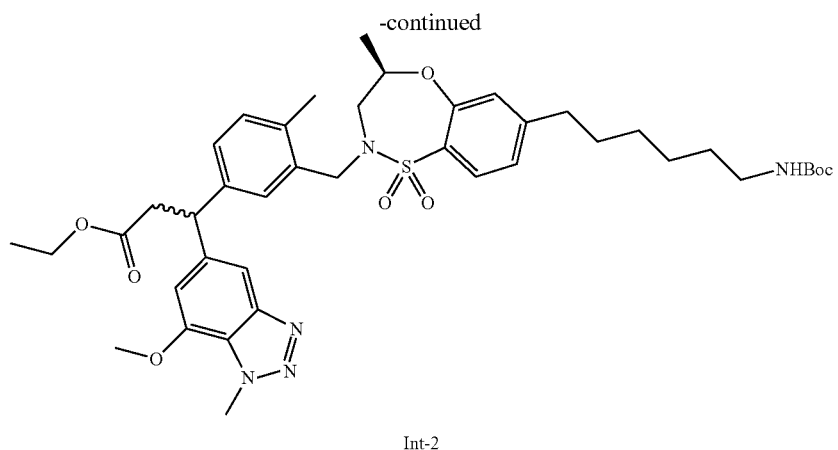

Int-2

To a solution of Int-1 (88 mg, 0.21 mmol) and ethyl 3-(3-(hydroxymethyl)-4-methylphenyl)-3-(7-methoxy-1-methyl-1H-benzo[d][1,2,3]triazol-5-yl)propanoate (82 mg, 0.21 mmol) in THF (2 mL), DIAD (85 mg, 0.42 mmol) and PPh$_3$ (110 mg, 0.42 mmol) were added at room temperature. The reaction mixture was stirred for 30 mins before evaporation under vacuum. The residue was purified by flash chromatography to yield Int-2 (100 mg, 0.13 mmol, 61%).

LC/MS m/z calculated for [M+H]$^+$ 778.4, found 778.4.

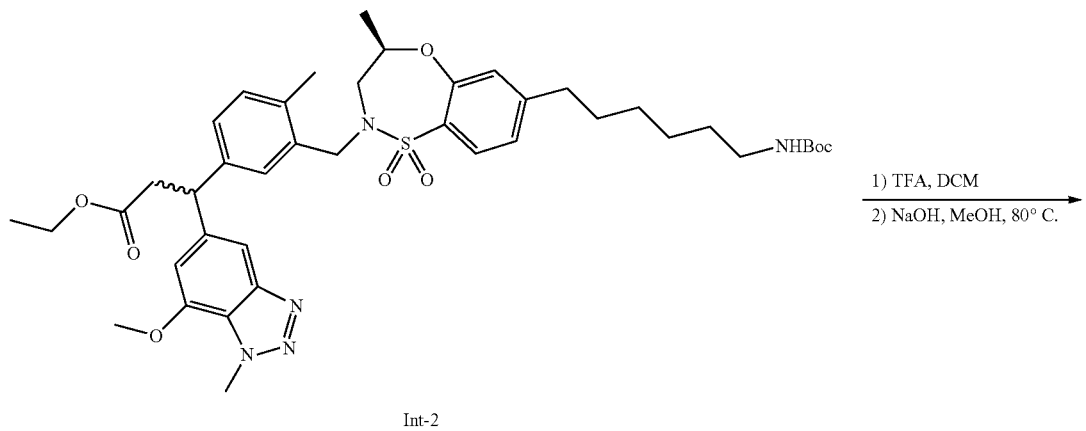

Int-2

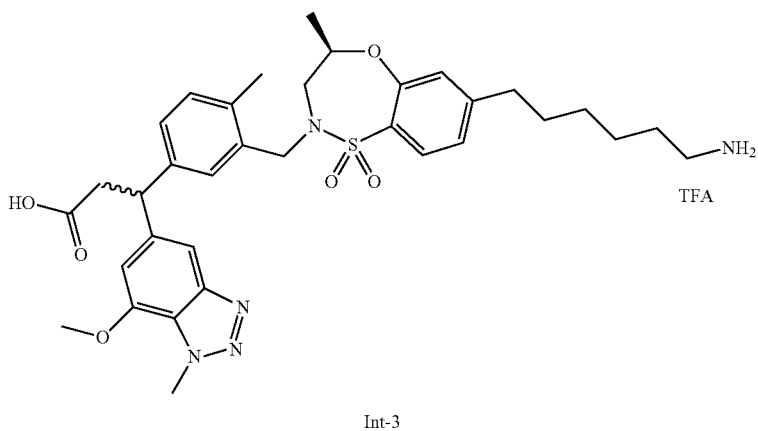

Int-3

To a solution of Int-2 (100 mg, 0.13 mmol) in DCM (2 mL), TFA (1 mL) was added dropwise at room temperature. After 1 hour, the mixture was evaporated under vacuum. To a solution of the obtained residue in MeOH (2 mL), NaOH (0.2 mL, 2N aq.) was added at room temperature. Then the mixture was heated up to 80° C. for 30 mins. After it was allowed to cool down, the mixture was purified by HPLC to yield Int-3 (67 mg, 0.10 mmol, 79%) as a TFA salt.

LC/MS m/z calculated for [M+H]$^+$ 650.3, found 650.3.

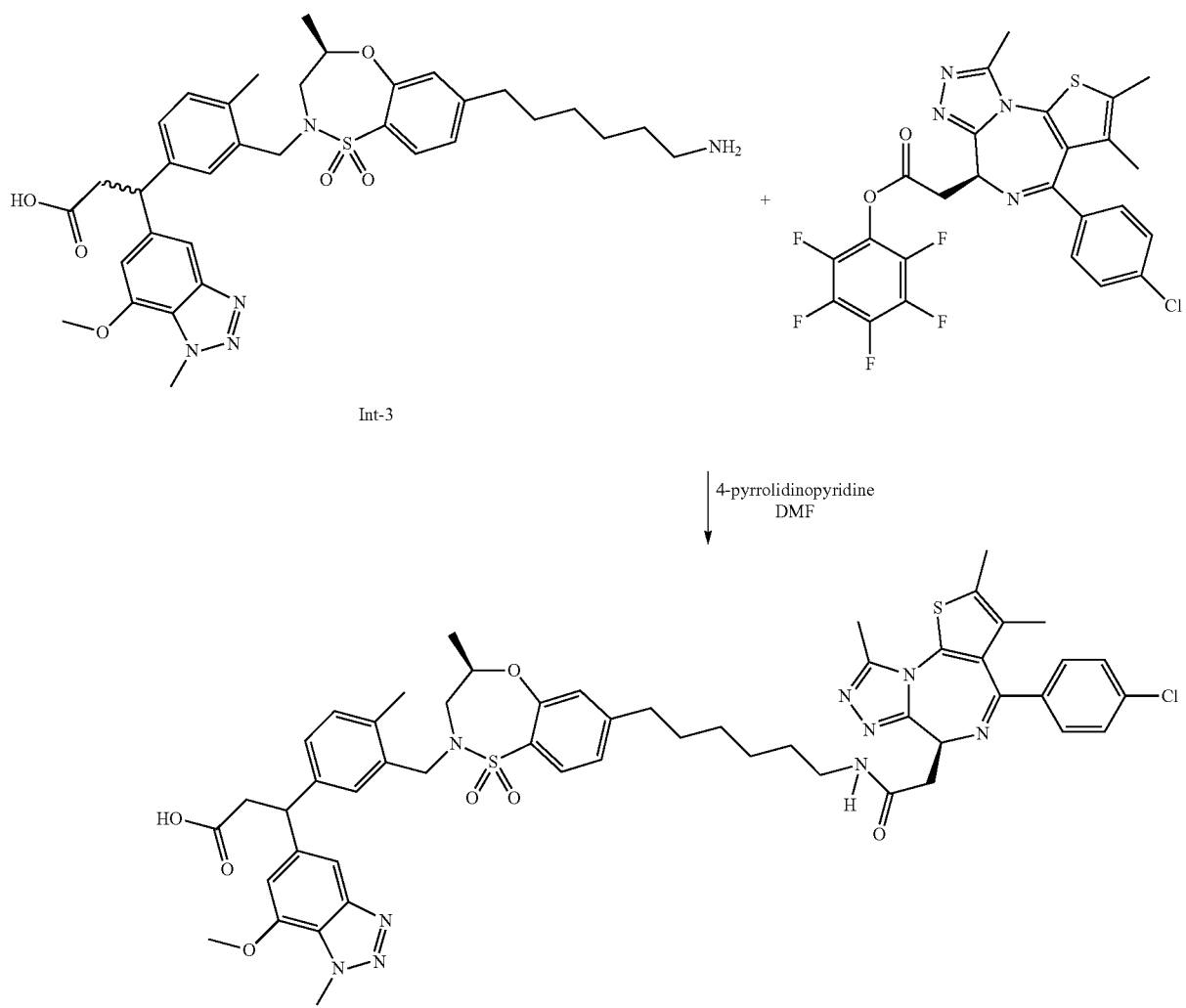

To a solution of Int-3 (24 mg, 0.031 mmol) and (S)-perfluorophenyl 2-(4-(4-chlorophenyl)-2,3,9-trimethyl-6H-thieno[3,2-f][1,2,4]triazolo[4,3-a][1,4]diazepin-6-yl)acetate (17 mg, 0.031 mmol) in DMF (2 mL), 4-pyrrolidinopyridine (9 mg, 0.062 mmol) was added at room temperature. After 3 hours, the mixture was purified by HPLC to yield bifunctional compound 1 (22 mg, 0.021 mmol, 68%) as TFA salt.

LC/MS m/z calculated for [M+H]$^+$ 1032.4, found 1032.4.

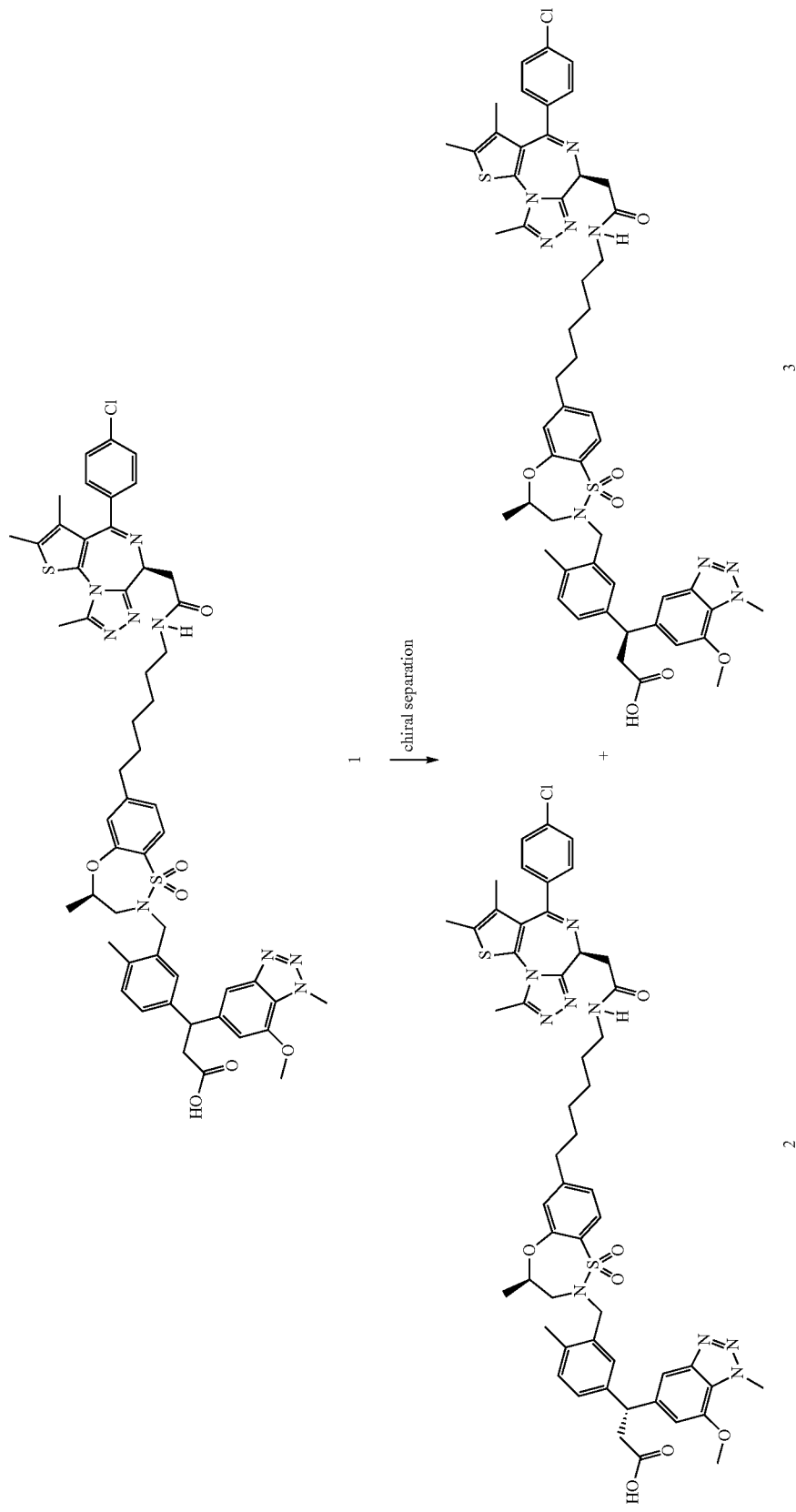

The diastereomers of bifunctional compound 1 were separated by chiral column chromatography (CHIRALPAK IA, Hexane/IPA/TFA=60/40/0.1) to yield bifunctional compound 2 (98.7% ee) and bifunctional compound 3 (95.3% ee).

LC/MS m/z calculated for [M+H]$^+$ 1032.4, found 1032.4.

Example 3: Synthesis of ethyl 3-(7-(2-((2-(2-(2-(4-(4-((5-chloro-4-((2-(isopropylsulfonyl)phenyl)amino)pyrimidin-2-yl)amino)phenyl)piperazin-1-yl)ethoxy)ethoxy)ethyl)amino)-2-oxoethoxy)-1-methyl-1H-benzo[d][1,2,3]triazol-5-yl)-3-(4-methyl-3-((4-methyl-1,1-dioxido-3,4-dihydro-2H-benzo[b][1,4,5]oxathiazepin-2-yl)methyl)phenyl)propanoate (11)

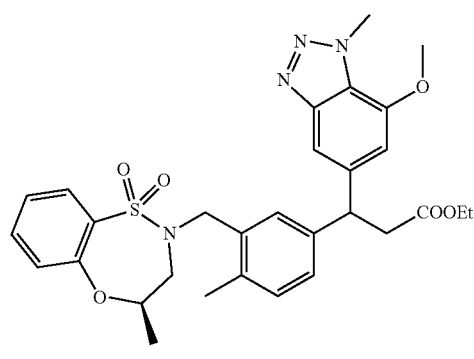

Int-4

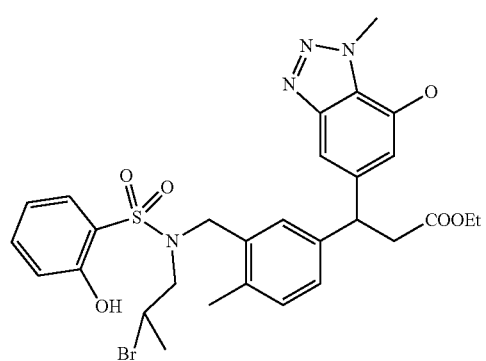

Int-5

To a solution of Int-4 (180 mg, 0.31 mmol) in DCM (2 mL), BBr$_3$ (1.56 mL, 1M in DCM, 1.56 mmol) was added dropwise at −78° C. The reaction was stirred at this temperature for 1 hour, then allowed to warm to room temperature. The mixture was stirred at room temperature for an additional 6 hours. The reaction was diluted with ethyl acetate, quenched with NaHCO$_3$ (sat. aq.), and extracted with EtOAc. The pooled organic layer was dried over MgSO$_4$, and concentrated under vacuum to yield ethyl 3-(3-((N-(2-bromopropyl)-2-hydroxyphenylsulfonamido)methyl)-4-methylphenyl)-3-(7-hydroxy-1-methyl-1H-benzo[d][1,2,3]triazol-5-yl)propanoate (Int-5) without any other purification.

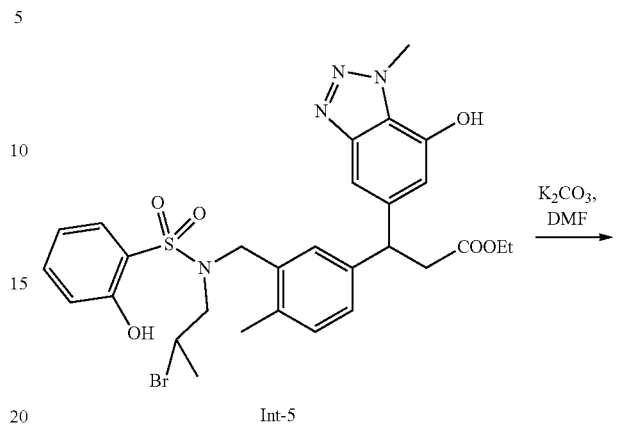

Int-5

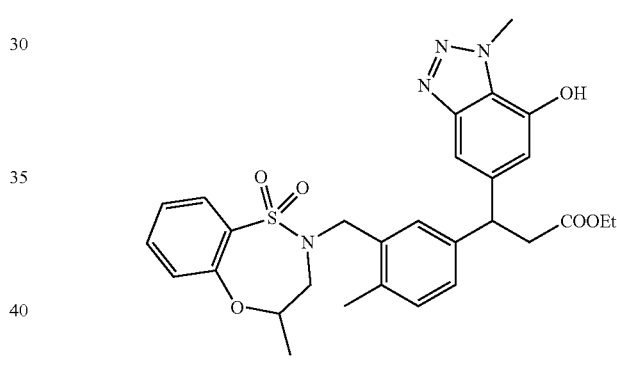

Int-6

To a solution of Int-5 (162 mg, 0.25 mmol) in DMF (3 mL), K$_2$CO$_3$ (104 mg, 0.75 mmol) was added in one portion at room temperature. The reaction was stirred at room temperature for 1 hour. The reaction was quenched with water, extracted with EtOAc, and dried with MgSO$_4$. The organic layer was concentrated under vacuum to give the crude Int-6 without any further purification.

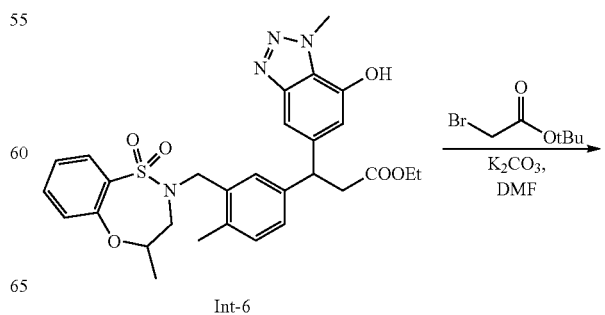

Int-6

89

-continued

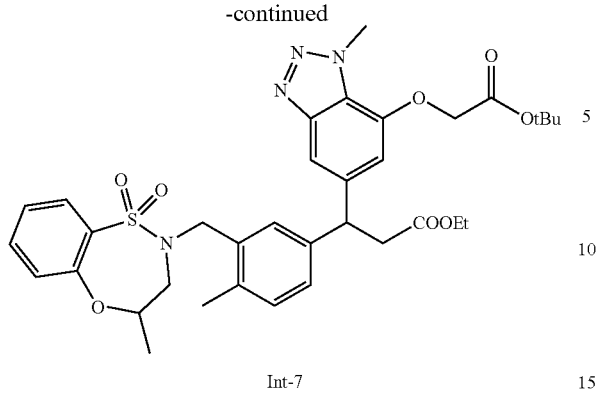

Int-7

To a solution of Int-6 (96 mg, 0.17 mmol) in DMF (1 mL), tert-butyl 2-bromoacetate (49.7 mg, 0.26 mmol) and K$_2$CO$_3$ (71.8 mg, 0.52 mmol) were added slowly at room temperature. The reaction was stirred overnight before filtration. The filtrate was concentrated under vacuum and purified by HPLC to yield intermediate Int-7 (90 mg, 0.13 mmol, 78%).

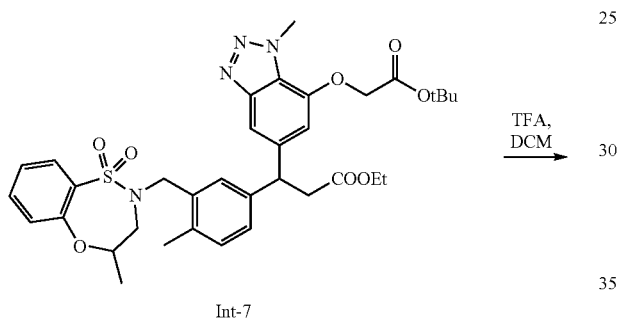

Int-7

90

-continued

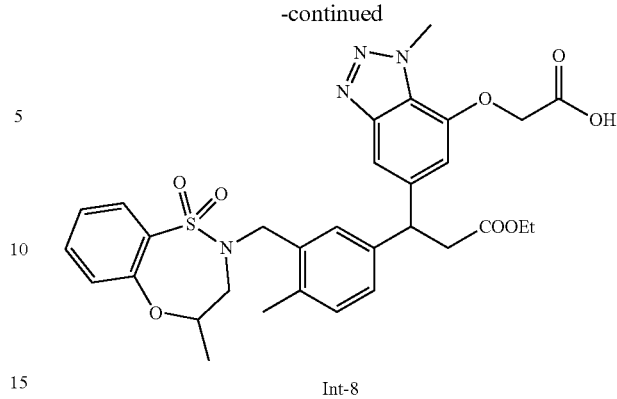

Int-8

To a solution of Int-7 (90 mg, 0.13 mmol) in DCM (1 mL), TFA (0.5 mL) was added dropwise at room temperature. The reaction was stirred for 1 hour. The solvent was removed under vacuum to yield the crude Int-8 without any further purification.

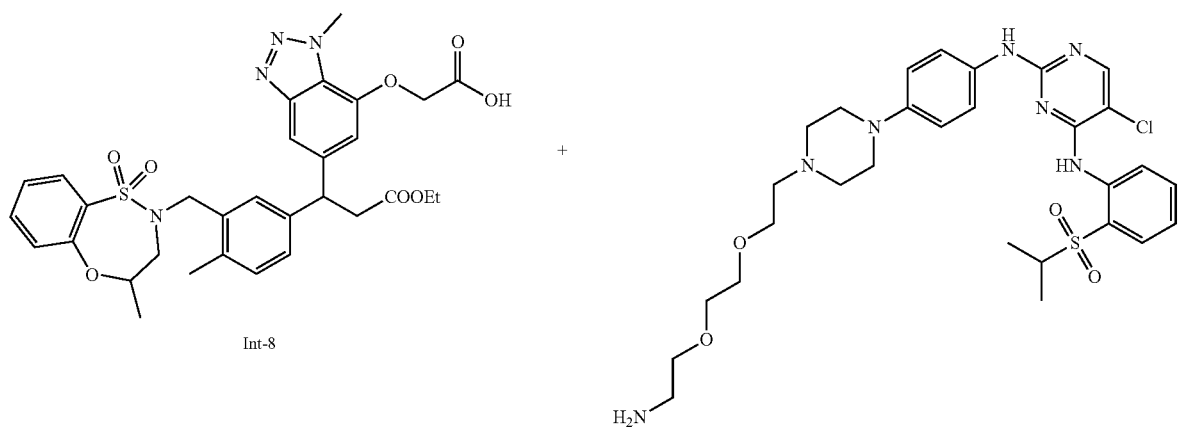

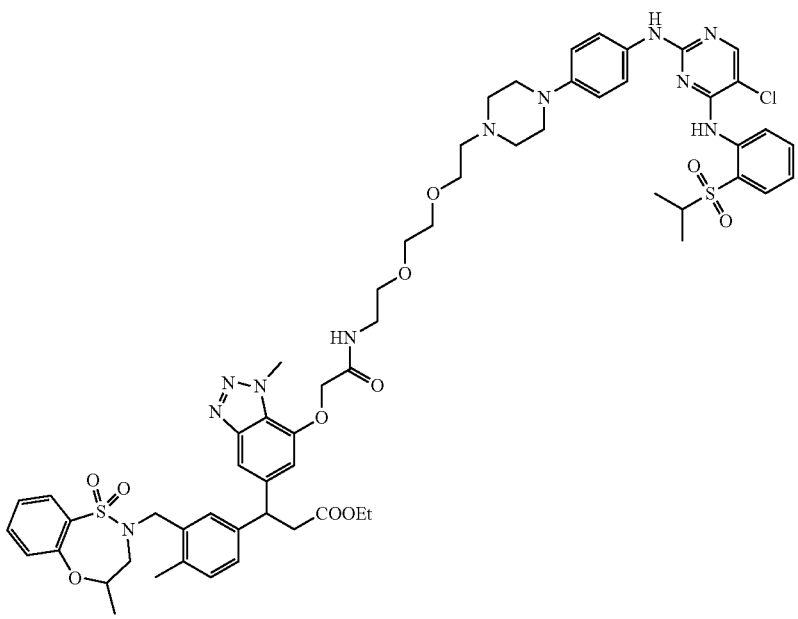

11

To a solution of Int-8 (81 mg, 0.13 mmol) and N2-(4-(4-(2-(2-(2-aminoethoxy)ethoxy)ethyl)piperazin-1-yl)phenyl)-5-chloro-N4-(2-(isopropylsulfonyl)phenyl)pyrimidine-2,4-diamine (97 mg, 0.13 mmol) in DMF (2 mL), N,N-diisopropylethylamine (DIEA) (84 mg, 0.65 mmol) and 1-[Bis(dimethylamino)methylene]-1H-1,2,3-triazolo[4,5-b]pyridinium 3-oxide hexafluorophosphate (HATU) (99 mg, 0.26 mmol) were added at room temperature. The reaction was stirred for 10 mins before purification by HPLC without any reaction workup to yield bifunctional compound 11 (122 mg, 0.10 mmol, 79%).

LC/MS m/z calculated for [M+H]$^+$ 1222.5, found 1222.5.

Example 4: Synthesis of 3-(7-(2-((2-(2-(2-(4-(4-((5-chloro-4-((2-(isopropylsulfonyl)phenyl)amino)pyrimidin-2-yl)amino)phenyl)piperazin-1-yl)ethoxy)ethoxy)ethyl)amino)-2-oxoethoxy)-1-methyl-1H-benzo[d][1,2,3]triazol-5-yl)-3-(4-methyl-3-((4-methyl-1,1-dioxido-3,4-dihydro-2H-benzo[b][1,4,5]oxathiazepin-2-yl)methyl)phenyl)propanoic acid (10)
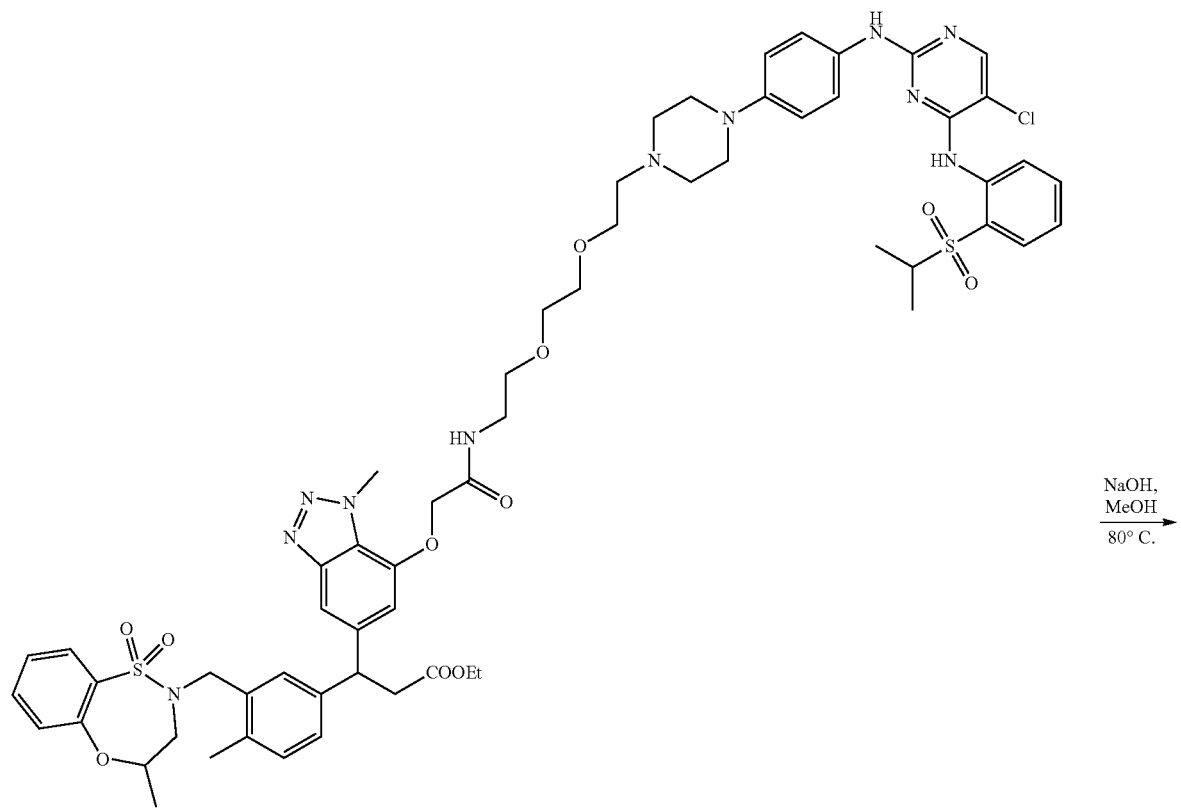

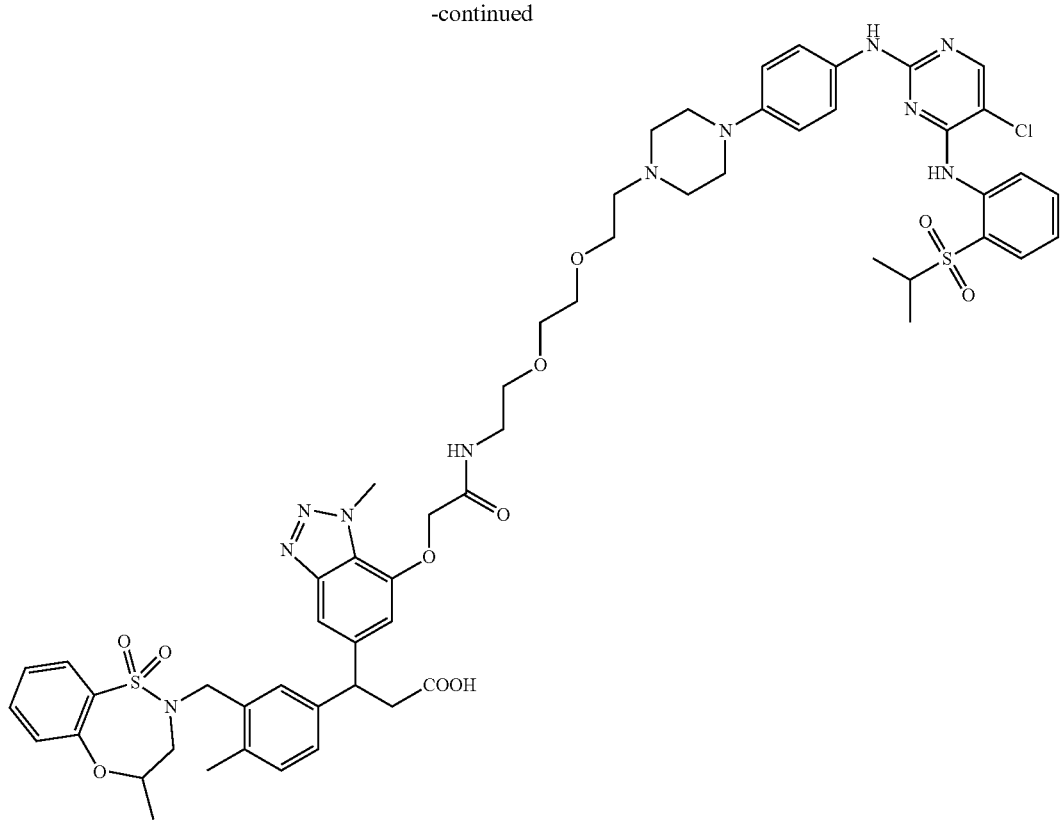

10

To a solution of bifunctional compound 11 (20 mg, 0.016 mmol) in MeOH (0.5 mL), NaOH (0.04 mL, 2M) was added at room temperature. The mixture was heated to 80° C. for 1 hour. The reaction was purified by HPLC without any reaction workup to yield bifunctional compound 10 (11 mg, 0.0092 mmol, 57%).

LC/MS m/z calculated for [M+H]$^+$ 1194.4, found 1194.4.

Example 5: Synthesis of 3-(7-(2-((6-(4-(4-((5-chloro-4-((2-(isopropylsulfonyl)phenyl)amino)pyrimidin-2-yl)amino)phenyl)piperazin-1-yl)hexyl)amino)-2-oxoethoxy)-1-methyl-1H-benzo[d][1,2,3]triazol-5-yl)-3-(4-methyl-3-((4-methyl-1,1-dioxido-3,4-dihydro-2H-benzo[b][1,4,5]oxathiazepin-2-yl)methyl)phenyl)propanoic acid (13)

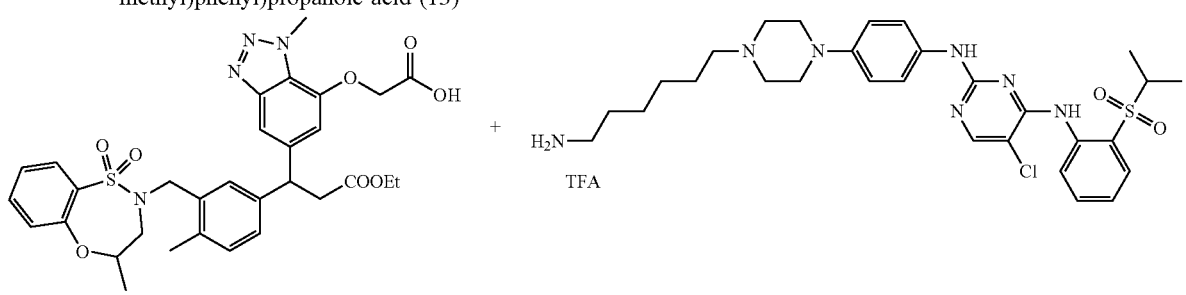

HATU•DIEA
DMF

-continued

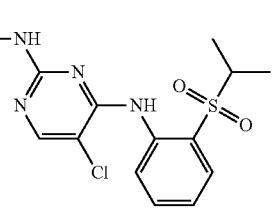
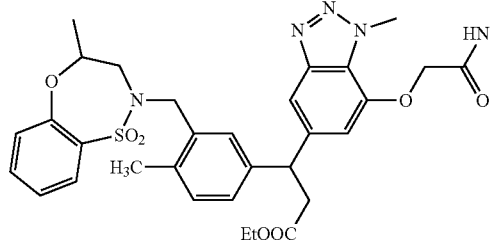

Int-9

To a solution of Int-8 (16 mg, 0.026 mmol) and N2-(4-(4-(6-aminohexyl)piperazin-1-yl)phenyl)-5-chloro-N4-(2-(isopropylsulfonyl)phenyl)pyrimidine-2,4-diamine TFA salt (21 mg, 0.026 mmol) in DMF (1 mL), DIEA (17 mg, 0.13 mmol) and HATU (20 mg, 0.052 mmol) were added at room temperature. The mixture was stirred for 10 mins. The reaction was purified by HPLC without any reaction workup to yield Int-9 (22 mg, 0.018 mmol, 68%).

LC/MS m/z calculated for [M+H]$^+$ 1190.5, found 1190.5.

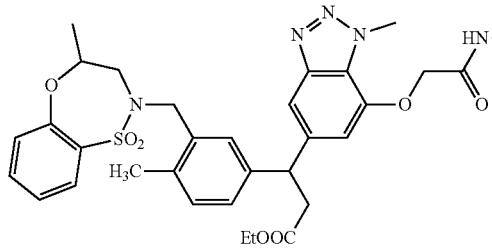

Int-9

NaOH, MeOH
80° C.

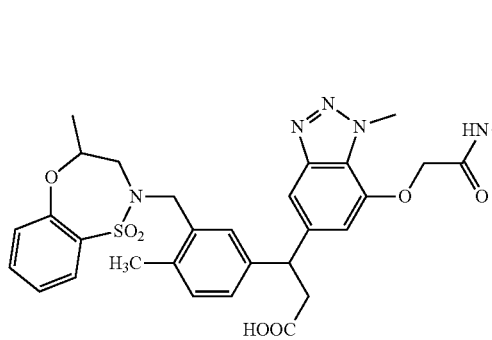

To a solution of Int-9 (22 mg, 0.018 mmol) in MeOH (0.5 mL), NaOH (0.046 mL, 2M) was added at room temperature. The mixture was heated to 80° C. for 1 hour. The reaction was purified by HPLC without any reaction workup to yield bifunctional compound 13 (10 mg, 0.0086 mmol, 48%).

LC/MS m/z calculated for [M+H]$^+$ 1162.4, found 1162.4.

Example 6: Synthesis of 3-(3-(((R)-7-(6-(2-(4-(4-((5-chloro-4-((2-(isopropylsulfonyl)phenyl)amino)pyrimidin-2-yl)amino)phenyl)piperazin-1-yl)acetamido)hexyl)-4-methyl-1,1-dioxido-3,4-dihydro-2H-benzo[b][1,4,5]oxathiazepin-2-yl)methyl)-4-methylphenyl)-3-(7-methoxy-1-methyl-1H-benzo[d][1,2,3]triazol-5-yl)propanoic acid (12)

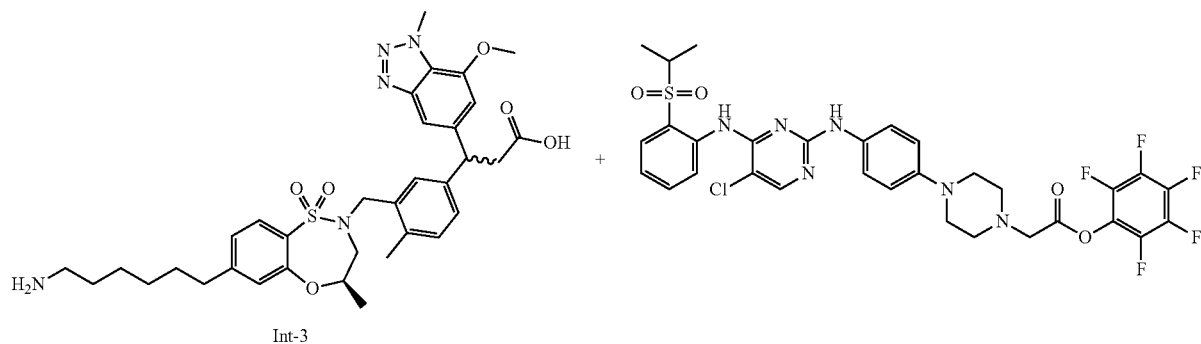

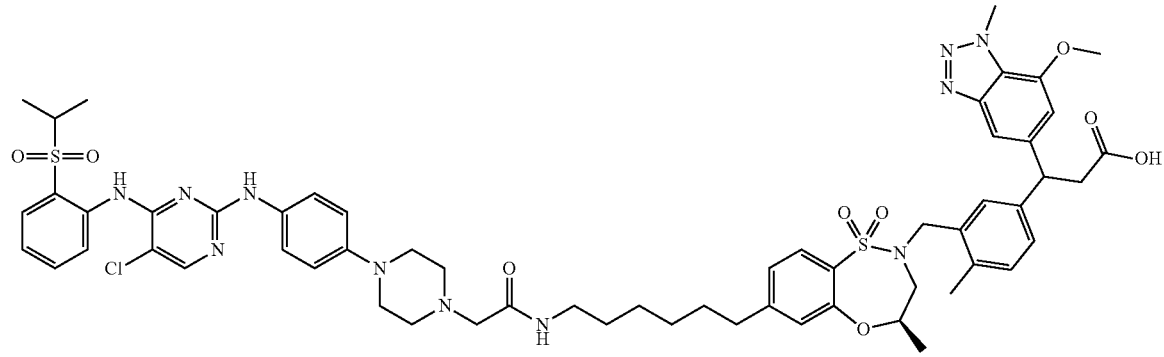

To a solution of Int-3 (3 mg, 0.005 mmol) and perfluorophenyl 2-(4-(4-(5-chloro-4-(2-(isopropylsulfonyl)phenylamino)pyrimidin-2-ylamino)phenyl)piperazin-1-yl)acetate (3.7 mg, 0.005 mmol) in DMF (0.5 mL), 4-pyrrolidinopyridine (1.5 mg, 0.010 mmol) was added at room temperature. After 2 hours, the mixture was purified by HPLC to yield bifunctional compound 12 (4 mg, 0.003 mmol, 60%).

LC/MS m/z calculated for [M+H]$^+$ 1176.4, found 1176.4.

Example 7: Synthesis of 3-(7-(2-(6-(4-(4-(5-chloro-4-(2-(isopropylsulfonyl)phenylamino)pyrimidin-2-ylamino)phenyl)piperazin-1-yl)hexylamino)-2-oxoethoxy)-1-methyl-1H-benzo[d][1,2,3]triazol-5-yl)-3-(4-methyl-3-((N-methylphenylsulfonamido)methyl)phenyl)propanoic acid (15)

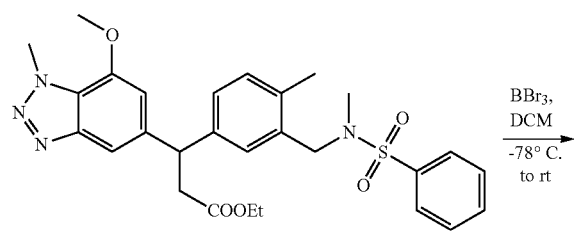

To a solution of ethyl 3-(7-methoxy-1-methyl-1H-benzo[d][1,2,3]triazol-5-yl)-3-(4-methyl-3-((N-methylphenylsulfonamido)methyl)phenyl)propanoate (230 mg, 0.43 mmol) in DCM (3 mL), BBr$_3$ (4.3 mL, 1M in DCM, 4.3 mmol) was added dropwise at −78° C. The reaction was stirred at this temperature for 1 hour and then allowed to warm to room temperature slowly. The mixture was stirred at room temperature for an additional 6 hours. The reaction was diluted with EtOAc and quenched with NaHCO$_3$ (sat. aq.). The mixture was extracted with EtOAc and dried over MgSO$_4$. The organic layer was concentrated under vacuum to yield ethyl 3-(7-hydroxy-1-methyl-1H-benzo[d][1,2,3]triazol-5-yl)-3-(4-methyl-3-((N-methylphenylsulfonamido)methyl)phenyl)propanoate as yellow oil without any further purification.

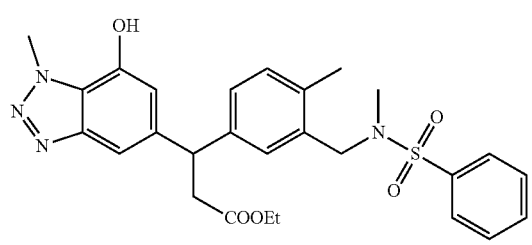

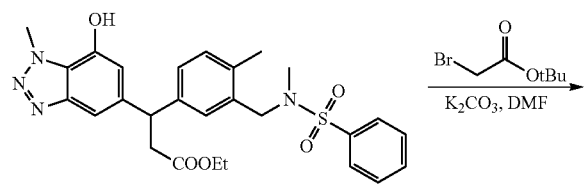

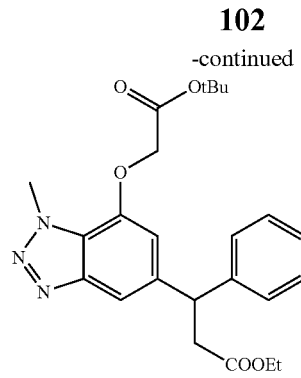

To a suspension of ethyl 3-(7-hydroxy-1-methyl-1H-benzo[d][1,2,3]triazol-5-yl)-3-(4-methyl-3-((N-methylphenylsulfonamido)methyl)phenyl)propanoate (24 mg, 0.046 mmol) and K$_2$CO$_3$ (19 mg, 0.138 mmol) in DMF (1 mL), tert-butyl 2-bromoacetate (10 μL, 0.69 mmol) was added dropwise at room temperature. The reaction was stirred at room temperature for 1 hour. The reaction was quenched with water, extracted with EtOAc, and dried over MgSO$_4$. The organic layer was concentrated under vacuum to get the crude intermediate ethyl 3-(7-(2-tert-butoxy-2-oxoethoxy)-1-methyl-1H-benzo[d][1,2,3]triazol-5-yl)-3-(4-methyl-3-((N-methylphenylsulfonamido)methyl)phenyl)propanoate without any further purification.

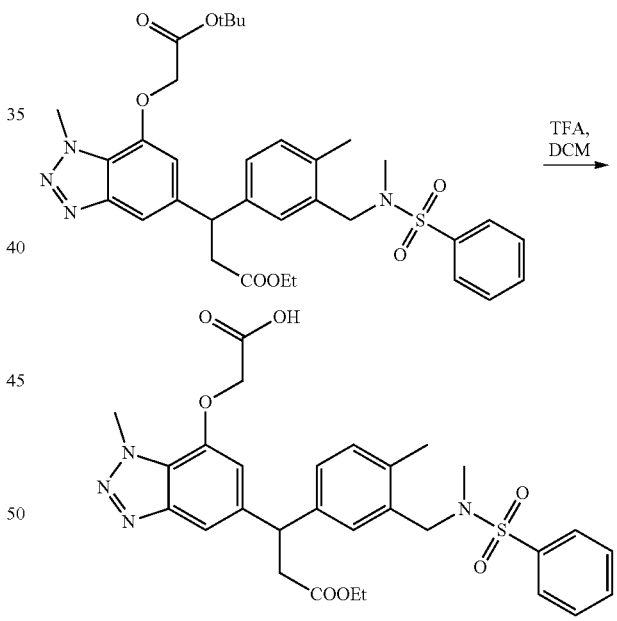

To a solution of ethyl 3-(7-(2-tert-butoxy-2-oxoethoxy)-1-methyl-1H-benzo[d][1,2,3]triazol-5-yl)-3-(4-methyl-3-((N-methylphenylsulfonamido)methyl)phenyl)propanoate (40 mg, 0.063 mmol) in DCM (1 mL), TFA (0.5 mL) was added dropwise at room temperature. The reaction was stirred for 1 hour. The solvent was removed under vacuum to yield the crude 2-(5-(3-ethoxy-1-(4-methyl-3-((N-methylphenylsulfonamido)methyl)phenyl)-3-oxopropyl)-1-methyl-1H-benzo[d][1,2,3]triazol-7-yloxy)acetic acid without any further purification.

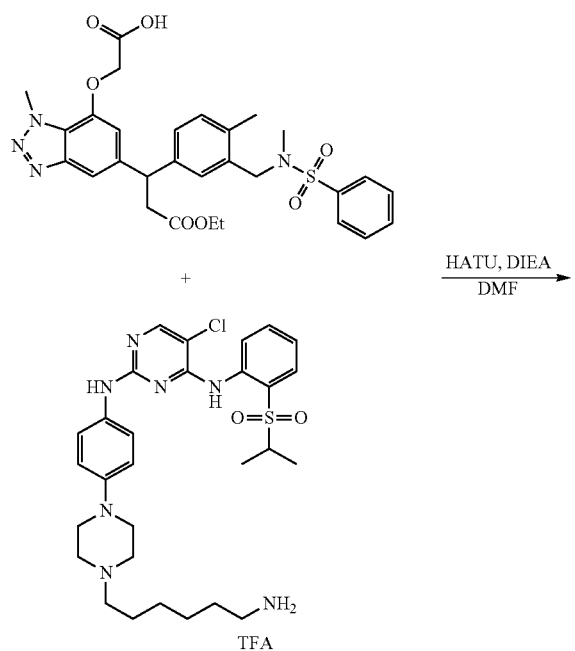

HATU, DIEA
―――――――→
DMF

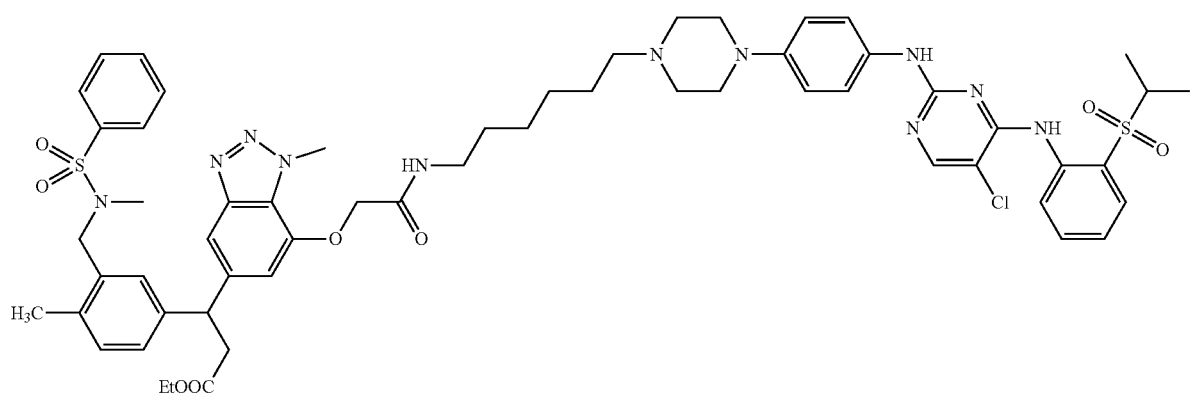

To a solution of 2-(5-(3-ethoxy-1-(4-methyl-3-((N-methylphenylsulfonamido)methyl)phenyl)-3-oxopropyl)-1-methyl-1H-benzo[d][1,2,3]triazol-7-yloxy)acetic acid (20 mg, 0.034 mmol) and N2-(4-(4-(6-aminohexyl)piperazin-1-yl)phenyl)-5-chloro-N4-(2-(isopropylsulfonyl)phenyl)pyrimidine-2,4-diamine TFA salt (25 mg, 0.034 mmol) in DMF (1 mL), DIEA (22 mg, 0.17 mmol) and HATU (26 mg, 0.068 mmol) were added at room temperature. The reaction was stirred for 10 mins. The reaction mixture was purified by HPLC without any workup to yield ethyl 3-(7-(2-(6-(4-(4-(5-chloro-4-(2-(isopropylsulfonyl)phenylamino)pyrimidin-2-ylamino)phenyl)piperazin-1-yl)hexylamino)-2-oxoethoxy)-1-methyl-1H-benzo[d][1,2,3]triazol-5-yl)-3-(4-methyl-3-((N-methylphenylsulfonamido)methyl)phenyl)propanoate (25 mg, 0.022 mmol, 64%).

LC/MS m/z calculated for [M+H]$^+$ 1148.4, found 1148.4.

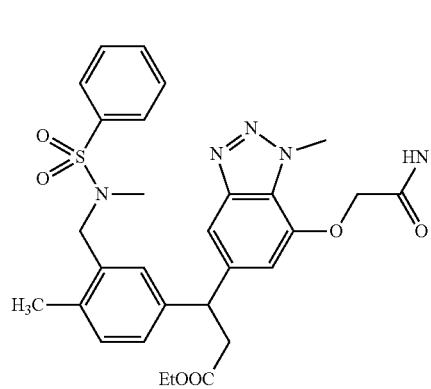
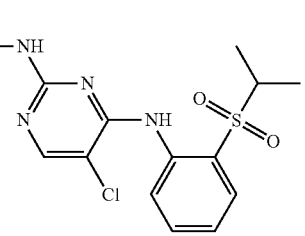

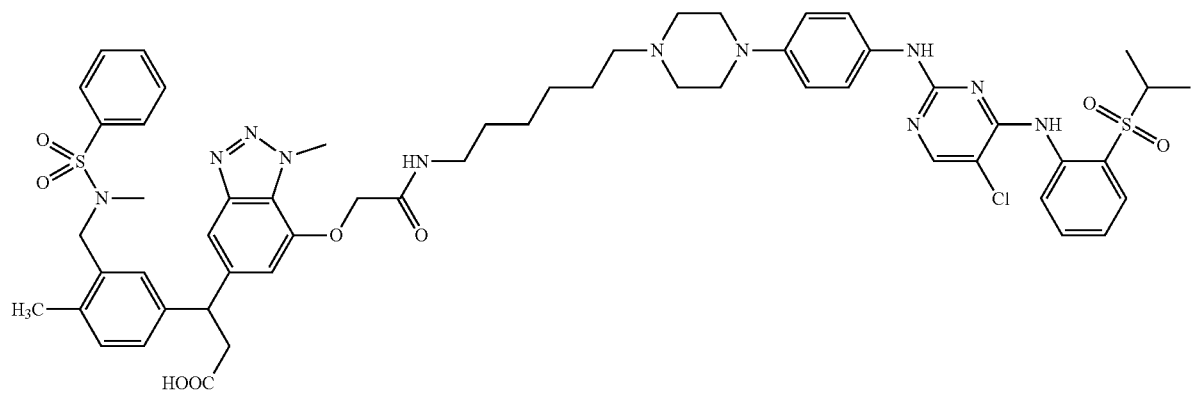

15

To a solution of ethyl 3-(7-(2-(6-(4-(4-(5-chloro-4-(2-(isopropylsulfonyl)phenylamino)pyrimidin-2-ylamino)phenyl)piperazin-1-yl)hexylamino)-2-oxoethoxy)-1-methyl-1H-benzo[d][1,2,3]triazol-5-yl)-3-(4-methyl-3-((N-methylphenylsulfonamido)methyl)phenyl)propanoate (25 mg, 0.022 mmol) in MeOH (0.5 mL), NaOH (0.022 mL, 2M) was added at room temperature. The reaction was heated to 80° C. for 1 hour. The reaction mixture was purified by HPLC without any workup to yield bifunctional compound 15 (12 mg, 0.011 mmol, 50%).

LC/MS m/z calculated for [M+H]$^+$ 1120.4, found 1120.4.

Example 8: Synthesis of 3-(3-((4-(6-(((6S)-4-(4-chlorophenyl)-6-(2-methoxy-2-oxoethyl)-3,9-dimethyl-6H-thieno[3,2-f][1,2,4]triazolo[4,3-a][1,4]diazepine-2-carboxamido)hexyloxy)-N-methylphenylsulfonamido)methyl)-4-methylphenyl)-3-(7-methoxy-1-methyl-1H-benzo[d][1,2,3]triazol-5-yl)propanoic acid (4)

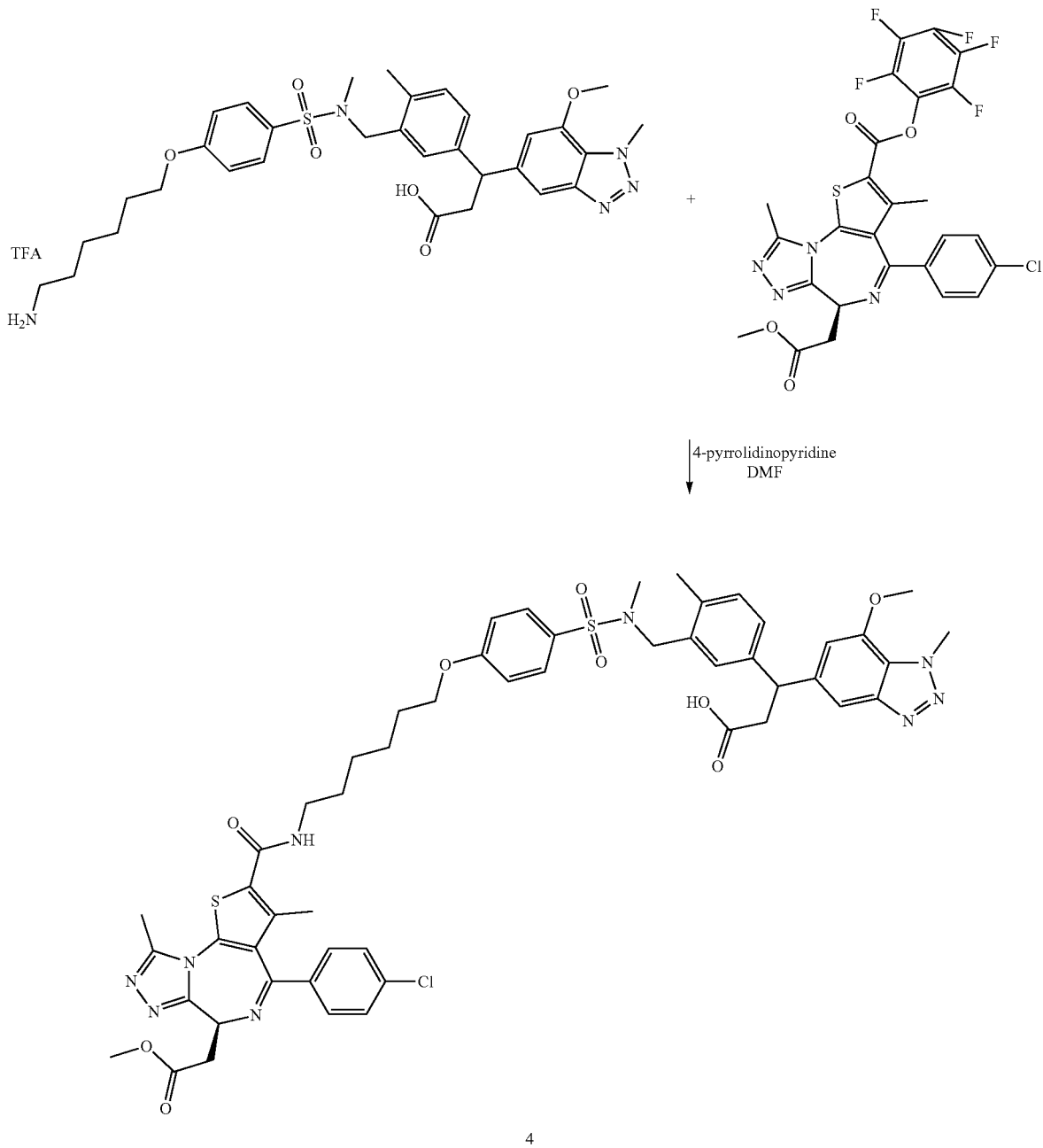

4

To a solution of 3-(3-((4-(6-aminohexyloxy)-N-methylphenylsulfonamido)methyl)-4-methylphenyl)-3-(7-methoxy-1-methyl-1H-benzo[d][1,2,3]triazol-5-yl)propanoic acid TFA salt (8 mg, 0.011 mmol) and (6S)-perfluorophenyl 4-(4-chlorophenyl)-6-(2-methoxy-2-oxoethyl)-3,9-dimethyl-6H-thieno[3,2-f][1,2,4]triazolo[4,3-a][1,4]diazepine-2-carboxylate (6.8 mg, 0.011 mmol) in DMF (1 mL), 4-pyrrolidinopyridine (3.3 mg, 0.022 mmol) was added at room temperature. After 3 hours, the mixture was purified by HPLC to yield bifunctional compound 4 (8.4 mg, 0.008 mmol, 73%).

LC/MS m/z calculated for [M+H]$^+$ 1050.3, found 1050.3.

Example 9: Synthesis of 3-(3-((4-(3-(((6S)-4-(4-chlorophenyl)-6-(2-methoxy-2-oxoethyl)-3,9-dimethyl-6H-thieno[3,2-f][1,2,4]triazolo[4,3-a][1,4]diazepine-2-carboxamido)propoxy)-N-methylphenylsulfonamido)methyl)-4-methylphenyl)-3-(7-methoxy-1-methyl-1H-benzo[d][1,2,3]triazol-5-yl)propanoic acid (6)

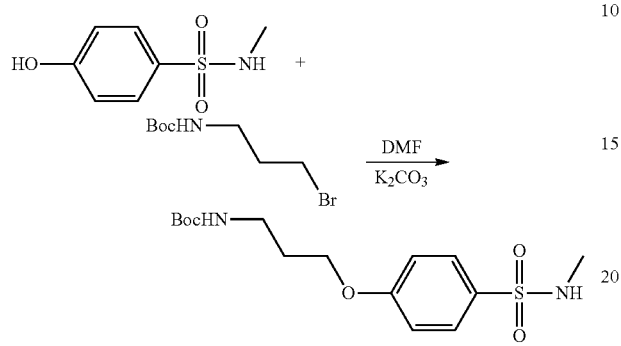

To a solution 4-hydroxy-N-methylbenzenesulfonamide (50 mg, 0.27 mmol) and tert-butyl 3-bromopropylcarbamate (64 mg, 0.27 mmol) in DMF (2 mL), K₂CO₃ (75 mg, 0.54 mmol) was added at room temperature. The mixture was stirred overnight. The reaction was filtered and the filtrate was concentrated under vacuum. The residue was purified by flash chromatography to yield tert-butyl 3-(4-(N-methylsulfamoyl)phenoxy)propylcarbamate (81 mg, 0.24 mmol, 87%).

LC/MS m/z calculated for [M+H]⁺ 345.1, found 345.1.

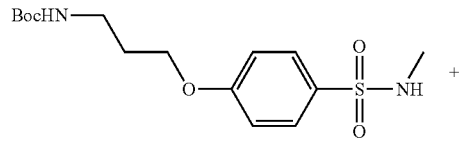

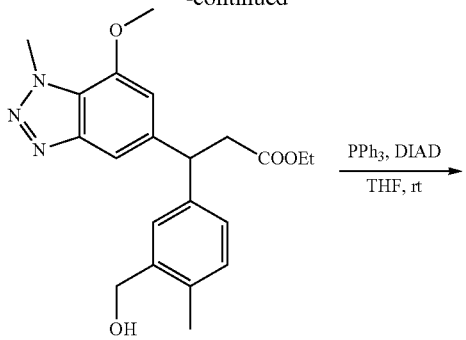

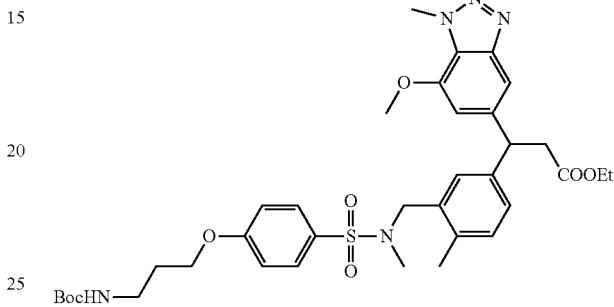

To a solution of tert-butyl 3-(4-(N-methylsulfamoyl)phenoxy)propylcarbamate (81 mg, 0.24 mmol) and ethyl 3-(3-(hydroxymethyl)-4-methylphenyl)-3-(7-methoxy-1-methyl-1H-benzo[d][1,2,3]triazol-5-yl)propanoate (90 mg, 0.24 mmol) in THF (2 mL), DIAD (97 mg, 0.48 mmol) and PPh₃ (126 mg, 0.48 mmol) were added at room temperature. The reaction mixture was stirred for 30 mins. The mixture was concentrated under vacuum and the residue was purified by flash chromatography to yield ethyl 3-(3-((4-(3-(tert-butoxycarbonylamino)propoxy)-N-methylphenylsulfonamido)methyl)-4-methylphenyl)-3-(7-methoxy-1-methyl-1H-benzo[d][1,2,3]triazol-5-yl)propanoate (97 mg, 0.14 mmol, 57%).

LC/MS m/z calculated for [M+H]⁺ 710.3, found 710.3.

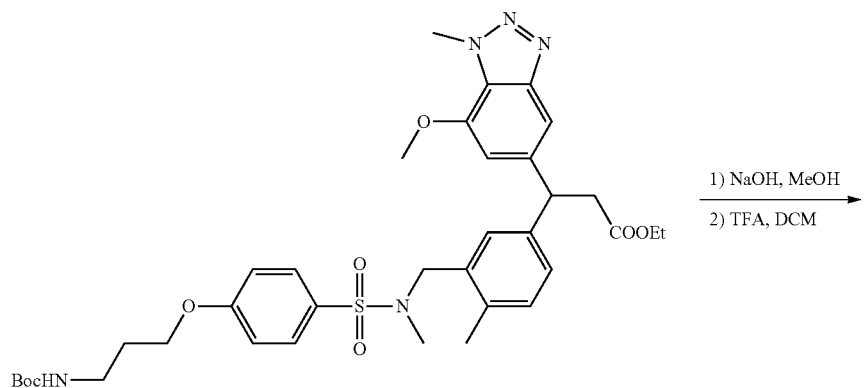

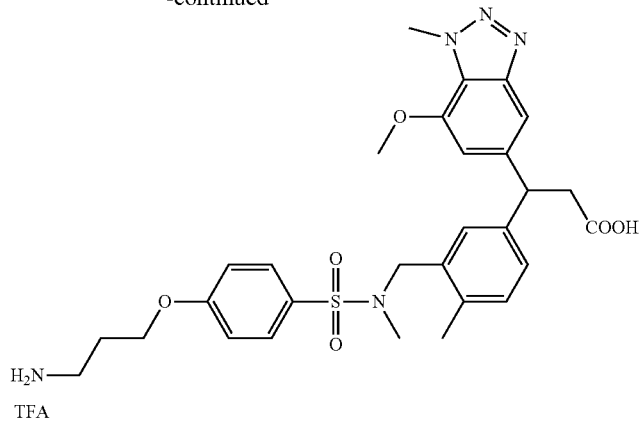

To a solution of ethyl 3-(3-((4-(3-(tert-butoxycarbonylamino)propoxy)-N-methylphenylsulfonamido)methyl)-4-methylphenyl)-3-(7-methoxy-1-methyl-1H-benzo[d][1,2,3]triazol-5-yl)propanoate (97 mg, 0.14 mmol) in MeOH (2 mL), NaOH (0.14 mL, 2M) was added at room temperature. The reaction was heated at 80° C. for 30 mins. The reaction mixture was concentrated under vacuum to yield the crude product without any further purification. The residue was dissolved in DCM (2 mL) and TFA (1 mL) was added dropwise at room temperature. After 1 hour, the reaction was concentrated under vacuum. The residue was purified by HPLC to yield 3-(3-((4-(3-aminopropoxy)-N-methylphenylsulfonamido)methyl)-4-methylphenyl)-3-(7-methoxy-1-methyl-1H-benzo[d][1,2,3]triazol-5-yl)propanoic acid (49 mg, 0.084 mmol, 60%) as a TFA salt.

LC/MS m/z calculated for [M+H]+ 582.2, found 582.2.

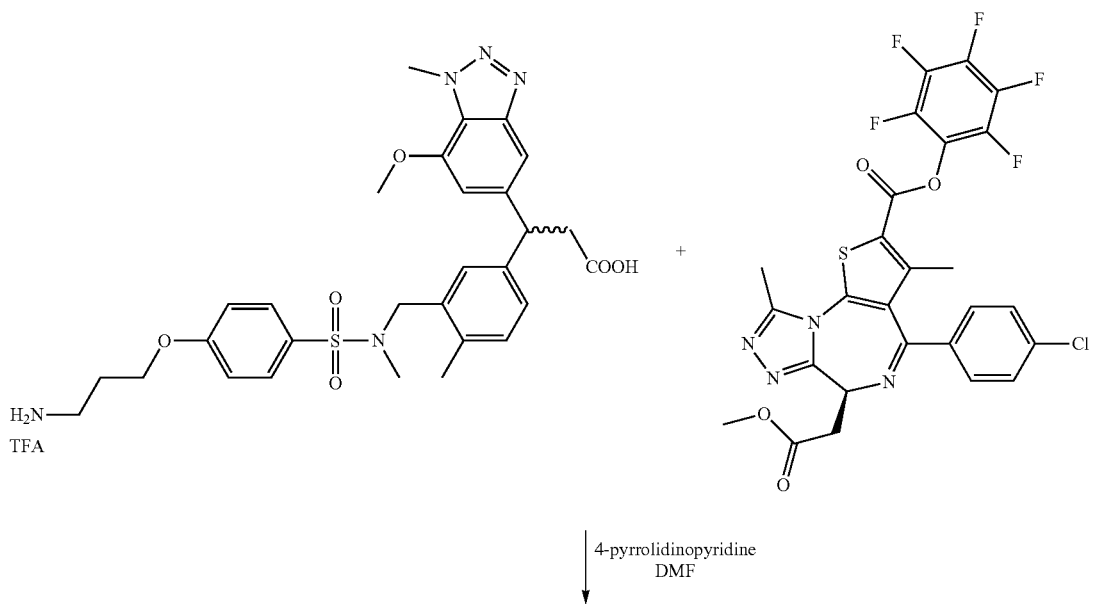

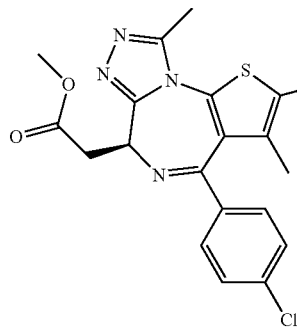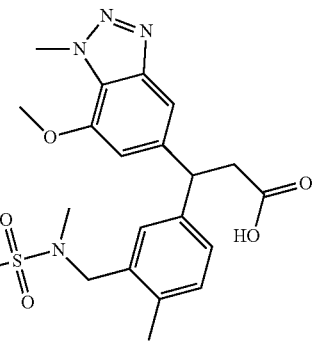

6

To a solution of 3-(3-((4-(3-aminopropoxy)-N-methylphenylsulfonamido)methyl)-4-methylphenyl)-3-(7-methoxy-1-methyl-1H-benzo[d][1,2,3]triazol-5-yl)propanoic acid TFA salt (8 mg, 0.010 mmol) and (6S)-perfluorophenyl 4-(4-chlorophenyl)-6-(2-methoxy-2-oxoethyl)-3,9-dimethyl-6H-thieno[3,2-f][1,2,4]triazolo[4,3-a][1,4]diazepine-2-carboxylate (6.1 mg, 0.010 mmol) in DMF (1 mL), 4-pyrrolidinopyridine (3 mg, 0.020 mmol) was added at room temperature. After 3 hours, the mixture was purified by HPLC to yield bifunctional compound 6 (8 mg, 0.008 mmol, 80%).

LC/MS m/z calculated for [M+H]$^+$ 1008.3, found 1008.3.

Example 10: Synthesis of 3-(3-((4-(3-(2-(((6S)-4-(4-chlorophenyl)-2,3,9-trimethyl-6H-thieno[3,2-f][1,2,4]triazolo[4,3-a][1,4]diazepin-6-yl)acetamido)propoxy)-N-methylphenylsulfonamido)methyl)-4-methylphenyl)-3-(7-methoxy-1-methyl-1H-benzo[d][1,2,3]triazol-5-yl)propanoic acid (5)

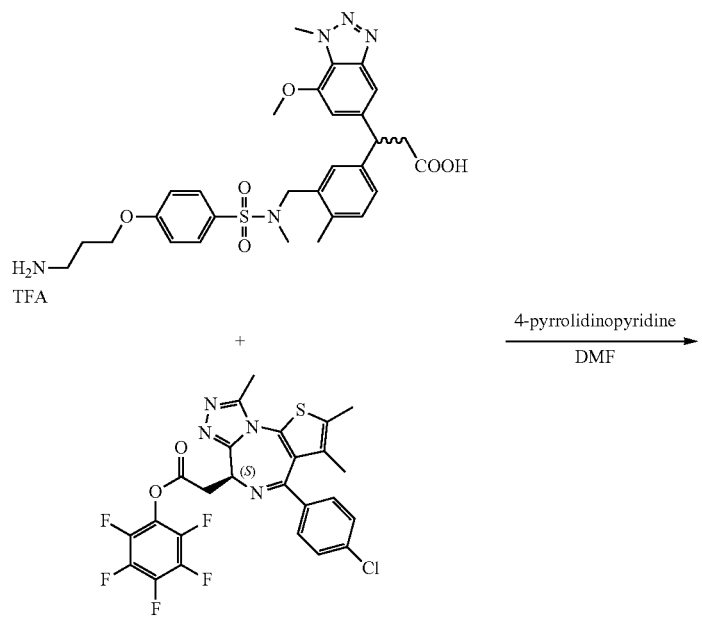

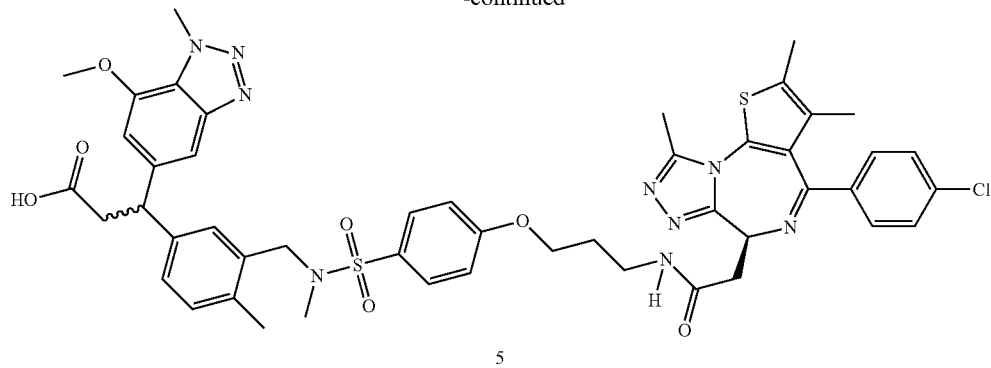

5

To a solution of 3-(3-((4-(3-aminopropoxy)-N-methylphenylsulfonamido)methyl)-4-methylphenyl)-3-(7-methoxy-1-methyl-1H-benzo[d][1,2,3]triazol-5-yl)propanoic acid TFA salt (8 mg, 0.010 mmol) and (S)-perfluorophenyl 2-(4-(4-chlorophenyl)-2,3,9-trimethyl-6H-thieno[3,2-f][1,2,4]triazolo[4,3-a][1,4]diazepin-6-yl)acetate (5.6 mg, 0.010 mmol) in DMF (1 mL), 4-pyrrolidinopyridine (3 mg, 0.020 mmol) was added at room temperature. After 3 hours, the mixture was purified by HPLC to yield bifunctional compound 5 (7 mg, 0.007 mmol, 70%).

LC/MS m/z calculated for [M+H]$^+$ 964.3, found 964.3.

Example 11: Synthesis of 3-(3-((4-(1-((6S)-4-(4-chlorophenyl)-2,3,9-trimethyl-6H-thieno[3,2-f][1,2,4]triazolo[4,3-a][1,4]diazepin-6-yl)-2-oxo-6,9,12-trioxa-3-azatetradecan-14-yloxy)-N-methylphenylsulfonamido)methyl)-4-methylphenyl)-3-(7-methoxy-1-methyl-1H-benzo[d][1,2,3]triazol-5-yl)propanoic acid (7)

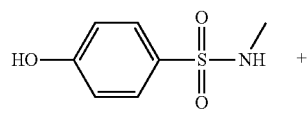 +

To a solution 4-hydroxy-N-methylbenzenesulfonamide (50 mg, 0.27 mmol) and tert-butyl 2-(2-(2-(2-bromoethoxy)ethoxy)ethoxy)ethylcarbamate (96 mg, 0.27 mmol) in DMF (2 mL), K$_2$CO$_3$ (75 mg, 0.54 mmol) was added at room temperature. The mixture was stirred overnight. The reaction was filtered, and the filtrate was concentrated under vacuum. The residue was purified by flash chromatography to yield tert-butyl 2-(2-(2-(2-(4-(N-methylsulfamoyl)phenoxy)ethoxy)ethoxy)ethoxy)ethylcarbamate.

LC/MS m/z calculated for [M+H]$^+$ 463.2, found 463.2.

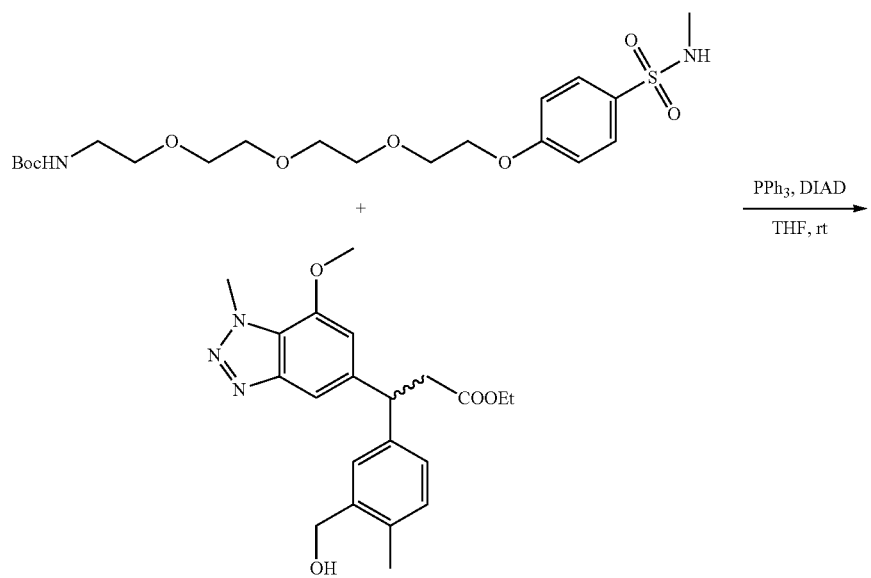

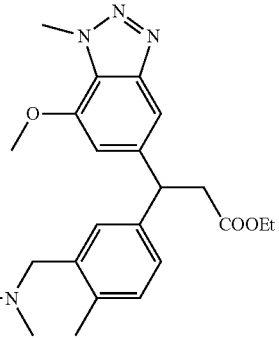

To a solution of tert-butyl 2-(2-(2-(2-(4-(N-methylsulfamoyl)phenoxy)ethoxy)ethoxy)ethoxy)ethylcarbamate (130 mg, 0.28 mmol) and ethyl 3-(3-(hydroxymethyl)-4-methylphenyl)-3-(7-methoxy-1-methyl-1H-benzo[d][1,2,3]triazol-5-yl)propanoate (108 mg, 0.28 mmol) in THF (2 mL), DIAD (113 mg, 0.56 mmol) and PPh₃ (147 mg, 0.56 mmol) were added at room temperature. The reaction mixture was stirred for 30 mins. The mixture was concentrated under vacuum and the residue was purified by flash chromatography to yield ethyl 3-(3-((4-(2,2-dimethyl-4-oxo-3,8,11,14-tetraoxa-5-azahexadecan-16-yloxy)-N-methylphenylsulfonamido)methyl)-4-methylphenyl)-3-(7-methoxy-1-methyl-1H-benzo[d][1,2,3]triazol-5-yl)propanoate (50 mg, 0.06 mmol, 21%).

LC/MS m/z calculated for [M+H]⁺ 828.4, found 828.4.

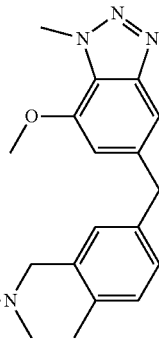

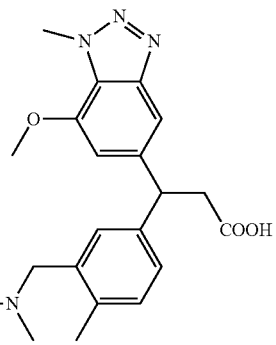

To a solution of ethyl 3-(3-((4-(2,2-dimethyl-4-oxo-3,8,11,14-tetraoxa-5-azahexadecan-16-yloxy)-N-methylphenylsulfonamido)methyl)-4-methylphenyl)-3-(7-methoxy-1-methyl-1H-benzo[d][1,2,3]triazol-5-yl)propanoate (50 mg, 0.06 mmol) in MeOH (2 mL), NaOH (0.12 mL, 2M) was added at room temperature. The mixture was heated to 80° C. for 30 mins. The reaction was concentrated under vacuum to yield the crude product without any further purification. The residue was dissolved in DCM (2 mL) and TFA (1 mL) was added dropwise at room temperature. After 1 hour, the reaction was concentrated under vacuum. The residue was purified by HPLC to yield 3-(3-((4-(2-(2-(2-(2-aminoethoxy)ethoxy)ethoxy)ethoxy)-N-methylphenylsulfonamido)methyl)-4-methylphenyl)-3-(7-methoxy-1-methyl-1H-benzo[d][1,2,3]triazol-5-yl)propanoic acid (33 mg, 0.047 mmol, 78%) as TFA salt.

LC/MS m/z calculated for [M+H]$^+$ 700.3, found 700.3.

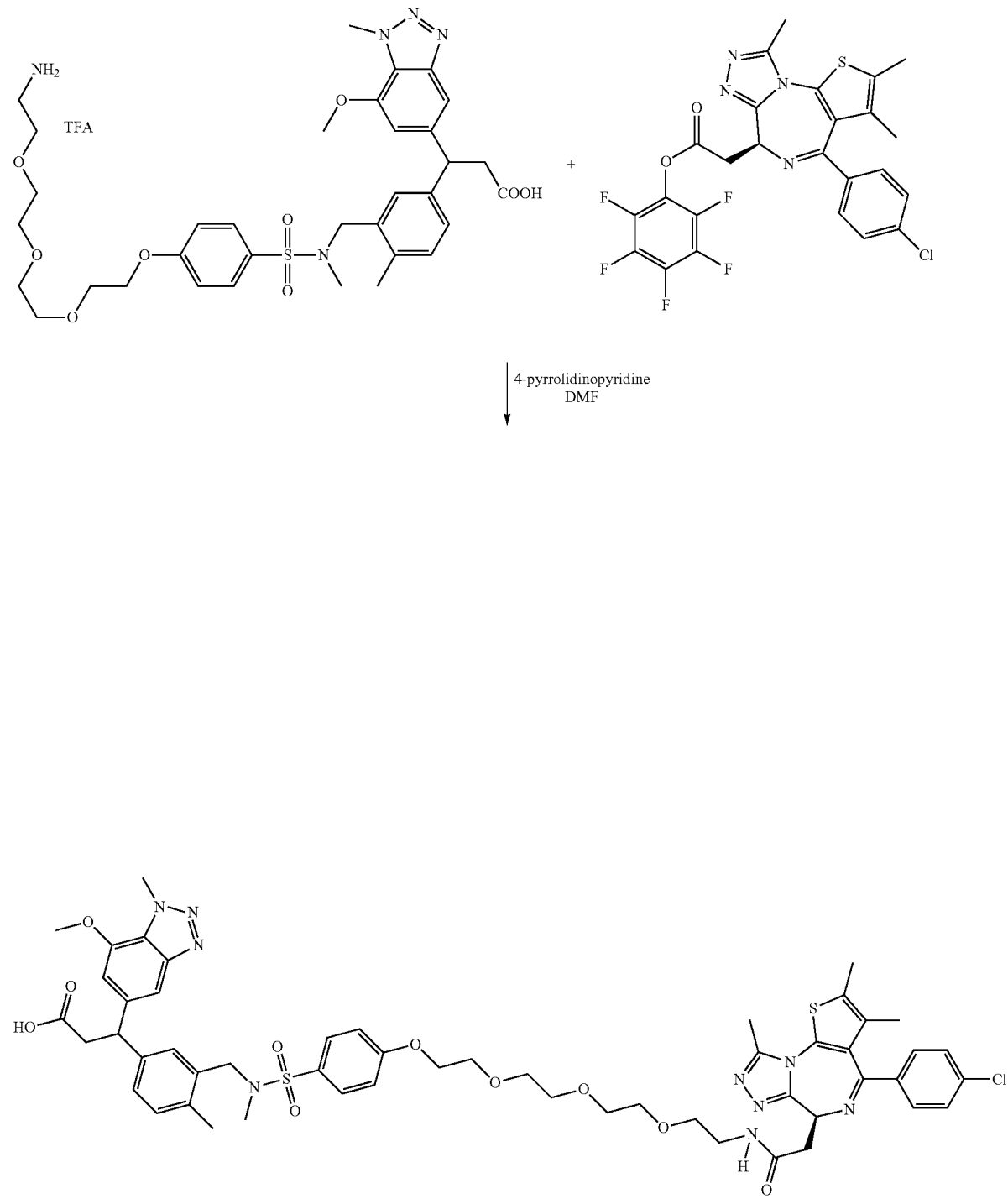

To a solution of 3-(3-((4-(2-(2-(2-(2-aminoethoxy)ethoxy)ethoxy)ethoxy)-N-methylphenylsulfonamido)methyl)-4-methylphenyl)-3-(7-methoxy-1-methyl-1H-benzo[d][1,2,3]triazol-5-yl)propanoic acid (10 mg, 0.012 mmol) and (S)-perfluorophenyl 2-(4-(4-chlorophenyl)-2,3,9-trimethyl-6H-thieno[3,2-f][1,2,4]triazolo[4,3-a][1,4]diazepin-6-yl)acetate (7 mg, 0.012 mmol) in DMF (1 mL), 4-pyrrolidinopyridine (3.6 mg, 0.024 mmol) was added at room temperature. After 3 hours, the mixture was purified by HPLC to yield bifunctional compound 7 (9 mg, 0.0083 mmol, 69%).

LC/MS m/z calculated for [M+H]$^+$ 1082.4, found 1082.4.

Example 12: Synthesis of 3-(3-((4-(2-(2-(2-(2-(6-chloro-8-fluoro-7-(3-hydroxynaphthalen-1-yl)-4-(4-methylpiperazin-1-yl)quinazolin-2-ylamino)ethoxy)ethoxy)ethoxy)ethoxy)-N-methylphenylsulfonamido)methyl)-4-methylphenyl)-3-(7-methoxy-1-methyl-1H-benzo[d][1,2,3]triazol-5-yl)propanoic acid (19)

To a solution of 3-(3-((4-(2-(2-(2-(2-aminoethoxy)ethoxy)ethoxy)ethoxy)-N-methylphenylsulfonamido)methyl)-4-methylphenyl)-3-(7-methoxy-1-methyl-1H-benzo[d][1,2,3]triazol-5-yl)propanoic acid (56 mg, 0.069 mmol) and 7-bromo-2,6-dichloro-8-fluoro-4-(4-methylpiperazin-1-yl)quinazoline (18 mg, 0.069 mmol) in isopropanol (IPA) (0.75 mL), DIEA (48 μL, 0.275 mmol) was added at room temperature. The reaction was heated to 90° C. for 1 hour. The mixture was purified by HPLC to yield 3-(3-((4-(2-(2-(2-(2-(7-bromo-6-chloro-8-fluoro-4-(4-methylpiperazin-1-yl)quinazolin-2-ylamino)ethoxy)ethoxy)ethoxy)ethoxy)-N-methylphenylsulfonamido)methyl)-4-methylphenyl)-3-(7-methoxy-1-methyl-1H-benzo[d][1,2,3]triazol-5-yl)propanoic acid (9 mg, 0.0085 mmol, 12%).

LC/MS m/z calculated for [M+H]$^+$ 1056.3, found 1056.3.

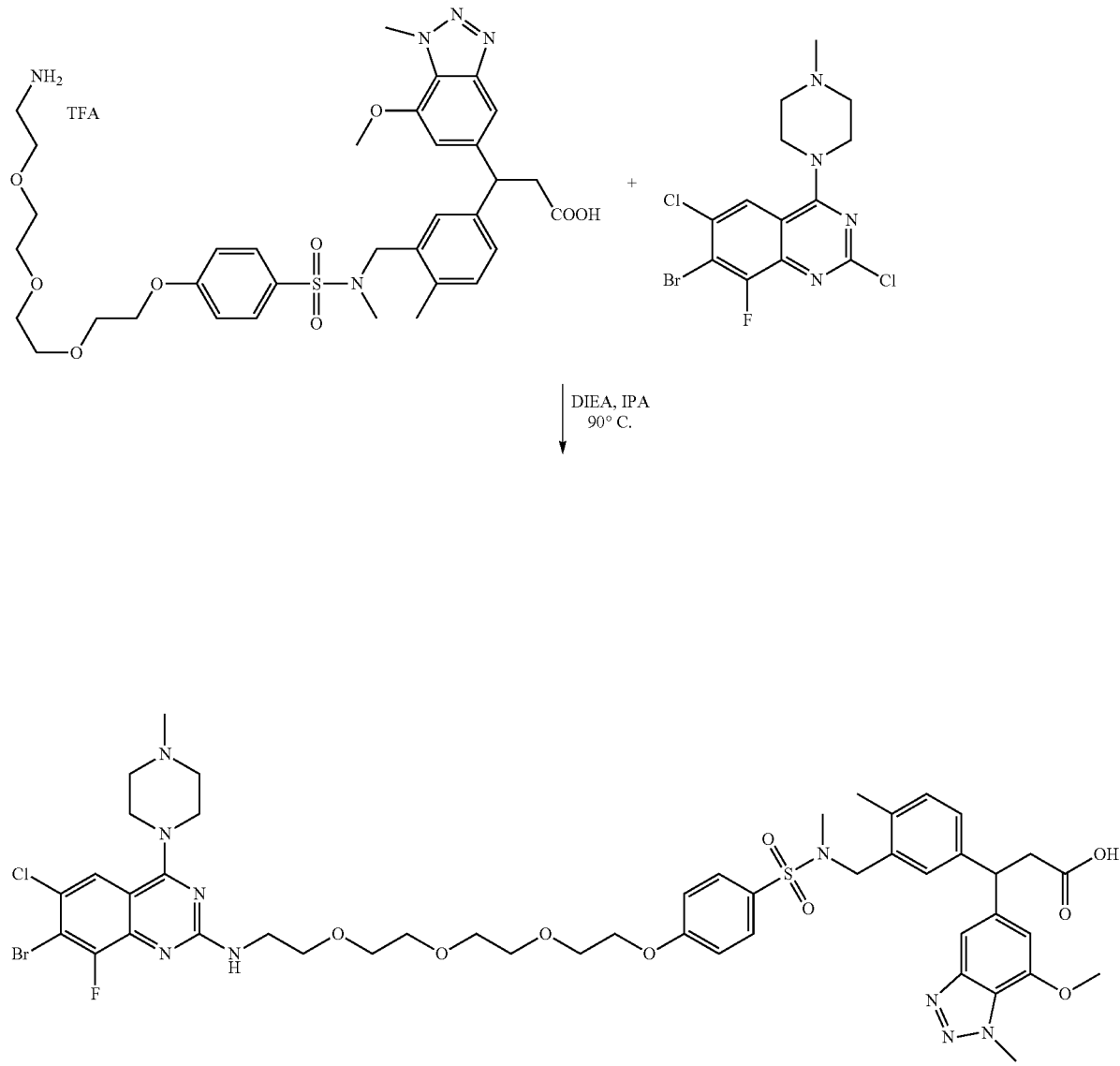

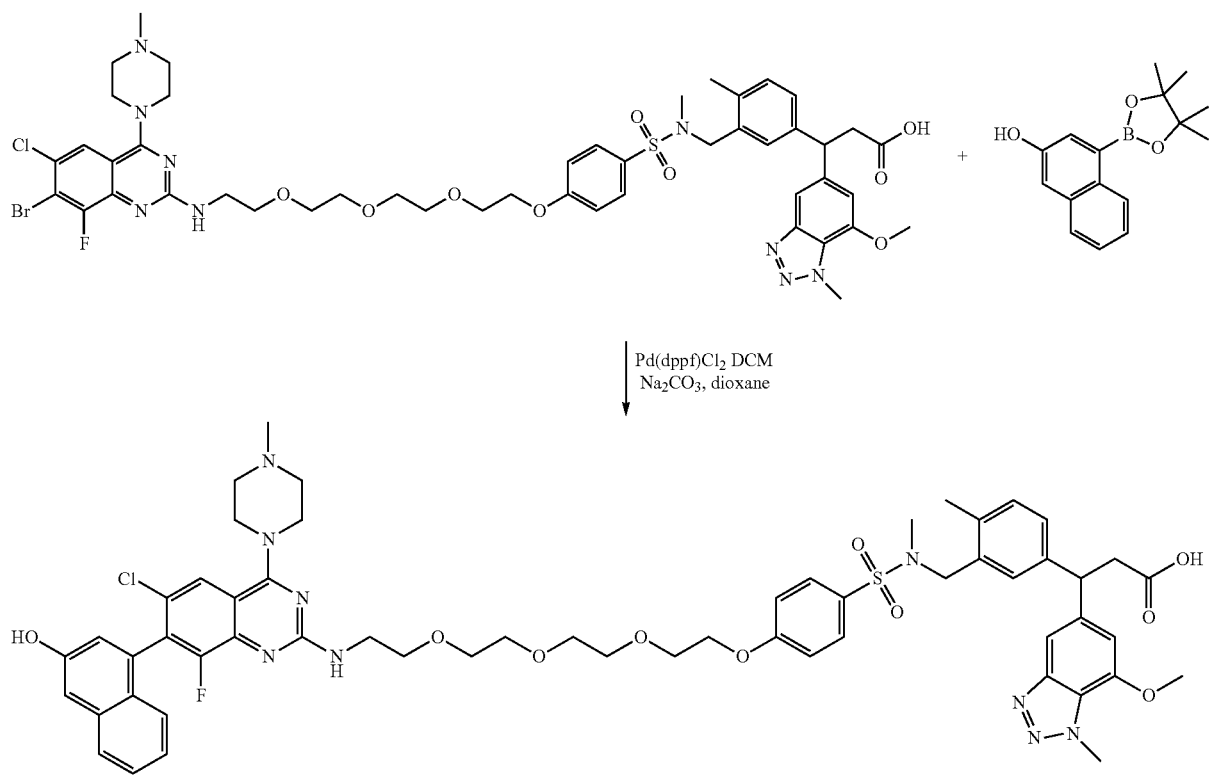

To the solution of 3-(3-((4-(2-(2-(2-(2-(7-bromo-6-chloro-8-fluoro-4-(4-methylpiperazin-1-yl)quinazolin-2-ylamino)ethoxy)ethoxy)ethoxy)ethoxy)-N-methylphenylsulfonamido)methyl)-4-methylphenyl)-3-(7-methoxy-1-methyl-1H-benzo[d][1,2,3]triazol-5-yl)propanoic acid (9 mg, 0.0085 mmol) in dioxane (1 mL), 4-(4,4,5,5-tetramethyl-1,3,2-dioxaborolan-2-yl)naphthalen-2-ol (3 mg, 0.011 mmol), Na$_2$CO$_3$ (100 μL, 1M aq.) and Pd(dppf)Cl$_2$·DCM (1.4 mg, 0.0017 mmol) were added in a vial. The reaction system was degassed and purged with N$_2$. The reaction mixture was then heated to 80° C. for 90 mins. The reaction mixture was filtered and purified by HPLC to yield bifunctional compound 19 (7 mg, 0.0062 mmol, 73%).

LC/MS m/z calculated for [M+H]$^+$ 1120.4, found 1120.4.

Example 13: Synthesis of 3-(3-(((4-(2-(2-(2-(2-((S)-4-(4-chlorophenyl)-2,3,9-trimethyl-6H-thieno[3,2-f][1,2,4]triazolo[4,3-a][1,4]diazepin-6-yl)acetamido)ethoxy)ethoxy)ethoxy)-N-methylphenyl)sulfonamido)methyl)-4-methylphenyl)-3-(7-methoxy-1-methyl-1H-benzo[d][1,2,3]triazol-5-yl)propanoic acid (8)

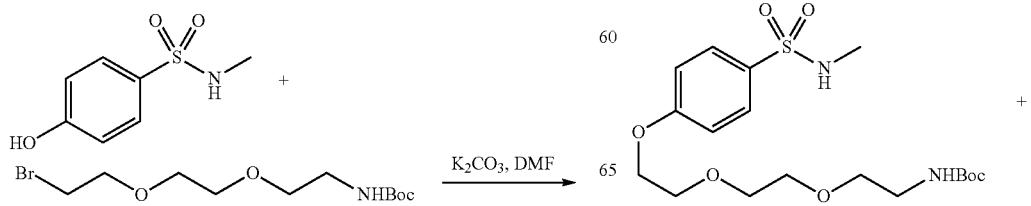

-continued

To a solution of tert-butyl (2-(2-(2-bromoethoxy)ethoxy)ethyl)carbamate in DMF (3 mL) was added K$_2$CO$_3$ (146 mg, 1.06 mmol) and 4-hydroxy-N-methylbenzenesulfonamide (100 mg, 0.53 mmol). The reaction mixture was stirred overnight at room temperature and then quenched with water. The mixture was extracted with ethyl acetate (3×10 mL), washed with brine, dried over sodium sulfate and concentrated under vacuum. Purification by silica gel chromatography yielded tert-butyl (2-(2-(2-(4-(N-methylsulfamoyl)phenoxy)ethoxy)ethoxy)ethyl)carbamate (139 mg, 0.33 mmol, 63% yield).

LC/MS m/z calculated for [M+Na]$^+$ 441.2, found 441.4.

125

-continued

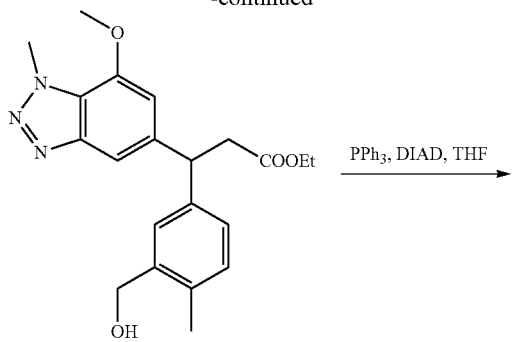

PPh₃, DIAD, THF →

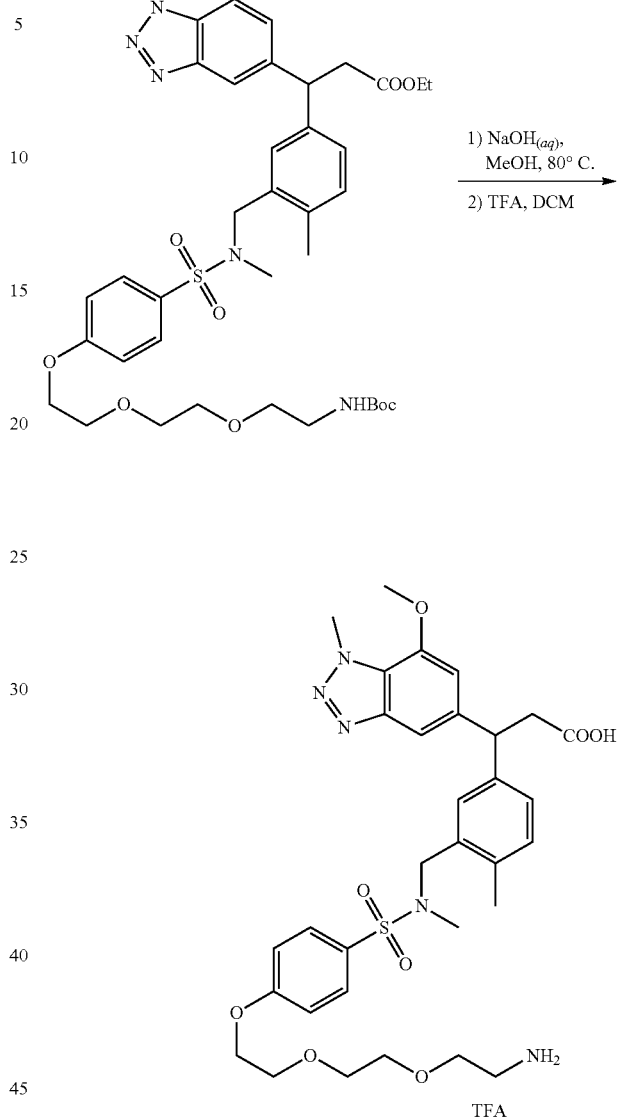

1) NaOH(aq), MeOH, 80° C. →
2) TFA, DCM

To a solution of ethyl 3-(3-(hydroxymethyl)-4-methylphenyl)-3-(7-methoxy-1-methyl-1H-benzo[d][1,2,3]triazol-5-yl)propanoate (126 mg, 0.33 mmol) and tert-butyl (2-(2-(2-(4-(N-methylsulfamoyl)phenoxy)ethoxy)ethoxy)ethyl)carbamate (139 mg, 0.33 mmol) in THF (2 mL), PPh₃ (173 mg, 0.66 mmol) and DIAD (133 mg, 0.66 mmol) were added at room temperature. The mixture stirred for 40 minutes before being concentrated under vacuum to yield ethyl 3-(3-(((4-((2,2-dimethyl-4-oxo-3,8,11-trioxa-5-azatridecan-13-yl)oxy)-N-methylphenyl)sulfonamido)methyl)-4-methylphenyl)-3-(7-methoxy-1-methyl-1H-benzo[d][1,2,3]triazol-5-yl)propanoate, which was used in the next step without further purification.

LC/MS m/z calculated for [M+H]⁺ 783.4, found 783.6.

To a solution of ethyl 3-(3-(((4-((2,2-dimethyl-4-oxo-3,8,11-trioxa-5-azatridecan-13-yl)oxy)-N-methylphenyl)sulfonamido)methyl)-4-methylphenyl)-3-(7-methoxy-1-methyl-1H-benzo[d][1,2,3]triazol-5-yl)propanoate (259 mg, 0.33 mmol) in methanol (3 mL) was added aqueous NaOH (0.5 mL, 3 N). The reaction mixture was stirred at 80° C. for 2 hours. The solution was then acidified with aqueous HCl before extraction with ethyl acetate (3×10 mL), washing with brine, and drying with sodium sulfate. After concentration under vacuum, the resulting residue was then dissolved in DCM (1 mL) and TFA (1 mL), and stirred at room temperature for 1 hour. The reaction mixture was concentrated under vacuum and the crude product purified by HPLC to yield 3-(3-(((4-(2-(2-(2-aminoethoxy)ethoxy)ethoxy)-N-methylphenyl)sulfonamido)methyl)-4-methylphenyl)-3-(7-methoxy-1-methyl-1H-benzo[d][1,2,3]triazol-5-yl)propanoic acid as a TFA salt (35 mg, 0.045 mmol, 14% yield over three steps).

LC/MS m/z calculated for [M+H]⁺ 656.3, found 656.4.

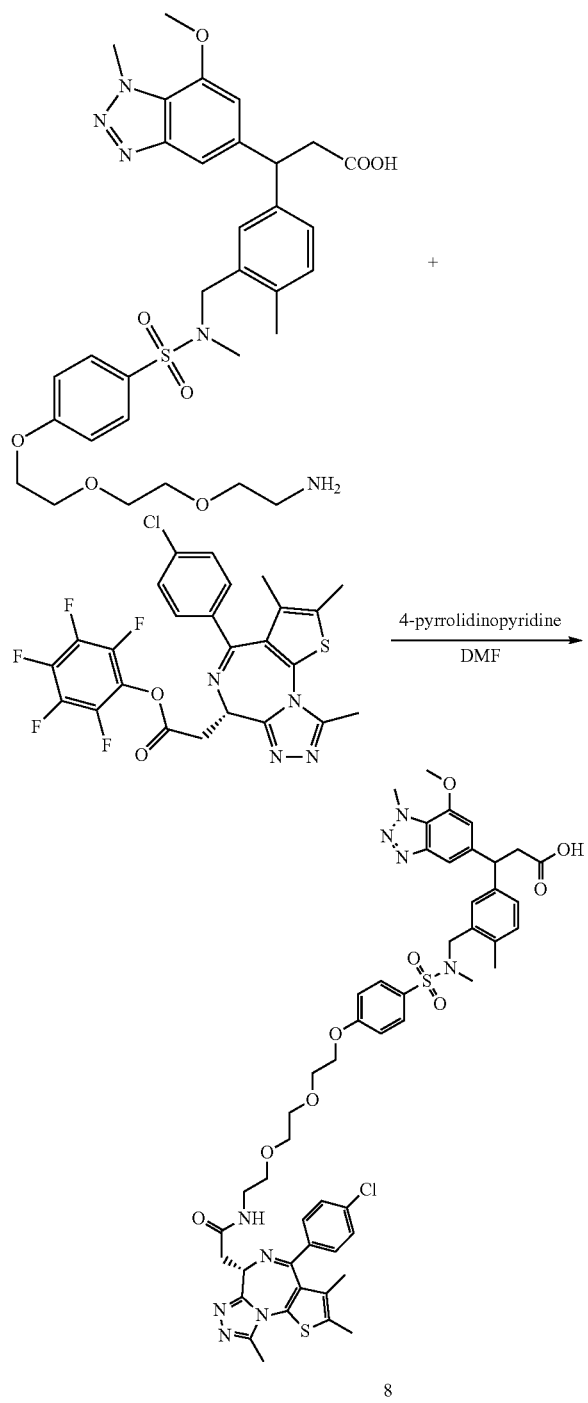

Example 14: Synthesis of 3-(3-(((4-(2-(2-(2-(2-((S)-4-(4-chlorophenyl)-2,3,9-trimethyl-6H-thieno[3,2-f][1,2,4]triazolo[4,3-a][1,4]diazepin-6-yl)acetamido)ethoxy)ethoxy)ethoxy)-N-methylphenyl)sulfonamido)methyl)-4-methylphenyl)-3-(7-methoxy-1-methyl-1H-benzo[d][1,2,3]triazol-5-yl)propanoic acid (16)

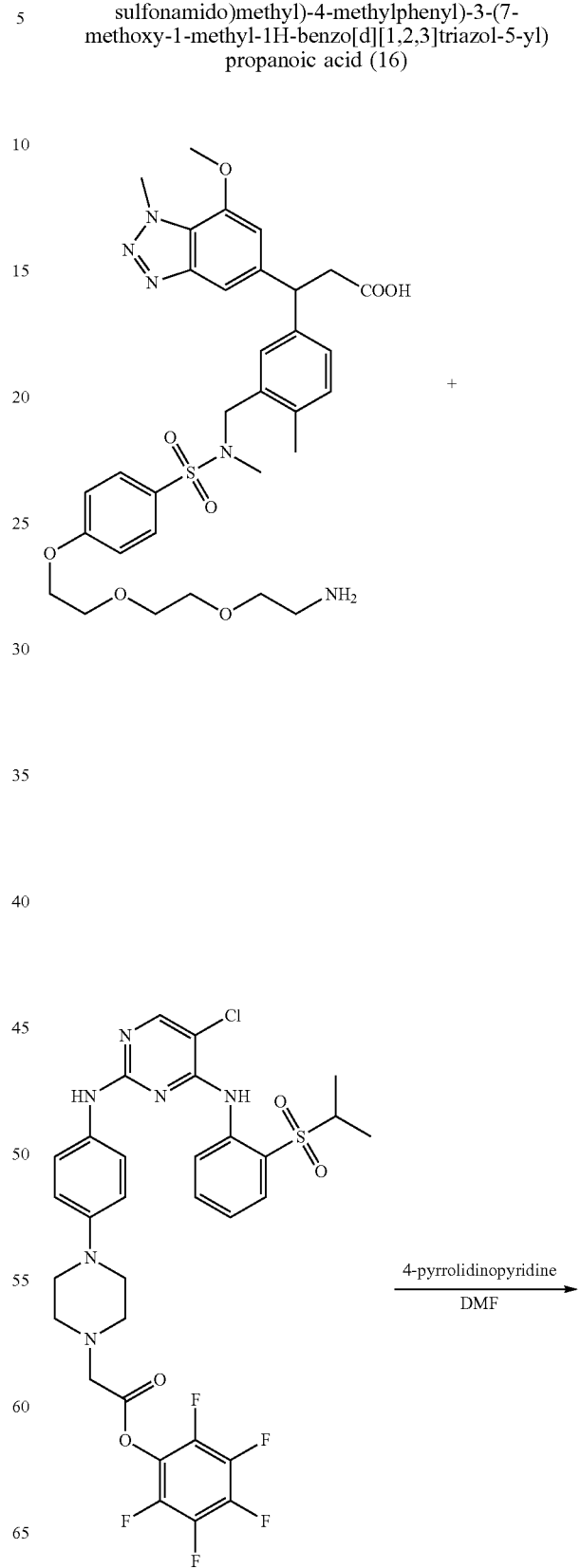

A solution of perfluorophenyl (S)-2-(4-(4-chlorophenyl)-2,3,9-trimethyl-6H-thieno[3,2-f][1,2,4]triazolo[4,3-a][1,4]diazepin-6-yl)acetate (15 mg, 0.027 mmol) in DMF (0.5 mL) was added to a solution of 3-(3-(((4-(2-(2-(2-aminoethoxy)ethoxy)ethoxy)-N-methylphenyl)sulfonamido)methyl)-4-methylphenyl)-3-(7-methoxy-1-methyl-1H-benzo[d][1,2,3]triazol-5-yl)propanoic acid (17.4 mg, 0.027 mmol) and 4-pyrrolidinopyridine (7.5 mg, 0.053 mmol) in DMF (1.5 mL). After stirring overnight the reaction mixture was purified by HPLC to yield bifunctional compound 8 (19.6 mg, 0.017 mmol, 63% yield).

LC/MS m/z calculated for [M+H]+ 1038.3, found 1037.9.

-continued

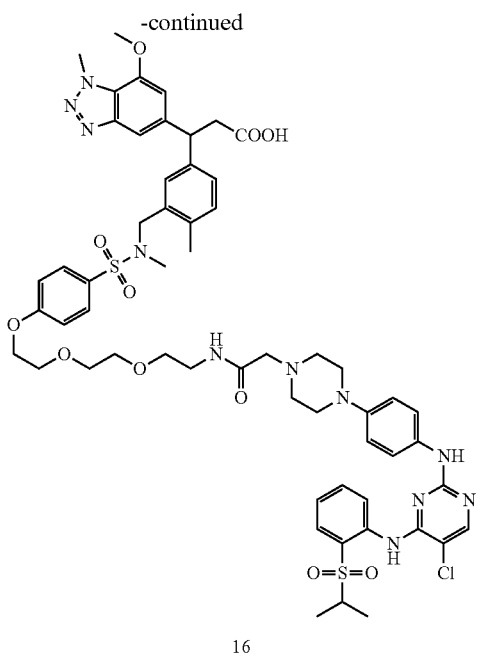

16

To a solution of perfluorophenyl 2-(4-(4-((5-chloro-4-((2-(isopropylsulfonyl)phenyl)amino)pyrimidin-2-yl)amino)phenyl)piperazin-1-yl)acetate and 3-(3-(((4-(2-(2-(2-aminoethoxy)ethoxy)ethoxy)-N-methylphenyl)sulfonamido)methyl)-4-methylphenyl)-3-(7-methoxy-1-methyl-1H-benzo[d][1,2,3]triazol-5-yl)propanoic acid in DMF (2 mL), 4-pyrrolidinopyridine (7.5 mg, 0.053 mmol) was added. The reaction mixture was stirred at room temperature for 3 hours and then purified by HPLC to yield bifunctional compound 16 (15.5 mg, 0.012 mmol, 44% yield).

LC/MS m/z calculated for [M+H]$^+$ 1182.4, found 1181.7.

Example 15: Synthesis of 3-(3-(((4-(2-(2-(2-(2-(4-(4-((5-chloro-4-((2-(isopropylsulfonyl)phenyl)amino)pyrimidin-2-yl)amino)phenyl)piperazin-1-yl)acetamido)ethoxy)ethoxy)ethoxy)-N-methylphenyl)sulfonamido)methyl)-4-methylphenyl)-3-(7-methoxy-1-methyl-1H-benzo[d][1,2,3]triazol-5-yl)propanoic acid (14)

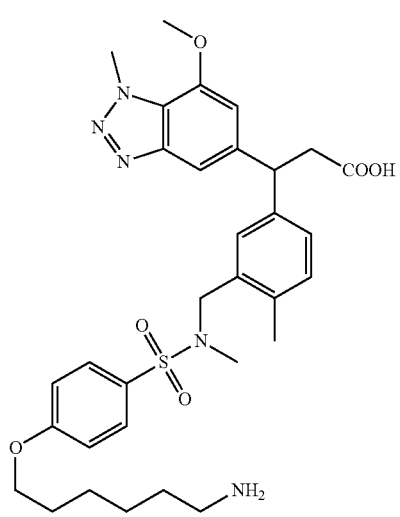

+

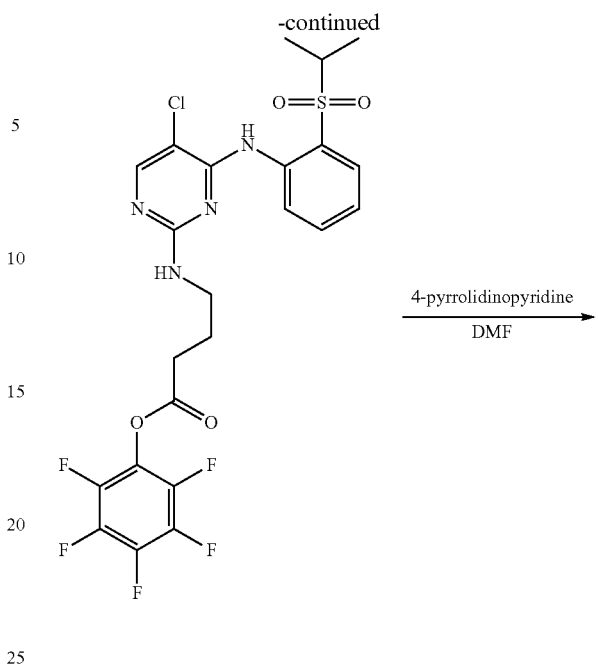

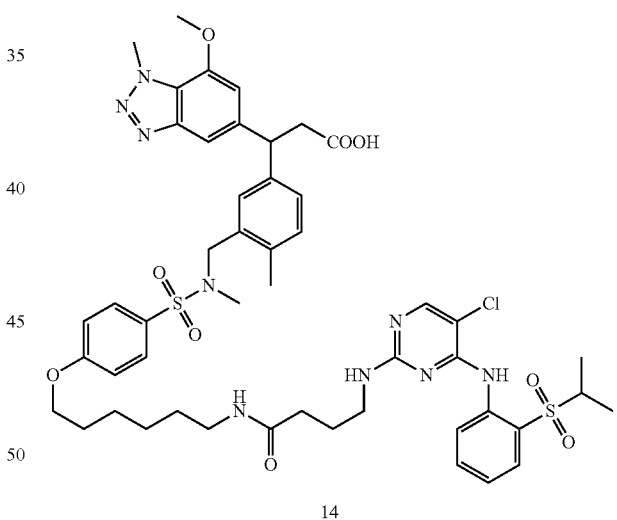

14

To a solution of 3-(3-(((4-((6-aminohexyl)oxy)-N-methylphenyl)sulfonamido)methyl)-4-methylphenyl)-3-(7-methoxy-1-methyl-1H-benzo[d][1,2,3]triazol-5-yl)propanoic acid (11.6 mg, 0.020 mmol) and perfluorophenyl 4-((5-chloro-4-((2-(isopropylsulfonyl)phenyl)amino)pyrimidin-2-yl)amino)butanoate (12.5 mg, 0.020 mmol) in DMF (2 mL), 4-pyrrolidinopyridine (6.0 mg, 0.040 mmol) was added. After stirring at room temperature for 3 hours, the reaction mixture was then purified by HPLC to yield bifunctional compound 14 (4.8 mg, 0.004 mmol, 21% yield).

LC/MS m/z calculated for [M+H]$^+$ 1018.4, found 1017.5.

Example 16: Synthesis of 3-(3-((4-(6-(2-(4-(4-(6-(3-(4-tert-butylbenzamido)-2-methylphenyl)-4-methyl-3-oxo-3,4-dihydropyrazin-2-ylamino)benzoyl)piperazin-1-yl)acetamido)hexyloxy)-N-methylphenylsulfonamido)methyl)-4-methylphenyl)-3-(7-methoxy-1-methyl-1H-benzo[d][1,2,3]triazol-5-yl)propanoic acid (18)

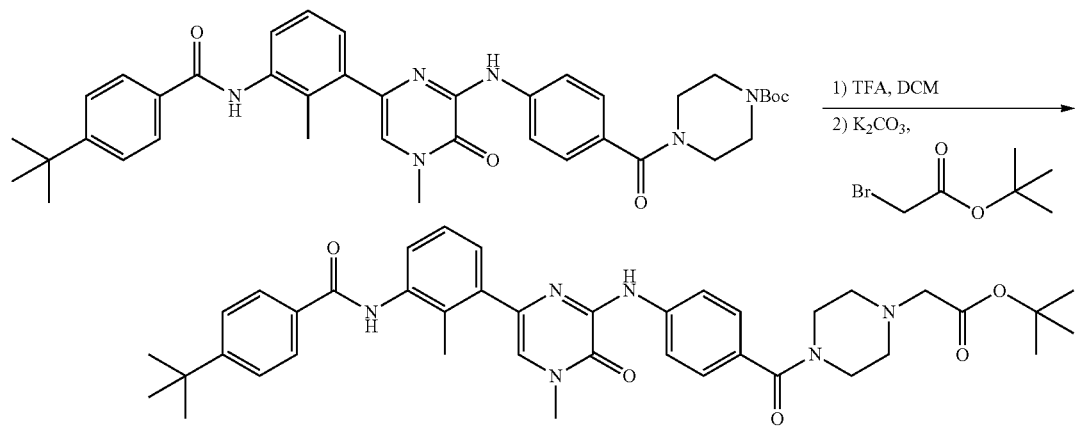

To a solution of tert-butyl 4-(4-(6-(3-(4-tert-butylbenzamido)-2-methylphenyl)-4-methyl-3-oxo-3,4-dihydropyrazin-2-ylamino)benzoyl)piperazine-1-carboxylate (30 mg, 0.044 mmol) in DCM (0.5 mL), TFA (0.5 mL) was added at room temperature. After 1 hour, the solution was concentrated under vacuum to get the crude product. To the solution of this residue in acetone (1 mL), tert-butyl 2-bromoacetate (6.5 μL, 0.044 mmol) and K₂CO₃ (12.1 mg, 0.088 mmol) were added at room temperature. After 14 hours, the reaction was quenched with water and extracted with EtOAc (3×5 mL). The organic layer was washed with brine and dried with Na₂SO₄. The mixture was concentrated under vacuum and the residue was purified with flash chromatography to yield tert-butyl 2-(4-(4-(6-(3-(4-tert-butylbenzamido)-2-methylphenyl)-4-methyl-3-oxo-3,4-dihydropyrazin-2-ylamino)benzoyl)piperazin-1-yl)acetate (27.7 mg, 0.040 mmol, 91%).

LC/MS m/z calculated for [M+H]$^+$ 693.4, found 693.4.

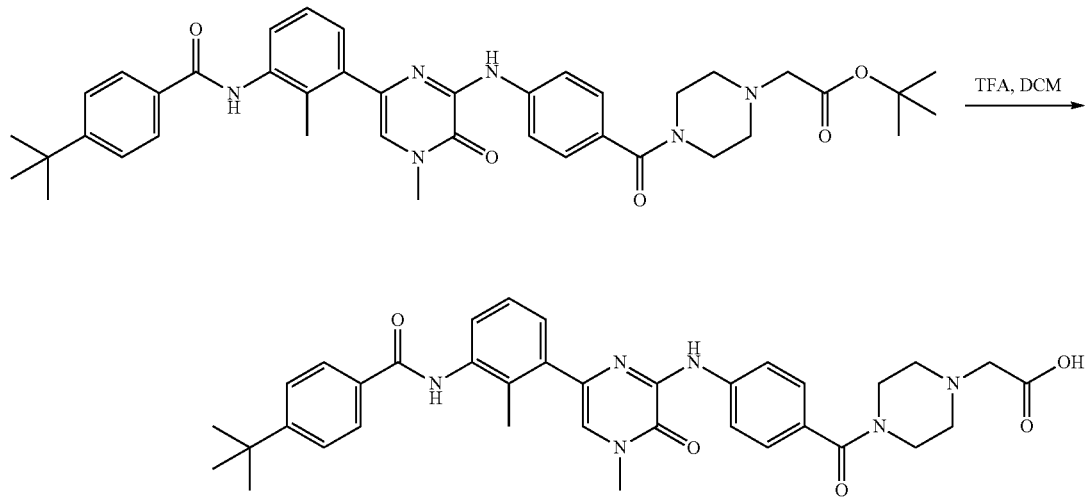

To a solution of tert-butyl 2-(4-(4-(6-(3-(4-tert-butylbenzamido)-2-methylphenyl)-4-methyl-3-oxo-3,4-dihydropyrazin-2-ylamino)benzoyl)piperazin-1-yl)acetate (27.7 mg, 0.040 mmol) in DCM (0.5 mL), TFA (0.5 mL) was added at room temperature. After 1 hour, the solution was concentrated under vacuum to get the crude product without any further purification.

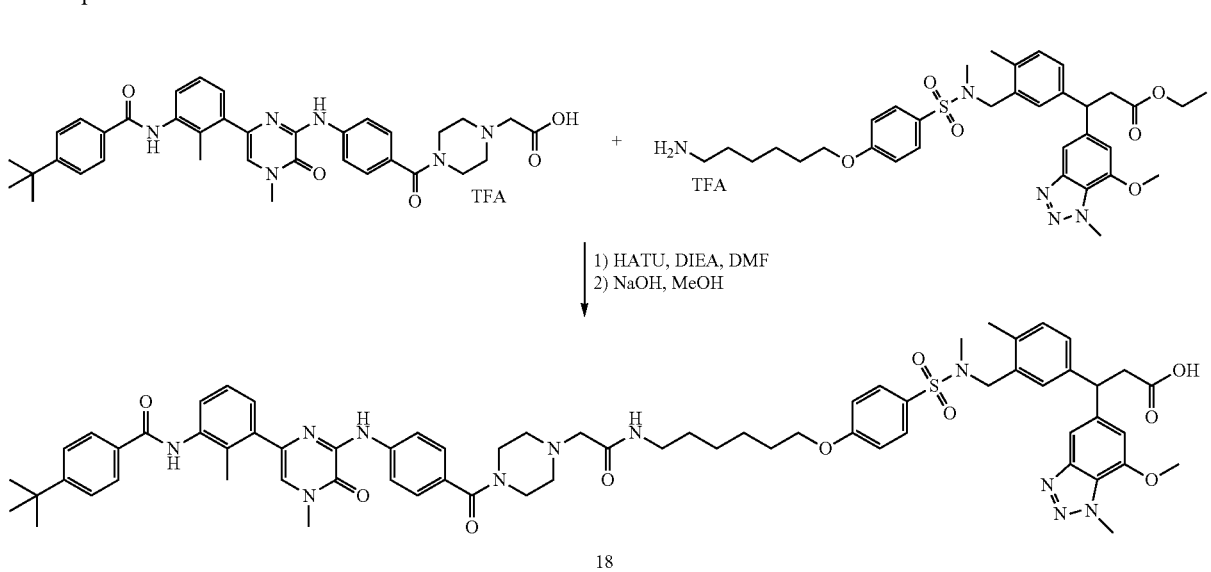

18

To a solution of 2-(4-(4-(6-(3-(4-tert-butylbenzamido)-2-methylphenyl)-4-methyl-3-oxo-3,4-dihydropyrazin-2-ylamino)benzoyl)piperazin-1-yl)acetic acid TFA salt (30 mg, 0.04 mmol) and ethyl 3-(3-((4-(6-aminohexyloxy)-N-methylphenylsulfonamido)methyl)-4-methylphenyl)-3-(7-methoxy-1-methyl-1H-benzo[d][1,2,3]triazol-5-yl)propanoate (30.6 mg, 0.04 mmol) in DMF (1 mL), HATU (30.4 mg, 0.08 mmol) and DIEA (258 mg, 0.20 mmol) were added at room temperature. After 10 mins, the reaction was quenched with water and extracted with EtOAc (3×5 mL). The organic layer was washed with brine and dried with $Na_2SO_4$. The mixture was concentrated under vacuum to get the crude product without any further purification. To the solution of resulted residue in MeOH (1 mL), NaOH (200 μL, 2N aq.) was added at room temperature. The reaction was heated to 80° C. for 1 hour. The solution was concentrated under vacuum and purified with HPLC to yield bifunctional compound 18 (11 mg, 0.0081 mmol, 20%).

LC/MS m/z calculated for [M+H]$^+$ 1242.6, found 1242.6.

Example 17: Synthesis of 3-(3-(((4-((6-(2-(4-(4-((5-chloro-4-(2,4-dimethylthiazol-5-yl)pyrimidin-2-yl)amino)phenyl)piperazin-1-yl)acetamido)hexyl)oxy)-N-methylphenyl)sulfonamido)methyl)-4-methylphenyl)-3-(7-methoxy-1-methyl-1H-benzo[d][1,2,3]triazol-5-yl)propanoic acid (17)

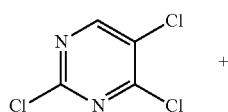

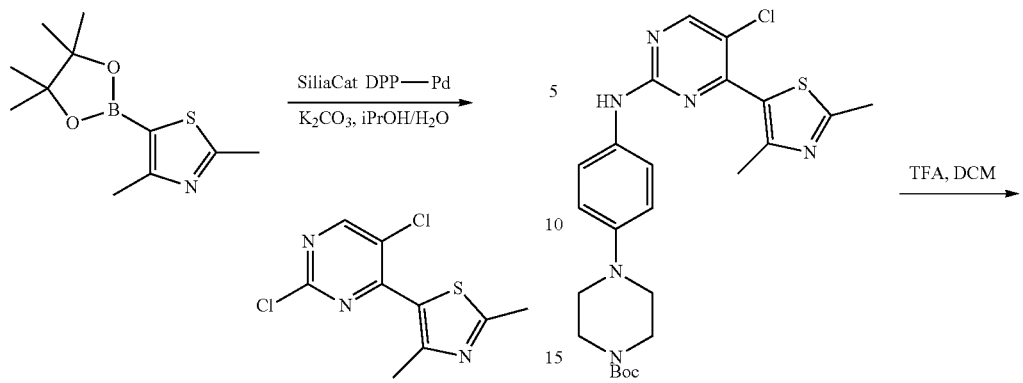

To the solution of 2,4,5-trichloropyrimidine (100 mg, 0.54 mmol), 2,4-dimethyl-5-(4,4,5,5-tetramethyl-1,3,2-dioxaborolan-2-yl)thiazole (130 mg, 0.54 mmol) and potassium carbonate (149 mg, 1.08 mmol) in iPrOH/H$_2$O (3.5 mL, 1 mL), SiliaCat DPP-Pd (43 mg, 0.0108 mmol) was added at room temperature. The reaction mixture was heated up to 85° C. for 30 mins. The reaction mixture was filtered, extracted with ethyl acetate, and concentrated to give 5-(2,5-dichloropyrimidin-4-yl)-2,4-dimethylthiazole as the crude product which was used without further purification.

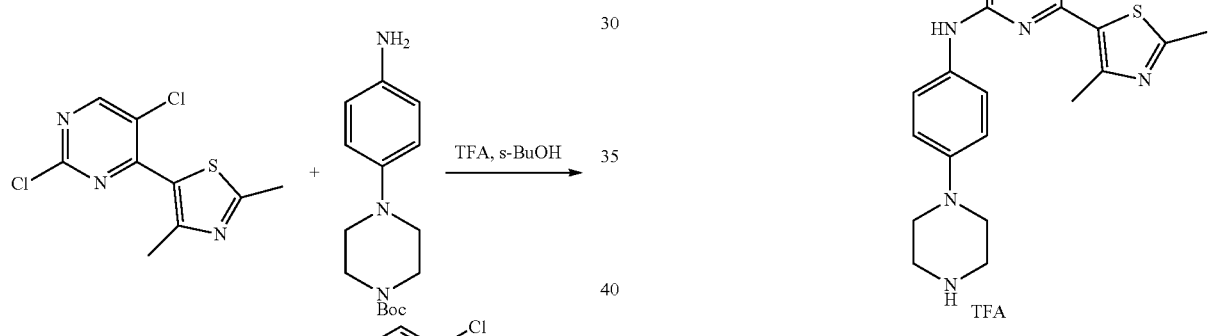

To the solution of 5-(2,5-dichloropyrimidin-4-yl)-2,4-dimethylthiazole (150 mg, 0.58 mmol) and tert-butyl 4-(4-aminophenyl)piperazine-1-carboxylate (241 mg, 0.87 mmol) in s-BuOH (2 mL), TFA (99 mg, 087 mmol) was added at room temperature. Then the reaction mixture was heated to 80° C. for 2 hours. The reaction mixture was cooled to room temperature and purified with flash chromatography to yield tert-butyl 4-(4-((5-chloro-4-(2,4-dimethylthiazol-5-yl)pyrimidin-2-yl)amino)phenyl)piperazine-1-carboxylate.

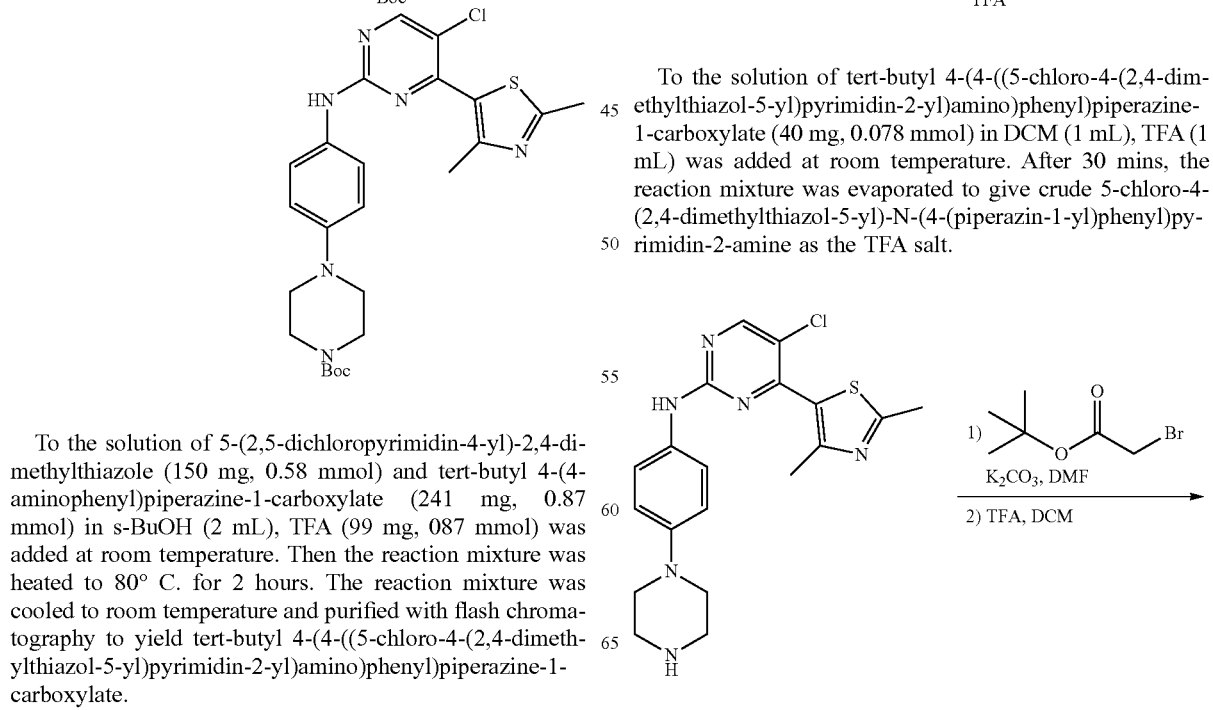

To the solution of tert-butyl 4-(4-((5-chloro-4-(2,4-dimethylthiazol-5-yl)pyrimidin-2-yl)amino)phenyl)piperazine-1-carboxylate (40 mg, 0.078 mmol) in DCM (1 mL), TFA (1 mL) was added at room temperature. After 30 mins, the reaction mixture was evaporated to give crude 5-chloro-4-(2,4-dimethylthiazol-5-yl)-N-(4-(piperazin-1-yl)phenyl)pyrimidin-2-amine as the TFA salt.

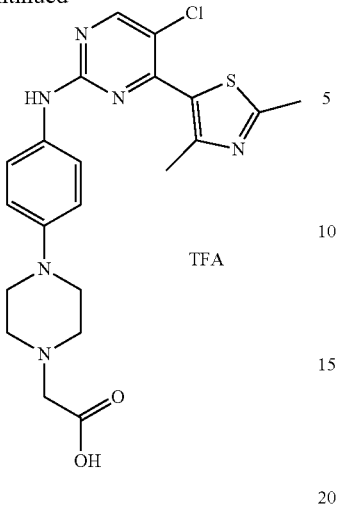

TFA

To the solution of 5-chloro-4-(2,4-dimethylthiazol-5-yl)-N-(4-(piperazin-1-yl)phenyl)pyrimidin-2-amine TFA salt (40 mg, 0.078 mmol) and potassium carbonate (33.1 mg, 0.24 mmol) in DMF (1 mL), tert-butyl 2-bromoacetate (17 µL, 0.12 mmol) was added at room temperature. After overnight stirring, the reaction mixture was evaporated to get the residue without further purification. The residue was dissolved in DCM (1 mL) and TFA (1 mL). The reaction was stirred at room temperature for 2 hours and then evaporated to give 2-(4-(4-((5-chloro-4-(2,4-dimethylthiazol-5-yl)pyrimidin-2-yl)amino)phenyl)piperazin-1-yl)acetic acid as the TFA salt.

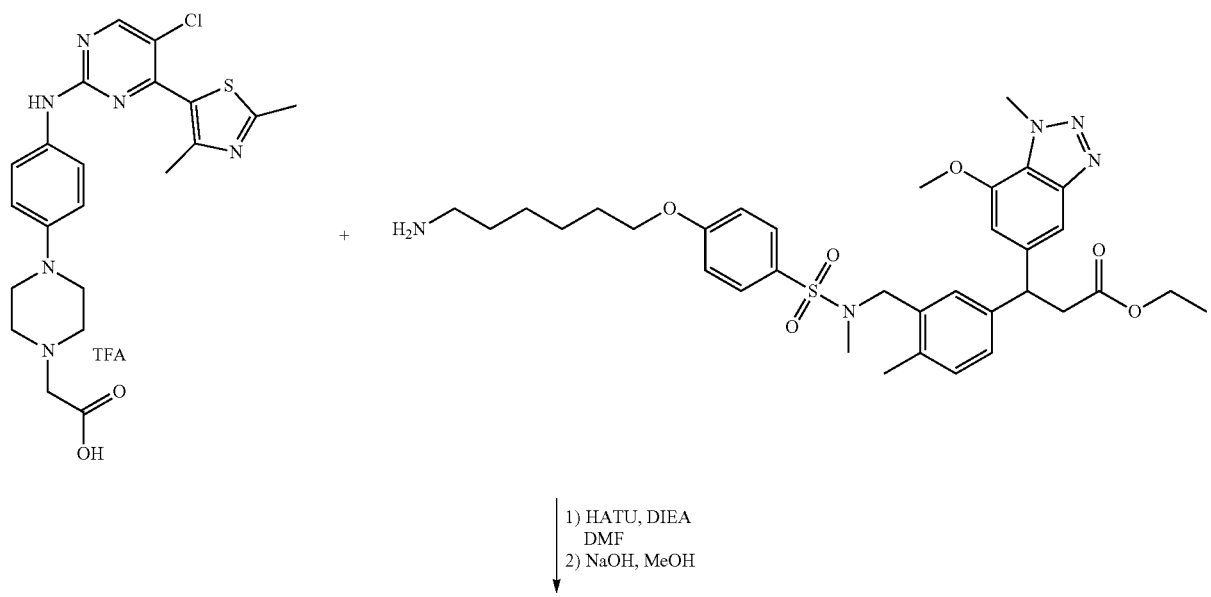

1) HATU, DIEA
   DMF
2) NaOH, MeOH

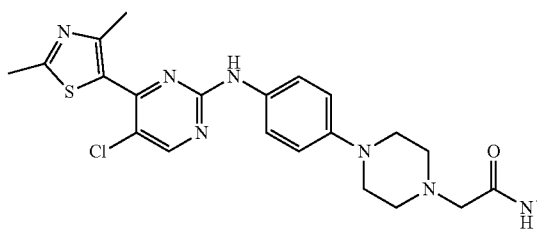
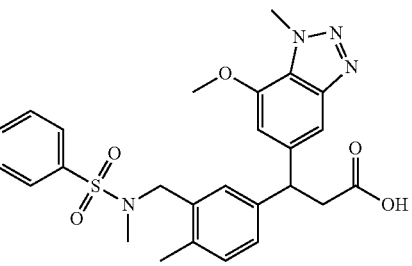

17

To the solution of 2-(4-(4-((5-chloro-4-(2,4-dimethylthiazol-5-yl)pyrimidin-2-yl)amino)phenyl)piperazin-1-yl)acetic acid TFA salt(18.8 mg, 0.033 mmol), ethyl 3-(3-(((4-((6-aminohexyl)oxy)-N-methylphenyl)sulfonamido)methyl)-4-methylphenyl)-3-(7-methoxy-1-methyl-1H-benzo[d][1,2,3]triazol-5-yl)propanoate TFA (25 mg, 0.033 mmol) and DIEA (22 mg, 0.165 mmol) in DMF (1 mL), HATU (25.3 mg, 0.066 mmol) was added at room temperature. After 5 minutes, the mixture was evaporated to give the crude product without any further purification. The residue was dissolved in MeOH (0.5 mL) and NaOH (2 M aq., 7 µL, 0.014 mmol). The reaction was heated to 80° C. for 1 hour. The mixture was purified with reverse phase pre-HPLC to get desired bifunctional compound 17.

LC/MS m/z calculated for [M+H]$^+$ 1064.4, found 1064.4.

Example 18: Synthesis of methyl 2-((6S)-4-(4-chlorophenyl)-2-((8-(2-((2-(2,6-dioxopiperidin-3-yl)-1,3-dioxoisoindolin-4-yl)oxy)acetamido)octyl)carbamoyl)-3,9-dimethyl-6H-thieno[3,2-f][1,2,4]triazolo[4,3-a][1,4]diazepin-6-yl)acetate (20)

(20)

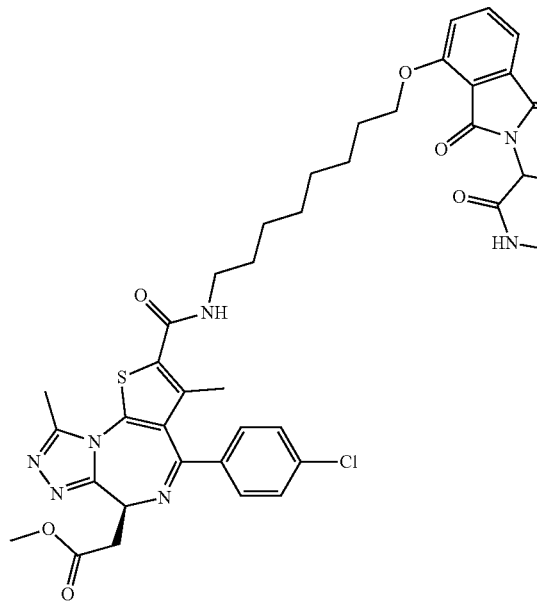

Compound 20 ("dBET23") was synthesized according to Nowak et al., Nat. Chem. Biol. 7:706-714 (2018).

Example 19: Synthesis of (S)-3-(3-(((R)-7-(3-(2-((S)-4-(4-chlorophenyl)-2,3,9-trimethyl-6H-thieno[3,2-f][1,2,4]triazolo[4,3-a][1,4]diazepin-6-yl)acetamido)propyl)-4-methyl-1,1-dioxido-3,4-dihydro-2H-benzo[b][1,4,5]oxathiazepin-2-yl)methyl)-4-methylphenyl)-3-(7-methoxy-1-methyl-1H-benzo[d][1,2,3]triazol-5-yl)propanoic acid (21)

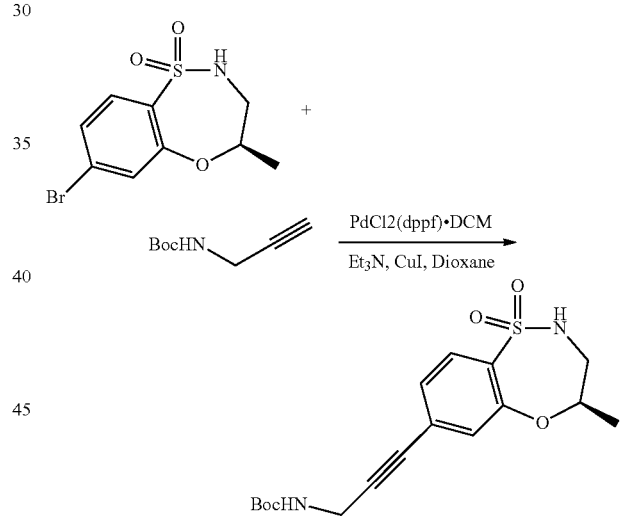

(R)-7-bromo-4-methyl-3,4-dihydro-2H-benzo[b][1,4,5]oxathiazepine 1,1-dioxide (300 mg, 1.03 mmol) was dissolved in dioxane (5 mL). N-Boc-propargylamine (191 mg, 1.23 mmol), Et$_3$N (430 µL, 3.09 mmol), CuI (39 mg, 190 mmol), and PdCl2(dppf)·DCM (84 mg, 0.103 mmol) were then added. The mixture was degassed and sparged with N$_2$ and stirred at 80° C. for 5 h. The reaction mixture was then filtered, diluted with water and extracted with ethyl acetate. Combined extracts were washed with brine, dried over Na$_2$SO$_4$, and concentrated before purification by silica gel chromatography using a gradient of 0-60% EtOAc/Hexanes. The resulting residue was then purified by HPLC to provide tert-butyl (R)-(3-(4-methyl-1,1-dioxido-3,4-dihydro-2H-benzo[b][1,4,5]oxathiazepin-7-yl)prop-2-yn-1-yl)carbamate as a colorless oil (279 mg, 0.76 mmol, 74%).

LC/MS m/z calculated for [M+H-COOC(CH$_3$)$_3$]$^+$ 266.06, found 266.87.

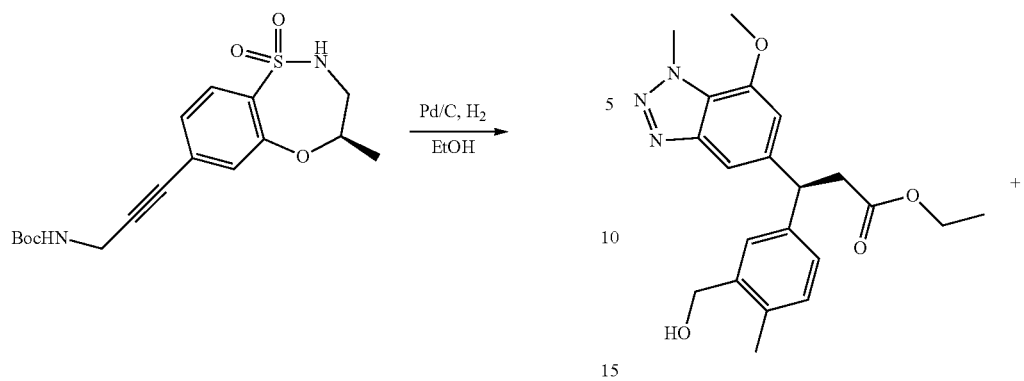

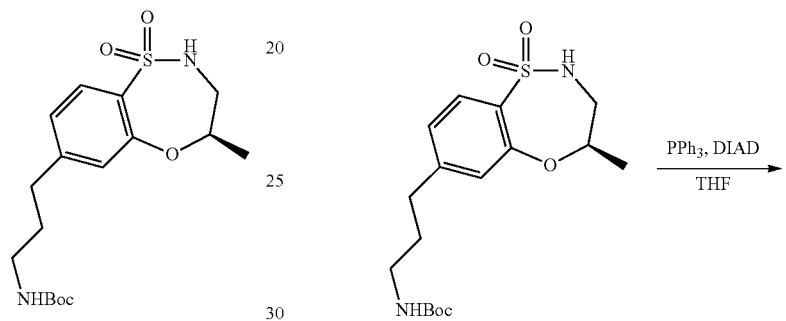

tert-butyl (R)-(3-(4-methyl-1,1-dioxido-3,4-dihydro-2H-benzo[b][1,4,5]oxathiazepin-7-yl)prop-2-yn-1-yl)carbamate (279 mg, 0.76 mmol) was dissolved in ethanol (20 mL), and palladium on carbon (50 mg, 10%) was added. The vessel was flushed with $H_2$ and stirred vigorously under $H_2$ (1 atm) overnight. Pd/C was removed by filtration through Celite and concentrated in vacuo to obtain tert-butyl (R)-(3-(4-methyl-1,1-dioxido-3,4-dihydro-2H-benzo[b][1,4,5]oxathiazepin-7-yl)propyl)carbamate as a colorless oil (245 mg, 0.65 mmol, 87%).

LC/MS m/z calculated for $[M+H-OC(CH_3)_3]^+$ 314.16, found 314.77.

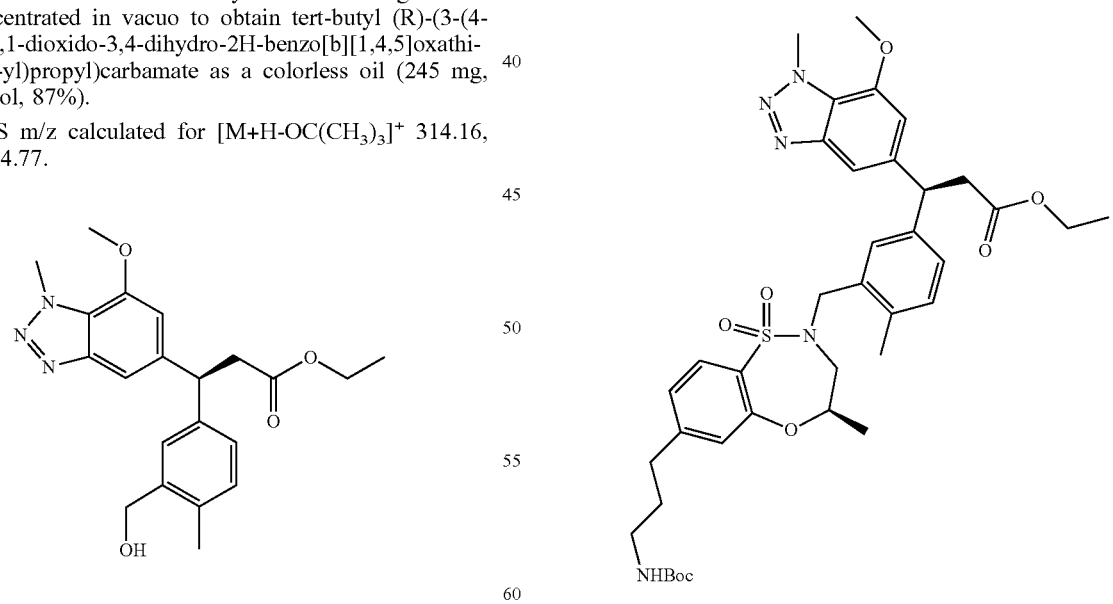

Ethyl 3-(3-(hydroxymethyl)phenyl)-3-(7-methoxy-1-methyl-1H-benzo[d][1,2,3]triazol-5-yl)propanoate, whose preparation is described previously, was purified by chiral column chromatography to obtain both (R) and (S) enantiomers. Ethyl (S)-3-(3-(hydroxymethyl)phenyl)-3-(7-methoxy-1-methyl-1H-benzo[d][1,2,3]triazol-5-yl)propanoate is used in the following examples.

tert-butyl (R)-(3-(4-methyl-1,1-dioxido-3,4-dihydro-2H-benzo[b][1,4,5]oxathiazepin-7-yl)propyl)carbamate (56 mg, 0.15 mmol) was dissolved in THF (2 mL) and ethyl (S)-3-(3-(hydroxymethyl)phenyl)-3-(7-methoxy-1-methyl-1H-benzo[d][1,2,3]triazol-5-yl)propanoate (58 mg, 0.15 mmol) was added. Triphenylphosphine (79 mg, 0.30 mmol) was added, followed by DIAD (61 mg, 0.030 mmol). After 20 minutes, DMSO was added and the solution was purified by HPLC to provide ethyl (S)-3-(3-(((R)-7-(3-((tert-butoxycarbonyl)amino)propyl)-4-methyl-1,1-dioxido-3,4-dihydro-2H-benzo[b][1,4,5]oxathiazepin-2-yl)methyl)phenyl)-3-(7-methoxy-1-methyl-1H-benzo[d][1,2,3]triazol-5-yl)propanoate as a brown oil (54 mg, 0.073 mmol, 49%).

LC/MS m/z calculated for [M+H]$^+$ 736.33, found 735.81.

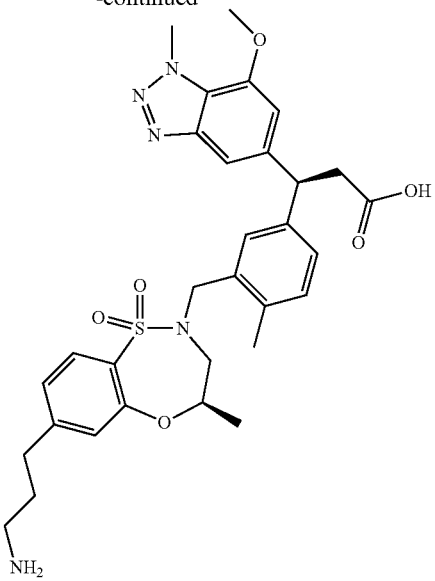

ethyl (S)-3-(3-(((R)-7-(3-((tert-butoxycarbonyl)amino)propyl)-4-methyl-1,1-dioxido-3,4-dihydro-2H-benzo[b][1,4,5]oxathiazepin-2-yl)methyl)phenyl)-3-(7-methoxy-1-methyl-H-benzo[d][1,2,3]triazol-5-yl)propanoate (54 mg, 0.073 mmol) was dissolved in MeOH and aqueous NaOH (100 μL, 5M) was added, and the suspension stirred at 80° C. for 3 hours. After cooling, aqueous HCl (100 μL, 6M) was used to acidify the mixture. The solvent was then evaporated, and the solids were suspended in ethanol, then filtered to remove salt. After evaporation, the residue was dissolved in DCM (1 mL), TFA (1 mL) was added and the solution stirred at rt for 2 hours. The solvent was then removed to provide (S)-3-(3-(((R)-7-(3-aminopropyl)-4-methyl-1,1-dioxido-3,4-dihydro-2H-benzo[b][1,4,5]oxathiazepin-2-yl)methyl)phenyl)-3-(7-methoxy-1-methyl-1H-benzo[d][1,2,3]triazol-5-yl)propanoic acid as the TFA salt as an amber oil (64 mg, 0.078 mmol, 106%).

LC/MS m/z calculated for [M+H]$^+$ 608.25, found 607.99.

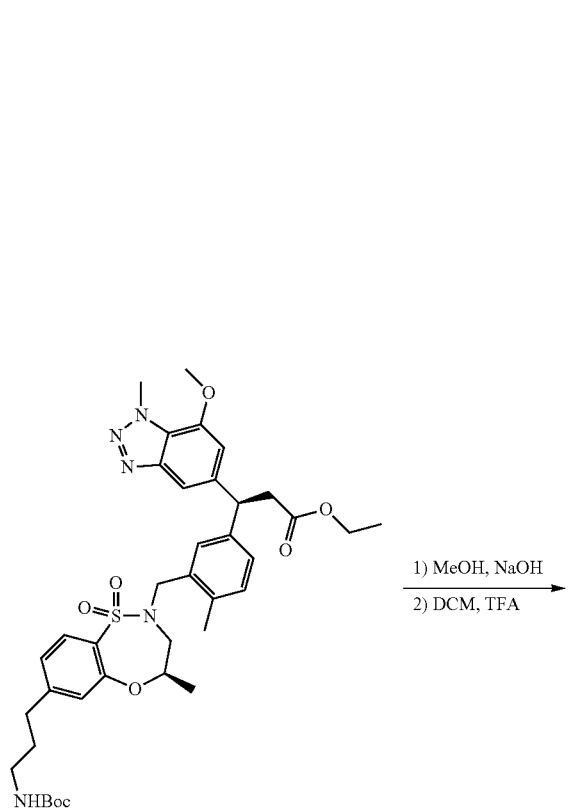

1) MeOH, NaOH
2) DCM, TFA

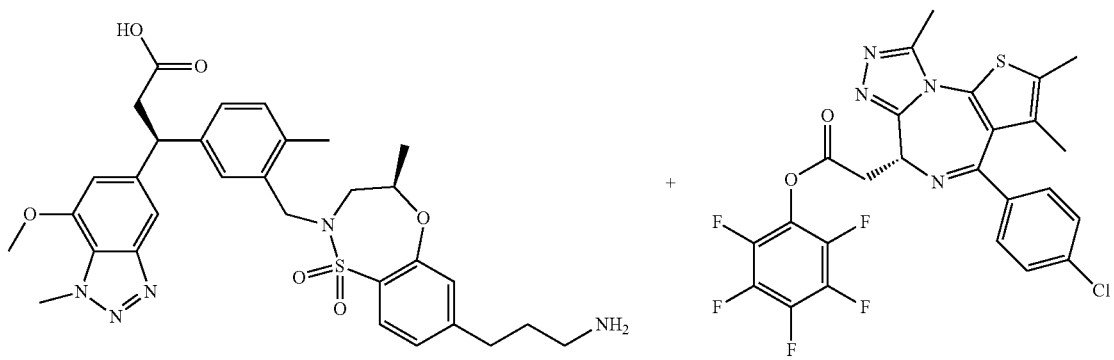

4-pyrrolidinopyridine
DMF

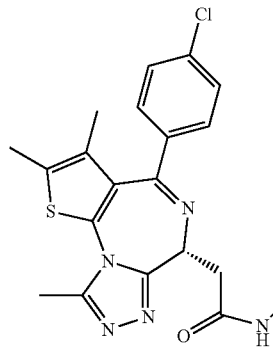

21

(S)-3-(3-(((R)-7-(3-aminopropyl)-4-methyl-1,1-dioxido-3,4-dihydro-2H-benzo[b][1,4,5]oxathiazepin-2-yl)methyl)phenyl)-3-(7-methoxy-1-methyl-1H-benzo[d][1,2,3]triazol-5-yl)propanoic acid (18 mg, 0.025 mmol) in DMF (1 mL) was combined with 4-pyrrolidinopyridine (15 mg, 0.10 mmol) and perfluorophenyl (S)-2-(4-(4-chlorophenyl)-2,3,9-trimethyl-6H-thieno[3,2-f][1,2,4]triazolo[4,3-a][1,4]diazepin-6-yl)acetate (14 mg, 0.025 mmol) in THF (300 µL), was added. The reaction was stirred for 15 minutes, then purified by HPLC to provide bifunctional compound 21 as a white solid (8.0 mg, 0.0087 mmol, 39%).

LC/MS m/z calculated for [M+H]$^+$ 990.31, found 989.53. $^1$H NMR (500 MHz, DMSO-d6) δ 12.02 (s, 1H), 8.22 (t, J=5.6 Hz, 1H), 7.60 (d, J=8.0 Hz, 1H), 7.42-7.32 (m, 5H), 7.27 (d, J=2.1 Hz, 1H), 7.21 (dd, J=7.8, 1.9 Hz, 1H), 7.14 (dd, J=8.1, 1.6 Hz, 1H), 7.10 (d, J=1.6 Hz, 1H), 7.04 (d, J=7.8 Hz, 1H), 6.85 (d, J=1.2 Hz, 1H), 4.49-4.38 (m, 2H), 4.35 (d, J=14.0 Hz, 1H), 4.32-4.26 (m, 1H), 4.26 (s, 3H), 3.86 (s, 3H), 3.72 (d, J=14.0 Hz, 1H), 3.52 (dd, J=15.4, 10.1 Hz, 1H), 3.20 (dd, J=7.1, 3.8 Hz, 2H), 3.09 (q, J=6.5 Hz, 2H), 3.05-2.97 (m, 2H), 2.70-2.58 (m, 3H), 2.53 (s, 3H), 2.34 (s, 3H), 2.16 (s, 3H), 1.80-1.63 (m, 2H), 1.55 (s, 3H), 1.01 (d, J=6.3 Hz, 3H).

Example 20: Synthesis of (S)-3-(3-(((R)-7-(4-(2-((S)-4-(4-chlorophenyl)-2,3,9-trimethyl-6H-thieno[3,2-f][1,2,4]triazolo[4,3-a][1,4]diazepin-6-yl)acetamido)butyl)-4-methyl-1,1-dioxido-3,4-dihydro-2H-benzo[b][1,4,5]oxathiazepin-2-yl)methyl)-4-methylphenyl)-3-(7-methoxy-1-methyl-1H-benzo[d][1,2,3]triazol-5-yl)propanoic acid (22)

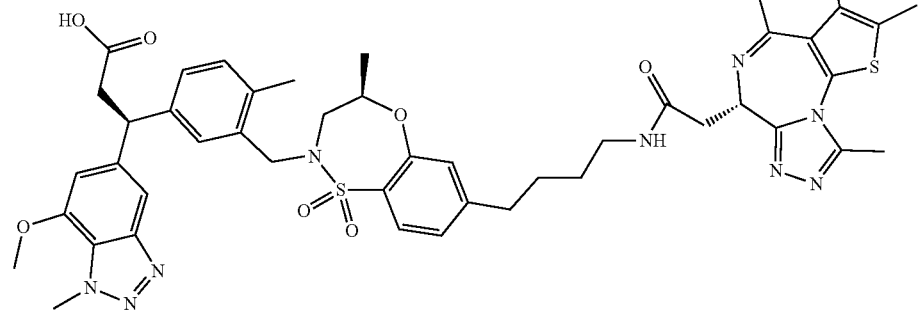

22

Bifunctional compound 22 was synthesized starting from tert-butyl but-3-yn-1-ylcarbamate and (R)-7-bromo-4-methyl-3,4-dihydro-2H-benzo[b][1,4,5]oxathiazepine 1,1-dioxide using the same procedure as used for bifunctional compound 22.

LC/MS m/z calculated for [M+H]+ 1004.33, found 1003.53. $^1$H NMR (500 MHz, DMSO-d6) δ 12.00 (s, 1H), 8.15 (t, J=5.7 Hz, 1H), 7.57 (d, J=7.9 Hz, 1H), 7.41 (d, J=8.8 Hz, 2H), 7.39-7.31 (m, 3H), 7.28 (d, J=2.0 Hz, 1H), 7.21 (dd, J=7.8, 1.9 Hz, 1H), 7.10 (d, J=8.1 Hz, 1H), 7.07 (s, 1H), 7.04 (d, J=7.9 Hz, 1H), 6.85 (s, 1H), 4.48-4.38 (m, 2H), 4.38-4.27 (m, 2H), 4.26 (s, 3H), 3.86 (s, 3H), 3.71 (d, J=14.0 Hz, 1H), 3.61-3.41 (m, 1H), 3.24-2.93 (m, 6H), 2.69-2.55 (m, 3H), 2.52 (s, 3H), 2.32 (s, 3H), 2.16 (s, 3H), 1.62-1.54 (m, 2H), 1.54-1.48 (m, 3H), 1.43 (p, J=7.1 Hz, 2H), 1.01 (d, J=6.3 Hz, 3H).

Example 21: (S)-3-(3-(((R)-7-(5-(2-((S)-4-(4-chlorophenyl)-2,3,9-trimethyl-6H-thieno[3,2-f][1,2,4]triazolo[4,3-a][1,4]diazepin-6-yl)acetamido)pentyl)-4-methyl-1,1-dioxido-3,4-dihydro-2H-benzo[b][1,4,5]oxathiazepin-2-yl)methyl)-4-methylphenyl)-3-(7-methoxy-1-methyl-1H-benzo[d][1,2,3]triazol-5-yl)propanoic acid (23)

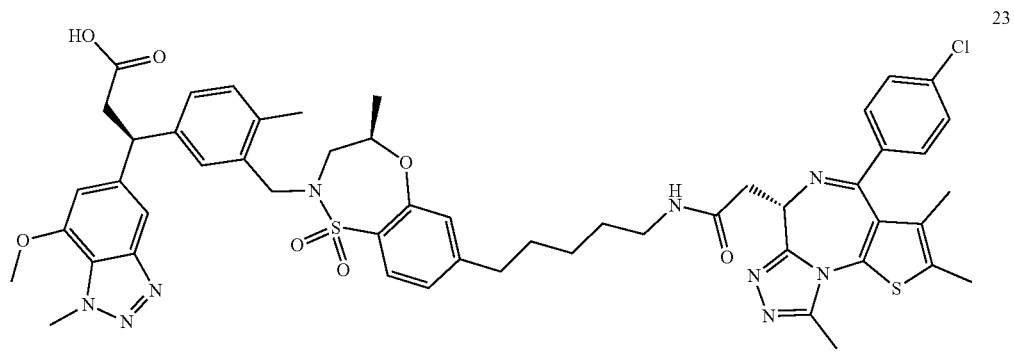

Bifunctional compound 23 was synthesized starting from tert-butyl pent-4-yn-1-ylcarbamate and (R)-7-bromo-4-methyl-3,4-dihydro-2H-benzo[b][1,4,5]oxathiazepine 1,1-dioxide using the same procedure as used for bifunctional compound 22.

LC/MS m/z calculated for [M+H]+ 1018.34, found 1017.53. $^1$H NMR (500 MHz, DMSO-d6) δ 12.01 (s, 1H), 8.13 (t, J=5.7 Hz, 1H), 7.59 (d, J=8.0 Hz, 1H), 7.46-7.39 (m, 2H), 7.39-7.33 (m, 3H), 7.27 (s, 1H), 7.21 (dd, J=7.8, 1.9 Hz, 1H), 7.09 (d, J=8.0, 1.6 Hz, 1H), 7.07-6.99 (m, 2H), 6.85 (d, J=1.2 Hz, 1H), 4.48-4.38 (m, 2H), 4.36-4.27 (m, 2H), 4.26 (s, 3H), 3.86 (s, 3H), 3.71 (d, J=14.0 Hz, 1H), 3.51 (dd, J=15.4, 10.1 Hz, 1H), 3.22-2.96 (m, 6H), 2.64 (d, J=14.8 Hz, 1H), 2.60-2.54 (m, 2H), 2.52 (s, 3H), 2.33 (s, 3H), 2.16 (s, 3H), 1.59-1.50 (m, 5H), 1.43 (m, 2H), 1.29 (m, 2H), 1.01 (d, J=6.3 Hz, 3H).

Example 22: Synthesis of (S)-3-(3-(((R)-7-(3-(2-(2-((S)-4-(4-chlorophenyl)-2,3,9-trimethyl-6H-thieno[3,2-f][1,2,4]triazolo[4,3-a][1,4]diazepin-6-yl)acetamido)ethoxy)propyl)-4-methyl-1,1-dioxido-3,4-dihydro-2H-benzo[b][1,4,5]oxathiazepin-2-yl)methyl)-4-methylphenyl)-3-(7-methoxy-1-methyl-1H-benzo[d][1,2,3]triazol-5-yl)propanoic acid (24)

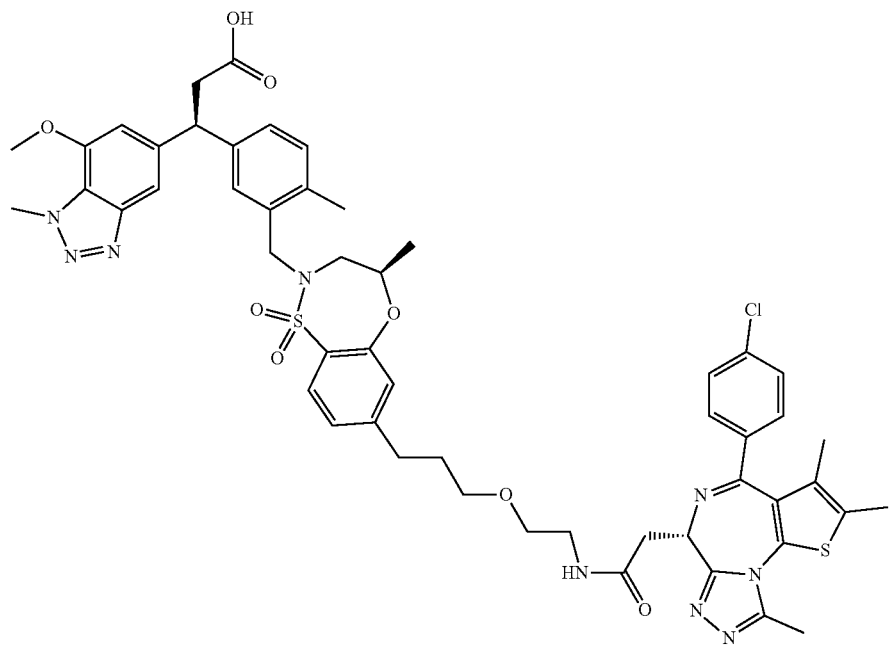

24

Bifunctional compound 24 was synthesized starting from tert-butyl (2-(prop-2-yn-1-yloxy)ethyl)carbamate and (R)-7-bromo-4-methyl-3,4-dihydro-2H-benzo[b][1,4,5]oxathiazepine 1,1-dioxide using the same procedure as used for bifunctional compound 21.

LC/MS m/z calculated for [M+H]$^+$ 1034.34, found 1033.54. $^1$H NMR (500 MHz, DMSO-d6) δ 12.02 (s, 1H), 8.22 (t, J=5.7 Hz, 1H), 7.58 (d, J=8.0 Hz, 1H), 7.41 (d, J=8.8 Hz, 2H), 7.38-7.32 (m, 3H), 7.27 (s, 1H), 7.21 (d, J=7.8 Hz, 1H), 7.11 (d, J=7.2 Hz, 1H), 7.07 (s, 1H), 7.04 (d, J=7.9 Hz, 1H), 6.85 (s, 1H), 4.49-4.39 (m, 2H), 4.37-4.27 (m, 2H), 4.26 (s, 3H), 3.85 (s, 3H), 3.71 (d, J=14.0 Hz, 1H), 3.51 (dd, J=15.4, 10.1 Hz, 1H), 3.38 (dh, J=6.1, 3.2, 2.6 Hz, 4H), 3.31-3.12 (m, 4H), 3.04-2.98 (m, 2H), 2.69-2.59 (m, 3H), 2.51 (s, 3H), 2.33 (s, 3H), 2.16 (s, 3H), 1.83-1.73 (m, 2H), 1.54 (s, 3H), 1.01 (d, J=6.3 Hz, 3H).

Example 23: (S)-3-(3-(((R)-7-(3-(2-(2-(2-((S)-4-(4-chlorophenyl)-2,3,9-trimethyl-6H-thieno[3,2-f][1,2,4]triazolo[4,3-a][1,4]diazepin-6-yl)acetamido)ethoxy)ethoxy)propyl)-4-methyl-1,1-dioxido-3,4-dihydro-2H-benzo[b][1,4,5]oxathiazepin-2-yl)methyl)-4-methylphenyl)-3-(7-methoxy-1-methyl-1H-benzo[d][1,2,3]triazol-5-yl)propanoic acid (25)

25

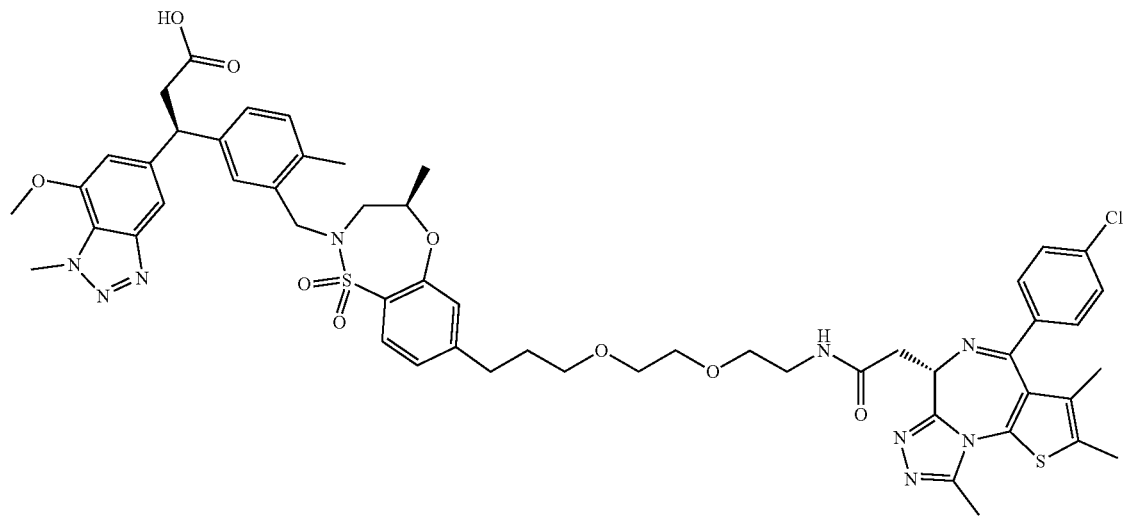

Bifunctional compound 25 was synthesized starting from tert-butyl (2-(2-(prop-2-yn-1-yloxy)ethoxy)ethyl)carbamate and (R)-7-bromo-4-methyl-3,4-dihydro-2H-benzo[b][1,4,5]oxathiazepine 1,1-dioxide using the same procedure as used for bifunctional compound 21.

LC/MS m/z calculated for [M+H]+ 1078.36, found 1077.65. $^1$H NMR (500 MHz, DMSO-d6) δ 12.03 (s, 1H), 8.22 (t, J=5.7 Hz, 1H), 7.58 (d, J=8.0 Hz, 1H), 7.41 (d, J=8.9 Hz, 2H), 7.38-7.32 (m, 3H), 7.27 (s, 1H), 7.21 (d, J=7.8 Hz, 1H), 7.09 (d, J=8.3 Hz, 1H), 7.07 (s, 1H), 7.04 (d, J=7.9 Hz, 1H), 6.85 (d, J=1.1 Hz, 1H), 4.47-4.39 (m, 2H), 4.31 (dd, J=20.9, 12.2 Hz, 2H), 4.26 (s, 3H), 3.85 (s, 3H), 3.71 (d, J=14.0 Hz, 1H), 3.52-3.47 (m, 3H), 3.46 (dd, J=5.6, 3.3 Hz, 2H), 3.42 (t, J=5.9 Hz, 2H), 3.35 (t, J=6.3 Hz, 2H), 3.30-3.10 (m, 4H), 3.07-2.97 (m, 2H), 2.68-2.59 (m, 3H), 2.51 (s, 3H), 2.33 (s, 3H), 2.15 (s, 3H), 1.81-1.71 (m, 2H), 1.56-1.51 (m, 3H), 1.01 (d, J=6.4 Hz, 3H).

Example 24: (S)-3-(3-(((R)-7-(1-((S)-4-(4-chlorophenyl)-2,3,9-trimethyl-6H-thieno[3,2f][1,2,4]triazolo[4,3-a][1,4]diazepin-6-yl)-2-oxo-6,9,12-trioxa-3-azapentadecan-15-yl)-4-methyl-1,1-dioxido-3,4-dihydro-2H-benzo[b][1,4,5]oxathiazepin-2-yl)methyl)-4-methylphenyl)-3-(7-methoxy-1-methyl-1H-benzo[d][1,2,3]triazol-5-yl)propanoic acid (26)

26

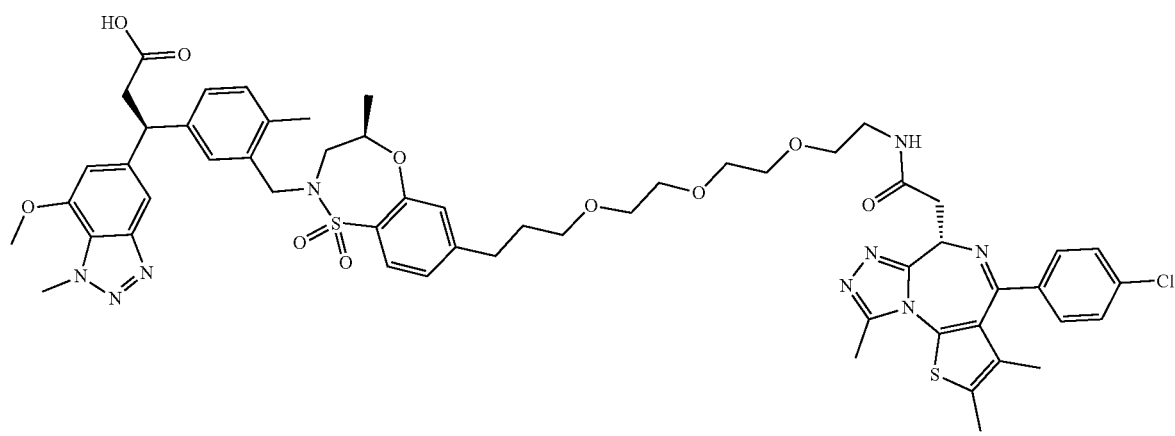

Bifunctional compound 26 was synthesized starting from tert-butyl (2-(2-(2-(prop-2-yn-1-yloxy)ethoxy)ethoxy)ethyl) carbamate and (R)-7-bromo-4-methyl-3,4-dihydro-2H-benzo[b][1,4,5]oxathiazepine 1,1-dioxide using the same procedure as used for bifunctional compound 26.

LC/MS m/z calculated for [M+H]$^+$ 1122.39, found 1121.66. $^1$H NMR (500 MHz, DMSO-d6) δ 12.03 (s, 1H), 8.20 (t, J=5.7 Hz, 1H), 7.58 (d, J=8.0 Hz, 1H), 7.41 (d, J=8.7 Hz, 2H), 7.38-7.31 (m, 3H), 7.27 (s, 1H), 7.21 (d, J=7.9 Hz, 1H), 7.10 (d, J=8.3 Hz, 1H), 7.07 (s, 1H), 7.03 (d, J=7.9 Hz, 1H), 6.85 (s, 1H), 4.48-4.36 (m, 2H), 4.36-4.27 (m, 2H), 4.26 (s, 3H), 3.85 (s, 3H), 3.71 (d, J=14.0 Hz, 1H), 3.48 (d, J=4.7 Hz, 5H), 3.46-3.30 (m, 10H), 3.29-3.09 (m, 2H), 3.06-2.94 (m, 2H), 2.69-2.55 (m, 3H), 2.51 (s, 3H), 2.32 (s, 3H), 2.15 (s, 3H), 1.81-1.71 (m, 2H), 1.54 (s, 3H), 1.01 (d, J=6.3 Hz, 3H).

Example 25: ethyl (S)-3-(3-(((R)-7-(6-(2-((S)-4-(4-chlorophenyl)-2,3,9-trimethyl-6H-thieno[3,2-f][1,2,4]triazolo[4,3-a][1,4]diazepin-6-yl)acetamido) hexyl)-4-methyl-1,1-dioxido-3,4-dihydro-2H-benzo[b][1,4,5]oxathiazepin-2-yl)methyl)-4-methylphenyl)-3-(7-methoxy-1-methyl-1H-benzo[d][1,2,3]triazol-5-yl)propanoate (27)

HPLC to provide bifunctional compound 27 as a white solid (9.4 mg, 0.0089 mmol, 52%).

LC/MS m/z calculated for [M+H]$^+$ 1060.39, found 1059.74. $^1$H NMR (500 MHz, DMSO-d6) δ 8.18 (t, J=5.6 Hz, 1H), 7.66 (d, J=7.9 Hz, 1H), 7.53-7.39 (m, 5H), 7.36 (d, J=2.0 Hz, 1H), 7.28 (d, J=7.8 Hz, 1H), 7.16 (d, J=8.1 Hz, 1H), 7.13-7.08 (m, 2H), 6.94 (s, 1H), 4.56-4.49 (m, 2H), 4.45-4.35 (m, 2H), 4.34 (s, 3H), 3.98-3.90 (m, 5H), 3.79 (d, J=14.1 Hz, 1H), 3.60 (dd, J=15.3, 10.1 Hz, 1H), 3.30-3.02 (m, 6H), 2.73 (d, J=15.0 Hz, 1H), 2.68-2.61 (m, 2H), 2.60 (s, 3H), 2.42-2.36 (m, 3H), 2.23 (s, 3H), 1.63-1.54 (m, 5H), 1.52-1.41 (m, 2H), 1.35 (p, J=3.6 Hz, 4H), 1.10 (d, J=6.3 Hz, 3H), 1.04 (t, J=7.1 Hz, 3H).

Example 26: Cellular Degradation of BRD4-BD2 Domain

To evaluate the activity of KEAP1-BRD targeting degraders in the cell, FACS-enabled stable reporter cell lines for single Bromodomain (BD) of the BRD2, 3 and 4 proteins were developed using the pCDNA5/FRT vector of the FLp-In system and followed the manufacturer's protocol.

A DNA sequence was constructed where a single BD (BD1 or BD2) of a BRD protein was tagged at the C-terminus with an enhanced Green Fluorescent Protein (eGFP).

27

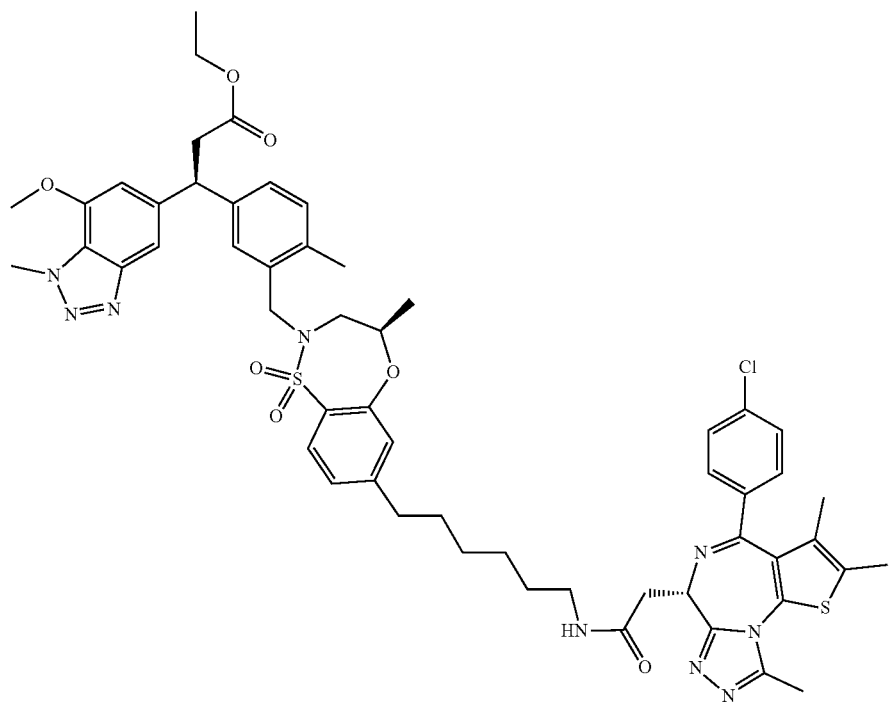

Ethyl (S)-3-(3-(((R)-7-(6-(2-((S)-4-(4-chlorophenyl)-2,3,9-trimethyl-6H-thieno[3,2-f][1,2,4]triazolo[4,3-a][1,4]diazepin-6-yl)acetamido)hexyl)-4-methyl-1,1-dioxido-3,4-dihydro-2H-benzo[b][1,4,5]oxathiazepin-2-yl)methyl)-4-methylphenyl)-3-(7-methoxy-1-methyl-1H-benzo[d][1,2,3]triazol-5-yl)propanoate (14 mg, 0.017 mmol) and (S)-2-(4-(4-chlorophenyl)-2,3,9-trimethyl-6H-thieno[3,2-f][1,2,4]triazolo[4,3-a][1,4]diazepin-6-yl)acetic acid (7 mg, 0.017 mmol) were dissolved in DMF (1 mL). DIEA (15 µL, 0.085 mmol) was added, followed by HATU (13 mg, 0.034 mmol). The mixture was stirred for 20 minutes, then purified by This sequence was followed by a P2A linker and a sequence that codes for mCherry fluorescent protein. The P2A linker that is located between the eGFP-tagged protein and the mCherry causes a single cut in the backbone amide bonds of the polypeptide during the translation of the mRNA, resulting in generation of two polypeptide chains, an eGFP-tagged protein and a mCherry protein. The expression level of these two polypeptides is therefore identical as they originate from a single mRNA, making the mCherry signal an expression level reporter as an internal reference.

Treatment of these reporter cell lines with compounds that have JQ1 as a warhead reports not only on their activities but also their specificity for each BD of the various BRD proteins.

The reporter cell lines were seeded on a 48-well plate the day before. The adherent FLp-In cells were then treated with a concentration series of bifunctional compound 9, starting at 20 µM with a 5× dilution in every step, consisting 5 dilution steps and one zero-compound condition for each reporter cell line, for 24 hours at 37° C. The final concentration of DMSO was normalized at 0.2% in all conditions.

The treated cells were then harvested by trypsin digest, brought to a volume of 200 µL with DMEM medium supplemented with 10% FBS and transferred to a 96-well assay plate for FACS reading. The eGFP/RFP ratio for each condition was then calculated and normalized against the zero-compound condition and plotted.

FIG. 1A shows that bifunctional compound 9 had a modest preference for BRD2$^{BD1}$ and BRD4$^{BD1}$.

Figure 1B:
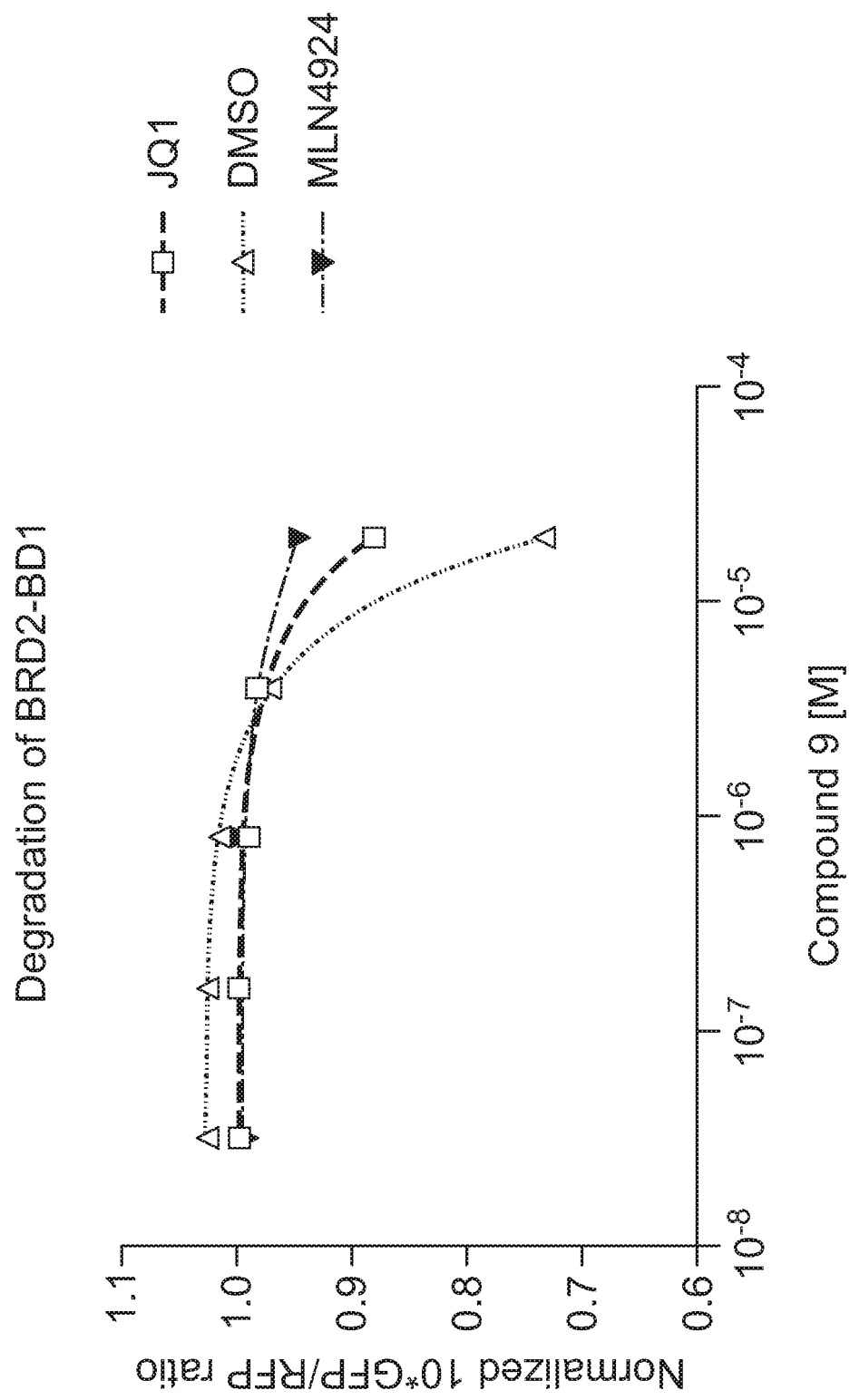
FIG. 1B is a graph that shows the rescue of BRD2$^{BD1}$ degradation by the targeting ligands JQ1 and MLN4924 as inhibitors, measured in terms of normalized 10* GFP/RFP ratio as a function of concentration (expressed in units of M), assayed in reporter cell lines, each expressing one of the bromodomains of BRD2/3/4 (BRD2-BD1, BRD2-BD2, BRD3-BD1, BRD3-BD2, BRD4-BD1, BRD4-BD2) as GFP fusion proteins together with RFP.

FIG. 1B shows the rescue of BRD2$^{BD1}$ degradation with two commercially available inhibitors, JQ1 and MLN4924. The experiment was set up as in above, except that the cells were first pre-treated with 10 µM final concentration of JQ1, MLN4924 or 0.1% DMSO control for 1 hour. The pre-treated cells were then treated with concentration series of bifunctional compound 9 that was prepared in the presence of inhibitors, for another 24 hours.

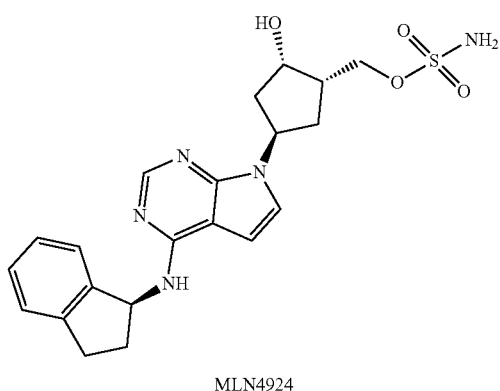 [SMILES: NS(=O)(=O)OC[C@@H]1C[C@@H](n2ccc3c(N[C@H]4CCc5ccccc54)ncnc32)C[C@@H]1O]

MLN4924

Since the degradation via bifunctional compound 9 can be rescued by JQ1 which competes with the degrader compound for binding to bromodomains of BRD proteins, these results confirm that the decrease in eGFP/RFP observed is a specific and direct effect of bifunctional compound 9. In addition, the degradation is rescued by the neddylation inhibitor, MLN4924, which is a mechanistic inhibitor of CRBN activity, further confirmed that the decrease in eGFP/RFP ratio in treated cells depends on the E3 ligase protein degradation pathway.

Example 27: Cellular Degradation of BRD2, BRD3 and BRD4-BD2

The experimental protocol is as in Example 16.

The degradation of various BRD-BD with bifunctional compound 1 was compared, starting at 20 µM with a 5× dilution in every step, consisting 5 dilution steps and one zero-compound condition for each reporter cell line, for 24 hours at 37° C. The final concentration of DMSO was normalized at 0.2% in all conditions.

The treated cells were then harvested by trypsin digest, brought to a volume of 200 µL with DMEM medium supplemented with 10% FBS and transferred to a 96-well assay plate for FACS reading. The eGFP/RFP ratio for each condition was then calculated and normalized against the zero-compound condition and plotted.

Figure 2A:
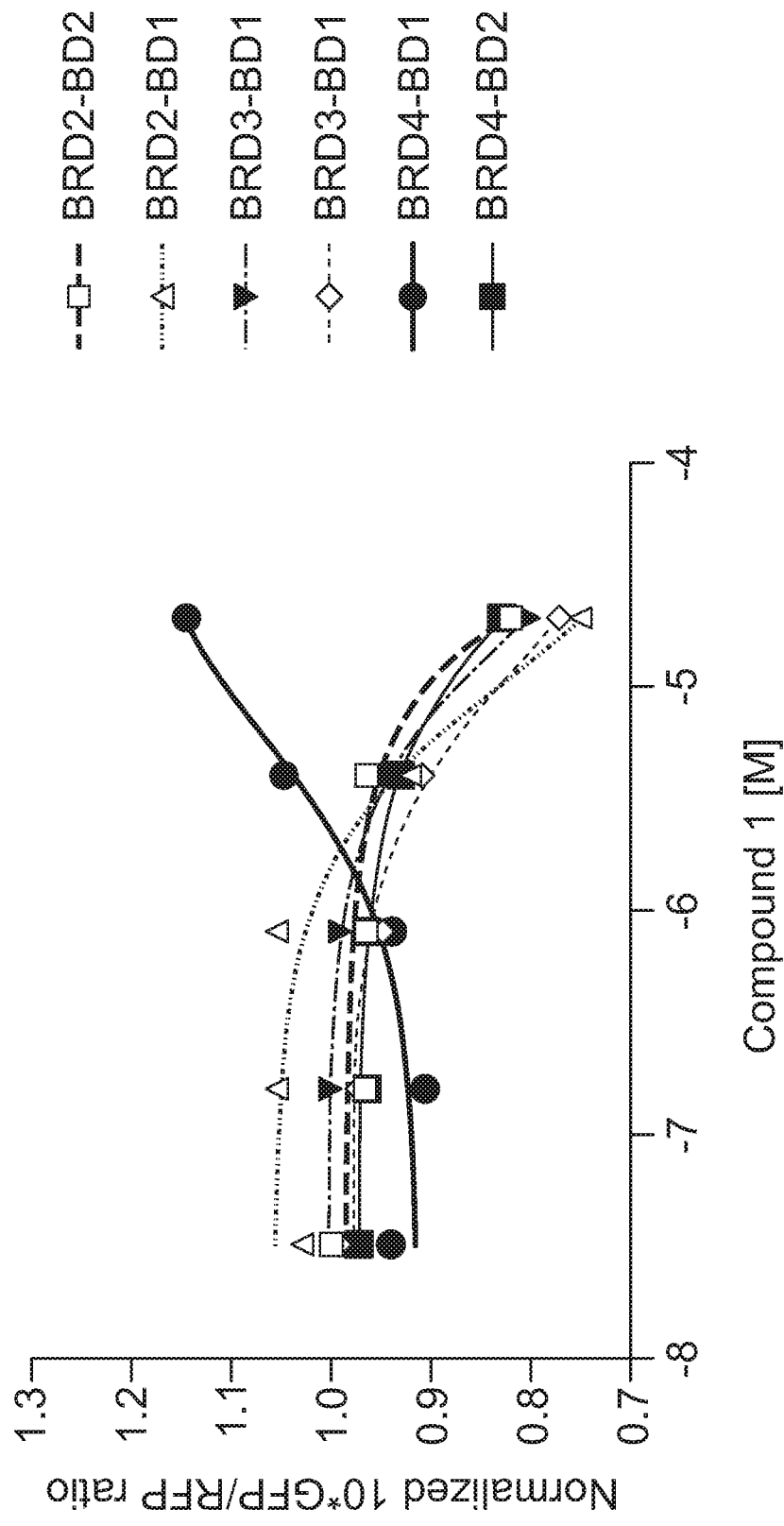
FIG. 2A is a graph that shows degradation of BRD proteins (BRD2, BRD3 and BRD4) by an inventive bifunctional compound 1 compared to controls, measured in terms of normalized 10* GFP/RFP ratio as a function of concentration (expressed in units of M), assayed in reporter cell lines, each expressing one of the bromodomains of BRD2/3/4 (BRD2-BD1, BRD2-BD2, BRD3-BD1, BRD3-BD2, BRD4-BD1, BRD4-BD2) as GFP fusion proteins together with RFP.

FIG. 2A shows that with the exception of BRD4BD1, bifunctional compound 1 targeted BRD-BD proteins with similar efficiency.

The rescue of BRD2BD2 degradation with two inhibitors JQ1 and MLN4924 was then determined. The experiment was set up as in above, except that the cells were first pre-treated with 10 µM final concentration of JQ1, MLN4924 or 0.1% DMSO control for 1 hour. The pre-treated cells were then treated with concentration series of bifunctional compound 1 that was prepared in the presence of inhibitors, for another 24 hours.

Figure 2B:
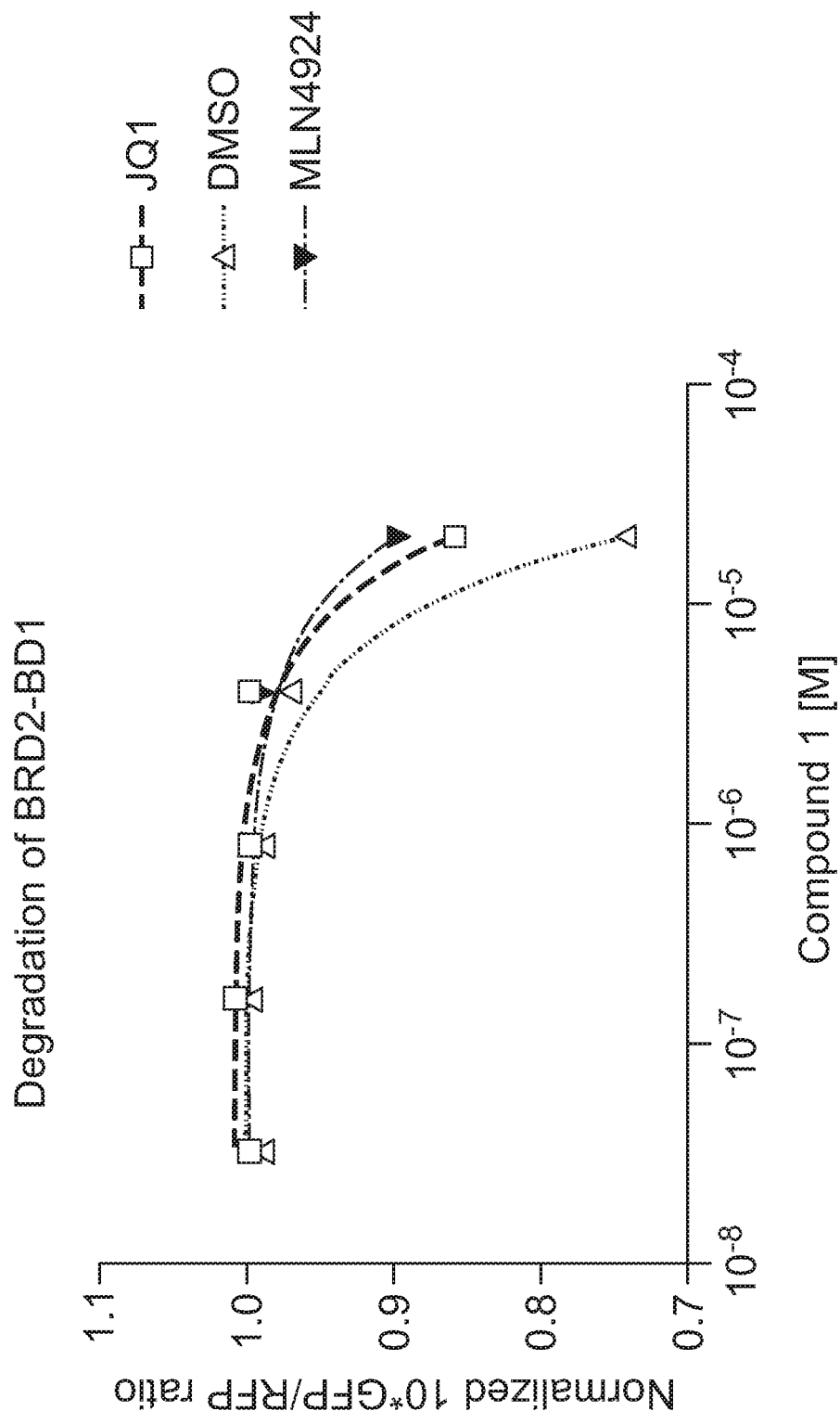
FIG. 2B is a graph that shows the rescue of BRD2-BD1 degradation by inhibitors MLN4924 and JQ1, measured in terms of normalized 10* GFP/RFP ratio as a function of concentration (expressed in units of M), assayed in reporter cell lines, each expressing one of the bromodomains of BRD2/3/4 (BRD2-BD1, BRD2-BD2, BRD3-BD1, BRD3-BD2, BRD4-BD1, BRD4-BD2) as GFP fusion proteins together with RFP.

Since the degradation via bifunctional compound 1 can be rescued by JQ1 which competes with the degrader compound for binding to BRD domains, these results (FIG. 2B) confirm that the decrease in eGFP/RFP observed is a specific and direct effect of bifunctional compound 1. In addition, the degradation is rescued by the neddylation inhibitor, MLN4924, which is a mechanistic inhibitor of CRBN activity, further confirms that the decrease in eGFP/RFP ratio in treated cells depends on the E3 ligase protein degradation pathway.

Example 28: Cellular Degradation of BRD4, BRD3 and BRD2 Domain

Figure 3B:
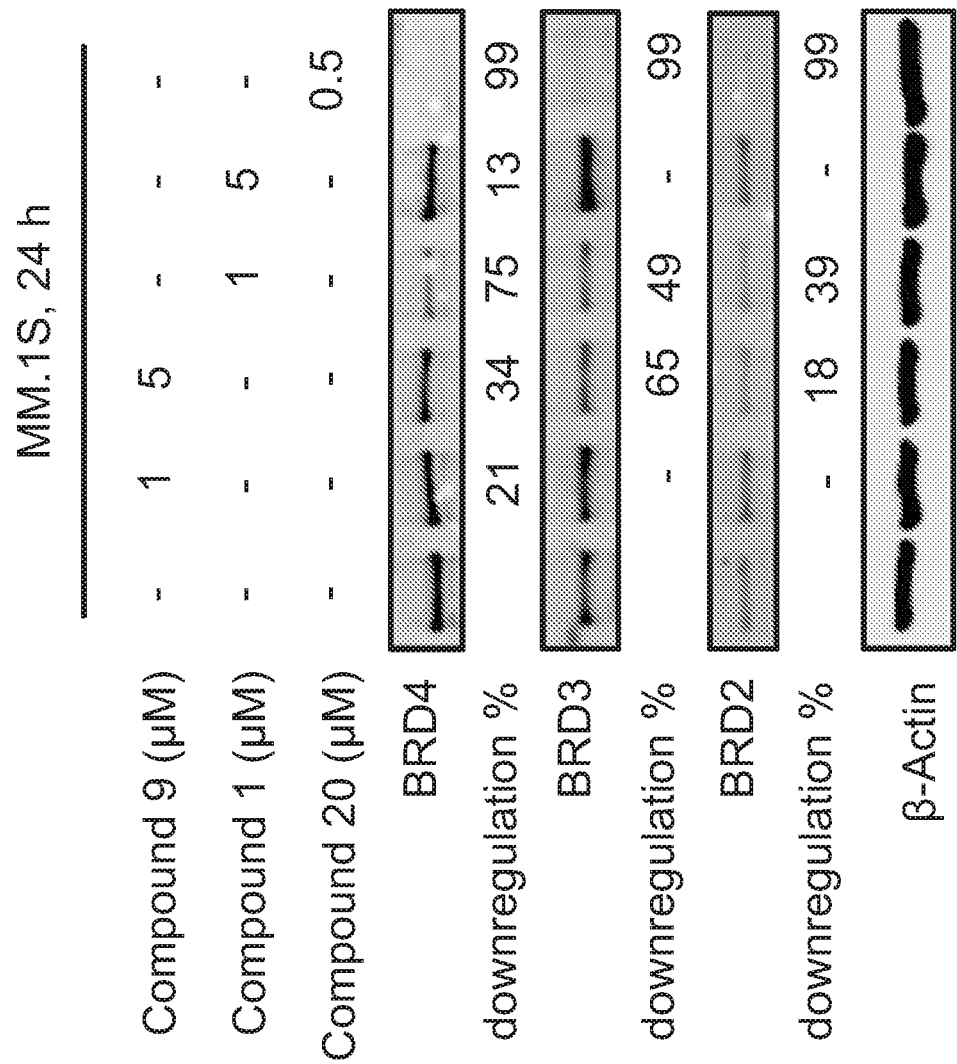

MM.1S multiple myeloma cells were treated with 0, 1, 5 µM bifunctional compound 1 and 9 or bifunctional compound 20 (0.5 µM, as a positive control, known degrader of BRD) for 14 or 24 h, then lysed and immunoblotted with antibodies to BRD2, BRD3, BRD4 and β-Actin. The results (FIG. 3A-FIG. 3B) indicated that bifunctional compound 1 strongly induced the degradation of BRD3 and BRD4, and slightly decreased the abundance of BRD2 after both 14 and 24 h treatment at the concentration of 1 µM. Notably, at the concentration of 5 µM, a decrease in BRD2, BRD3 and BRD4 degradation were observed (known as the 'hook effect'). A second degrader compound 9 slightly degraded BRD2, BRD3 and BRD4 after 24 h treatment at the concentration of 5 µM.

Example 29: Cellular Degradation of BRD4, BRD3 and BRD2 Domain

Figure 3C:
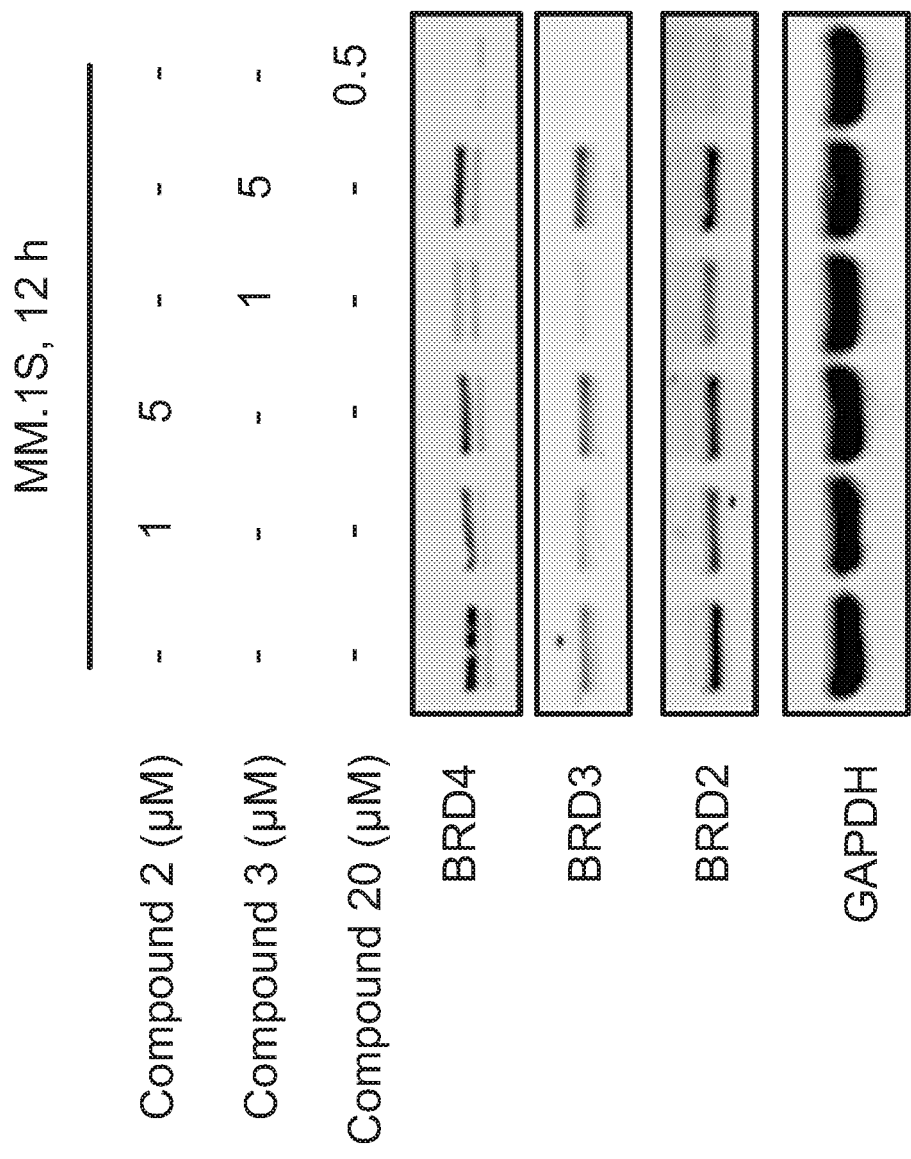
FIG. 3C-FIG. 3D are Western blots that show the degradation of BRD4, BRD3 and BRD2 by inventive bifunctional compounds 2 and 3 over time (12 hours and 24 hours) and as a function of concentration (μM) as compared to controls.
Figure 3D:
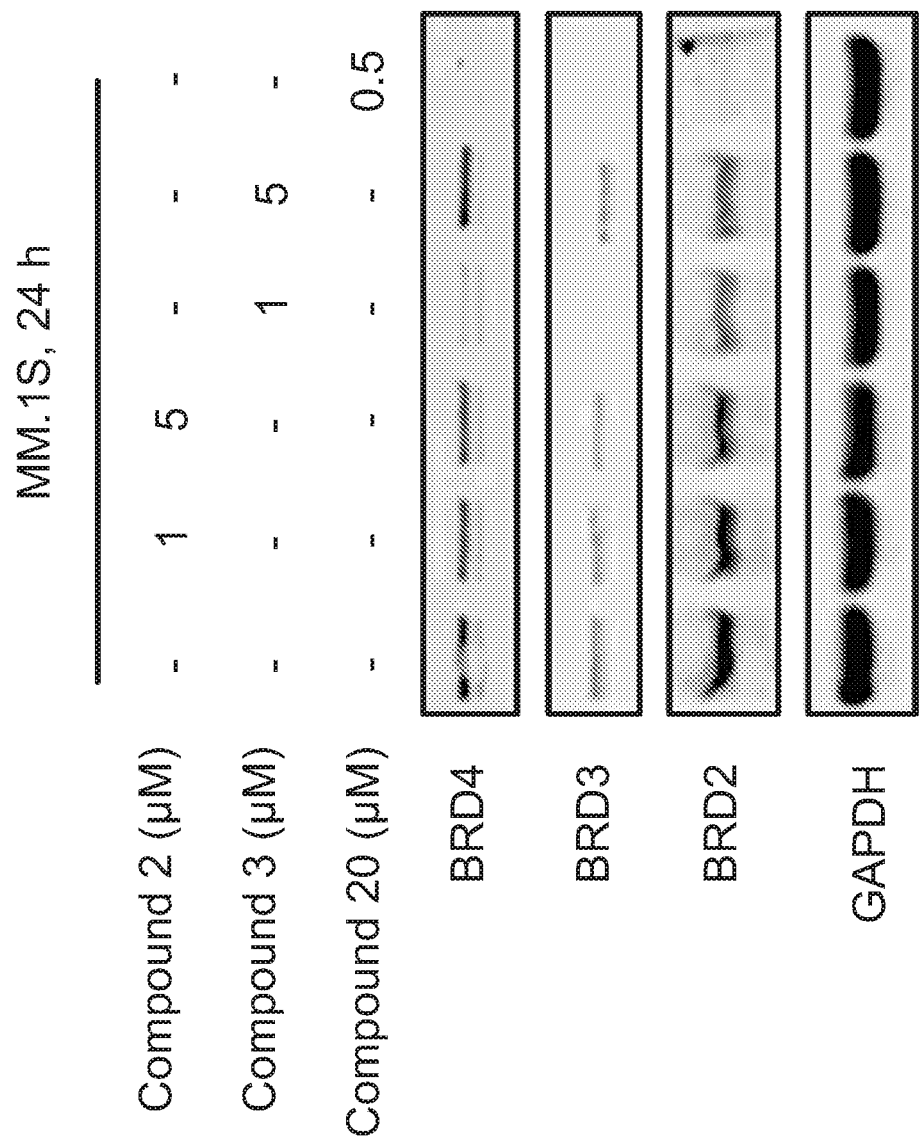

MM.1S multiple myeloma cells were treated with 0, 1, 5 µM bifunctional compound 1 and 9 or bifunctional compound 20 (0.5 µM, as a positive control) for 14 or 24 h, then lysed and immunoblotted with antibodies to BRD2, BRD3, BRD4 and β-Actin. The results (FIG. 3C-FIG. 3D) indicated that bifunctional compound 1 strongly induced the degradation of BRD3 and BRD4, and slightly decreased the abundance of BRD2 after both 14 and 24 h treatment at the concentration of 1 µM. Notably, at the concentration of 5 µM, a decrease in BRD2, BRD3 and BRD4 degradation were observed (known as the 'hook effect'). A second degrader compound 9 slightly degraded BRD2, BRD3 and BRD4 after 24 h treatment at the concentration of 5 µM.

Example 30: Analysis of Change to Cellular Protein Abundance in Response to Treatment with Bifunctional Compound 9

Lysis buffer (8 M Urea, 50 mM NaCl, 50 mM 4-(2hydroxyethyl)-1-piperazineethanesulfonic acid (EPPS) pH 8.5.

Protease and Phosphatase inhibitors from Roche) was added to the cell pellets and homogenized by 20 passes through a 21 gauge (1.25 in. long) needle to achieve a cell lysate with a protein concentration between 1-4 mg/mL. A micro-BCA assay (Pierce™) was used to determine the final protein concentration in the cell lysate. 200 µg of protein for each sample were reduced and alkylated as previously described. Proteins were precipitated using methanol/chloroform. In brief, four volumes of methanol were added to the cell lysate, followed by one volume of chloroform, and finally three volumes of water. The mixture was vortexed and centrifuged to separate the chloroform phase from the aqueous phase. The precipitated protein was washed with three volumes of methanol, centrifuged and the resulting washed precipitated protein was allowed to air dry.

Precipitated protein was resuspended in 4 M urea, 50 mM HEPES pH 7.4, followed by dilution to 1 M urea with the addition of 200 mM EPPS, pH 8. Proteins were first digested with LysC (1:50; enzyme:protein) for 12 hours at room temperature. The LysC digestion was diluted to 0.5 M Urea with 200 mM EPPS pH 8 followed by digestion with trypsin (1:50; enzyme:protein) for 6 hours at 37° C. Tandem mass tag (TMT) reagents (Thermo Fisher Scientific™) were dissolved in anhydrous acetonitrile (ACN) according to manufacturer's instructions. Anhydrous ACN was added to each peptide sample to a final concentration of 30% v/v, and labeling was induced with the addition of TMT reagent to each sample at a ratio of 1:4 peptide:TMT label. The 10-plex labeling reactions were performed for 1.5 hours at room temperature and the reaction quenched by the addition of hydroxylamine to a final concentration of 0.3% for 15 minutes at room temperature. The sample channels were combined at a 1:1:1:1:1:1:1:1:1:1 ratio, desalted using $C_{18}$ solid phase extraction cartridges (Waters™) and analyzed by LC-MS for channel ratio comparison.

Samples were then combined using the adjusted volumes determined in the channel ratio analysis and dried down in a speed vacuum. The combined sample was then resuspended in 1% formic acid, and acidified (pH 2-3) before being subjected to desalting with C18 SPE (Sep-Pak™ Waters™). Samples were then offline fractionated into 96 fractions by high pH reverse-phase HPLC (Agilent™ LC1260) through an aeris peptide xb-c18 column (Phenomenex®) with mobile phase A containing 5% acetonitrile and 10 mM $NH_4HCO_3$ in LC-MS grade $H_2O$, and mobile phase B containing 90% acetonitrile and 10 mM $NH_4HCO_3$ in LC-MS grade $H_2O$ (both pH 8.0). The 96 resulting fractions were then pooled in a non-continuous manner into 24 fractions and these fractions were used for subsequent mass spectrometry analysis. Data were collected using an Orbitrap Fusion Lumos mass spectrometer (Thermo Fisher Scientific™, San Jose, CA, USA) coupled with a Proxeon EASY-nLC 1200 LC pump (Thermo Fisher Scientific™). Peptides were separated on a 75 µM inner diameter microcapillary column packed with ~50 cm of Accucore C18 resin (1.8 µM, 100 Å, Thermo Fisher Scientific™). Peptides were separated using a 190 mi gradient of 6-27% acetonitrile in 1.0% formic acid with a flow rate of 400 nL/min. Each analysis used an MS3-based TMT method as described previously.

The data (illustrated in FIGS. 4 and 5) were acquired using a mass range of m/z 340-1350, resolution 120,000, AGC target $1 \times 10^6$, maximum injection time 100 ms, dynamic exclusion of 120 seconds for the peptide measurements in the Orbitrap. Data dependent MS2 spectra were acquired in the ion trap with a normalized collision energy (NCE) set at 55%, AGC target set to $1.5 \times 10^5$ and a maximum injection time of 150 ms. MS3 scans were acquired in the Orbitrap with a HCD collision energy set to 55%, AGC target set to $1.5 \times 10^5$, maximum injection time of 150 ms, resolution at 50,000 and with a maximum synchronous precursor selection (SPS) precursors set to 10. Proteome Discoverer 2.2 (Thermo Fisher Scientific™) was used for RAW file processing and controlling peptide and protein level false discovery rates, assembling proteins from peptides, and protein quantification from peptides. MS/MS spectra were searched against a Uniprot human database (September 2016) with both the forward and reverse sequences. Database search criteria are as follows: tryptic with two missed cleavages, a precursor mass tolerance of 20 ppm, fragment ion mass tolerance of 0.6 Da, static alkylation of cysteine (57.02146 Da), static TMT labelling of lysine residues and N-termini of peptides (229.16293 Da), and variable oxidation of methionine (15.99491 Da). TMT reporter ion intensities were measured using a 0.003 Da window around the theoretical m/z for each reporter ion in the MS3 scan. Peptide spectral matches with poor quality MS3 spectra were excluded from quantitation (summed signal-to-noise across 10 channels<200 and precursor isolation specificity <0.5), and resulting data was filtered to only include proteins that had a minimum of 3 unique peptides identified. Reporter ion intensities were normalised and scaled using in-house scripts in the R framework. Statistical analysis was carried out using the limma package within the R framework.

Figure 4:
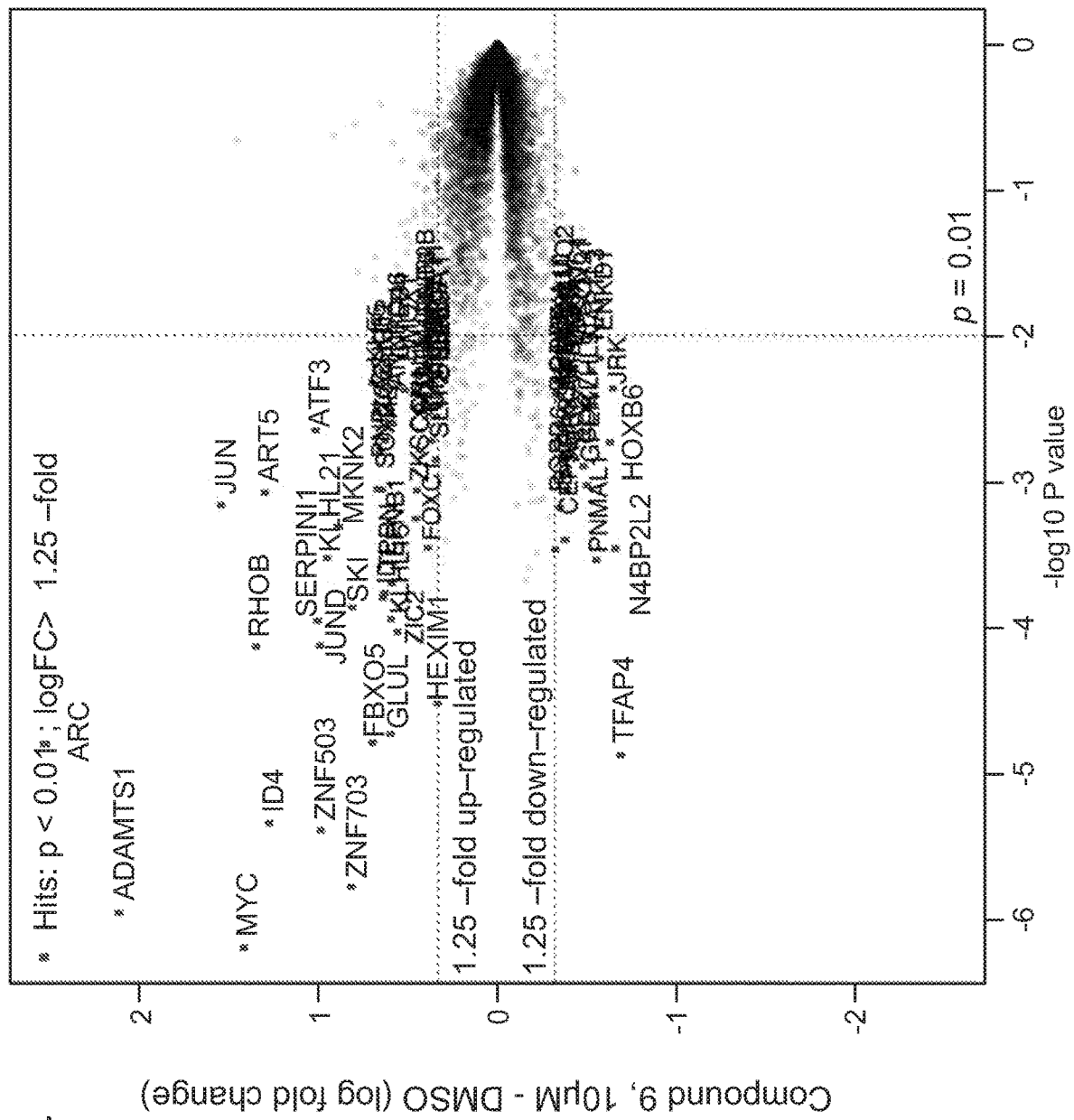
FIG. 4 is a scatter plot that shows the change in relative protein abundance with treatment of inventive bifunctional compound 9 (10 μM, 6 hours×2), compared to dimethyl sulfoxide (DMSO) control. Significant changes were assessed by moderated t-test and displayed with log 2 fold change on the y-axis and negative $\log_{10}$ P values on the x-axis for two independent biological replicates of compound 9 and three independent biological replicates of DMSO.

HEK293T cells were treated with DMSO control (biological replicates) or 10 µM bifunctional compound 9 for 6 hours (biological duplicates). FIG. 4 is a scatter plot depicting the change in relative protein abundance with treatment of bifunctional compound 9 (10 µM, 6 hours, ×2) compared to DMSO control. Proteins with changes that meet the significance threshold (>1.25–FC and p<0.01) are displayed as a red dot with the corresponding protein name next to it. Log 2FC is displayed on the y-axis and −Clog 10 P-value is displayed on the x-axis.

Figure 5:
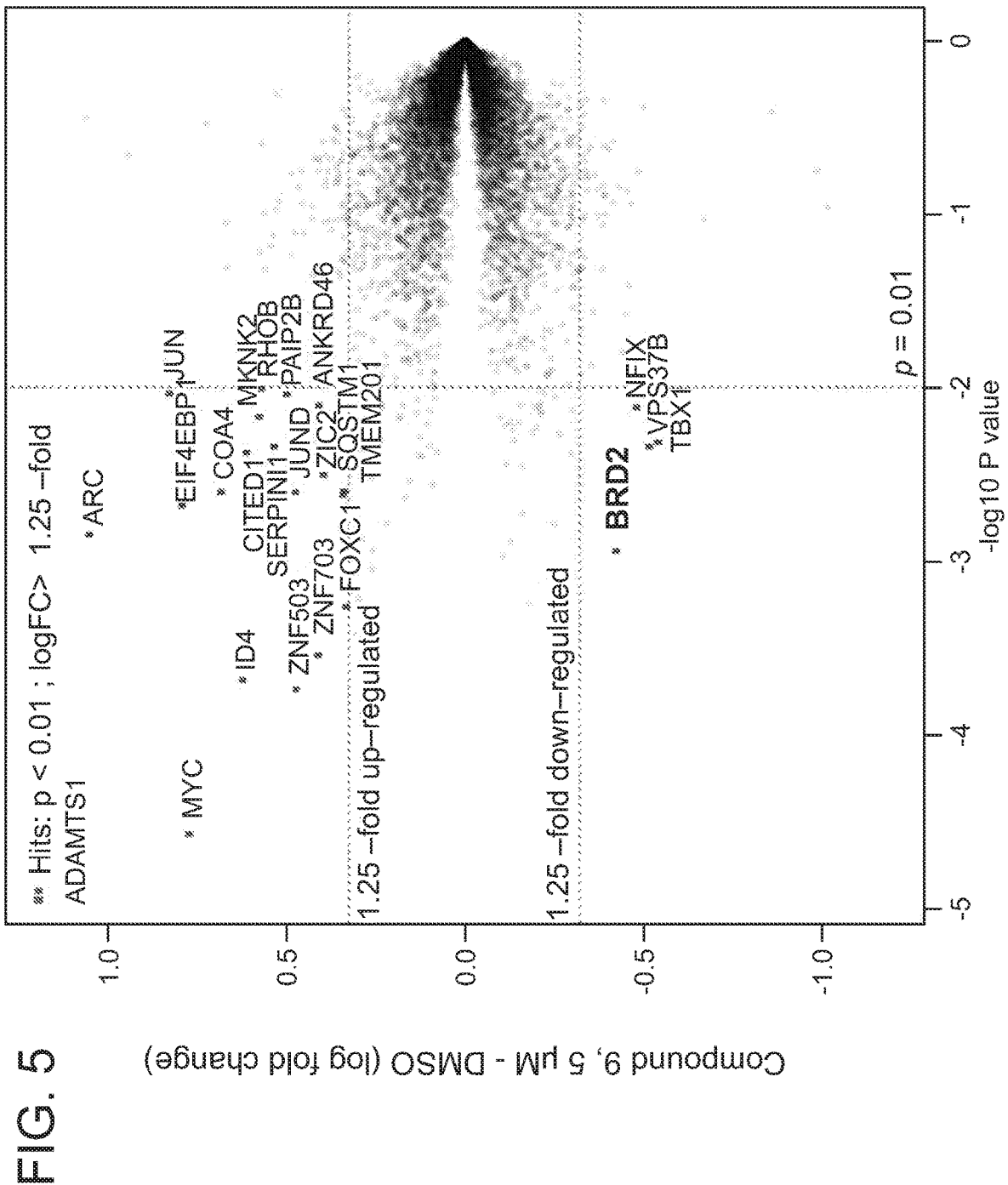
FIG. 5 is a scatter plot that shows the change in relative protein abundance with treatment of inventive bifunctional compound 9 (5 μM, 6 hours×2), compared to DMSO control. Significant changes were assessed by moderated t-test and displayed with log 2 fold change on the y-axis and negative $\log_{10}$ P values on the x-axis for two independent biological replicates of bifunctional compound 9 and three independent biological replicates of DMSO.

HEK293T cells were treated with DMSO control (biological replicates) or 5 µM bifunctional compound 9 for 6 hours (biological duplicates). FIG. 5 is a scatter plot depicting the change in relative protein abundance with treatment of bifunctional compound 9 (5 µM, 6 hours, ×2) compared to DMSO control. Proteins with changes that meet the significance threshold (>1.25–FC and p<0.01) are displayed as a red dot with the corresponding protein name next to it. BRD2 is enlarged and shown in bold.

Since BRD2 degradation was observed in the 5 µM treatment, but not the 10 µM treatment, it is suggestive that 10 µM is in the range of the bifunctional compound "hook effect". Log 2FC is displayed on the y-axis and −log 10 P-value is displayed on the x-axis.

Example 31: Analysis of Change to Cellular Protein Abundance in Response to Treatment with Bifunctional Compound 1

The experimental protocol is as in Example 21. MM1s cells were treated with DMSO control (biological replicates) or 1 µM bifunctional compound 1 for 5 hours (biological replicates).

Figure 6:
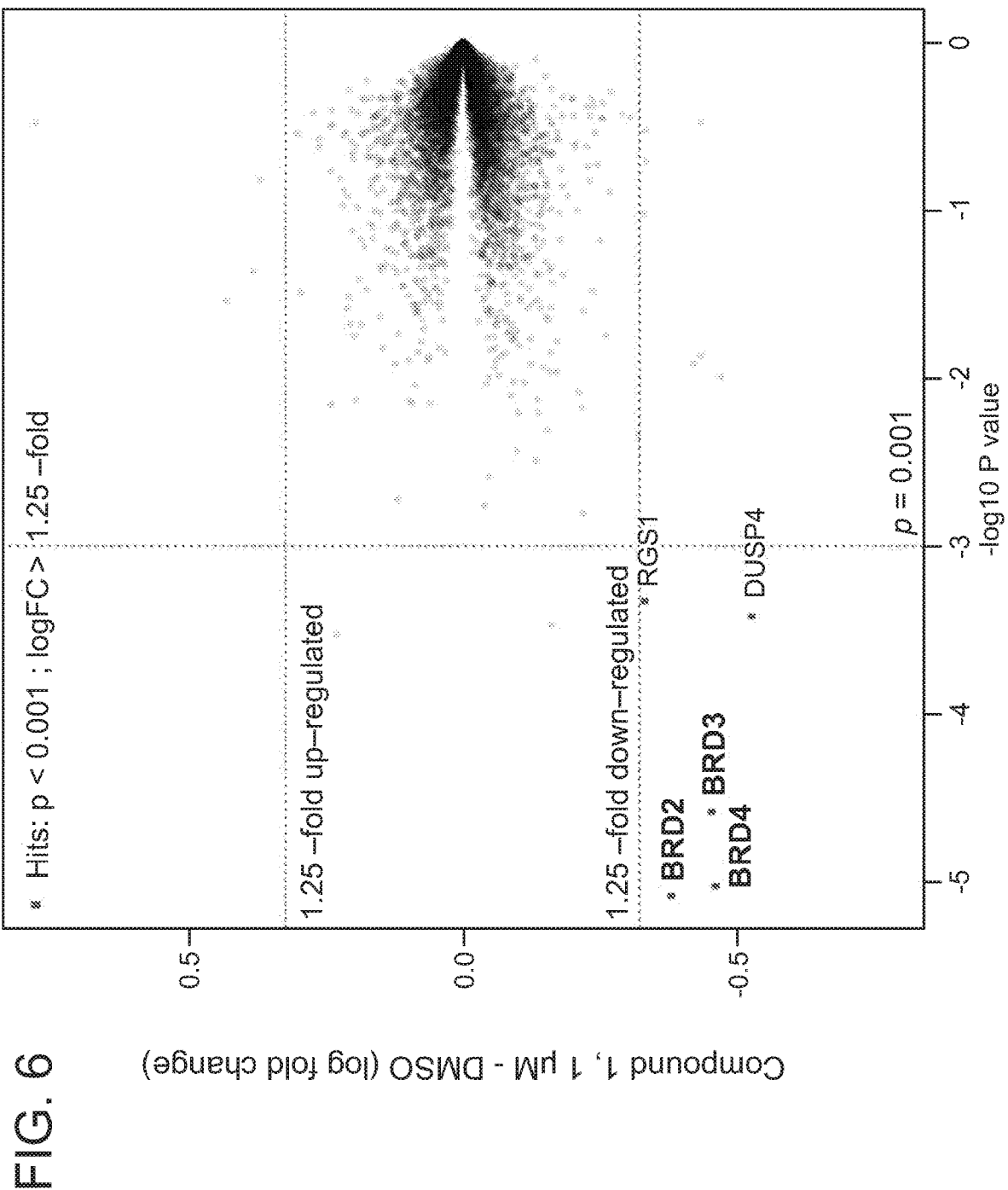
FIG. 6 is a scatter plot that shows the change in relative protein abundance with treatment of inventive bifunctional compound 1 (1 μM, 5 hours×2), compared to DMSO control. Significant changes were assessed by moderated t-test and displayed with log 2 fold change on the y-axis and negative $\log_{10}$ P values on the x-axis for three independent biological replicates of bifunctional compound 1 and three independent biological replicates of DMSO.

FIG. 6 is a scatter plot depicting the change in relative protein abundance with treatment of bifunctional compound 1 (1 µM, 5 hours, ×3) compared to DMSO control. Proteins with changes that met the significance threshold (>1.25–FC and p<0.001) are displayed as a red dot with the corresponding protein name next to it. BRD2, BRD3 and BRD4 are enlarged and shown in bold. Log 2FC is displayed on the y-axis and −log 10 P-value is displayed on the x-axis.

All patent publications and non-patent publications are indicative of the level of skill of those skilled in the art to which this invention pertains. All these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

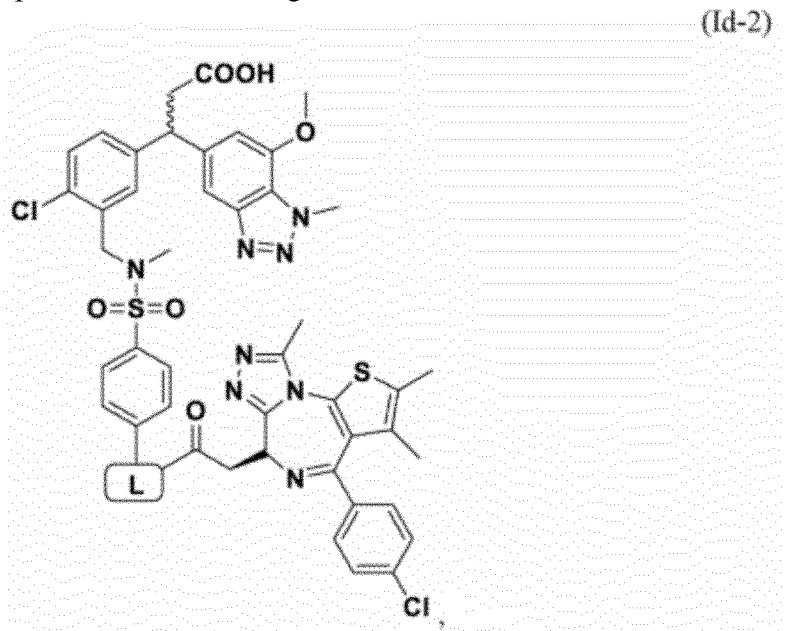

What is claimed is:

1. A bifunctional compound of formula (I):

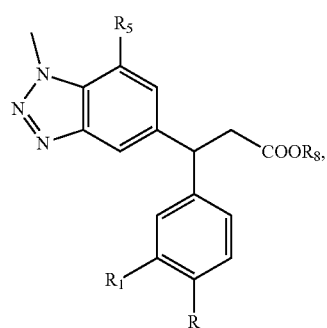

(I)

wherein:
R is methyl or halo;

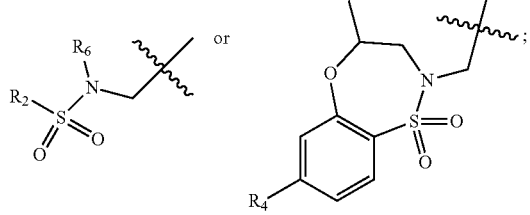

$R_2$ is methyl,

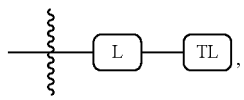

wherein L is a linker comprising an alkylene chain or a bivalent alkylene chain which may be interrupted by, and/or terminate at either or both termini in at least one of —O—, —S—, —N(R')—, —C(O)—, —C(O)O—, —OC(O)—, —OC(O)O—, —C(NOR')—, —C(O)N(R')—, —C(O)N(R')C(O)—, —C(O)N(R')C(O)N(R')—, —N(R')C(O)—, —N(R')C(O)N(R')—, —N(R')C(O)O—, —OC(O)N(R')—, —C(NR')—, —N(R')C(NR')—, —C(NR')N(R')—, —N(R')C(NR')N(R')—, —S(O)$_2$—, —OS(O)—, —S(O)O—, —S(O)—, —OS(O)$_2$—, —S(O)$_2$O—, —N(R')S(O)$_2$—, —S(O)$_2$N(R')—, —N(R')S(O)—, —S(O)N(R')—, —N(R')S(O)$_2$N(R')—, —N(R')S(O)N(R')—, $C_{3-12}$ carbocyclene, 3- to 12-membered heterocyclene, 5- to 12-membered heteroarylene or any combination thereof, wherein R' is H or $C_1$-$C_6$ alkyl; and TL is a targeting ligand of the structure:

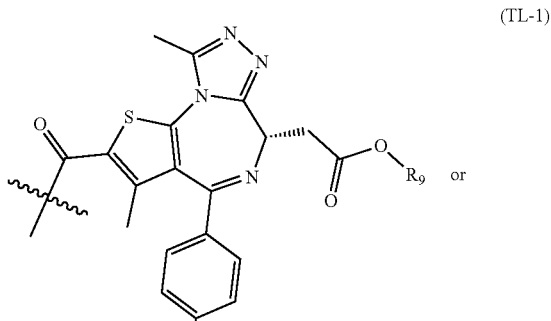

(TL-1)

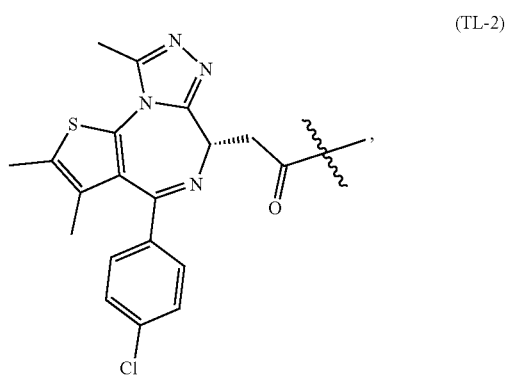

(TL-2)

wherein $R_9$ is methyl, or tertiary butyl, or

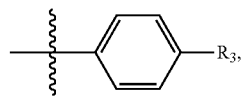

wherein $R_3$ is H or

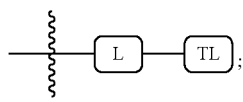

$R_4$ is H, halo or

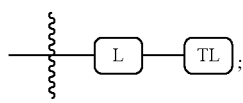

$R_5$ is methoxy or

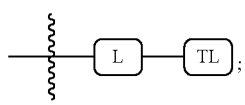;

$R_6$ is H or methyl; and
$R_8$ is H or ethyl,
provided that one of $R_2$, $R_3$, $R_4$ and $R_5$ is

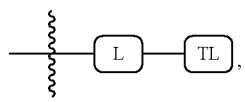, or a pharmaceutically acceptable salt or stereoisomer thereof.

2. The bifunctional compound of claim 1, wherein R is methyl;
$R_1$ is

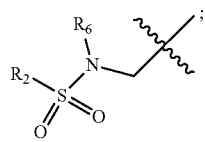

$R_2$ is

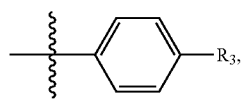

wherein
$R_3$ is

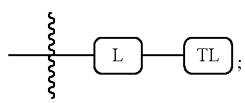;

$R_5$ is methoxy; and $R_6$ is methyl,
the bifunctional compound is represented by formula (Ia):

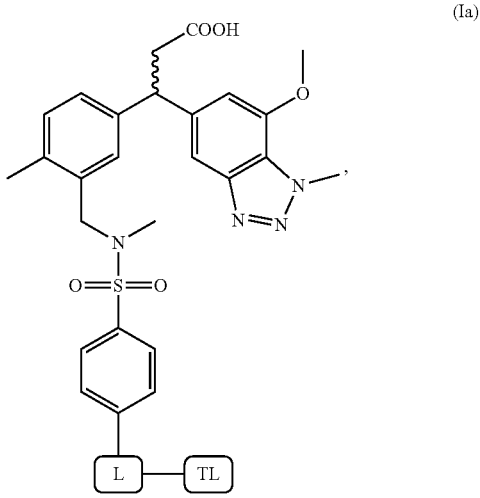

or a pharmaceutically acceptable salt or stereoisomer thereof.

3. The bifunctional compound of claim 1, wherein R is methyl;
$R_1$ is

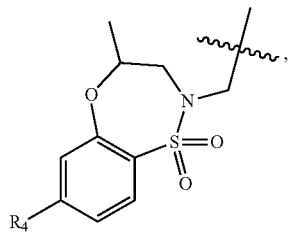

wherein
$R_4$ is

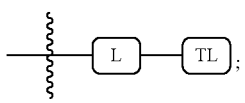;

$R_5$ is methoxy; and $R_8$ is H,
the bifunctional compound is represented by formula (Ib):

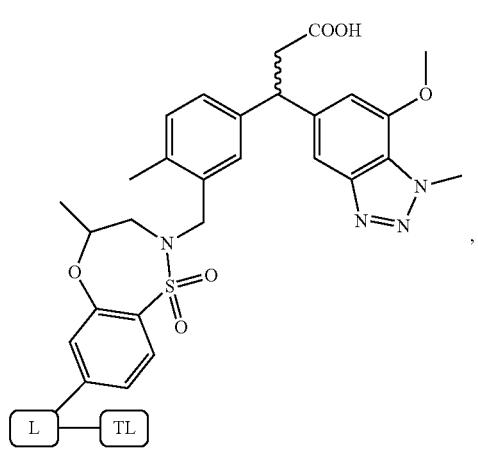

or a pharmaceutically acceptable salt or stereoisomer thereof.

4. The bifunctional compound of claim 1, wherein R is methyl;
$R_1$ is

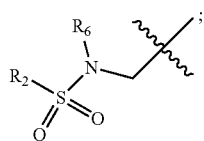

$R_2$ is

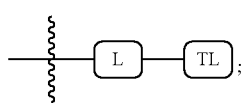

$R_5$ is methoxy;
$R_6$ is H; and $R_8$ is H,
the bifunctional compound is represented by formula (Ic):

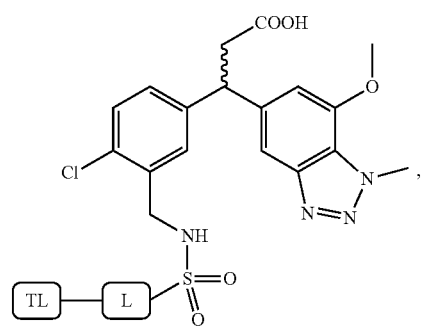

or a pharmaceutically acceptable salt or stereoisomer thereof.

5. The bifunctional compound of claim 1, wherein R is Cl, $R_1$ is

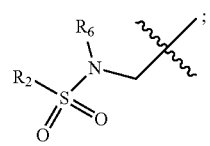

$R_2$ is

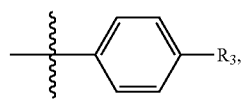

$R_3$ is

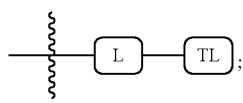

$R_5$ is methoxy;
$R_6$ is methyl; and $R_8$ is H,
the bifunctional compound is represented by formula (Id):

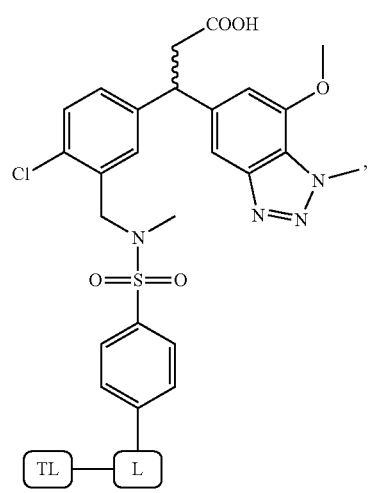

or a pharmaceutically acceptable salt or stereoisomer thereof.

6. The bifunctional compound of claim 1, wherein R is Cl;
$R_1$ is

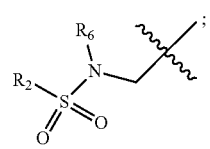

wherein
R₂ is

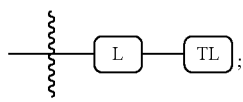

R₅ is methoxy;
R₆ is H; and R₈ is H,
the bifunctional compound is represented by formula (Ie):

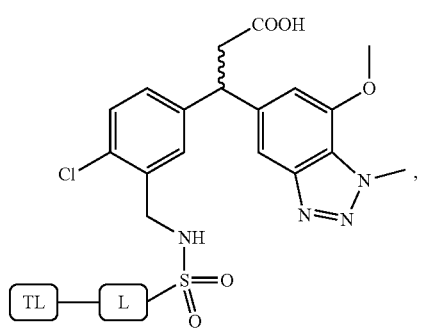

or a pharmaceutically acceptable salt or stereoisomer thereof.

7. The bifunctional compound of claim 1, wherein R is methyl;
R₁ is

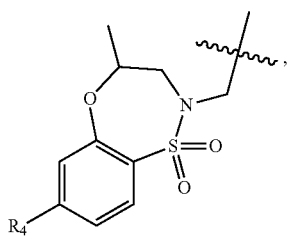

R₄ is H; and
R₅ is

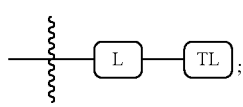

and R₈ is H,
the bifunctional compound is represented by formula (If):

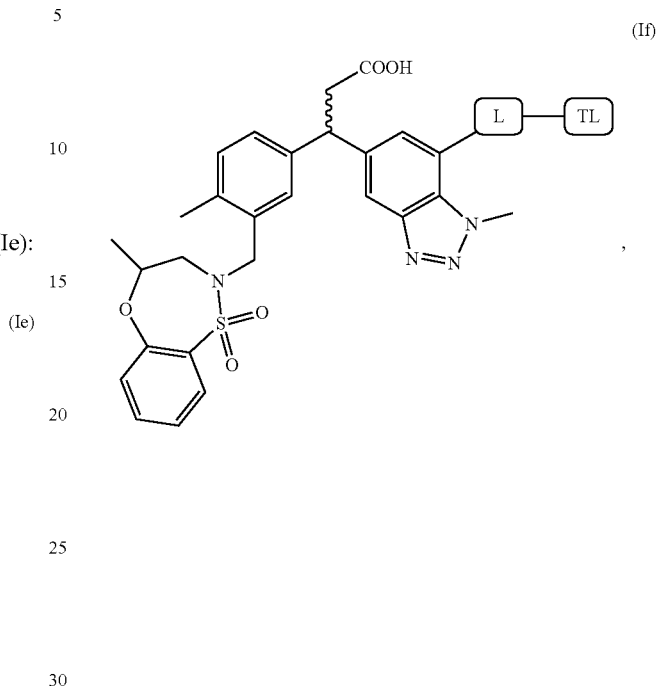

or a pharmaceutically acceptable salt or stereoisomer thereof.

8. The bifunctional compound of claim 1, wherein the targeting ligand binds BRD4, BRD3 and BRD2, and wherein the bifunctional compound is represented by a structure selected from the group consisting of:

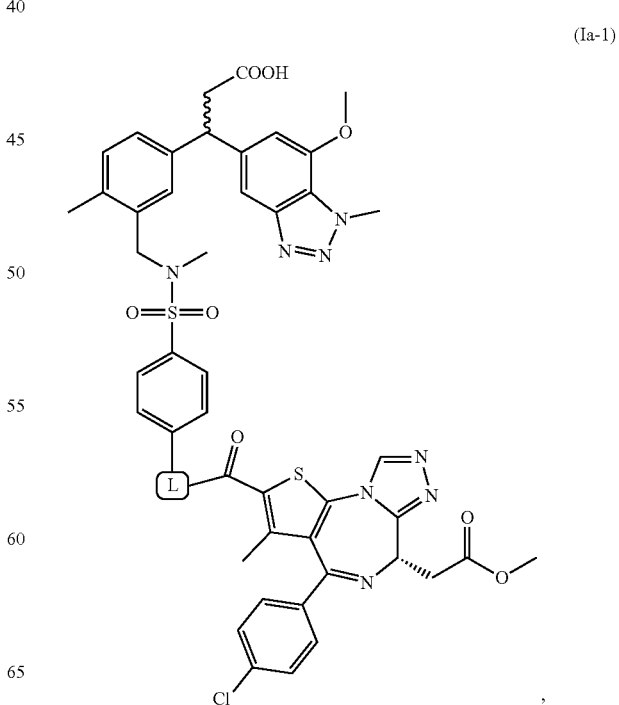

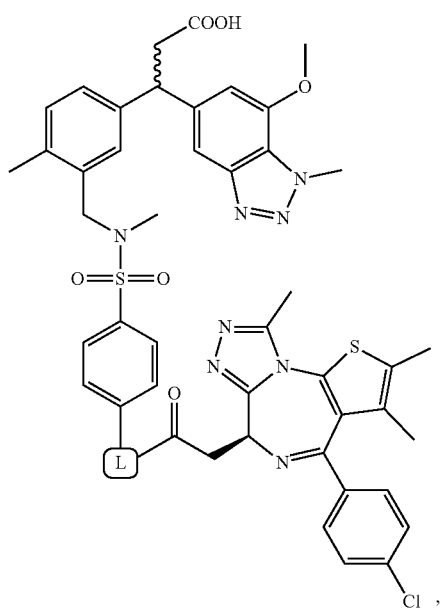
(Ia-2)
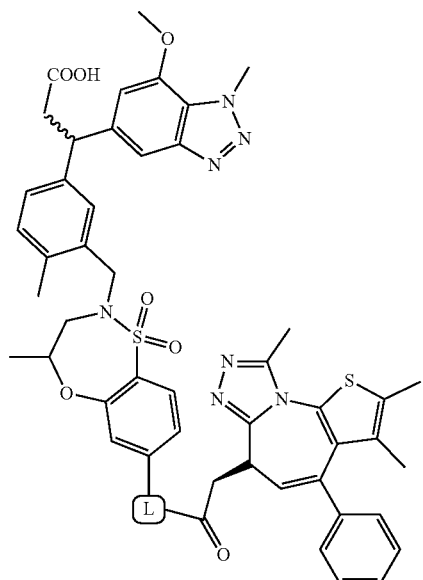
(Ib-2)
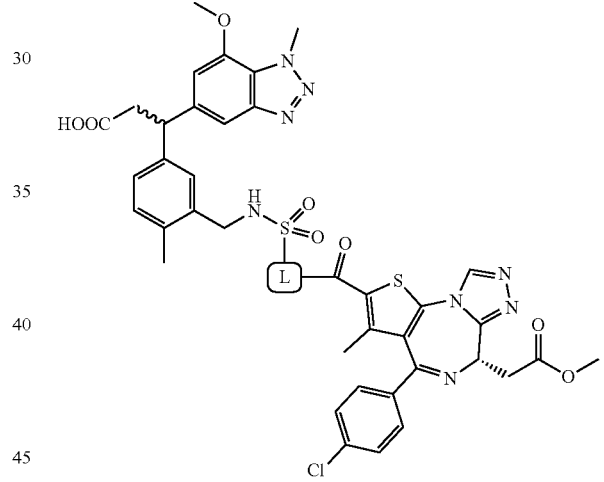
(Ic-1)
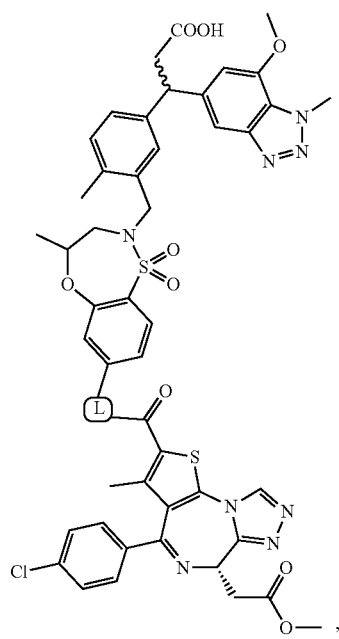
(Ib-1)
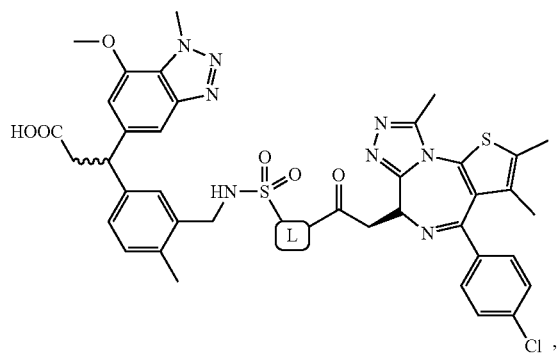
(Ic-2)

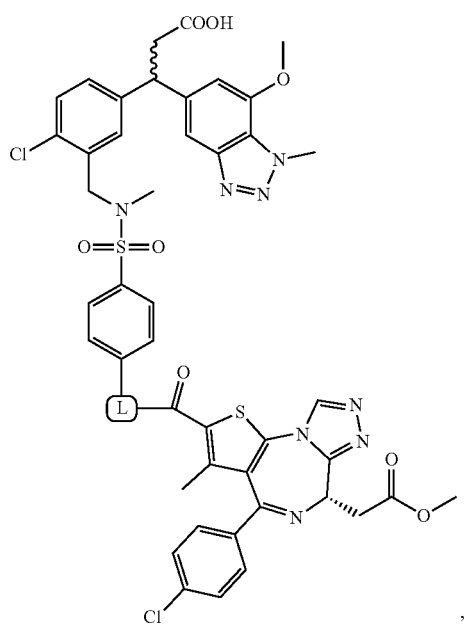
(Id-1)
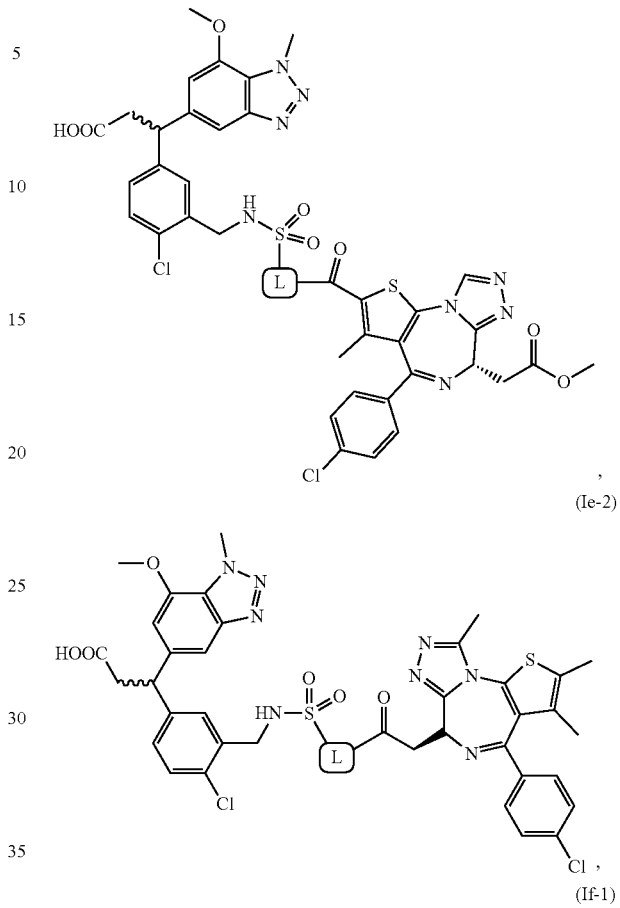
(Ie-1),
(Ie-2),
(If-1)
and
(If-2);
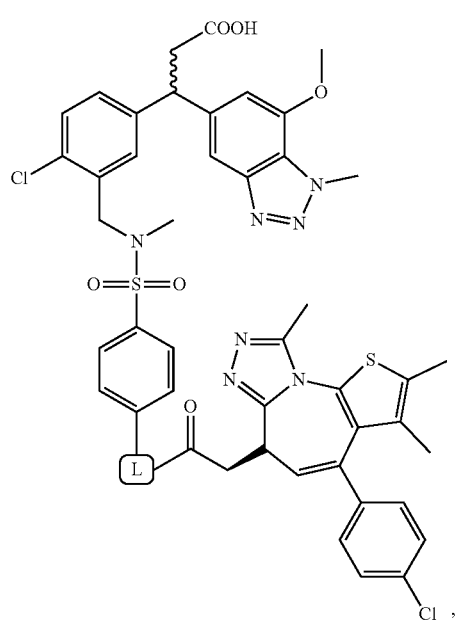
(Id-2)

or a pharmaceutically acceptable salt or stereoisomer thereof.
9. The bifunctional compound of claim 1, wherein the targeting ligand binds BRD4, BRD3 and BRD2, and wherein the bifunctional compound is represented by a structure selected from the group consisting of:
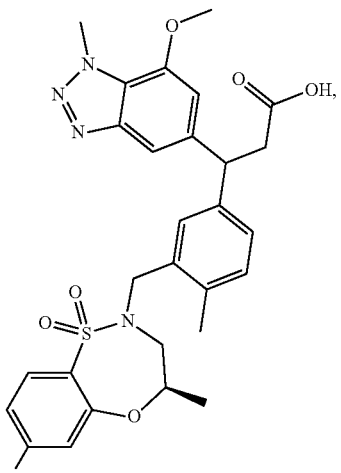
(1)
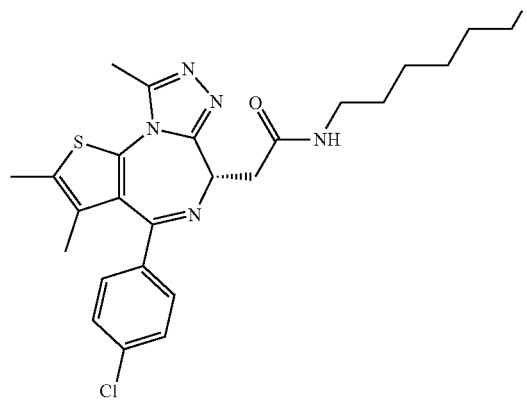
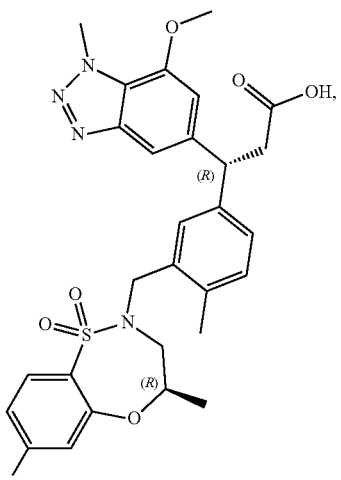
(2)

-continued
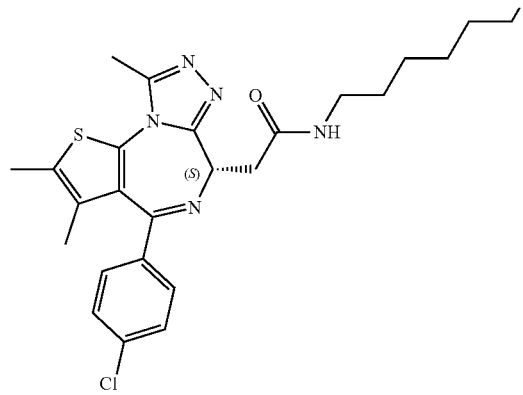
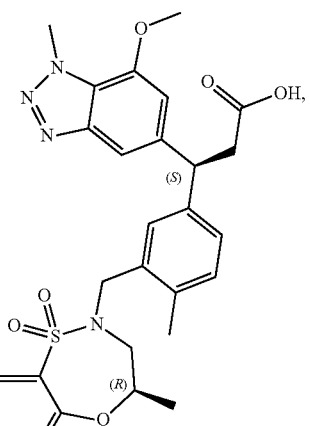
(3)
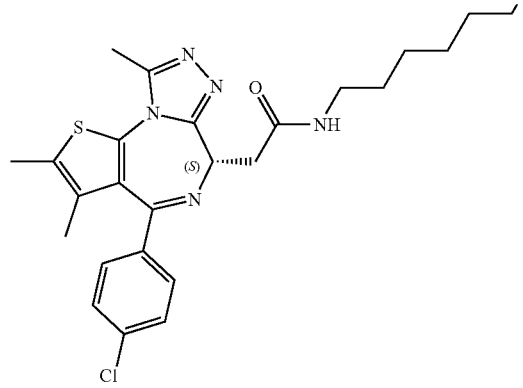
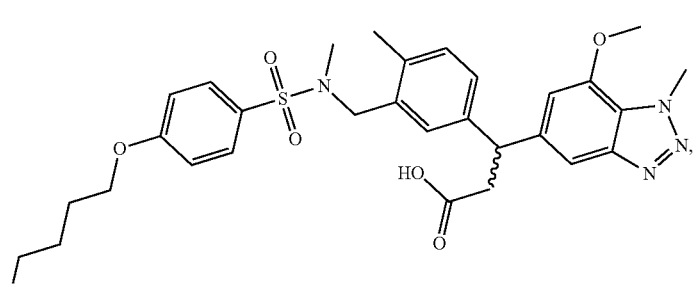
(4)

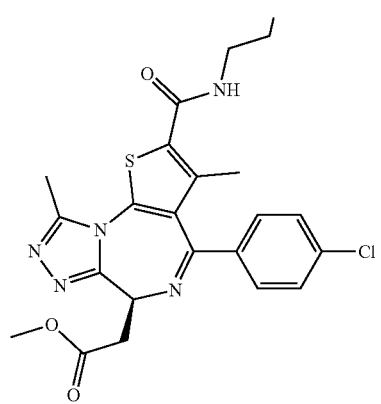
(5)
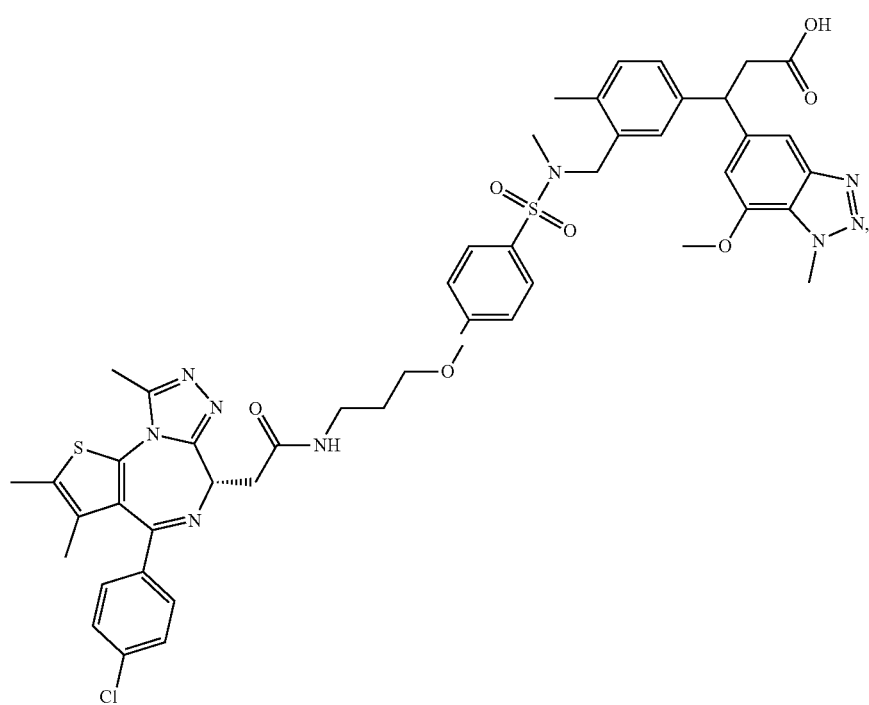
(6)
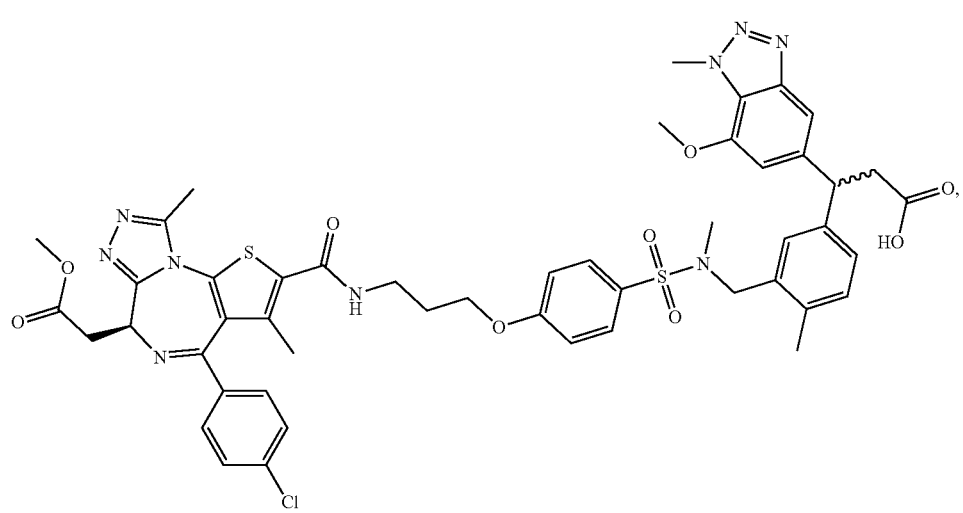

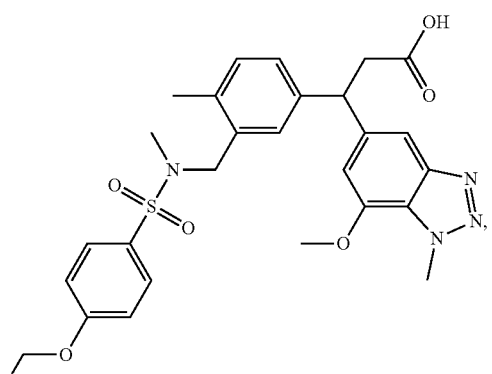
(7)
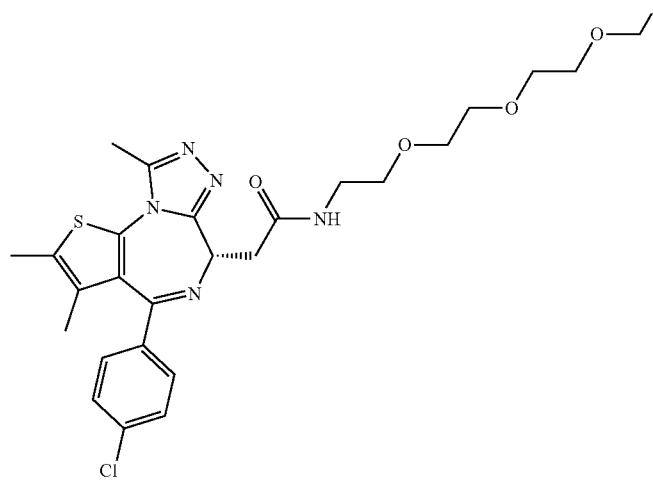
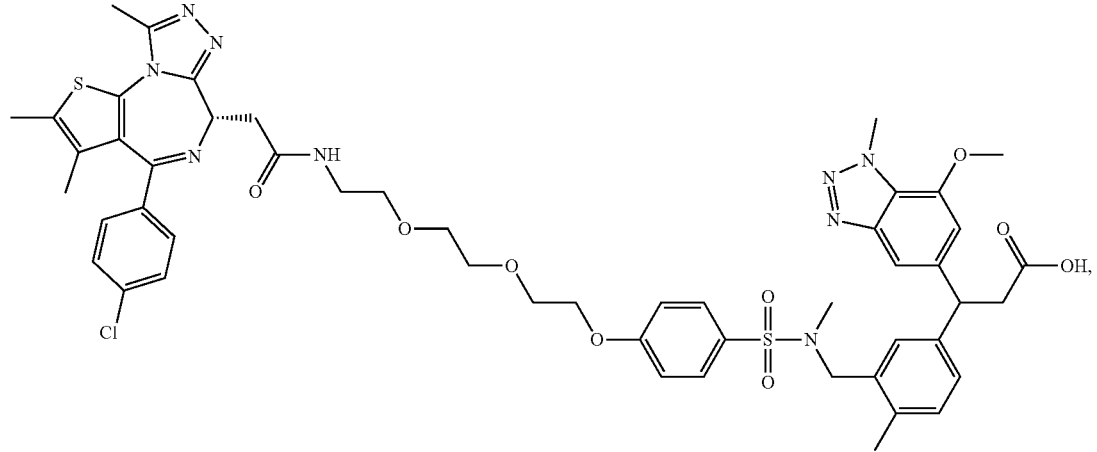
(8)

-continued
(9)
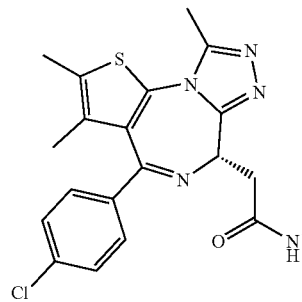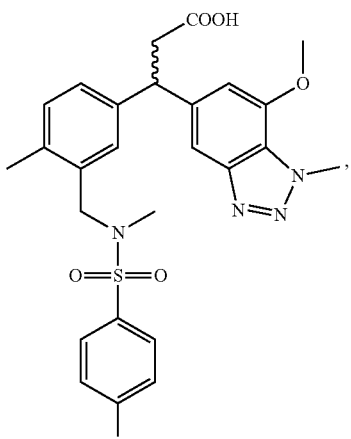
(21)
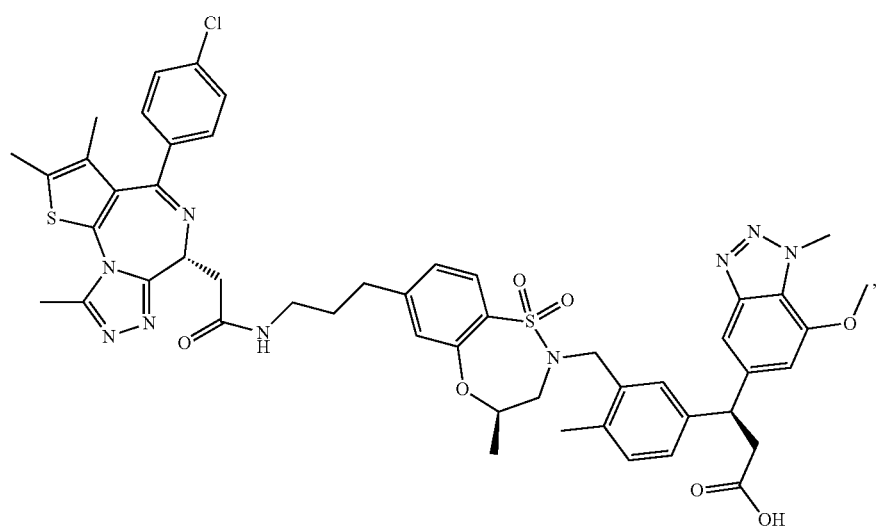
(22)
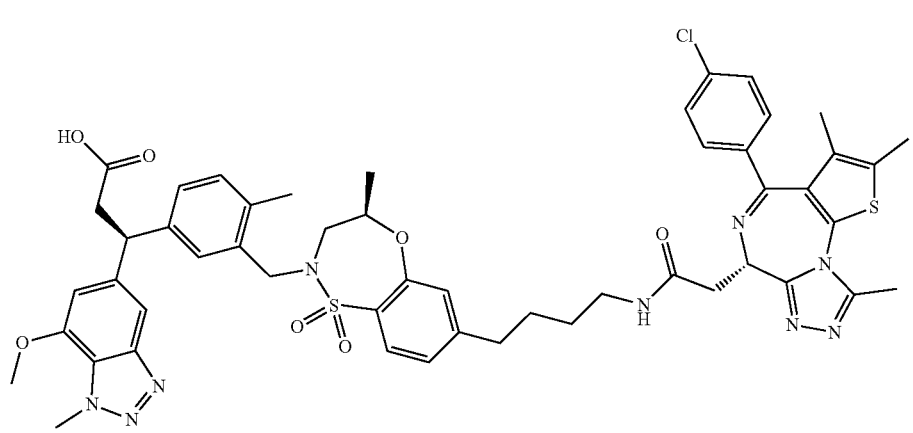

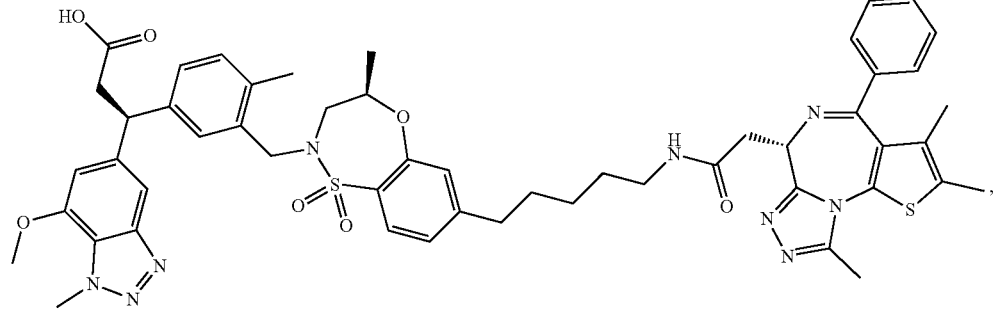
(23)
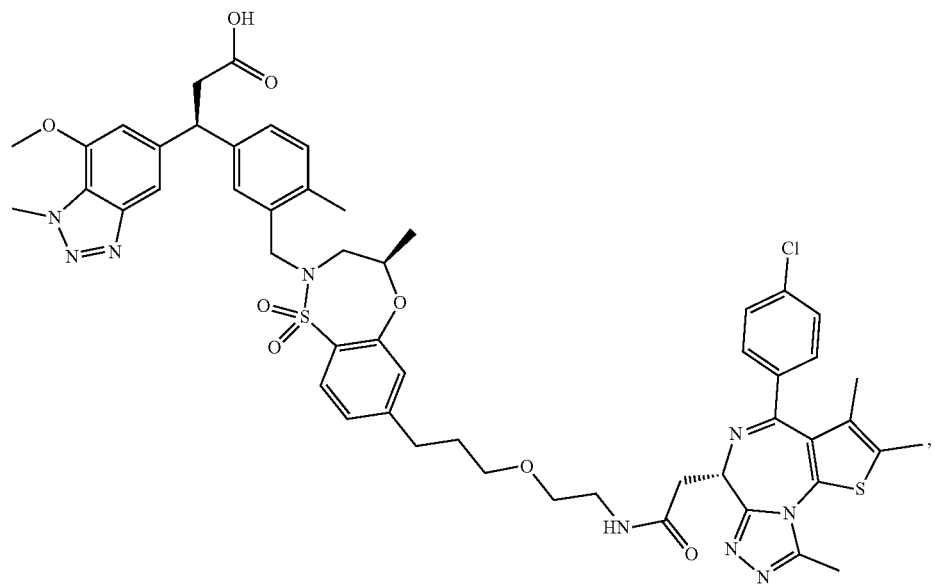
(24)
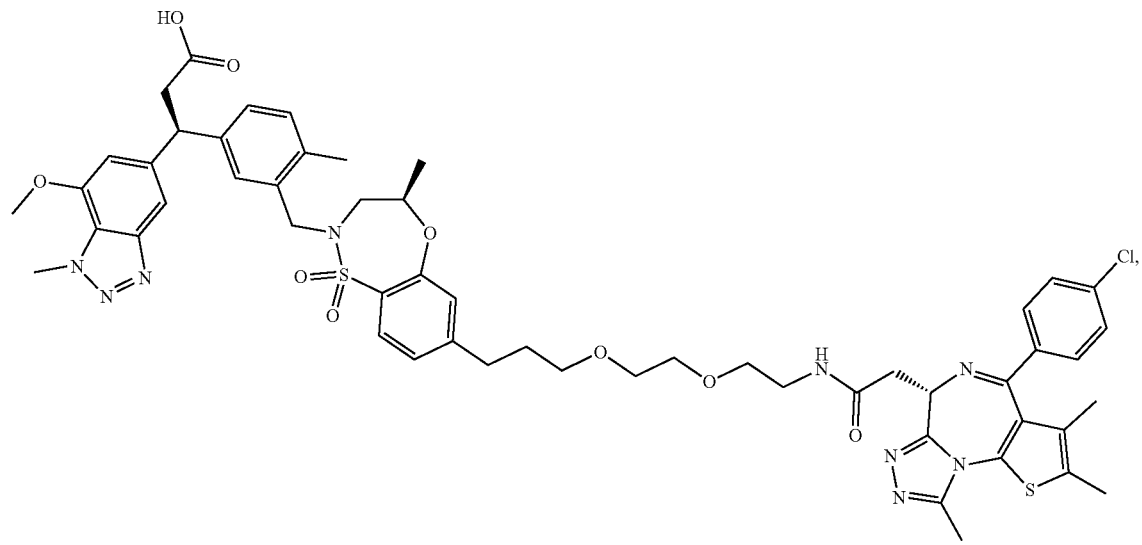
(25)

(26)

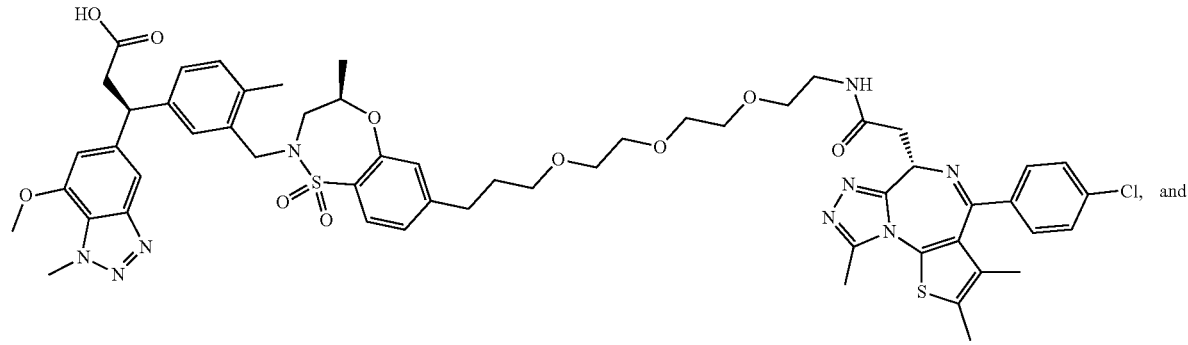

and (27)

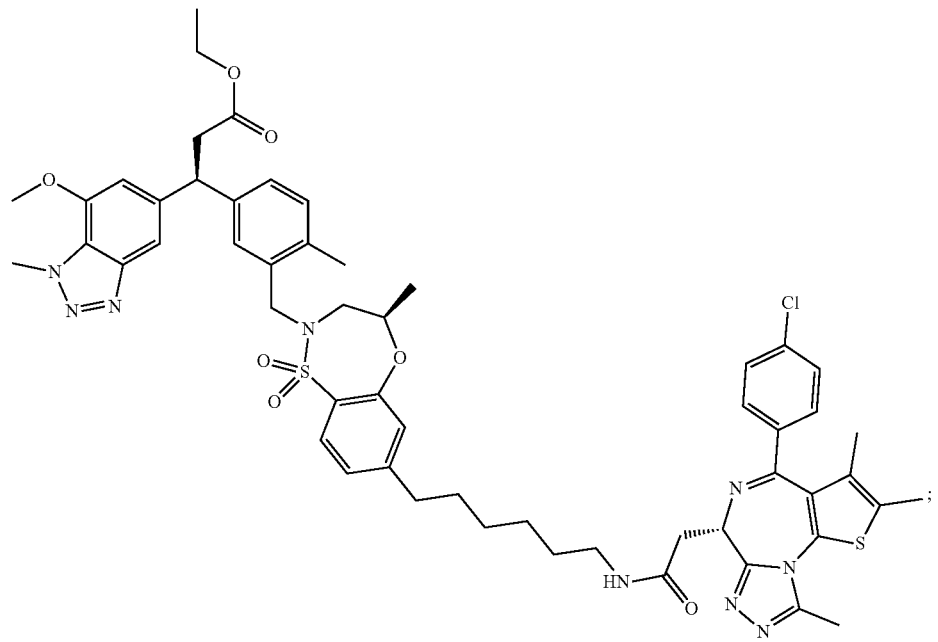

;

a pharmaceutically acceptable salt or stereoisomer thereof.

10. A pharmaceutical composition comprising a therapeutically effective amount of the bifunctional compound of claim 1, and a pharmaceutically acceptable carrier.

11. A method of treating a disease or disorder characterized by an aberrant or dysfunctional BRD4, BRD3 or BRD2, comprising administering to a subject in need thereof a therapeutically effective amount of the bifunctional compound of claim 1.

* * * * *

UNITED STATES PATENT AND TRADEMARK OFFICE
CERTIFICATE OF CORRECTION

PATENT NO. : 12,365,677 B2
APPLICATION NO. : 17/258340
DATED : July 22, 2025
INVENTOR(S) : Nathanael S. Gray et al.

Page 1 of 2

It is certified that error appears in the above-identified patent and that said Letters Patent is hereby corrected as shown below:

In the Claims

In Column 169, Lines 40-65:
Delete the following structure:

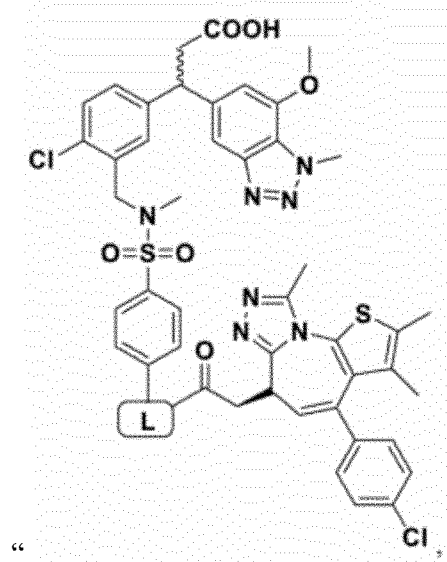

" ", ,

Signed and Sealed this
Sixteenth Day of September, 2025

Coke Morgan Stewart
*Acting Director of the United States Patent and Trademark Office*

CERTIFICATE OF CORRECTION (continued)
U.S. Pat. No. 12,365,677 B2

Replace with the following structure: